(12) United States Patent
Kolmar et al.

(10) Patent No.: US 8,278,262 B2
(45) Date of Patent: Oct. 2, 2012

(54) USE OF MICROPROTEINS AS TRYPTASE INHIBITORS

(75) Inventors: Harald Kolmar, Mühltal (DE);
Christian Sommerhoff, München (DE);
Alexander Wentzel, Göttingen (DE)

(73) Assignee: BioNTech AG (DE)

( * ) Notice: Subject to any disclaimer, the term of this patent is extended or adjusted under 35 U.S.C. 154(b) by 649 days.

(21) Appl. No.: 11/663,435

(22) PCT Filed: Sep. 19, 2005

(86) PCT No.: PCT/EP2005/010087
§ 371 (c)(1),
(2), (4) Date: Sep. 19, 2007

(87) PCT Pub. No.: WO2006/032436
PCT Pub. Date: Mar. 30, 2006

(65) Prior Publication Data
US 2009/0130692 A1 May 21, 2009

(30) Foreign Application Priority Data
Sep. 21, 2004 (EP) .................................... 04022455

(51) Int. Cl.
*A61K 38/00* (2006.01)
*G01N 33/567* (2006.01)
(52) U.S. Cl. ........................................ 514/1.1; 435/7.21
(58) Field of Classification Search ........................ None
See application file for complete search history.

(56) References Cited

U.S. PATENT DOCUMENTS
2009/0156476 A1* 6/2009 Kolmar et al. .................. 514/12

FOREIGN PATENT DOCUMENTS
EP        0 401 109 A1    12/1990
(Continued)

OTHER PUBLICATIONS

Asherie. Protein Crystallization and Phase Diagrams. Methods. 2004. vol. 34, pp. 266-272.*

(Continued)

*Primary Examiner* — Marcela M Cordero Garcia
(74) *Attorney, Agent, or Firm* — McAndrews, Held & Malloy, Ltd.

(57) ABSTRACT

Disclosed are uses of microproteins preferably microproteins forming a cystine knot (i.e. belonging to the family of inhibitor cystine knot (ICK) polypeptides) or polynucleotides encoding said microproteins for the preparation of a pharmaceutical composition for treating or preventing a disease that can be treated or prevented by inhibiting the activity of tryptase as well as corresponding methods of treatment. Also disclosed are uses of the microproteins for inhibiting tryptase activity, for purifying tryptase, as a carrier molecule for tryptase and for deleting or quantifying tryptase in a sample, including corresponding diagnostic applications. Furthermore disclosed are fusion proteins comprising an inactive barnase as well as fusion proteins comprising barnase and a microprotein. Also encompassed are nucleic acid molecules encoding such a fusion protein, as well as corresponding vectors, host cells, preparation methods and uses of the fusion protein. Moreover, the present application discloses a crystal of a microprotein fused with barnase, preferably inactive barnase. The disclosure also refers to corresponding preparation methods for the crystal, structure analysis methods using the crystal data storage media comprising the structure data obtained, as well as to in silico methods using the structure data for characterizing the binding of microproteins to target molecules. Furthermore, disclosed are pharmaceutical compositions comprising the crystal and corresponding medical uses.

Figure 2:
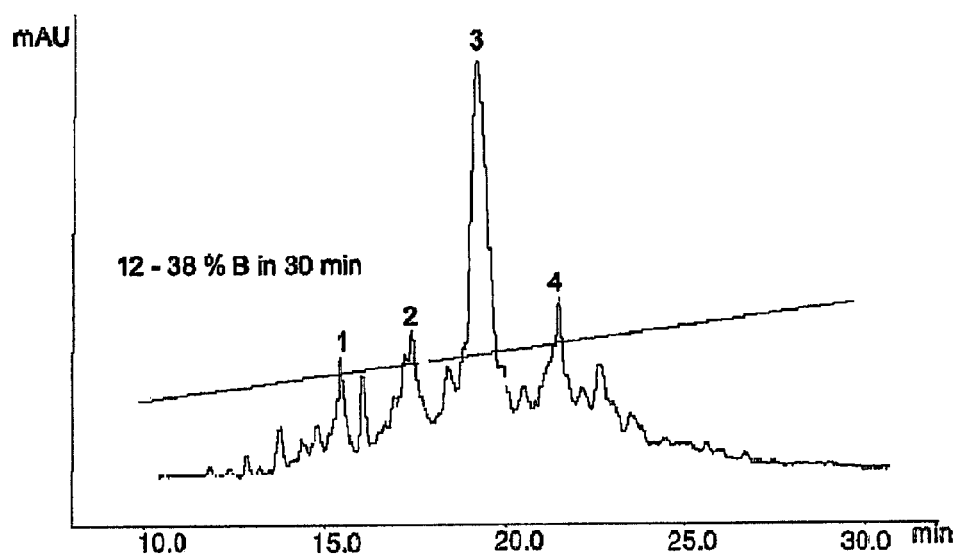

31 Claims, 20 Drawing Sheets
(5 of 20 Drawing Sheet(s) Filed in Color)

FOREIGN PATENT DOCUMENTS

WO    WO 01/27147 A1    4/2001

OTHER PUBLICATIONS

H.J.C. Berendsen. A Glimpse of the Holy Grail? Science (1998) 282, pp. 642-643.*

Rudinger. In: Peptide Hormones, JA Parsons, Ed. (1976), pp. 1-7.*

SIGMA. Designing Custom Peptides. http://www.sigma-genosys.com/peptide_design.asp (Accessed Dec. 16, 2004), 2 pages.*

W.S. Messer, "Vasopressin and Oxytocin", web document updated Apr. 3, 2000; http://www.neurosci.pharm.utoledo.edu/MBC3320/vasopressin.htm; 5 pages.*

D.E. Smilek, et al. Proc. Natl. Acad. Sci. USA (1991) 88, pp. 9633-9637.*

D. Voet and J.G. Voet. Biochemistry, 2nd Edition.(1995), pp. 235-241.*

Hernandez J-F et al., Squash trypsin Inhibitors from *Momordica cochinchinensis* exhibit an atypical macrocyclic structure, Biochemistry, vol. 39, 2000, pp. 5722-5730.

Craik J et al., The cyclotides: novel macrocyclic peptides as scaffold in drug design, Current Opinion in Drug Discovery and Development, vol. 5, No. 2, 2002, pp. 251-260.

Schmoldt H-U et al., A fusion protein system for the recombinant production of short disulfide bond rich cystine knot peptides using barnase as a purification handle, Protein Expression and Purification, vol. 39, Jan. 2005, pp. 82-89.

Deyev S. et al., Design of multivalent complexes using the barnase-barstar module, Nature Biotechnology, vol. 21, No. 12, Dec. 2003, pp. 1486-1492.

Axe D. et al., A Search for single substitutions that eliminate enzymatic function in a bacterial ribonuclease, Biochemistry, vol. 37, 1988, pp. 7157-7166.

* cited by examiner

A
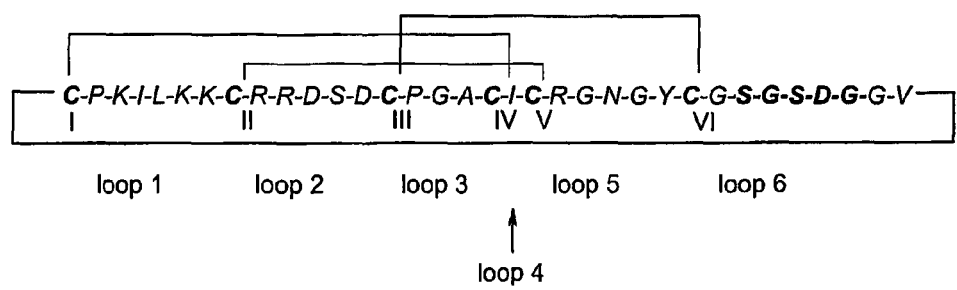
B
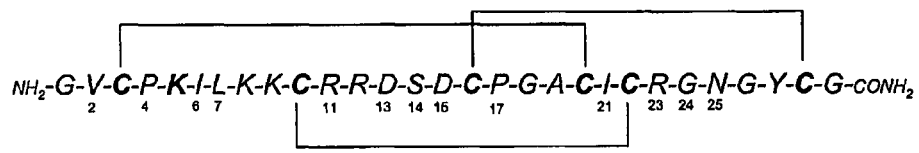
C
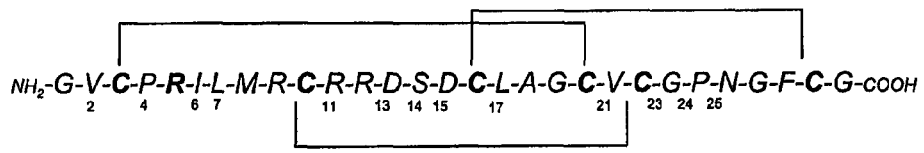
Figure 1

```
        GGGtccgtttgcccgaaaatcctgaaaaaatgtcgacgtgactccgactgcctggctggc
  1     ---------+---------+---------+---------+---------+---------+    60
        CCCaggcaaacgggcttttaggactttttttacagctgcactgaggctgacggaccgaccg
        GlySerValCysProLysIleLeuLysLysCysArgArgAspSerAspCysLeuAlaGly tgcgtttgcgggcccaacggtttctgcgggtcctaa
 61     ---------+---------+---------+------                              96
        acgcaaacgcccgggttgccaaagacgcccaggatt
        CysValCysGlyProAsnGlyPheCysGlySerEnd
```

Figure 5

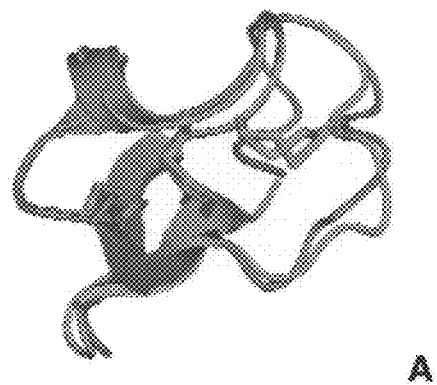
A
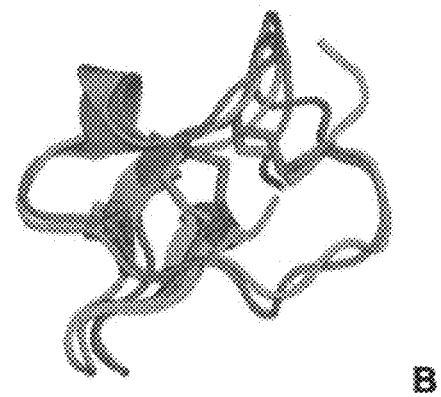
B
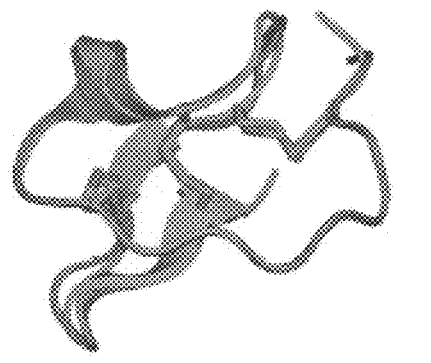
C
Figure 20

USE OF MICROPROTEINS AS TRYPTASE INHIBITORS

The present application claims priority to International Application No. PCT/EP2005/010087 filed Sep. 19, 2005, which claims priority to European Patent Application No. 04022455.2 filed Sep. 21, 2004. The contents of both applications are expressly incorporated herein by reference in their entireties.

The present application relates to the use of microproteins, preferably microproteins forming a cystine knot (i.e. belonging to the family of inhibitor cystine knot (ICK) polypeptides), or polynucleotides encoding said microproteins for the preparation of a pharmaceutical composition for treating or preventing a disease that can be treated or prevented by inhibiting the activity of tryptase as well as to corresponding methods of treatment. The present invention also relates to uses of the microproteins for inhibiting tryptase activity, for purifying tryptase, as a carrier molecule for tryptase and for detecting or quantifying tryptase in a sample, including corresponding diagnostic applications. The present invention furthermore relates to fusion proteins comprising an inactive barnase as well as to fusion proteins comprising barnase and a microprotein. Also encompassed by the present invention are nucleic acid molecules encoding such a fusion protein, as well as corresponding vectors, host cells, preparation methods and uses of the fusion protein. Moreover, the present invention relates to a crystal of a microprotein fused with barnase, preferably inactive barnase. The present invention also refers to corresponding preparation methods for the crystal, structure analysis methods using the crystal, data storage media comprising the structure data obtained, as well as to in silico methods using the structure data for characterizing the binding of microproteins to target molecules. Furthermore, the invention relates to pharmaceutical compositions comprising the crystal and corresponding medical uses.

Asthma is a complex disease involving multiple biochemical mediators for both its acute and chronic manifestations. Increasingly, asthma is recognized as an inflammatory disorder (see, e.g., Hood, et al., 1984). Asthma is frequently characterized by progressive development of hyperresponsiveness of the trachea and bronchi to both immunospecific allergens and chemical or physical stimuli. The hyperresponsiveness of asthmatic bronchiolar tissue is thought to result from chronic inflammation reactions, which irritate and damage the epithelium lining the airway wall and promote pathological thickening of the underlying tissue. Bronchial biopsy studies have indicated that even patients with mild asthma have features of inflammation in the airway wall.

One initiator of the inflammatory sequence is an allergic response to inhaled allergens. Leukocytes carrying IgE receptors, mast cells and basophils, but also monocytes, macrophages, and eosinophils, are present in the epithelium and underlying smooth muscle tissues of bronchi where they are activated initially by binding of specific inhaled antigens to the IgE receptors. Activated mast cells release a number of preformed or primary chemical mediators of the inflammatory response and enzymes. Furthermore, numerous secondary mediators of inflammation are generated in situ by enzymatic reactions of activated mast cells, including superoxide and lipid derived mediators. In addition, several large molecules are released by degranulation of mast cells: proteoglycans, peroxidase, arylsulfatase B, and notably the proteases tryptase and chymotryptic proteinase (chymase).

This release of compounds from mast cells probably accounts for the early bronchiolar constrictor response that occurs in susceptible individuals after exposure to airborne allergens. The early asthmatic reaction is maximal at around fifteen minutes after allergen exposure; recovery occurs over the ensuing one to two hours. In 25-35% of individuals, the early asthmatic reaction is followed by a further decline in respiratory function which begins within a few hours and is maximal between six and twelve hours post-exposure. This late asthmatic reaction is accompanied by a marked increase in the number of inflammatory cells infiltrating bronchiolar smooth muscle and epithelial tissues, and spilling into the airways. These cells include eosinophils, neutrophils, and lymphocytes, all of which are attracted to the site by release of mast cell derived chemotactic agents. The infiltrating cells themselves become activated during the late reaction phase. The late asthmatic response is believed to be a secondary inflammatory reaction mediated in part by the secretory activity of macrophages.

Human tryptase is a serine proteinase which is the predominant protein present in human mast cells. The term tryptase covers four closely related enzymes ($\alpha$, I, II/$\beta$, III; possessing 90 to 98% sequence identity) (Miller et al. 1989; Vanderslice et al., 1990).

Tryptase is the major secretory protease of human mast cells and is proposed to be involved in neuropeptide processing and tissue inflammation. Mature human tryptase is a tetrameric glycosylated molecule, is heparin-associated and composed of heterogenous, catalytically active subunits (see, e.g., Vanderslice et al., 1990; Miller et al., 1989, 1990, Sommerhoff et al., 1999).

Tryptase is stored in mast cell secretory granules. After mast cell activation, human tryptase can be found in various biologic fluids. Tryptase levels in lung lavage fluid obtained from atopic asthmatics increase after endobronchial allergen challenge. Some smokers of cigarettes have striking elevations of bronchoalveolar lavage fluid tryptase levels compared to nonsmoker control groups, a finding that provides some support for the hypothesis that release of proteinases from activated mast cells could contribute to lung destruction in smoker's emphysema, (Kalenderian, et al., Chest 94:119-123, 1988). In addition, tryptase has been shown to be a potent mitogen for fibroblasts, suggesting its involvement in pulmonary fibrosis and interstitial lung diseases (Ruoss et al., 1991).

Tryptase has been implicated in a variety of biological processes, including degradation of vasodilating and bronchorelaxing neuropepudes (see Caughey, et al., 1988; Franconi, et al., 1989; and Tam, et al. 1990) and modulation of bronchial responsiveness to histamine (see Sekizawa, et al., 1989) and psoriasis. These studies suggest that tryptase possibly increases bronchoconstriction in asthma by destroying bronchodilating peptides.

Elevated levels of mast-cell tryptase have been found
  in the plasma of patients with mastocytosis, after systemic anaphylaxis (Schwartz et al., 1987, 1989).
  in the duodenal mucosa of psoriasis patients (Michaelsson et al., 1997).
  in bronchoalveolar lavage fluid of patients with asthma (Broide et al., 1991; Wenzel et al., 1988), interstitial lung diseases (Walls et al., 1991), and after antigen challenge of allergic patients (Castells & Schwartz 1988).
  in the skin blister fluid after cutaneous antigen challenge in patients with atopic and allergic skin disease (Shalit et al., 1990; Atkins et al., 1990; Brockow et al., 2002).
  in nasal lavage fluid after local antigen challenge of patients with seasonal allergic rhinitis (Juliusson et al., 1991; Howarth, 1995)
  in the crevicular fluid of patients with gingivitis and periodontitis (Cox & Eley, 1989) and in the lesional skin of patients with psoriasis (Michaelsson et al., 1997).

in the mucosa of the ileum and colon of patients with inflammatory bowel disease (IBD), which was accompanied by great changes of the content in mast cells such as dramatically increased expression of TNFalpha, IL-16 and substance P. The evidence of mast cell degranulation was found in the wall of intestine from patients with IBD with immunohistochemistry technique. The highly elevated histamine and tryptase levels were detected in mucosa of patients with IBD, strongly suggesting that mast cell degranulation is involved in the pathogenesis of IBD (He, 2004).

in myeloblasts in patients with acute myeloid leukaemia (AML) that produce significant amounts of tryptase(s). In these patients, myeloblasts express alpha-tryptase mRNA in excess over beta-tryptase mRNA, and secrete the respective protein (=pro-alpha-tryptase) in a constitutive manner (Sperr et al., 2001, 2002).

Human tryptase is inhibited by small molecular weight substances (e.g. leupeptin and diisopropyl fluorophosphate). Divalent cations, such as calcium, and benzamidine and its derivatives are competitive inhibitors of human mast cell tryptase (Schwartz, 1994). Several low-molecular-weight compounds have been described as tryptase inhibitors in the patent literature (summarized in Newhouse 2002). However, none of the compounds have made their way into later stage clinical trials. This is explained by undesired side reactions, insufficient selectivity, high toxicity, low stability and/or low bioavailability of the different inhibitor compounds described (Newhouse 2002).

Although tryptase has trypsin-like properties, most protein-based inhibitors do not inhibit it. Although having trypsin-like properties, it is a characteristic of human tryptase not to be inhibited by potent trypsin inhibitors such as bovine pancreatic trypsin inhibitor (Di Marco & Priestle, 1997). Endogenous inhibitors that target the catalytic sites of mast cell tryptase have yet to be reported. Human tryptase activity is inhibited by lactoferrin and myeloperoxidase (both neutrophil-derived) and by antithrombin-III, all of which antagonise the glycosaminoglycans (heparin or chondroitin sulfate) that stabilize the mast cell tryptase (MCT) tetramer (Alter et al., 1990; Cregar et al., 1999; Elrod et al., 1997). The only two known protein-based human tryptase inhibitors which inhibit tryptase via tight binding to its active site are the leech derived tryptase Inhibitor (LDTI) and the tick-derived protease inhibitor protein (rTdPI) (WO 95/03333 and WO 01/05832). LDTI is a 46 residue protein, where two LDTI monomers interact with one tryptase tetramer. A recombinant form of this Kazal-type protein has been found to efficiently inhibit 2 of the 4 catalytic sites of the tetrameric tryptase (Stubbs et al., 1997; Auerswald et al., 1994; Sommerhoff et al., 1994) with a Ki of 1.4 nM, while the remaining two sites are inhibited with Ki values of 560 and 10,000 nM, respectively. The efficient binding of only two catalytic sites out of four in the tryptase tetramer has so far prevented any therapeutic uses of LDTI.

Thus, it would be desirable to provide further inhibitors to tryptase, especially for therapeutic purposes. In case of proteinaceous inhibitors, it would be furthermore desirable to provide the inhibitor in crystalline form so as to facilitate structure analysis and have a basis for studying and improving tryptase binding. In addition, it would be desirable to provide corresponding means and methods that may be useful for improving the production of such inhibitors or crystals thereof.

In view of the above explanations, it is clear that there is still an on-going need for efficient inhibitors of tryptase. Thus, the technical problem underlying the present invention is to make available further tryptase inhibitors that can be used to prevent or treat diseases that can be prevented or treated by inhibiting tryptase activity. Preferably, such inhibitors should overcome drawbacks associated with tryptase inhibitors of the prior art such as undesired side reactions, insufficient selectivity, high toxicity, low stability, low bioavailability and/or insufficient binding affinity.

This technical problem is solved by the provision of the embodiments as characterized in the claims.

Accordingly, the present invention relates to the use of a microprotein or a polynucleotide encoding said microprotein for the preparation of a pharmaceutical composition for treating or preventing a disease that can be treated or prevented by inhibiting the activity of tryptase.

The present invention is based on the surprising finding that microproteins are capable of efficiently binding tryptase. This is shown for many exemplary specimens in Example 3, infra. Three of the microproteins of the invention were furthermore positively tested for tryptase selectivity (see Table 2 in Example 3, infa). Thus, the use of the present invention refers to the use of microproteins which are capable of significantly inhibiting the activity of tryptase. Preferably, the microproteins are able to bind all four catalytic sites of the tryptase tetramer. The provision of the present invention, i.e. the recognition that microproteins can be used to inhibit tryptase in particular for therapeutic purposes, overcomes disadvantages that are known for low-molecular weight tryptase inhibitors (see, e.g., Newhouse, 2002). For instance, such small molecules may show a toxic effect to the organism to which they are applied due to a relatively low binding specificity causing binding to molecules other than tryptase. Compared to the small molecules, microproteins show a larger interaction surface so that a more selective binding can be expected for them. Furthermore, protein-based binding molecules typically have a lower dissociation rate constant than low-molecular weight molecules, thus, binding for a longer time to the target and therefore having more advantageous binding properties.

In addition, a further advantage over low-molecular weight tryptase inhibitors lies in the fact that microproteins can be expected not to be able to cross the membrane barrier. This prevents microproteins from binding to tryptase stored within mast cells which may potentially influence the physiological state of the mast cell negatively. Small molecules, by contrast, can often cross membranes. Moreover, especially cystine knot proteins are notoriously stable against enzymic or thermal degradation.

The term "microprotein" generally refers to polypeptides with a relatively small size of not more than 50 amino acids and a defined structure based on intra-molecular disulfide bonds. Microproteins are typically highly stable and resistant to heat, pH and proteolytic degradation. The current knowledge on microproteins, in particular in regard to their structure and occurrence, is for instance reviewed in Craik (2001); Pallaghy (1994); and Craik (J. Mol. Biol. 294 (1999), 1327-1336).

In a preferred embodiment, the microprotein in the use of the invention comprises at least six cysteine residues, of which six cysteine residues are connected via disulphide bonds so as to form a cystine knot.

Such microproteins are also known as inhibitor cystine knot (ICK) polypeptides and are also called like that in the following explanations.

Figure 11:
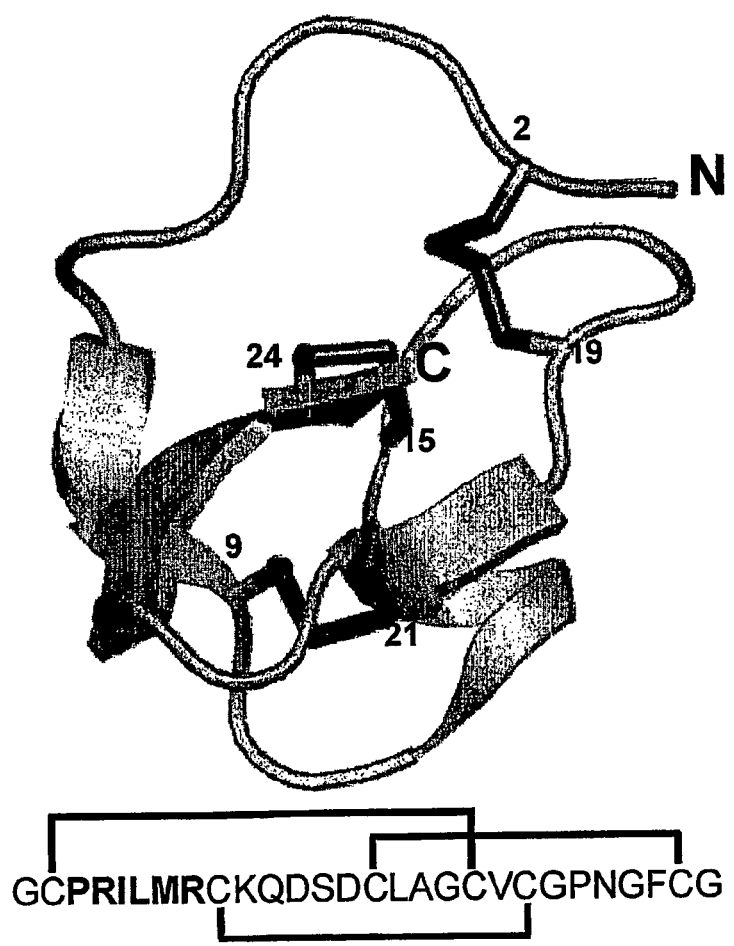

The term "cystine knot" refers to a three-dimensional structure formed by the ICK polypeptides which are characterized by a small triple β-sheet which is stabilized by a three-disulfide bond framework which comprises an embedded ring formed by two disulphide bonds and their connecting backbone segments, through which a third disulfide bond is threaded. Preferably, the cystine knot is formed by six conserved cysteine residues and the connecting backbone segments, wherein the first disulfide bond is between the first and the fourth cysteine residue, the second disulfide bond between the second and the fifth cysteine residue and the third disulfide bond between the third and the sixth cysteine residue, the third disulfide bond being threaded through the ring formed by the other two disulfide bonds and their connecting backbone segments. FIG. 11 shows an example of a corresponding cystine knot forming microprotein. If considered suitable, a disulfide bond may be replaced by a chemical equivalent thereof which likewise ensures the formation of the overall topology of a cystine knot. For testing whether a given microprotein has formed the correct cystine knot, a skilled person can determine which cystine residues are connected with one another. This can, for instance, be done according to techniques described in Gorasson (J. Biol. Chem. 278 (2003), 48188-48196) and Horn (J. Biol. Chem. 279 (2004), 35867-35878). Microproteins with a cystine knot are for instance described in Craik (2001); Pallaghy (1994); and Craik (J. Mol. Biol. 294 (1999), 1327-1336).

The microproteins for use in connection with the present invention may have a peptide backbone with an open or a circular conformation. The open conformation preferably refers to microproteins with an amino-group at the N-terminus and a carboxyl-group at the C-terminus. However, any modifications of the termini, along with what a skilled person envisages based on the state of the art in peptide chemistry, is also contemplated, as long as the resulting microprotein shows tryptase-inhibiting activity. In the closed conformation, the ends of the peptide backbone of the microproteins are connected, preferably via a covalent bond, more preferably via an amide (i.e. peptide) bond. Microproteins with a closed conformation having a cystine knot topology are known in the prior art as "cyclotides" and their knot as "cyclic cystine knot (CCK)". Such cyclotides are for instance described in WO 01/27147 and Craik (Curr. Opinion in Drug Discovery & Development 5 (2002), 251-260).

It is furthermore preferred that the microproteins for use in the present invention comprise the amino acid motif $CX_3$-$CX_4$-$CX_{4-7}$-$CX_1$-$CX_{4-5}$-$CX_{5-7}$ (SEQ ID NO: 18), with X meaning independently from each other any amino acid residue. C means, in accordance with the standard nomenclature, cysteine. Preferably, the amino acids X are not cysteine. It is furthermore preferred that the cysteine residues C in that sequence form a cystine knot as defined above.

In accordance with a further preferred embodiment of the invention, the microprotein has a length of between 28 and 40 amino acids.

It has been shown in experiments conducted in connection with the present invention that microproteins not exceeding a certain maximum size show a particularly good performance, especially in regard to the capacity to bind all four catalytic sites of the tryptase tetramer. Accordingly, it is particularly preferred that the microproteins for use in connection with the present invention have a length of up to 35 amino acids, more preferably of up to 32 amino acids, and most preferably of up to 30 amino acids.

Furthermore, it is preferred that the microprotein for use in connection with the present invention and in accordance with the aforementioned definitions comprises an amino acid sequence selected from the group consisting of:
(a) the amino acid sequence depicted in any one of SEQ ID NOs: 1 to 15;
(b) the amino acid sequence depicted in SEQ ID NO: 16 or 17;
(c) a fragment of the amino acid sequence of (a) or (b), said fragment being capable of inhibiting tryptase activity; and
(d) a functional equivalent in which at least one residue of the amino acid sequence or of the fragment of any one of (a) to (c) is substituted, added and/or deleted, said functional equivalent being capable of inhibiting tryptase activity.

The microproteins defined under (a) having the amino acid sequence of any one of SEQ ID NOs: 1 to 13 have been shown experimentally to efficiently inhibit tryptase (see Example 3 and Table 1, infra). Their use is therefore particularly preferred in connection with the present invention. The nucleotide sequence of a particularly preferred microprotein is shown in FIG. 5 (SEQ ID NO: 20). In addition, it is particularly preferred that the microprotein for use in connection with the present invention comprises the amino acid sequence of any one of SEQ ID NOs: 1, 14 and 15. These are the amino acid sequences of the microproteins McoTI-I, McoTI-II and McoTI-III described in Hernandez (2000).

The consensus sequence of SEQ ID NO: 16 referred to under (b) has been derived from the amino acid sequence of the microprotein MCoTI-KKV (SEQ ID NO: 7) which showed to have the highest tryptase inhibiting activity among the microproteins tested. It is conceived that at positions 1, 2, 8, 11, 12, 14 and 15 of SEQ ID NO: 16 amino acid residues lysine (K) or arginine (R) may reside interchangeably. The consensus sequence referred to under SEQ ID NO: 17 differs from that of SEQ ID NO: 16 in its C-terminal part.

The present invention also refers to the use of microproteins comprising a fragment of an amino acid sequence as defined in (a) or (b), provided said fragment has tryptase-inhibiting activity. The term "fragment" has a clear meaning to a person skilled in the art and refers to a partial continuous sequence of amino acid residues within the amino acid sequence with reference to which the fragment is defined. Thus, compared to the reference amino acid sequence, the fragment lacks at least one amino acid residue at the N-terminus, at the C-terminus or at both termini. In the case of a circular reference sequence, the fragment lacks at least one amino acid residue at one position of said sequence, whereby the fragment may be circular or linear. Preferably, the fragment retains the six conserved cysteine residues and, by their presence, is capable of forming the cystine knot topology.

The term "functional equivalent" refers to variants of a microprotein as defined in any one of (a) to (c), in which at least one residue of the amino acid sequence or the fragment of any one of (a) to (c) is substituted, added and/or deleted, said variant being capable of inhibiting tryptase activity. Preferably, the functional equivalent has an amino acid sequence which comprises six cysteine residues which are connected via disulfide bonds so as to form a cystine knot.

A functional fragment for use in the present invention may for example be a polypeptide which is encoded by a polynucleotide the complementary strand of which hybridises with a nucleotide sequence encoding a microprotein as defined in any one of (a) to (c), wherein said polypeptide has the activity of inhibiting tryptase activity.

In this context, the term "hybridization" means hybridization under conventional hybridization conditions, preferably under stringent conditions, as for instance described in Sambrook and Russell (2001), Molecular Cloning: A Laboratory Manual, CSH Press, Cold Spring Harbor, N.Y., USA. In an especially preferred embodiment, the term "hybridization" means that hybridization occurs under the following conditions:
Hybridization buffer: 2×SSC; 10×Denhardt solution (Fikoll 400+PEG+BSA; ratio 1:1:1); 0.1% SDS; 5 mM EDTA; 50 mM $Na_2HPO_4$;

250 µg/ml of herring sperm DNA; 50 µg/ml of tRNA;
or
0.25 M of sodium phosphate buffer, pH 7.2;
1 mM EDTA
7% SDS
Hybridization temperature T=60° C.
Washing buffer: 2×SSC; 0.1% SDS
Washing temperature T=60° C.

Polynucleotides encoding a functional equivalent which hybridize with a nucleotide sequence encoding a microprotein as defined in any one of (a) to (c) can, in principle, be derived from any organism expressing such a protein or can encode modified versions thereof. Such hybridizing polynucleotides can for instance be isolated from genomic libraries or cDNA libraries of bacteria, fungi, plants or animals.

Such hybridizing polynucleotides may be identified and isolated by using the polynucleotides encoding the microproteins described herein or parts or reverse complements thereof, for instance by hybridization according to standard methods (see for instance Sambrook and Russell (2001), Molecular Cloning: A Laboratory Manual, CSH Press, Cold Spring Harbor, N.Y., USA).

Such hybridizing polynucleotides also comprise fragments, derivatives and allelic variants of one of the polynucleotides encoding a microprotein as defined in any one of (a) to (c), as long as the polynucleotide encodes a polypeptide being capable of inhibiting tryptase. In this context, the term "derivative" means that the sequences of these polynucleotides differ from the sequence of one of the polynucleotides encoding a microprotein as defined supra in one or more positions and show a high degree of homology to these sequences, preferably within sequence ranges that are essential for protein function. Particularly preferred is that the derivative encodes an amino acid sequence comprising six cysteine residues which are connected via disulfide bonds so as to form a cystine knot.

The property of a polynucleotide to hybridize a nucleotide sequence may likewise mean that the polynucleotide encodes a polypeptide, which has a homology, that is to say a sequence identity, of at least 30%, preferably of at least 40%, more preferably of at least 50%, even more preferably of at least 60% and particularly preferred of at least 70%, especially preferred of at least 80% and even more preferred of at least 90% to the amino acid sequence of a microprotein as defined in any one of (a) to (c), supra. Moreover, the property of a polynucleotide to hybridize a nucleotide sequence may mean that the polynucleotides has a homology, that is to say a sequence identity, of at least 40%, preferably of at least 50%, more preferably of at least 60%, even more preferably of more than 65%, in particular of at least 70%, especially preferred of at least 80%, in particular of at least 90% and even more preferred of at least 95% when compared to a nucleotide sequence encoding a microprotein as defined in any one of (a) to (c), supra.

Preferably, the degree of homology is determined by comparing the respective sequence with the amino acid sequence of any one of SEQ ID NOs: 1 to 17. When the sequences which are compared do not have the same length, the degree of homology preferably refers to the percentage of amino acid residues or nucleotide residues in the shorter sequence which are identical to the respective residues in the longer sequence. The degree of homology can be determined conventionally using known computer programs such as the DNAstar program with the ClustalW analysis. This program can be obtained from DNASTAR, Inc., 1228 South Park Street, Madison, Wis. 53715 or from DNASTAR, Ltd., Abacus House, West Ealing, London W13 0AS UK (support@dnastar.com) and is accessible at the server of the EMBL outstation.

When using the Clustal analysis method to determine whether a particular sequence is, for instance, 80% identical to a reference sequence the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

Preferably, the degree of homology of, the hybridizing polynucleotide is calculated over the complete length of its coding sequence. It is furthermore preferred that such a hybridizing polynucleotide, and in particular the coding sequence comprised therein, has a length of at least 75 nucleotides and preferably at least 100 nucleotides.

Preferably, sequences hybridizing to a polynucleotide encoding a microprotein for use in connection with the invention comprise a region of homology of at least 90%, preferably of at least 93%, more preferably of at least 95%, still more preferably of at least 98% and particularly preferred of at least 99% identity to a polynucleotide encoding a specifically disclosed microprotein, wherein this region of homology has a length of at least 75 nucleotides and preferably of at least 100 nucleotides. Homology, moreover, means that there is a functional and/or structural equivalence between the compared polynucleotides or the polypeptides encoded thereby. Polynucleotides which are homologous to the above-described molecules and represent derivatives of these molecules are normally variations of these molecules having the same biological function. They may be either naturally occurring variations, preferably orthologs of a polynucleotide encoding a microprotein as defined in any one of (a) to (c), supra, for instance sequences from other alleles, varieties, species, etc., or may comprise mutations, wherein said mutations may have formed naturally or may have been produced by deliberate mutagenesis. The variants, for instance allelic variants, may be naturally occurring variants or variants produced by chemical synthesis or variants produced by recombinant DNA techniques or combinations thereof. Deviations from the polynucleotides encoding the above-described specific microproteins may have been produced, e.g., by deletion, substitution, insertion and/or recombination, e.g. by the fusion of portions of two or more different microproteins. Modification of nucleic acids, which can be effected to either DNA or RNA, can be carried out according to standard techniques known to the person skilled in the art (e.g. Sambrook and Russell, "Molecular Cloning, A Laboratory Manual"; CSH Press, Cold Spring Harbor, 2001 or Higgins and Hames (eds.) "Protein expression. A Practical Approach." Practical Approach Series No. 202. Oxford University Press, 1999). Preferably, amplification of DNA is accomplished by using polymerase chain reaction (PCR) and the modification is used by appropriate choice of primer oligonucleotides, containing e.g. mutations in respect to the template sequence (see, e.g. Landt, Gene 96 (1990), 125-128).

The polypeptides being variants of the concrete microproteins disclosed herein possess certain characteristics they have in common with said microproteins. These include for instance biological activity, molecular weight, immunological reactivity, conformation, etc., and physical properties, such as for instance the migration behavior in gel electrophoreses, chromatographic behavior, sedimentation coefficients, solubility, spectroscopic properties, stability, pH optimum, temperature optimum etc.

The biological activity of the microproteins for use in connection with the invention, in particular the activity of inhibiting tryptase can be tested by methods as described in the prior art and in the Examples.

A suitable assay for tryptase inhibition activity is described in Example 3. The calculation of the apparent Ki-values (also designated $Ki_{app}$) which are indicative for the tryptase inhibiting activity of a given microprotein may be conducted according to Morrison (1969). This calculation is described in further detail for the analogous measurement of trypsin inhibition in Example 4. Typically, microproteins encompassed by the uses of the present invention have a tryptase inhibiting activity with a Ki of not more than 1 mM, preferably not more than 0.5 mM, more preferably not more than 0.2 mM, still more preferably not more than 0.1 mM, further preferred not more than 0.05 mM, particularly preferred not more than 0.02 mM, especially preferred not more than 0.005 mM. Most preferred is a Ki of not more than 0.002 mM. It is understood that the values determined in the activity assays may vary within an error range typical for the particular assay system applied, preferably within a range of +/−20%, further preferred with +/−10% and particularly preferred within 5%.

It is further preferred that a microprotein for use in connection with the present invention additionally shows an inhibitory activity on trypsin. As is outlined in Example 4 (infra), a test for trypsin inhibition may be indicative for the formation of the correct folding topology. A suitable trypsin inhibition assay is described in Example 4 (infra) which is based on the methods described in Van Nostrand (1990) and Sinha (1991). Preferably, the microproteins for use in connection with the present invention show a Ki for trypsin in the range of not more than 1 nM and preferably of not more than 0.5 nM. Advantageously, in view of a high selectivity for tryptase which may be desirable for therapeutic applications, it is preferred that the microproteins for the uses of the invention show a comparatively low inhibitory activity with regard to other proteases, such as trypsin or blood co-aggulation factors.

The term "tryptase" includes the four closely related enzymes so far known which are α-, I-, II/β- and III-tryptase sharing a sequence identity between 90 and 98% (Miller, 1998; Vanderslice, 1990). Tryptase is the major secretory protease of human mast cells and is proposed to be involved in neuropeptide processing and tissue inflammation. Mature human tryptase is a tetrameric glycosylated molecule, is heparin-associated and composed of heterogenous, catalytically active subunits (see, e.g. Vanderslice et al., 1990; Miller et al., 1989, Sommerhoff et al., 1999). Tryptase is stored in mast cell secretory granules. After mast cell activation, human tryptase can be found in various biologic fluids. In connection with the present invention, the preferred target of the microproteins is mast cell tryptase, more preferably β-tryptase or α-tryptase.

The microproteins for use in connection with the present invention may consist solely of amino acids, preferably naturally occurring amino acids. However, encompassed are also microproteins which are derivatized in accordance with techniques familiar to one skilled in peptide and polypeptide chemistry. Such derivatives may for instance include the replacement of one or more amino acids with analogues such as chemically modified amino acids, the cyclisation at the N- and C-termini or conjugation with functional moieties that may for instance improve the therapeutical effect of the microproteins. The inclusion of derivatized moieties may, e.g., improve the stability, solubility, the biological half life or absorption of the polypeptide. The moieties may also reduce or eliminate any undesirable side effects of the microprotein. An overview for suitable moieties can be found, e.g., in Remington's Pharmaceutical Sciences by E. W. Martin (18$^{th}$ ed., Mack Publishing Co., Easton, Pa. (1990)). Polyethylene glycol (PEG) is an example for such a chemical moiety which may be used for the preparation of therapeutic proteins. The attachment of PEG to proteins has been shown to protect them against proteolysis (Sada et al., J. Fermentation Bioengineering 71 (1991), 137-139). Various methods are available for the attachment of certain PEG moieties to proteins (for review see: Abuchowski et al., in "Enzymes as Drugs"; Holcerberg and Roberts, eds. (1981), 367-383). Generally, PEG molecules are connected to the protein via a reactive group found on the protein. Amino groups, e.g. on lysines or the amino terminus of the protein are convenient for this attachment among others. Further chemical modifications which may be used for preparing therapeutically useful microproteins include the addition of cross-linking reagents such as glutaraldehyde, the addition of alcohols such as glycol or ethanol or the addition of sulhydroxide-blocking or modifying reagents such as phosphorylation, acetylation, oxidation, glucosylation, ribosylation of side chain residues, binding of heavy metal atoms and/or up to 10 N-terminal or C-terminal additional amino acid residues. Preferably, the latter residues are histidines or more preferably the residues RGS-(His)$_6$.

A further suitable derivatisation may be the fusion with one or more additional amino acid sequences. In such fusion proteins, the additional amino acid sequence may be linked to the microprotein sequence by covalent or non-covalent bonds, preferably peptide bonds. The linkage can be based on genetic fusion according to methods known in the art or can, for instance, be performed by chemical cross-linking as described in, e.g., WO 94/04686. The additional amino acid sequence may preferably be linked by a flexible linker, advantageously a polypeptide linker, wherein said polypeptide linker may comprise plural, hydrophilic, peptide-bonded amino acids of a length sufficient to span the distance between the C-terminal end of the tertiary structure formed by the additional sequence and the N-terminal end of the microprotein or vice versa. The fusion protein may comprise a cleavable linker or cleavage site for proteinases (e.g., CNBr cleavage or thrombin cleavage site; see Example 4, supra).

Furthermore, said additional amino acid sequence typically has a predefined specificity or function, e.g., nuclear localization signals, transactivating domains, DNA-binding domains, hormone-binding domains, protein tags (GST, GFP, h-myc peptide, FLAG, HA peptide).

In a preferred embodiment, the microprotein is fused to barnase, preferably to inactive barnase.

"Barnase" is an extracellular ribonuclease from *Bacillus amyloliquefaciens* (Fersht, 1993; Paddon, 1987). It has been shown in connection with the present invention that the fusion of a microprotein to barnase can bring about a number of advantages. In particular, when the microprotein is produced recombinantly by the expression in a host cell, such as *E. coli*, the fused barnase moiety has solubilizing effect. This may greatly reduce or completely avoid the need to isolate the expressed microprotein from inclusion bodies and to subsequently oxidize it to obtain the active disulphide-bonded conformation. Further advantages lie in the possibility to use barstar-barnase affinity for purifying the expressed microprotein from the crude extract (see Example 5, infra) as well as in the feasibility to crystallize the fusion protein and to analyze the three-dimensional structure by using the known barnase structure as an input for a facilitated structure modeling (see Example 6).

If the barnase fusion is constructed using an active barnase, it may be necessary to co-express the barnase inhibitor barstar in sufficient amount since otherwise the barnase has a lethal effect on the host cell (Martsev, 2004). In view of this, it may be preferable to use an inactive mutant of barnase such as the one having His-102 replaced by Ala (see Example 4, infra). Thereby, the advantages connected with barnase fusions are maintained, while it is not necessary to additionally co-express barstar.

The microprotein for use in connection with the present invention may, e.g., be a naturally purified product, or a product of chemical synthetic procedures, or produced by recombinant techniques from a prokaryotic or eukaryotic host (for example, by bacterial, yeast, higher plant, insect and mammalian cells in culture). For the provision of the microprotein via recombinant expression, an overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence.

It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance $E.$ $coli$, $S.$ $cerevisiae$) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Aced. Sci. USA (1983), 21-25), Ipl, rac (Boros et al., Gene 42 (1986), 97-100). Inducible promoters are preferably used for the synthesis of proteins. These promoters often lead to higher protein yields than do constitutive promoters. In order to obtain an optimum amount of protein, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature. Transformation or transfection of suitable host cells can be carried out according to one of the methods mentioned above. The host cell is cultured in nutrient media meeting the requirements of the particular host cell used, in particular in respect of the pH value, temperature, salt concentration, aeration, antibiotics, vitamins, trace elements etc. The microprotein can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the protein. Finally, high performance liquid chromatography (HPLC) can be employed for final purification steps.

Depending upon the host employed in a recombinant production procedure, the expressed polypeptide may be glycosylated or may be non-glycosylated. The polypeptide may also include an initial methionine amino acid residue.

Preferably, the microprotein is first recombinantly produced as a fusion protein, advantageously with barnase, and then released from the fusion partner by cleavage at the fusion linkage and subsequent separation.

Likewise, the microprotein may be produced by any suitable standard peptide synthesis procedure as described in the art (see, e.g., Merrifield, Methods Enzymol. 289 (1997), 3-13; Hancock, Mol. Biotechnol. 4 (1995), 73-86; and Merrifield, Adv. Enzymol. Relat. Areas Mol. Biol. 32 (1969), 221-296), such as for instance that used in Example 1 (infra).

For administration to a subject, the microprotein may be formulated as a pharmaceutical composition. Such pharmaceutical compositions comprise a therapeutically effective amount of the microprotein and, optionally, a pharmaceutically acceptable carrier. The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin (see supra). Such compositions will contain a therapeutically effective amount of the aforementioned microprotein, preferably in purified form, together with a suitable amount of carrier so as to provide the form for proper administration to the patient. The formulation should suit the mode of administration.

In another preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. The pharmaceutical composition for use in connection with the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Preferably, the pharmaceutical composition is administered directly or in combination with an adjuvant.

In the context of the present invention the term "subject" means an individual in need of inhibiting the activity of tryptase. Preferably, the subject is a vertebrate, even more preferred a mammal, particularly preferred a human.

The term "administered" means administration of a therapeutically effective dose of the aforementioned pharmaceutical composition comprising the microprotein to an individual. By "therapeutically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

The methods are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents may be administered alone or in combination with other treatments. The administration of the pharmaceutical composition can be done in a variety of ways as discussed above, including, but not limited to, orally, subcutaneously, intravenously, intra-arterial, intranodal, intramedullary, intrathecal, intraventricular, intranasally, intrabronchial, transdermally, intranodally, intrarectally, intraperitoneally, intramuscularly, intrapulmonary, vaginally, rectally, or intraocularly. In some instances, for example, in the treatment of wounds and inflammation, the pharmaceutically effective agent may be directly applied as a solution dry spray. The attending physician and clinical factors will determine the dosage regimen. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg; however, doses below or above this exemplary range are envisioned, especially considering the aforementioned factors.

The dosages are preferably given once a week, however, during progression of the treatment the dosages can be given in much longer time intervals and in need can be given in much shorter time intervals, e.g., daily. In a preferred case the immune response is monitored using methods known to those skilled in the art and dosages are optimized, e.g., in time, amount and/or composition. Progress can be monitored by periodic assessment. The pharmaceutical composition may be administered locally or systemically. Administration will preferably be parenterally, e.g., intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In a preferred embodiment, the pharmaceutical composition is formulated as an aerosol for inhalation.

In a further preferred embodiment, the pharmaceutical composition is formulated for the oral route of administration.

In a preferred embodiment, the present invention refers to the-above-described use, wherein the microprotein is administered to the patient in the form of a gene delivery vector which expresses the microprotein. Furthermore preferred is that the cells are transformed with the vector ex vivo and the transformed cells are administered to the patient.

According to these embodiments, the pharmaceutical composition for use in connection with the present invention is a vector comprising and capable of expressing a polynucleotide encoding a microprotein as described above. Such a vector can be an expression vector and/or a gene delivery vector. Expression vectors are in this context meant for use in ex vivo gene therapy techniques, i.e. suitable host cells are transfected outside the body and then administered to the subject. Gene delivery vectors are referred to herein as vectors suited for in vivo gene therapeutic applications, i.e. the vector is directly administered to the subject, either systemically or locally. The vector referred to herein may only consist of nucleic acid or may be complexed with additional compounds that enhance, for instance, transfer into the target cell, targeting, stability and/or bioavailability, e.g. in the circulatory system. Examples of such additional compounds are lipidic substances, polycations, membrane-disruptive peptides or other compounds, antibodies or fragments thereof or receptor-binding molecules specifically recognizing the target cell, etc. Expression or gene delivery vectors may preferably be derived from viruses such as retroviruses, vaccinia virus, adeno-associated virus, herpes viruses or bovine papilloma virus, and may be used for delivery into a targeted cell population, e.g. into cells of the respiratory tract. Methods which are well known to those skilled in the art can be used to construct recombinant expression or gene delivery vectors; see, for example, the techniques described in Sambrook and Russell, Molecular Cloning: A Laboratory Manual, Cold Spring Harbor Laboratory (2001) N.Y. and Ausubel, Current Protocols in Molecular Biology, Green Publishing Associates and Wiley Interscience, N.Y. (1989). Alternatively, the vectors can be reconstituted into liposomes for delivery to target cells. The vectors containing the a microprotein-encoding polynucleotide can be transferred into a host cell by well-known methods, which vary depending on the type of cellular host. For example, calcium chloride transfection is commonly utilized for prokaryotic cells, whereas calcium phosphate treatment or electroporation may be used for other cellular hosts (see Sambrook, supra).

Suitable vectors and methods for ex-vivo or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Isner, Lancet 348 (1996), 370-374; Muhlhauser, Circ. Res. 77 (1995), 1077-1086; Wang, Nature Medicine 2 (1996), 714-716; WO 94/29469; WO 97/00957 or Schaper, Current Opinion in Biotechnology 7 (1996), 635-640, and references cited therein. The vectors for use in this embodiment of the invention may be designed for direct introduction or for introduction via liposomes or viral vectors (e.g. adenoviral, retroviral) into the cell. Preferred gene delivery vectors include baclovirus-, adenovirus- and vaccinia virus-based vectors. These are preferrably non-replication competent.

The use of the present invention preferably refers to a disease selected from the group consisting of asthma, inflammation, psoriasis, pulmonary fibrosis, an interstitial lung disease, rheumatoid arthritis, gingivitis, peridontitis, an allergic reaction, allergic rhinitis, osteoarthritis, atherosclerosis, angiogenesis, multiple sclerosis and cancer.

Due to their capacity to inhibit tryptase, the microproteins described herein-above can be utilized according to the present invention in order to prevent or treat diseases or conditions in which tryptase is a pathology-mediating agent. This refers in particular to mast cell-mediated inflammatory disorders. One aspect in this context especially refers to inflammatory diseases associated with the respiratory tract, such as asthma, psoriasis or allergic rhinitis. It is in particular contemplated to use microproteins for preventing or treating the late phase bronchoconstriction and airway hyperresponsiveness associated with chronic asthma. In addition, the use of the present invention refers to the treating of other types of immunomediated inflammatory disorders, such as psoriasis, rheumatoid arthritis, conjunctivitis as well as inflammatory bowel disease. A further preferred use refers to the use of microproteins against acute myeloid leukemia (AML) where it has been shown that the myeloblasts of these patients express alpha-tryptase in excess over beta-tryptase and secrete pro-alpha-tryptase constitutively (Sperr, 2001, 2002). The present invention also includes the use of the above-described microproteins as anti-inflammatory agents. In this function, the microprotein may be a component of creams for topical administration, e.g., to insect, snake or scorpion bites, or to skin affected by dermatitis.

In a further aspect, the present invention relates to a method for the treatment of an individual in need of inhibiting the activity of tryptase comprising administering to said individual an effective amount of a pharmaceutical composition comprising the microprotein as defined above or a polynucleotide encoding said microprotein and, optionally, a pharmaceutically acceptable carrier.

With regard to this embodiment, the above explanations, in particular concerning the formulation of pharmaceutical compositions, mode of administration and diseases, likewise apply.

In accordance with the aforesaid, the present invention also refers to the use of the microprotein as defined above or a polynucleotide encoding said microprotein for inhibiting tryptase activity. This embodiment may refer to tryptase inhibition in vivo or in vitro, preferably in vitro.

Another embodiment of the present invention relates to the use of the microprotein as defined above for purifying tryptase.

For this purpose, the microprotein is preferably bound to a solid support. The term "purifying" includes in this context also removing, isolating or extracting tryptase. The support may comprise any suitable inert material and includes gels, magnetic and other beads, microspheres, binding columns and resins. For carrying out the present embodiment, standard protocols for affinity purification of proteins known to a skilled person are applicable.

In a further aspect, the present invention relates to the use of the microprotein as defined above as a carrier molecule for tryptase or a derivative thereof.

This application may in particular refer to the use of the microprotein as a carrier molecule for tryptase and tryptase-related compounds, such as in creams, oils, powders or pills, to provide slow release of the bound components.

Also, the present invention relates to the use of microproteins as defined above for detecting and/or quantifying tryptase in a sample.

The quantification of tryptase levels, preferably human mast cell tryptase levels may, for example, be applicable for blood, nasal lavage fluids, tissues or food products. In connection with this application, the microproteins may be employed together with means of detection (for example radiolabel, antibodies, enzymes such as alkaline phosphatases, peroxidases and luciferases) that allow the accurate quantification of tryptase in the sample to be tested. Accordingly, the present invention refers to corresponding kits comprising one or more microproteins and, preferably, suitable detection means. Such kits may resemble radioimmunoassay or ELISA kits, with the proteins of the invention acting as binding molecules, instead of antibodies directed against tryptase. The detection of tryptase may in particular be used for the detection of mast cells.

Any technique common to the art may be used in a detection method according to the present embodiment and may comprise immunocytochemical and histological techniques, in which the microprotein may be used in combination with antisera (such as anti-McoTI-II antisera), or in which the molecule is directly coupled to a label or dye, such as a fluorescent dye, e.g. FITC. In another embodiment, the microprotein may be fused either genetically or synthetically to another protein such as an alkaline phosphatase, luciferase or peroxidase in order to facilitate its detection. Other methods to detect tryptase-containing cells or samples may involve blotting techniques (Towbin et al, 1979), gel retardation, affinity chromatography, or any of the other suitable methods that are used in the art.

Moreover, the present invention relates to a method for diagnosing a disorder associated with an aberrant abundance of tryptase in a given cell, tissue, organ or organism, comprising (a) contacting a sample from said cell, tissue, organ or organism with a microprotein as defined above under conditions allowing binding between tryptase and the microprotein;
(b) determining the amount of the microprotein bound to tryptase; and
(c) diagnosing a disorder when the determined amount is above or below a standard amount.

In this context, the microprotein may be used in the form of a diagnostic composition which optionally comprises suitable means for detection. The microproteins described above can be utilized in liquid phase or bound to a solid phase carrier. Corresponding affinity assays may be carried out either in a competitive or a non-competitive fashion. Such affinity assays may be devised in a way analogous to the radioimmunoassay (RIA), the sandwich (immunometric assay) or the Western blot assay. The microproteins can be bound to many different carriers or used to isolate cells specifically bound to said polypeptides. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

The term "aberrant abundance" refers to a concentration of tryptase in a given cell, tissue, organ or organism which is significantly below or above a standard concentration of tryptase for said cell, tissue, organ or organism of a healthy individual so that it is associated with a disease to be diagnosed, preferably one of the diseases mentioned above. Preferably, the tryptase concentration when aberrantly abundant is reduced to not more than 75%, preferably not more than 50%, more preferably not more than 25%, and particularly preferred to not more than 10% of the standard concentration. Alternatively, the tryptase concentration in the aberrant state is preferably increased to at least 150%, more preferably to at least 200% and still further preferred to at least 500% of the standard concentration.

According to the above, the present invention also refers to the use of the microproteins as defined above or a polynucleotide encoding said microprotein for diagnosing a disease related to an aberrant expression of tryptase.

In a further aspect, the present invention also refers to a kit comprising a microprotein as defined above and a manual for carrying out the above-defined diagnostic method or the corresponding use and, optionally, means of detection or a standard tryptase sample.

The components of the kit of the present invention may be packaged in containers such as vials, optionally in buffers and/or solutions. If appropriate, one or more of said components may be packaged in one and the same container. Additionally or alternatively, one or more of said components may be adsorbed to a solid support such as, e.g., a nitrocellulose filter or nylon membrane, or to the well of a microtitre-plate.

A further embodiment of the present invention relates to a fusion protein comprising an inactive barnase.

The advantages of using a fusion protein comprising an inactive barnase have already been mentioned above in connection with the production of microprotein fusions. Accordingly, the fusion of a given protein to be expressed to inactive barnase can be summarized as follows:

(i) Fusion with barnase may lead to an improved solubility of the protein to be expressed. This may be explained by a chaperone-like effect the barnase has on its fusion partner. It is of, note that this effect is observed irrespective of whether the barnase is fused to the N- or to the C-terminus of the fusion partner. The solubilizing function of barnase may facilitate the recombinant production of a desired protein, in particular when it is to be expressed in the cytoplasm of a host organism, wherein the host organism preferably is a microorganism, advantageously a bacterium, such as E. coli. For instance, the problem of resolving inclusion bodies concomitant with a subsequent renaturation of the expressed protein may be overcome by using a barnase fusion. The useful effect of improving solubility of expressed proteins is already described for active barnase (Martsev, 2004).

(ii) A particular improvement associated with the use of inactive barnase compared to an active one lies in the fact that the experimental requirements for the expression of the fusion protein are significantly reduced because it is no longer necessary to co-express the barnase inhibitor barstar. Without its co-expression, barnase activity has a lethal effect on the host cell (Martsev, 2004). Inactive barnase is already known in the art, e.g. from Jucovic (1995). However, it could not have been foreseen whether an inactivated barnase would show the advantages of the active barnase in a fusion protein expression. This, however, has been shown convincingly in the experiments described in Examples 2 and 4, infra. The barnase fusion clones mentioned in Martsev (2004) to bear functionally significant mutations in the barnase module are preferably no subject-matter of the present invention.

(iii) A further surprising advantage of a fusion with inactive barnase is the fact that the expression product of this fusion can easily be recovered from the crude preparation by applying the strong binding interaction between barnase and barstar. Such an approach has not yet been described for barnase fusions in general. In addition, it would have been uncertain whether inactivated barnase would indeed work in an affinity chromatography with barstar as binding moiety. However, this has convincingly been proven in the experiment described in Example 5, infra.

(iv) Furthermore, based on the barnase moiety within the fusion protein, the fusion protein can be combined non-covalently, but nevertheless stably under physiological conditions with a second fusion protein which comprises barstar. Thereby, bi- or multivalent functions, such as for instance multiple microproteins, can be combined within one structure. This principle is described in Deyev (2003).

In a further aspect, the present invention also relates to fusion proteins comprising barnase and a microprotein. Preferably, said barnase is inactive.

Microproteins are known to a person skilled in the art. Preferred microproteins are in this context those which have been defined above in connection with the tryptase inhibiting function of microproteins.

With regard to the microprotein-barnase fusions, the same applies in regard to advantages as that outlined above under (i) to (iv). In addition, these fusion proteins also have the advantage of generally facilitating the recombinant expression of microproteins which, without the fusion to barnase, might not be expressible at all or only to an unsatisfactory extent. Furthermore, the barnase fusion may also facilitate the elucidation of the three-dimensional structure of a crystal from the microprotein. This aspect is described in more detail further below.

With regard to the construction principles and ways of production of the fusion proteins of the invention, it is herewith referred to corresponding standard techniques known to a person skilled in the art and, in particular, to the above explanations concerning fusion proteins set out in connection with the aspect of the invention concerning the therapeutical use of microproteins for inhibiting tryptase. It is preferred that the fusion proteins of the invention contain a cleavable linker between the barnase and the other portion so that the two portions may be readily separated from one another after expression. Corresponding linker sequences are well-known to the skilled person and examples thereof are mentioned herein. Furthermore, it is contemplated that the fusion protein of the invention may contain additional amino acid sequences along with the particular function the user intends.

A preferred embodiment of the present invention relates to nucleic acid molecules comprising a nucleotide sequence encoding the above-defined fusion protein of the invention.

The nucleic acid molecules of the invention can be any type of polynucleotide, e.g. DNA molecules or RNA molecules or combinations thereof. These polynucleotides can be obtained by any suitable technique known in the art, they, for instance, may be produced synthetically or by recombinant techniques, in vivo or in vitro, such as PCR. Such polynucleotides may comprise any modification thereof that is known in the state of the art (see, e.g., U.S. Pat. No. 5,525,711, U.S. Pat. No. 4,711,955, U.S. Pat. No. 5,792,608 or EP 302175 for examples of modifications). Such polynucleotides may be single- or double-stranded, linear or circular, without any size limitation. Preferably, the nucleic acid molecules are DNA, cDNA or mRNA.

The nucleic acid molecule encoding a fusion protein of the invention will generally be a recombinant nucleic molecule. The term "recombinant nucleic acid molecule" refers to any nucleic acid molecule that has been produced by a technique useful for artificially combining nucleic acid molecules or parts thereof that were beforehand not connected as in the resulting recombinant nucleic acid molecule. Suitable techniques are for example available from the prior art, as represented by Sambrook and Russell, Molecular Cloning A Laboratory Manual, Cold Spring Harbor Laboratory (2001) N.Y. and Ausubel, Current Protocols in Molecular Biology, Green Publishing Associates and Wiley Interscience, N.Y. (1989).

In a preferred embodiment, the nucleic acid molecule comprised in the recombinant nucleic acid molecule is operably linked to expression control sequences allowing expression in prokaryotic or eukaryotic cells. Suitable expression control sequences include promoters that are applicable in the target host organism. Such promoters are well known to the person skilled in the art for diverse hosts from the kingdoms of prokaryotic and eukaryotic organisms and are described in literature. For example, such promoters can be isolated from naturally occurring genes or can be synthetic or chimeric promoters. Likewise, the promoter can already be present in the target genome and may be linked to the coding sequence by a suitable technique known in the art, such as for example homologous recombination.

The present invention also relates to vectors, particularly plasmids, cosmids, viruses and bacteriophages used conventionally in genetic engineering, that comprise a nucleic acid molecule of the invention.

In a preferred embodiment of the invention, the vectors of the invention are suitable for the transformation of fungal cells, plant cells, cells of microorganisms or animal cells, in particular mammalian cells. Preferably, such vectors are suitable for the transformation of microorganisms, such as yeast or bacteria, in particular of *E. coli*. Methods which are well known to those skilled in the art can be used to construct recombinant vectors; see, for example, the techniques described in Sambrook and Russell, Molecular Cloning A Laboratory Manual, Cold Spring Harbor Laboratory (2001) N.Y. and Ausubel, Current Protocols in Molecular Biology, Green Publishing Associates and Wiley Interscience, N.Y. (1989). Alternatively, the vectors may be liposomes into which the recombinant nucleic acid molecules of the invention can be reconstituted for delivery to target cells.

Advantageously, the nucleic acid molecules contained in the vectors and encoding a fusion protein of the invention are operably linked to one or more expression of the fusion protein in a host cell.

The expression of the nucleic acid molecules of the invention in prokaryotic or eukaryotic cells, for instance in *Escherichia coli*, may be interesting because it permits a more precise characterization of the biological activities of the proteins encoded by these molecules. In addition, it is possible to insert different additional mutations into the nucleic acid molecules by methods usual in molecular biology (see for instance Sambrook and Russell, 2001, Molecular Cloning, A Laboratory Manual, Cold Spring Harbor Laboratory Press, Cold Spring Harbor, N.Y.), leading to the synthesis of proteins possibly having modified biological properties. In this regard, it is on one hand possible to produce deletion mutants in which nucleic acid molecules are produced by progressive deletions from the 5' or 3' end of the coding DNA sequence, and said nucleic acid molecules lead to the synthesis of correspondingly shortened proteins. On the other hand, the introduction of point mutations is also conceivable at positions at which a modification of the amino acid sequence for instance influences the biological activity of the protein.

For genetic engineering in prokaryotic cells, the nucleic acid molecules of the invention or parts of these molecules can be introduced into plasmids which permit mutagenesis or sequence modification by recombination of DNA sequences. Standard methods (see Sambrook and Russell, 2001, Molecular Cloning: A laboratory manual, Cold Spring Harbor Laboratory Press, NY, USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

In a further embodiment, the invention relates to a method for producing cells capable of expressing a fusion protein according to the invention comprising genetically engineering cells with an above-described nucleic acid molecule, recombinant nucleic acid molecule or vector of the invention. Encompassed by the present invention are likewise cells obtainable by this method.

Another embodiment of the invention relates to host cells, in particular prokaryotic or eukaryotic cells, genetically engineered with an above-described nucleic acid molecule or vector of the invention, and to cells descended from such transformed cells and containing said nucleic acid molecule or vector of the invention and to cells obtainable by the above-mentioned method.

In a preferred embodiment the host cell is genetically engineered in such a way that it contains a nucleic acid molecule stably integrated into the genome. More preferably the nucleic acid molecule can be expressed so as to lead to the production of the encoded fusion protein.

An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antoine von Leuwenhoek 67 (1995), 261-279), Bussineau (Developments in Biological Standardization 83 (1994), 13-19), Gellissen et al. (Antoine van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication origin ensuring replication in the host selected, but also a bacterial or viral promoter and, in most cases, a termination signal for transcription. Between the promoter and the termination signal there is in general at least one restriction site or a polylinker which enables the insertion of a coding nucleotide sequence. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of proteins. These promoters often lead to higher protein yields than do constitutive promoters. In order to obtain an optimum amount of protein, a two-stage process is often used. First, the host cells are cultured under optimum conditions up to a relatively high cell density. In the second step, transcription is induced depending on the type of promoter used. In this regard, a tac promoter is particularly suitable which can be induced by lactose of IPTG (isopropyl-β-D-thiogalactopyranoside) (deBoer et al., Proc. Natl. Acad. Sci. USA 80 (1983), 21-25). Termination signals for transcription are also described in the literature.

The transformation of the host cell with a nucleic acid molecule or vector according to the invention can be carried out by standard methods, as for instance described in Sambrook and Russell, (Molecular Cloning: A Laboratory Manual (2001), Cold Spring Harbor Press, New York; Methods in Yeast Genetics, A Laboratory Course Manual, Cold Spring Harbor Laboratory Press, 1990). The host cell is cultured in nutrient media meeting the requirements of the particular host cell used, in particular in respect of the pH value, temperature, salt concentration, aeration, antibiotics, vitamins, trace elements etc. The protein according to the present invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromography and lectin chromatography. Depending on whether the protein is expressed intra- or extracellularly, the protein can be recovered from the cultured cells and/or from the supernatant of the medium. Protein refolding steps can be used, as necessary, in completing configuration of the protein. Finally, high performance liquid chromatography (HPLC) can be employed for final purification steps.

Accordingly, a further embodiment of the invention relates to a method for preparing a fusion protein comprising culturing the above-described host cells under conditions that the fusion protein encoded by the nucleic acid molecule with which said host cell is genetically engineered is expressed; and recovering the fusion protein from the culture.

In a particular preferred embodiment, the method of the invention for preparing a fusion protein comprises a step in which the fusion protein is purified by way of binding the barnase moiety of the fusion protein to barstar.

This application is in line with the above explanations according to which it is an advantageous property of the fusion protein of the invention that it can be purified by making use of the strong, but reversible binding activity between barnase and barstar. The feasibility of this principle has been demonstrated in Example 5, infra.

Moreover, the present invention relates to a fusion protein obtainable by the method for its production as described above.

The fusion protein of the present invention may be glycosylated or may be non-glycosylated. The fusion protein of the invention may also include an initial methionine amino acid residue. The fusion protein according to the invention may be further modified to contain additional chemical moieties not normally part of the protein. Those derivatized moieties may, e.g., improve the stability, solubility, the biological half life or absorption of the protein. The moieties may also reduce or eliminate any undesirable side effects of the protein and the like. An overview for these moieties can be found, e.g., in Remington's Pharmaceutical Sciences (18th edition, Mack Publishing Co., Easton, Pa. (1990)). Particular examples of suitable protein modifications are described above.

The present invention relates in a further embodiment to a method of detecting or purifying the fusion protein of the invention comprising the step of contacting the fusion protein with barstar. Preferably, in this method, barstar is immobilized.

For immobilization any conceivable solid support may be used along with the particular intended application, and may include any suitable inert material such as gels, magnetic or other beads, microspheres, binding columns and resins.

For detection purposes, barstar may preferably be coupled to a detectable moiety. Corresponding suitable moieties are described in the literature and examples are given above in connection with tryptase-detection and corresponding diagnostic methods.

Detection as well as purification may be carried out in accordance with techniques familiar to a skilled person.

Furthermore, the present invention also relates to the use of the fusion proteins of the invention for producing a crystal of said fusion protein.

In a further aspect, the present invention relates to a crystal of a microprotein fused with barnase.

The provision of the crystal of the invention is connected with a number of improvements over the prior art. For instance, the presence of the barnase in the microprotein fusion facilitates easy crystallizing of microproteins, apparently because barnase is good to crystallize. Heretofore, it was only in rare cases possible to achieve the crystallization of a solitary microprotein, i.e. without a bound target protein (e.g. trypsin) (Thaimattam, Acta Crystallogr. D. Biol. Crystallogr. 58 (2002), 1448-1461). The co-crystallization of a microprotein together with bound trypsin has been reported by Chakraborty (2001), Zhu (J. Protein Chem. 18 (1999), 505), Ay (Acta Crystallogr. D 59 (2003), 247) and Bode (FEBS L. 242 (1989), 285). Often crystallization of a microprotein is hampered because a target protein is not available in sufficient amounts or does not undergo crystallization. These difficulties have been overcome by the provision of the crystal of the invention since a solitary microprotein was shown to be well amenable to crystallization when it is fused to barnase (see Example 6, infra).

Moreover, it was surprisingly found that the presence of the barnase in the crystal does not influence the structure analysis of the fused microprotein.

A further advantage of the fusion to barnase lies in the fact that the already known barnase structure (Baudet, J. Mol. Biol. 219 (1991), 123-132; Martin, Acta Crystallogr. D. Biol. Crystallogr. 55 (1999), 386-398) may be utilized as a starting point for modelling the structure of the whole fusion protein, and thereby of the microprotein. The barnase structure data can be entered into the algorithm applied for determining the structure of the crystallized fusion protein. Thus, it is possible to resolve the structure of the microprotein without having any previous knowledge on its structure, because the diffraction data of the crystal can be interpreted starting from the known barnase structure.

The microprotein structure retrievable from the crystal of the invention may be of use for analyzing the topology of the binding site to the target molecule. Based on the information obtainable from such an analysis, it may for example be possible to optimize the binding of a microprotein by introducing chemical modifications in the structure of the microprotein, e.g. by changing one or more amino acid residues in the binding site. This has already been successfully practiced, for instance, with the microprotein EETI-II in connection with its inhibitory activity upon porcine pancreatic elastase (Hilpert, J. Biol. Chem. 278 (2003), 24986-24993).

Additionally, the elucidation of the microprotein structure promoted by the provision of the crystal of the invention may be beneficial for the construction of graftings onto microproteins. Microproteins are generally considered as being good carriers for peptide functions, such as peptides having a therapeutical effect. The introduction of such peptide sequences, also called "grafting", into sites not essential for folding of the microprotein may for instance improve stability and bioavailability of the peptide in the subject to whom it is administered. Corresponding microprotein grafting approaches are for example described in WO 01/27147 and WO 01/34829. By the elucidation of the microprotein structure based on the crystal of the invention, the design of such grafting constructs may be improved. For example, the selection of suitable sites for introducing such a peptide into a microprotein may now be done more specifically. Also, microproteins comprising a grafted peptide may likewise be contained in a crystal of the invention and therefore their structure can be directly determined. This may, for example, yield a further optimization of the peptide display and target binding by rational design methods.

Such specific interventions are now greatly facilitated by the provision of the crystals of the invention and corresponding methods for producing them. A further advantage of the use of a fusion to barnase is the fact that this fusion protein can be readily purified by affinity chromatography using barstar as binding moiety.

The crystal of the invention may harbor any microprotein known to a person skilled in the art. Preferably, it is a microprotein defined above in connection with the uses of the microproteins for inhibiting tryptase. In a particularly preferred embodiment, the microprotein-barnase fusion contained in the crystal comprises the amino acid sequence set forth in SEQ ID NO: 19. It is furthermore preferred that the barnase contained in the crystal of the invention is inactive. In accordance with the explanations given further above, the use of an inactive barnase has the advantage that the co-expression of barstar can be omitted.

In a preferred embodiment, the crystal of the present invention belongs to space group $C222_1$. Furthermore, it is preferred that the crystal of the invention, has the unit cell dimensions of a=73.981 Å, b=217.820 Å and c=58.322 Å, $\alpha=\beta=\gamma=90°$. A particularly preferred crystal of the invention has the crystal coordinates as depicted in Table 6, infra. Also preferred is a crystal the coordinates of which differ from the coordinates in Table 6 by a root mean square deviation of the C-alpha atoms by less than 3 Å, preferably by less than 2 Å and further preferred by less than 1 Å. Most preferably the crystal of the invention is obtainable by the method described in Example 6.

The term "crystal" as used herein refers to an ordered state of matter. Since it cannot be excluded that the crystallized proteins are not purified to homogeneity, corresponding impurities may be contained in the crystal. Even highly purified proteins may still be heterogeneous due to modifications, the binding of ligands or other effects. In addition, proteins are generally crystallized from complex solutions that may include not only the target molecule but also buffers, salts, precipitating agents and water. It is important to note that protein crystals are composed not only of protein, but also of a large percentage of solvents molecules, in particular water. The proportion of these other compounds within the crystal may vary from 30 to even 90%. Frequently, heterogeneous masses serve as nucleation centers and the crystals simply grow around them. The skilled person knows that some crystals diffract better than others. Crystals may vary in size from a barely observable 20 mm to 1 or more millimeters. Crystals useful for X-ray analysis are typically single, 0.05 mm or larger, and free of cracks and defects. However, advances in technology may allow analyzing increasingly smaller crystals.

The term "coordinate" as used herein, refers to the information of the three-dimensional organization of the atoms contained in the crystal of the invention which contribute to the protein structure. A common format for coordinate files is the so-called "PDP file format" (PDB=Protein Data Bank, http://www.pdb.org/) which is organized according to the instructions and guidelines given by the Research Collaboratory for Structural Bioinformatics (H. M. Berman, J. Westbrook, Z. Feng, G. Gilliland, T. N. Bhat, H. Weissig, I. N. Shindyalov, P. E. Bourne: Nucleic Acids Research, 28 pp. 235-242 (2000)) and which allows a graphical representation by programs such as O (Jones et al. Acta Crystallogr. 1991, 47:110-111), rasmol (Trends Biochem Sci. 1995: 20(9):374), moiscript (Kraulis, P. (1991), J. Appl. Cryst. 24, 946-950), bobscript or Pymol (Delano, W. L. (2002), The PyMOL Molecular Graphics System, DeLano Scientific, San Carlos, Calif., USA).

The term "root mean square deviation" (RMSD) is used as a mean of comparing two closely related structures and relates to a deviation in the distance between related atoms of the two structures after structurally minimizing this distance in an alignment. Related proteins with closely related structures will be characterized by relatively low RMSD values whereas more changes will result in an increase of the RMSD value.

Another aspect of the present invention refers to a method of preparing the crystal of the invention comprising the steps of:
(a) providing an aqueous solution comprising a microprotein fused with barnase;
(b) providing a reservoir solution comprising a precipitating agent;
(c) mixing a volume of said aqueous solution with a volume of said reservoir solution thereby forming a mixed volume; and
(d) crystallizing at least a portion of said mixed volume.

The growth of crystals may be effected according to standard protein crystallisation procedures described in the literature such as in DeLucas (J. Struct. Biol. 142 (2003), 188-206), Chemov (J. Struct. Biol. 142 (2003), 3-21), and McPherson (Structure 3 (1995), 759-768). In a preferred embodiment, the crystals are grown according to the method described in Example 6 (infra). Each of the steps identified in this protocol may be further and separately refined, as it will be apparent to the skilled practitioner.

The protein provided for crystallization should be sufficiently purified. Preparation and purification can be done according to conventional protocols such as those mentioned above in connection with expression techniques and vectors. Typically, a microorganism is transformed with an expression vector containing one or more copies of the gene encoding the respective microprotein-barnase fusion protein. The microorganisms, typically bacteria, may be grown under conditions that allow an optimized expression of the fusion protein. If the fusion protein is exported into the medium, it can be conveniently purified from the culture supernatant. Otherwise, the host cell has to be disrupted as the first step of the purification process. After recovery of a crude mixture from the cell culture, the fusion protein may be purified by using a combination of various purification steps. Some of these purification steps may be repeated, if appropriate. The fusion protein present in the crude extract is advantageously purified by employing a method comprising an affinity purification step. Such an affinity purification step may make use of the barnase-barstar binding interaction as already described above and in Example 5 (infra) in further detail. Alternatively, for example, antibodies raised against the microprotein or barnase may be used for the purification, wherein said antibodies (or fragments thereof) are preferentially coupled to a column material. Suitable antibodies may be obtained by conventional immunization protocols such as described, for example, in Harlowe and Lane, "Antibodies, A Laboratory Manual", CHS Press, 1988, Cold Spring Harbor. The affinity purification step may be combined with gel filtration and/or anion exchange chromatography steps, before or after the affinity purification step. The purification protocol may further comprise one or more dialysis steps. The order of purification steps is preferably selected as described in Example 4 or 5.

The reservoir solution may be provided with suitable ingredients in accordance with standard crystallization techniques. The conditions for crystallization are provided by the reservoir solution which generally contains at least one compound selected from the group consisting of a buffer, a salt and a precipitant. The buffer is preferably MES, however, it may be replaced by any other buffer with a similar buffer capacity and $pK_i$. The term "salt" refers to charged molecules composed of cation and anion and which are held together by ionic interactions. Preferably said salt contains molecules selected from the group consisting of Mg, Ca, Na, Cl, Br, I, Rb, P, S, K, Mn, Zn, Cu, B, Mo, Se, Si, Co, J, V, Ni, wherein these molecules are in their charged state and contain one or more counterions. The reservoir solution may additionally contain a detergent which is preferably selected from the group consisting of Triton X-100, NP 40 $C_{12}E_9$, $Cl_2E_8$, n-Dodecyl-β-D-maltoside, sucrose monolaurate, CTAB, Deoxy-BigChap, n-decyl-β-D-maltoside, Nony-β-D-glucoside, DDAO, n-Octanoylsucrose, MEGA-8, MEGA-9, IPTG, HEGA-8, HEGA-9, CHAPS, CHAPSO, BAM, CYMAL-2, $C_{14}E_8$, TWEEN and Brij59. The reservoir solution may further contain a reducing agent such as one selected from the group consisting of DTE, β-mercaptoethanol, cysteine and GSH.

Preferably, the reservoir solution comprises at least one compound selected from the group consisting of HEPES, NaCl, PEG 100, PEG 200, PEG 400, PEG 500, PEG 600, PEG 800, PEG 1000, PEG 2000, PEG 3000, PEG 4000, PEG 5000, PEG 6000, PEG 7000, PEG 8000, ammonium sulphate, ammonium acetate, sodium sulphate, organic solvents, isopropanol, citrate buffer, Tris buffer, cacodylate buffer, MES-buffer, dithiothreitol, octylglycopyranoside and uranylacetate.

As a preferred ingredience, the reservoir solution may contain PEG 400, advantageously at a concentration between 5 and 10%, more preferably at 7%. Further preferred ingredients are ammonium sulphate, preferably at a concentration of 1 to 2 M, more preferably at 1.3 M, as well as MES buffer. Further preferred is that the reservoir solution has a pH between 6 and 7, preferably of 6.5. Crystallization is preferably carried out according to the sitting drop method, but other methods such as the hanging drop method are not excluded from the scope of the present invention. Generally, grown crystals may be cryoprotected prior to undergoing X-ray diffraction studies. Before freezing, e.g. in liquid nitrogen, the crystal is typically contacted with a cryoprotectant such as a liquor containing 25% glycerol or a PEG and isopropanol-containing solution.

The person skilled in the art knows that additional factors such as temperature may be crucial for crystal formation. These and other conditions of crystallization as well as strategies to optimise conditions of crystallization are known by a skilled person and can be retrieved from the literature such as "Crystallization of Biological Macromolecules" by Alexander McPherson (Cold Spring Harbor Laboratory; 1st edition (1999).

The invention furthermore pertains to a crystal obtainable by the above-described method for preparing a crystal.

In a further embodiment, the invention relates to a method for determining the three-dimensional structure of a microprotein, comprising the steps of:
(a) performing an X-ray diffraction analysis of a crystal of a microprotein fused with barnase;
(b) computationally processing the diffraction data obtained in step (a) in order to determine the three-dimensional structure of the crystal components and thereby to obtain crystal coordinates; and
(c) storing the obtained crystal coordinates on a data storage medium.

Preferably, step (b) further comprises to use data on the three-dimensional structure of barnase not being fused to the microprotein for modelling the structure of the barnase moiety within the fusion protein. Thereby it is possible to elucidate the microprotein's structure without any previous knowledge thereon. The barnase structure data is retrievable, e.g. from the RCSB PDB Web site (protein data bank, repository for the processing and distribution of 3-D biological macromolecular structure data) WWW.rcsb.org, entry 1A2P.

Preferentially, the crystal used in the method of the present embodiment is a crystal of the invention as defined above.

X-ray diffraction may be performed on a beamline such as the DESY beamline BW6. Data may be further processed with XDS (W. Kabsch, *J. Appl. Cryst.* 21, 67 (1988)) and scaled with XCALE (Kabsch, 1993). Further refinement is possible by applying CNS (A. T. Brünger et al. Acta Cryst D 54, 905 (1998)). The structure can finally be solved with, for example, AmoRe (J. Navaza, Acta Crystallogr. A 50, 157 (1994)) and analysed with Xfit (D. E. McRee, J. Struct. Biol. 125, 156 (1999)) while structure validatation may be performed with PROCHECK (R. A. Laskowski, M. W. MacArthur, *J. Appl. Crystallogr.* 26, 283 (1993)) and WHATCHECK (R. W. W. Hooft, G. Vriend, C. Sander, E. E. Abola, *Nature* 381, 272 (1996)). The final map containing the atomic coordinates of the constituents of the crystal may be stored on a data carrier, typically the data is stored in PDB format or in x-plor format, both of which are known to the person skilled in the art. However, crystal coordinates may as well be stored in simple tables or text files.

In a preferred embodiment of the present invention, the method for structure determination comprises additional steps of computer modelling, wherein computer modelling may include the step of (a) using virtual-screening tools for the search of compounds that bind to the microprotein; (b) using homology-modelling tools that search for compounds similar to known microprotein ligands and that make molecular contacts to the binding sites of the microprotein under investigation; (c) using molecular-modelling algorithms that allow an estimation of the binding affinities of compounds to the microprotein; or (d) using ligand construction tools that build up organic molecules that fit into the ligand binding site of the target molecule of the microprotein, such as tryptase or other proteases.

The design of molecules with particular structural relationships to part of a protein molecule are well established and described in the literature (see for example Cochran, A. G. (2000), Chem. Biol. 7, 85-94; Grzybowski, B. A., Ishchenko, A. V., Shimada, J., Shakhnovich, E. I. (2002), Acc. Chem. Res. 35, 261-269; Velasquez-Campoy, A., Kiso, Y., Freire, E. (2001), Arch. Biochem. Biophys. 380, 169-175; D'Aquino, J. A., Freire, E., Amzel, L. M. (2000), Proteins: Struc. Func. Genet. Suppl. 4, 93-107.). Any of these so-called "molecular modelling" methods for rational drug design can be used to find a ligand to a microprotein or a ligand to the microprotein target molecule that behaves analogously or similar to the microprotein. Most of these molecular modelling methods take into consideration the shape, charge distribution and the distribution of hydrophobic groups, ionic groups and hydrogen bonds in the site of interest of the protein molecule. Using this information, that can be derived from the crystal structure of proteins and protein-ligand complexes, these methods either suggest improvements to existing proposed molecules, construct new molecules on their own that are expected to have good binding affinity, screen through virtual compound libraries for such molecules, or otherwise support the interactive design of new drug compounds in silico. Programs such as GOLD (G. Jones, et al., Development and J. Mol. Biol., 267, 727-748 (1997)); FLEXX (B. Kramer et al., Structure, Functions, and Genetics, Vol. 37, pp. 228-241, 1999); FLEXE (M. Rarey et al., JMB, 261, 470-489 (1996)) DOCK (Kuntz, I. D. Science 257: 1078-1082, 1992); AUTODOCK (Morris et al., (1998), J. Computational Chemistry, 19: 1639-1662) are virtual screening programs designed to calculate the binding position and conformation as well as the corresponding binding energy of an organic compound to a protein. These programs are specially trimmed to allow a great number of "dockings", that is calculations of the conformation with the highest binding energy of a compound to a binding site, per time unit. In this context, binding energy is not always a real value, but can be statistically related to a real binding energy through a validation procedure. These methods lead to molecules, termed here "hits" that have to be assessed by experimental biochemical, structural-biological, molecular-biological or physiological methods for their expected biological activity. Positively assayed molecules may thus constitute potential lead candidates for the design of bio-active compounds.

The terms "molecular modeling" and "molecular modeling techniques" refer to techniques that generate one or more 3D models of a ligand binding site or other structural feature of a macromolecule. Molecular modelling techniques can be performed manually, with the aid of a computer, or with a combination of these. Molecular modelling techniques can be applied to the atomic coordinates of a crystal of the present invention to derive a range of 3D models and to investigate the structure of ligand binding sites. A variety of molecular modelling methods are available to the skilled person for use in this regard (see e.g., G. Klebe and H. Gohlke, Angew. Chem. Int. Ed. 2002, 41, 2644-2676; Jun Zeng: Combinatorial Chemistry & High Throughput Screening, 2000, 3, 355-362 355; Andrea G Cochran, Current Opinion in Chemical Biology 2001, 5:654-659). At the simplest level, visual inspection of a computer model of the structure of a microprotein-barnase fusion can be used, in association with manual docking of models of functional groups into its binding pockets. Software for implementing molecular modelling techniques may also be used. Typical suites of software include CERIUS2 (available from Molecular Simulations Inc (http://www.msi-.com/)), SYBYL (available from Tripos Inc; http://www.tripos.com), AMBER (available from Oxford Molecular; http://www.oxmol.co.uk/), HYPERCHEM (available from Hypercube Inc; (http://www.hyper.com/), INSIGHT II (available from Molecular Simulations Inc; http://www.msi-.com/), CATALYST (available from Molecular Simulations Inc; http://www.msi.com/), CHEMSITE (available from Pyramid Learning; http://www.chemsite.org/), QUANTA (available from Molecular Simulations Inc; http://www.msi-.com/). These packages implement many different algorithms that may be used according to the invention (e.g. CHARMm molecular mechanics). Their uses in the methods of the invention include, but are not limited to: (a) interactive modelling of the structure with concurrent geometry optimization (e.g., QUANTA); (b) molecular dynamics simulation of microprotein structures (e.g. CHARMM, AMBER); (c) normal mode dynamics simulation of microprotein structures (e.g. CHARMM). Modelling may include one or more steps of energy minimization with standard molecular mechanics force fields, such as those used in CHARMM and AMBER. These molecular modelling techniques allow the construction of structural models that can be used for in silico drug design and modeling.

Moreover, elucidation of the structure of another crystal according to the present invention but being different from the specific MCoTi-II-barnase crystal described herein (Example 6) may be facilitated by employing the three-dimensional structure of said specific crystal as a search model to locate the structure of the further microprotein-barnase fusion in its own crystal unit cell by rotation and translation searches. In particular, if a given microprotein-barnase fusion having a structure similar to MCoTi-II-barnase has been crystallized and X-ray diffraction data have been produced, the molecular replacement method can be applied. In this method, the three-dimensional structure of MCoTi-II-barnase is used as a search model to locate the unknown structure of the microprotein-barnase fusion in its own crystal unit cell by rotation and translation searches. This may avoid the cumbersome search for heavy atom derivatives.

Generally, the method of "molecular replacement" is applicable if the crystal structure of one protein A is known and if crystals of a homologous protein B have been obtained. X-ray diffraction data of crystals of protein B are collected and the three-dimensional model of protein A is used to search for its orientation ("rotation") and position ("translation") in the crystal unit cell or protein B, utilizing the X-ray diffraction data of the latter. If the search has been successful as indicated by certain correlation coefficients, the model of protein A may be refined against the X-ray data of the homologous protein B until convergence is achieved as indicated by the crystallographic reliability (R)-factor. As a result, the three-dimensional structure of protein B can be obtained.

In a further aspect, the present invention relates to the use of the crystal of the invention as defined above or structure data obtainable therefrom for designing or identifying a compound as a drug. Preferably, said drug is capable of inhibiting a serine protease, preferentially a tryptase.

In accordance with the above explanations in connection with the method of the invention for identifying the three-dimensional structure of a microprotein, the structure data may be used to design or identify new drugs which have the same target as the microprotein, but shows pharmacological advantages such as an improved selectivity or degradation within the body. Thereby, the three-dimensional structure of the microprotein allows identifying points of contact with the target molecule. Based on these data, a drug having the desired characteristics may be designed or identified, by applying computational means, as referred to above.

In some cases, it may be advantageous to develop new ligands de novo, i.e. not on the basis and as a modification of a pre-existing compound. The term "de novo compound design" refers to a process whereby the binding pocket of the target macromolecule are determined, and its surfaces are used as a platform or basis for the rational design of compounds that will interact with those surfaces. The molecular modeling steps used in the methods of the invention may use the atomic coordinates of a crystal of the present invention and models or structures derived therefrom, to determine binding surfaces. In particular, the present invention also refers to structures, i.e. PDB-files, of a microprotein. Any such structure will preferably reveal van der Waals contacts, electrostatic interactions, and/or hydrogen bonding opportunities. Said binding surfaces will typically be used by grid-based techniques (e.g. GRID, CERIUS.sup.2; Goodford (1985) J. Med. Chem. 28: 849-857) and/or multiple copy simultaneous search (MCSS) techniques to map favorable interaction positions for functional groups. This preferably reveals positions in the binding pocket sites of the microprotein for interactions such as, but not limited to, those with protons, hydroxyl groups, amine groups, hydrophobic groups (e.g. methyl, ethyl, benzyl) and/or divalent cations. Based on this information, scaffolds may be generated which mimic the structure of the binding sites of the microprotein. These may comprise functional groups which are chemical groups that interact with one or more sites on an interaction surface of a macromolecule. Once functional groups which can interact with specific sites at the target molecule of the microprotein have been identified, they can be linked so as to form a single compound using either bridging fragments with the correct size and geometry or frameworks which can support the functional groups at favorable orientations, thereby providing a desired drug or lead compound for this. Whilst linking of functional groups in this way can be done manually, perhaps with the help of software such as QUANTA or SYBYL, the following software may be used for assistance: HOOK, which links multiple functional groups with molecular templates taken from a database, and/or CAVEAT, which designs linking units to constrain acyclic molecules. Other computer-based approaches to de novo compound design that can be used with the atomic coordinates of the present invention include LUDI (Bohm (1992) J. Comp. Aided Molec. Design 6: 593-606, SPROUT (available from http://chem-.leeds.ac.uk/ICAMS/SPROUT.html) and LEAPFROG (available from Tripos Inc; http://www.tripos.com). Suitable in silico libraries include the Available Chemical Directory (MDL Inc), the Derwent World Drug Index (WDI), BioByte-MasterFile, the National Cancer Institute database (NCI), and the Maybridge catalog. Compounds in these in silico libraries can also be screened for their ability to mimic the binding sites of the microprotein by using their respective atomic coordinates in automated docking algorithms.

Furthermore, the microprotein structure date may also be used for screening a compound that binds to a microprotein. An automated docking algorithm is one which permits the prediction of interactions of a number of compounds with a molecule having a given atomic structure. Suitable docking algorithms include: DOCK (Kuntz et al. (1982) J. Mol. Biol. 161: 269-288), AUTODOCK (Goodsell et al. (1990) Proteins: Structure, Function and Genetics 8: 195-202), MOE-DOCK (available from Chemical Computing Group Inc; http://www.chemcomp.com/) or FLEXX (available from Tripos Inc; http://www.tripos.com). Docking algorithms can also be used to verify interactions with ligands designed de novo.

The present invention further relates to a machine-readable data storage medium comprising the structure data of the crystal of the invention and which, when read by an appropriate machine, can be used to display a three-dimensional representation of the microprotein contained in the crystal or a portion thereof. Preferably, such a data storage medium is obtainable by the above-described method for determining the three-dimensional structure of a microprotein. The storage medium in which the structure may be provided is preferably random-access memory (RAM), but may also be read-only memory (ROM, e.g. a CDROM or DVD), a diskette or a hard drive. The storage medium may be local to the computer, or may be remote (e.g. a networked storage medium, including the internet). The recorded data are preferably the atomic co-ordinates as shown in Table 6. Any suitable computer can be used according to the present invention for representing or further processing the data recorded on the medium.

It is another aspect of the present invention to provide a device comprising (a) the above-defined machine-readable data storage medium; and (b) a computer program for the display of the 3-dimensional microprotein model; and optionally (c) software for the evaluation of potential ligands or, processed forms of the microprotein such as peptidomimetics.

It is yet another aspect of the present invention to provide the use of the device of the present invention for modelling a ligand to or a drug analogous to the microprotein.

In accordance with the above explanations, the present invention also refers to a method of identifying a compound capable of binding to a microprotein comprising the steps of:
(a) performing a fitting reaction by computational means between a microprotein and a candidate compound using the structure data of the microprotein obtainable from the crystal of the invention and structure data of said compound; and (b) determining whether the candidate compound is capable of binding the microprotein based on the data obtained in the fitting reaction.

Suitable methods for identifying a compound capable of binding microprotein have already been outlined in connection with the use of the present invention for designing or identifying a drug.

In a preferred embodiment, the present method also encompasses developing a ligand which comprises the step of modifying an identified ligand to alter, add or eliminate a portion thereof suspected of interacting with a binding site of the microprotein, thereby increasing or decreasing the affinity of the ligand to the binding site.

Accordingly, the present invention additionally relates to the use of the crystal of the invention or structure data obtainable therefrom or the data storage medium of the invention for identifying a compound capable of binding to a microprotein.

In a further aspect, the present invention refers to a method for optimizing the binding activity of a microprotein to a target molecule comprising the steps of:

(a) determining by computational means one or more residues of the microprotein which participate in the binding interaction with the target molecule using structure data of the microprotein obtainable from a crystal according to the invention and structure data of the target molecule; and (b) modifying in the microprotein one or more of said determined residues so as to optimize the binding activity of the microprotein to the target molecule.

Particularly preferred is that the structure data of the microprotein and the target molecule are obtained from a crystallized co-complex of said microprotein and target molecule.

It is furthermore preferred that the structure data of the microprotein the binding activity of which is to be optimized is obtained by computationally superimposing its structure on the structure data of another microprotein's crystal, which is preferably a crystal according to the present invention.

For this embodiment of the present invention, suitable techniques of the rational design may be applied. These are generally known to a person skilled in the art. "Optimizing" may refer to an increase or a decrease of the binding affinity to a given target molecule, as can be expressed for example by Ki-values (see supra), preferably an increase is meant. Alternatively, or in addition, "optimizing" may for example refer to an increased or decreased, preferably increased, selectivity for the target molecule. For example, the selectivity for β-tryptase may be increased by enhancing the binding affinity for this enzyme and concomitantly decreasing the affinity to other target molecules to which the microprotein under investigation shows significant binding, such as trypsin or other tryptase isoforms. In accordance with the present embodiment, the binding affinity of the microprotein can be significantly increased, preferably by orders of magnitude, by a series of rational measures known to the person skilled in the art. These include the modification of the microprotein with chemical groups so as to reduce their degrees of freedom lost upon binding to the target molecule site or the introduction of more potent electrostatic or hydrophobic binding groups.

Particularly preferred is to carry out the present embodiment, as follows:

In cases where the three-dimensional structure of the target and the ligand microprotein is known or, most preferably, where the structure of the co-complex of both compounds is known, predictions can be made to optimize the binding of the microprotein. As an illustration, it is herewith reported that for the McoETi tryptase inhibitor, the structure of McoETi was superimposed onto the structure of the EETI-II microprotein in complex with trypsin as is retrievable from the protein data bank www.rcsb.org, entry 1H9H. Next, the tryptase structure was superimposed to trypsin, making use of the software Insight II (Accelrys). As a result, a model of McoETI binding to tryptase was obtained. As expected, it was found that the side chain of lysine residue 5 contacts the catalytic serine 195 OH. Interestingly, the active site of tryptase contains a number of acidic residues and some of the basic residues of the McoETI inhibitor loop together with the two adjacent arginines seem to contribute to binding. Hence, a number of variants have been made, where either additional lysines were introduced at the amino-terminus or internal lysine/arginine residues were systematically replaced by alanine. By performing rational design in this way, a substantial improvement of affinity was thus achieved (see Table 1, infra). In this way, the microproteins depicted in Table 1 (infra) under items 8, 18, 19 and 20 (i.e. SEQ ID Nos: 4, 11, 12 and 13) have been produced.

According to the above, the present invention also relates to the use of the crystal of the invention or structure data derivable therefrom for optimizing the three-dimensional structure of said microprotein with respect to its binding and/or inhibiting activity to a target molecule, said target molecule preferably being a tryptase.

These pharmaceutical compositions may be formulated in an analogous manner as it is described above for the microprotein. A skilled person is aware of suitable ways for formulating proteinaceous compounds provided in crystallized form. The use of protein crystals in medicine is for example described in Gappa (Tissue Eng. 7 (2001), 35-44) and Brader (Nat. Biotechnol. 20 (2002), 800-804).

Accordingly, the present invention also relates to the use of a crystal of the invention for the preparation of a pharmaceutical composition for treating or preventing a disease that can be treated or prevented by inhibiting the activity of tryptase. Preferably, the disease is selected from the group consisting of asthma, inflammation, psoriasis, pulmonary fibrosis, an interstitial lung disease, rheumatoid arthritis, gingivitis, periodontitis, an allergic reaction, allergic rhinitis, osteoarthritis, atherosclerosis, angiogenesis, multiple sclerosis or cancer.

These and other embodiments are disclosed and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet, for example under http://www.ncbi.nim.nih.gov/PubMed/medline.html. Further databases and addresses, such as http://www.ncbi.nim.nih.gov/, http://www.infobiogen.fr/, http://www.fmi.ch/biology/research_tools.html, http://www.tigr.org/, are known to the person skilled in the art and can also be obtained using, e.g., http://www.google.de. An overview of patent information in biotechnology and a survey of relevant sources of patent information useful for retrospective searching and for current awareness is given in Berks, TIBTECH 12 (1994), 352-364.

Furthermore, the term "and/or" when occurring herein includes the meaning of "and", "or" and "all or any other combination of the elements connected by said term".

The present invention is further described by reference to the following non-limiting figures and examples.

The Figures show:

This patent or patent application contains at least one drawing in color. Copies of this patent or patent application in publication with color drawings will be provided by the office upon request and payment of the necessary fee.

FIG. 1 depicts the amino acid sequences of the McoTI-II cyclotide (SEQ ID NO: 22) (A), of an open chain variant of McoTi-II called McoTi-o (SEQ ID NO: 1) (B) and of a hybrid consisting of the aminoterminal part of McoTi-o and the ICK peptide EETI-II called McoEeTi (SEQ ID NO: 23) (C).

FIG. 2 shows a HPLC profile of crude linear peptide McoTI-o. Peak 3: linear target peptide. As products from incomplete coupling were detected: peak 1: missing Pro; peak 2: missing TyrCys; peak 4: additional $^t$Bu group.

Figure 3:
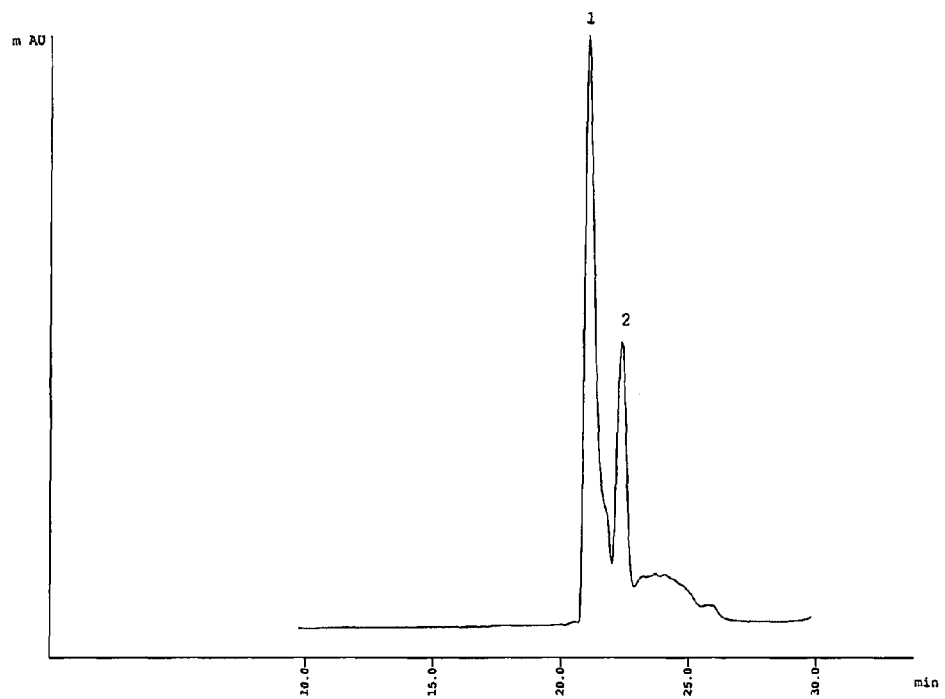

FIG. 3 is a profile of an HPLC purification of McoTi-o after oxidation of cysteine residues. The elution time and the absorption of the effluent at 217 nm are given on the abscissa and the ordinate, respectively. Peak 1 indicates the folded peptide McoTi-o, peak 2 a mixture of not complete or proper folded intermediates.

Figure 4:
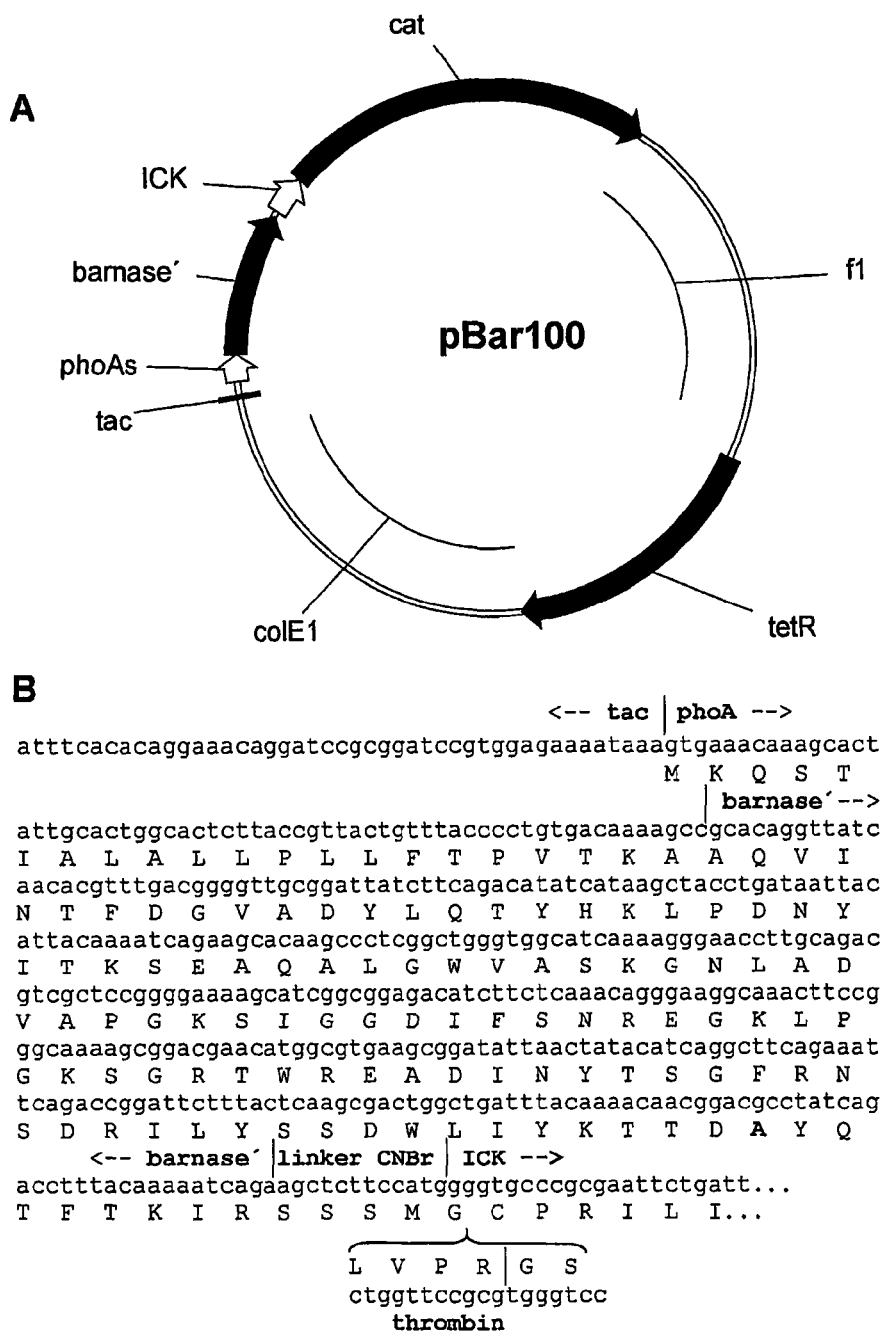

FIG. 4 illustrates the barnase'-ICK peptide fusion construct design. (A) Schematic representation of the plasmid pBar100 harboring the barnase' gene that leads to the expression of the enzymatically inactive H102A variant; f1, replication origin; cat, chloramphenicol resistance marker; tetR, tetracycline repressor encoding gene; colE1, colE1 replication origin; tac, tac promotor sequence; phoAs, alkaline phosphatase periplasmic signal sequence; ICK, ICK peptide encoding sequence. (B) DNA and protein sequence of the barnase'-ICK peptide fusion. The exchanged amino acid at position #102 of barnase (H102A) is indicated in bold letters. In the pBar100 series of expression vectors, a single methionine codon resides at the junction of barnase' and ICK peptide coding sequence that can be used for chemical cleavage of the fusion protein with cyanogen bromide. The pBar100Throm vector encodes in addition a thrombin recognition site (LVPRGS).

FIG. 5 depicts the nucleotide and corresponding amino acid sequence of a synthetic rMcoEeTi hybrid gene (SEQ ID NOs: 20 and 21).

Figure 6:
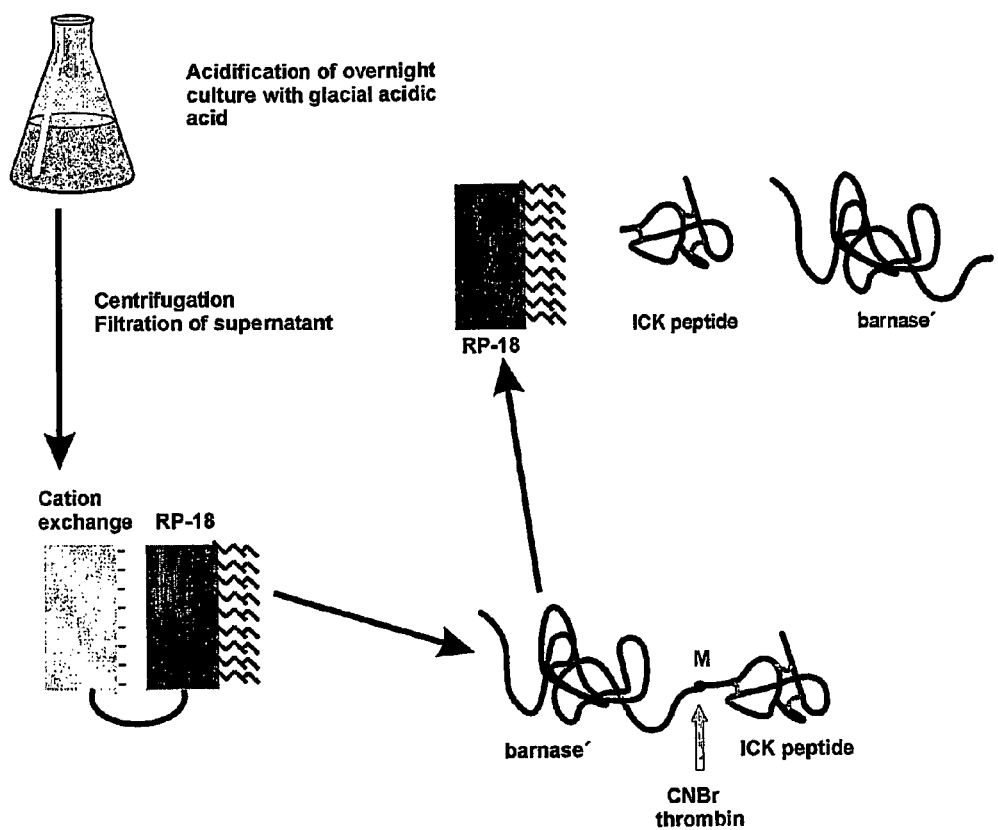

FIG. 6 represents a schematic outline of ICK peptide production and purification as described in Example 2. As a first step, the bacterial liquid culture of *E. coli* cells containing the respective pBar vector is acidified with glacial acidic acid which results in the release of the barnase'-ICK peptide fusion into the culture medium. The filtrated culture supernatant is subjected to a combined cation exchange/reverse-phase HPLC chromatography. To obtain pure fusion protein, a second cation exchange chromatography is performed after solubilization in 0.1 M Tris-HCl pH 7.8 containing 8 M urea and dialysis against 50 mM ammonium acetate. Cleavage of the fusion with CNBr or thrombin results in the release of the ICK peptide from the barnase' carrier and the ICK peptide is isolated by RP-HPLC.

Figure 7:
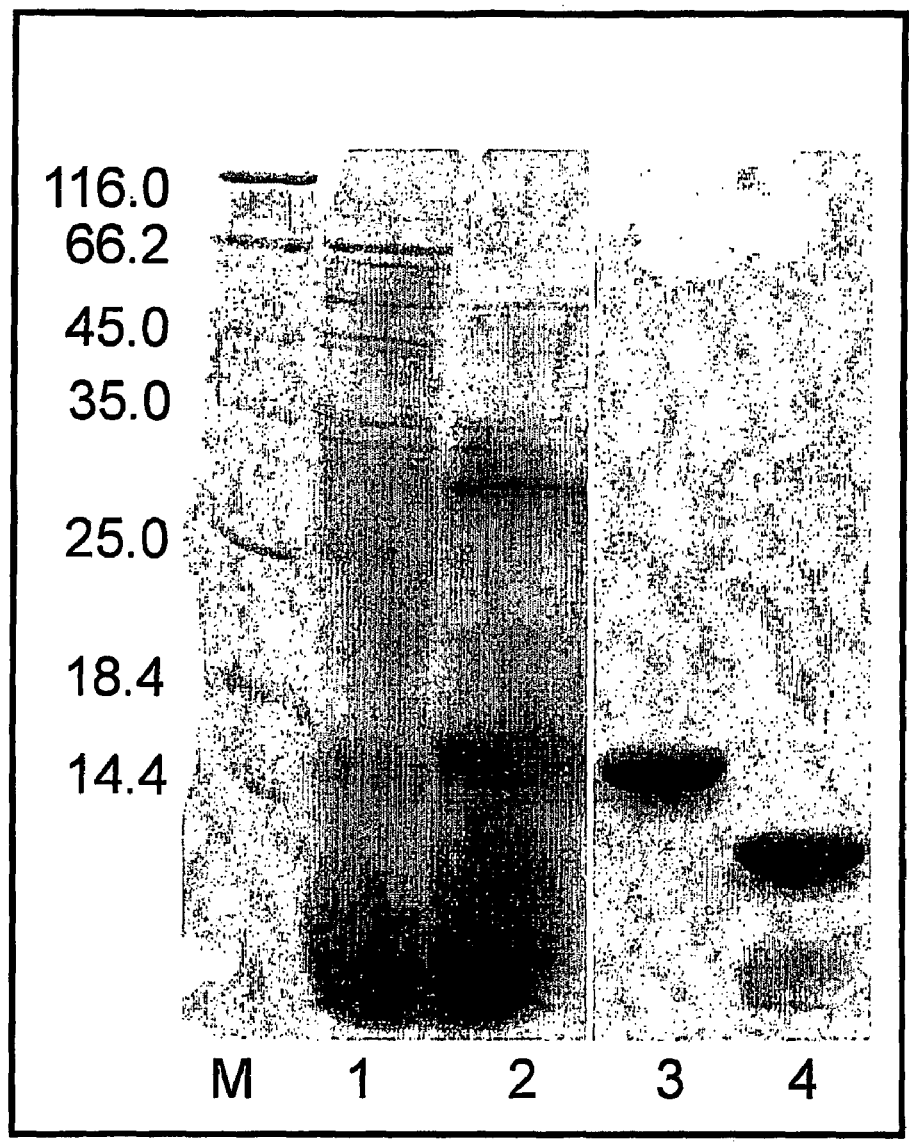

FIG. 7: displays an SDS-PAGE analysis of the purification of rMcoEeTi described in Example 2. M: Protein molecular weight marker (MBI Fermentas) with sizes indicated in kDa.; lane 1: culture supernatant (1.6 ml, precipitated with TCA); lane 2: culture supernatant after acidification (1.6 ml, precipitated with TCA); lane 3: purified barnase'-ThromMcoEeTI fusion protein; lane 4: fusion protein after overnight cleavage with thrombin.

Figure 8:
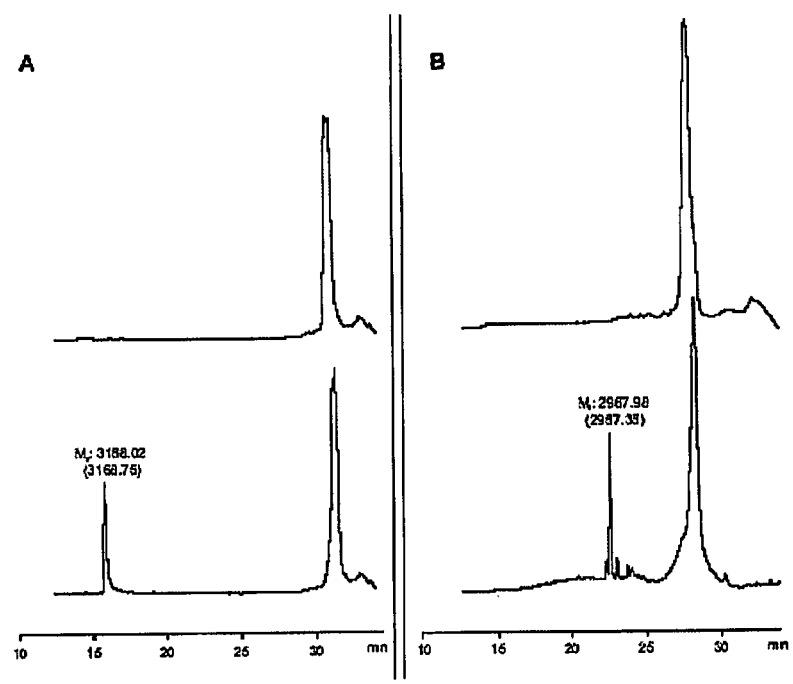

FIG. 8: shows an HPLC analysis of the barnase'-McoEeTI (A) and the barnase'-EETI-II M7I (B) peptide fusion prior to cleavage (upper trace) and after cleavage with CNBr or thrombin, respectively (lower trace). The experimentally determined molecular mass of the respective ICK peptide is given together with the calculated molecular mass (indicated in parentheses).

Figure 9:
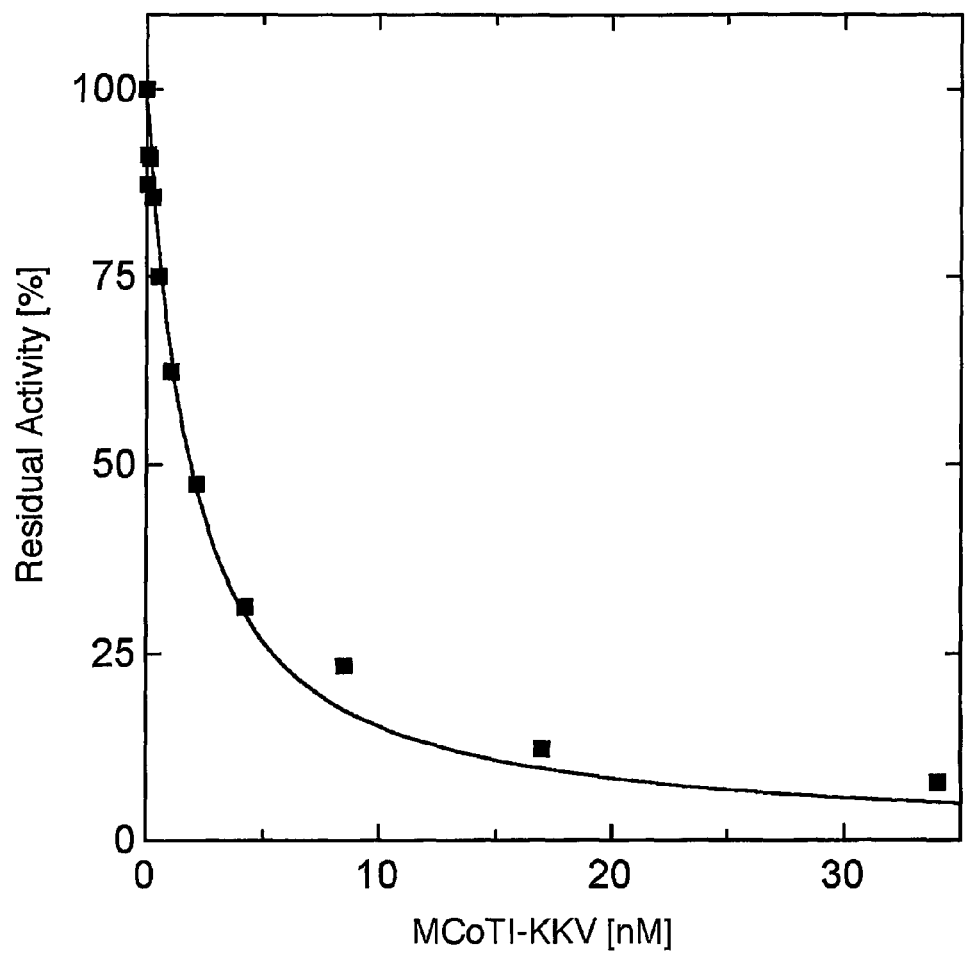

FIG. 9 shows the result of an assay for the inhibition of human tryptase by McoTi-KKV. Tryptase (0.2 nM) was pre- incubated with McoTi-KVV (0-34 nM) at 37 degree C. for 60 min, and the reaction was initiated by the addition of substrate tos-Gly-Pro-Arg-AMC. The residual steady state velocities were measured over 10 min and are expressed in % of the activity measured in the absence of the inhibitor.

Figure 10:
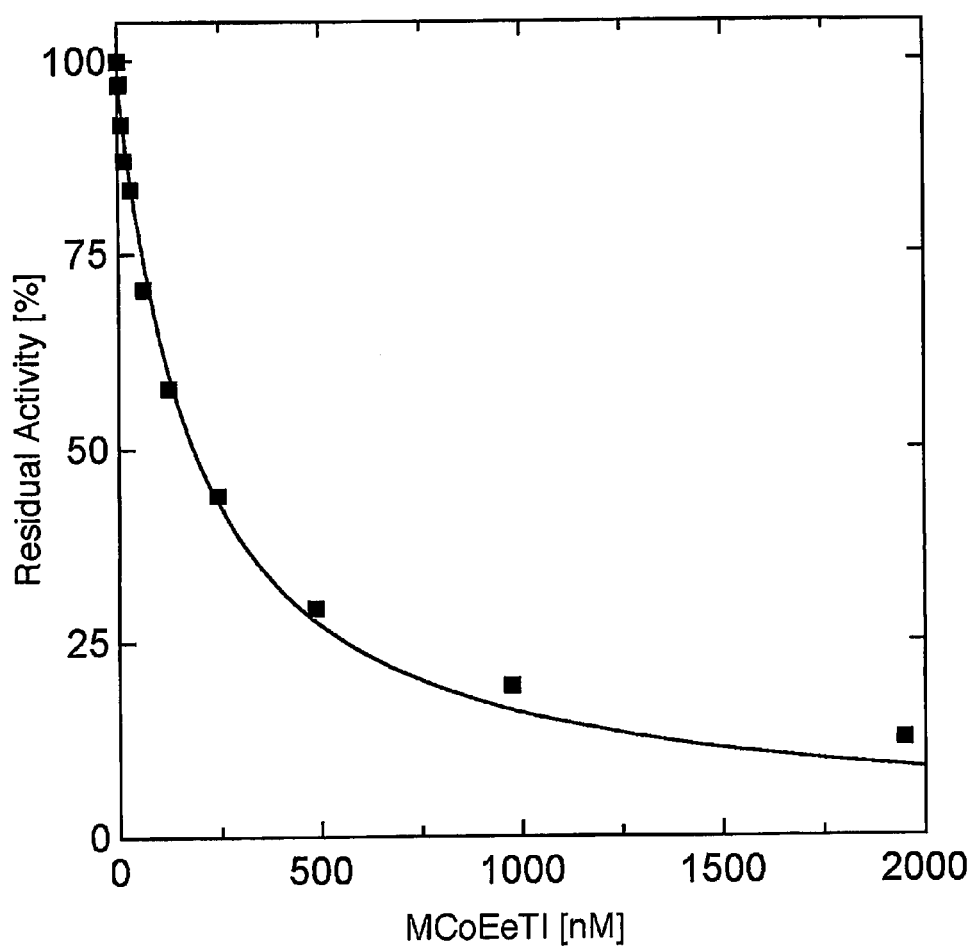

FIG. 10 shows the result of an assay for the inhibition of human tryptase by McoEeTI. Tryptase (0.2 nM) was preincubated with MCoEeTI (0-1950 nM) at 37 degree C. for 60 min, and the reaction was initiated by the addition of substrate tos-Gly-Pro-Arg-AMC. The residual steady state velocities were measured over 10 min and are expressed in % of the activity measured in the absence of the inhibitor.

FIG. 11 shows the amino acid sequence and three-dimensional structure of the ICK peptide EETI-II (SEQ ID NO: 24), a trypsin inhibitor from *Ecballium elaterium* (Chiche, 1989). The ribbon representation of the secondary structure elements of mature EETI-II was drawn with the program PYMOL (http://www.pymol.org). Disulfide bonds are shown as sticks. Cysteine linkage is also indicated in the amino acid sequence, where the inhibitor loop is marked in bold letters.

Figure 12:
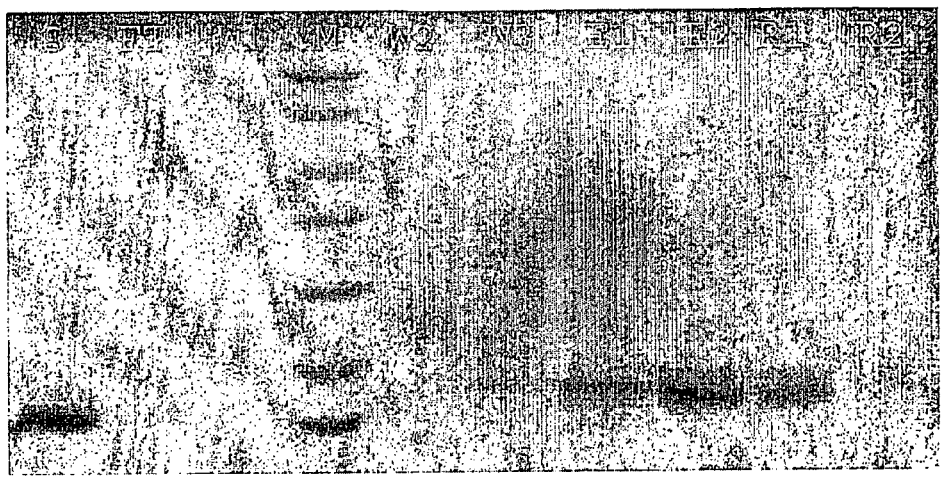

FIG. 12 is a depiction of an SDS-PAGE onto which samples were loaded taken during a purification of a barnase' fusion protein using barstar in the affinity column (see Example 5). S: Sample prior to column application; FT: Flow-through of sample applied to the column; W1: Wash 1; W2: Wash 2; W3: Wash 3; E1: Elution fraction 1; E2: Elution fraction 2; R1: Regeneration solution 1; and R2: Regeneration solution 2.

Figure 13:
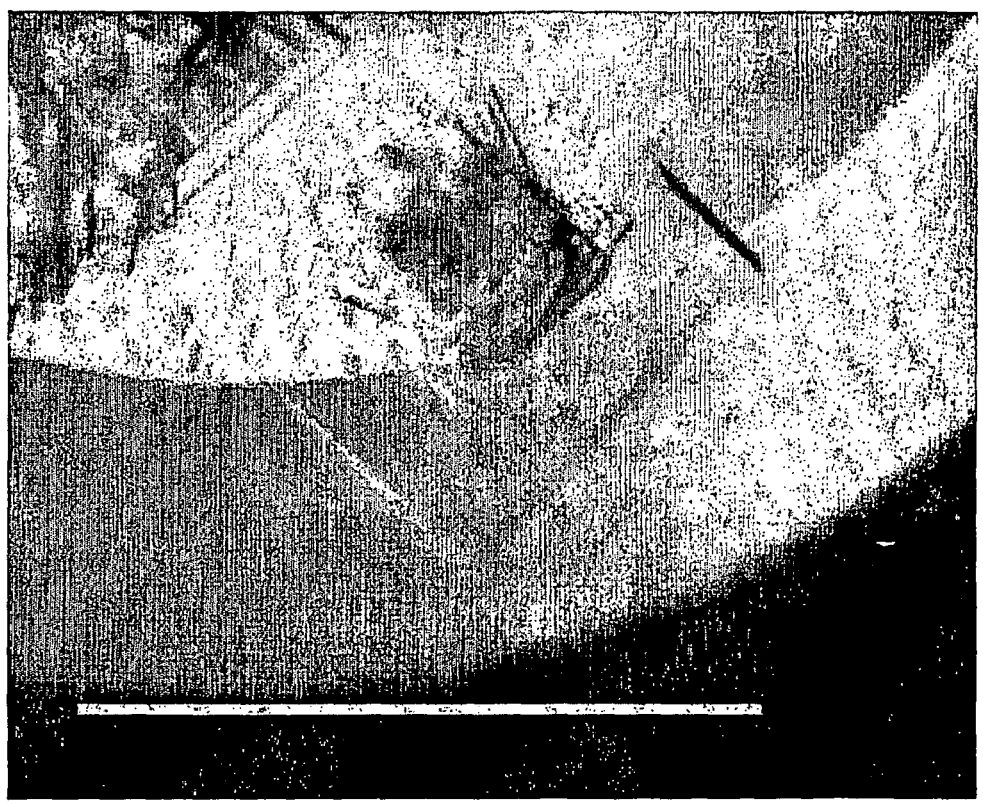

FIG. 13 shows a crystal of the barnase-MCoTi-II fusion used for data collection (see Example 6). Scale bat is 1 mm.

Figure 14:
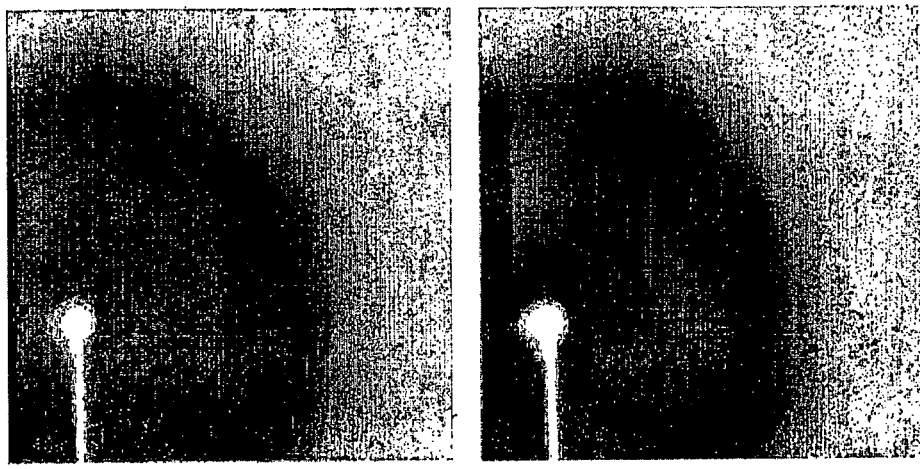

FIG. 14 illustrates the effect of crystal annealing. In house diffraction data before (left) and after (right) annealing recorded from the same crystal in approximately the same orientation. After annealing, spots are less smeared out and visible to higher resolution.

Figure 15:
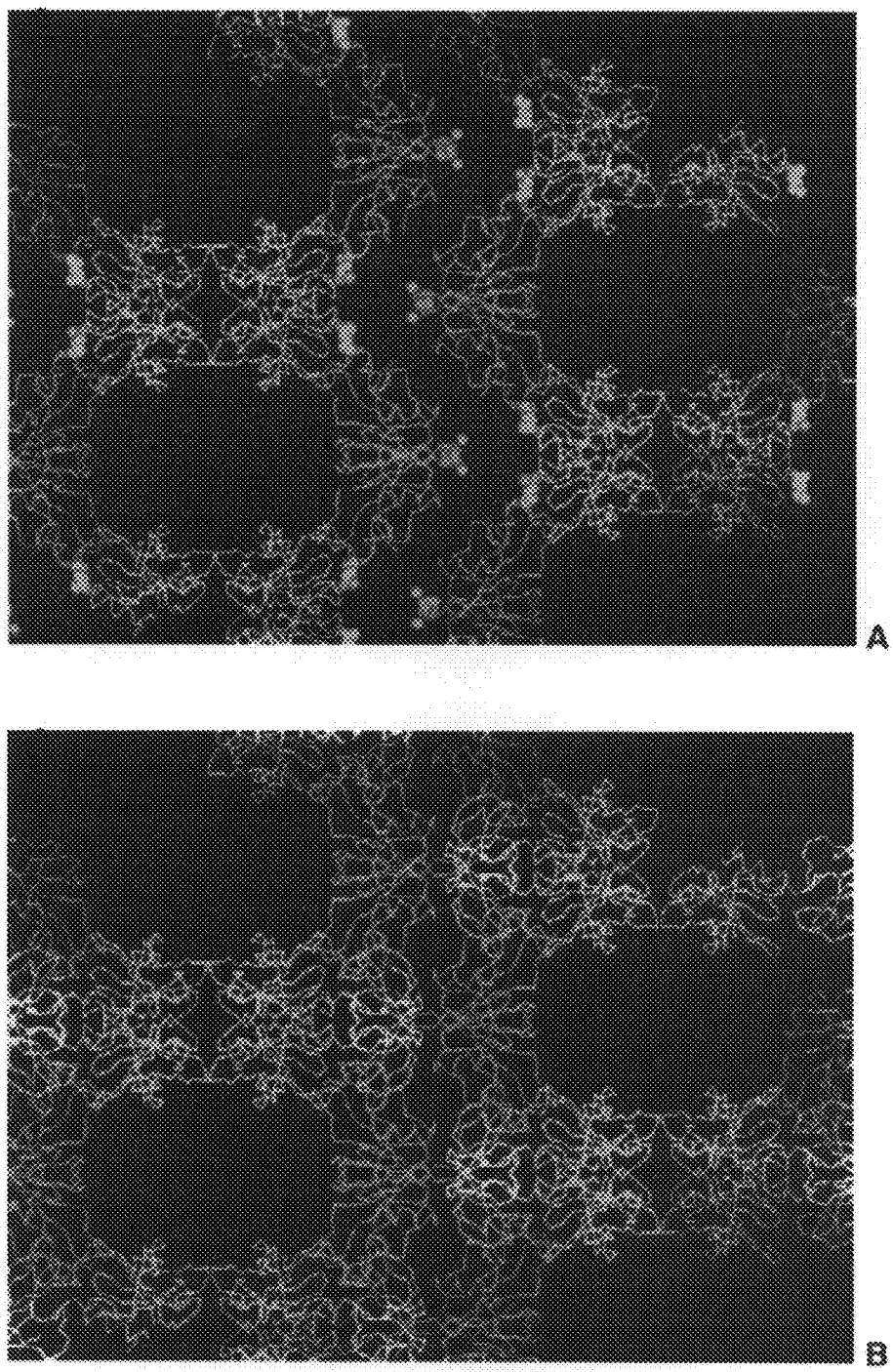

FIG. 15 shows the packing of the barnase-MCoTi-II crystal. Barnase and MCoTi-II of the first molecule are shown in blue and orange, respectively. Barnase and MCoTi-II of the second molecule are shown in green and yellow, respectively. FIG. 15A shows the packing of barnase as obtained by the molecular replacement. The C-terminal residue of barnase is shown in spheres. FIG. 15B shows the large solvent channels in the barnase-MCoTi-II crystal.

Figure 16:
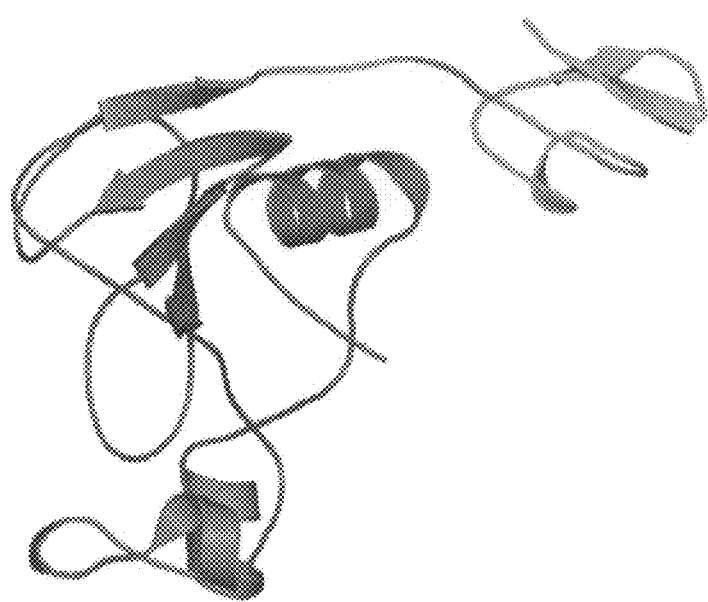

FIG. 16 gives an overall view of the barnase-MCoTi-II monomer. Barnase is shown with β-strands in blue and α-helices in red. The linker sequence (SSSM) is coloured orange, MCoTi-II is shown in green.

Figure 17:

FIG. 17 presents an overlay of the two monomers of barnase-MCoTi-II in the asymmetric unit shown in red and blue. The monomers were aligned on the barnase. The Figure illustrates that the difference between the two monomers is due to a rigid body movement of barnase (lower left) and MCoTi-II (upper right) relative to one another around residues of the linker.

Figure 18:
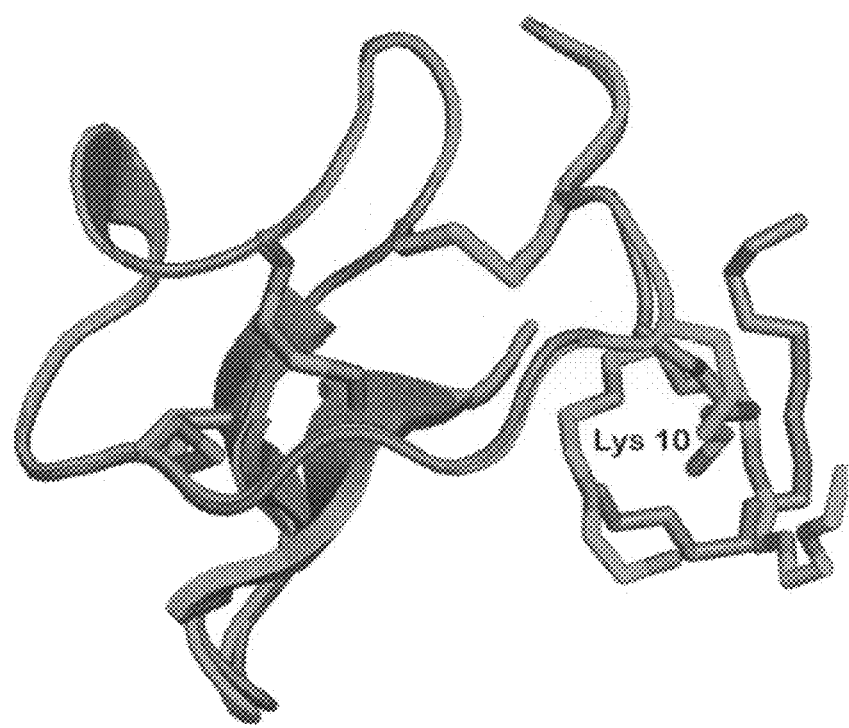

FIG. 18 presents an overlay of MCoTi-II from the two crystallographically independent molecules A (green) and molecule B (blue). In both monomers, Lys 10 is coordinated by a PEG molecule (shown in ball-and-stick representation), but the positioning of the PEG is different on both molecules.

Figure 19:
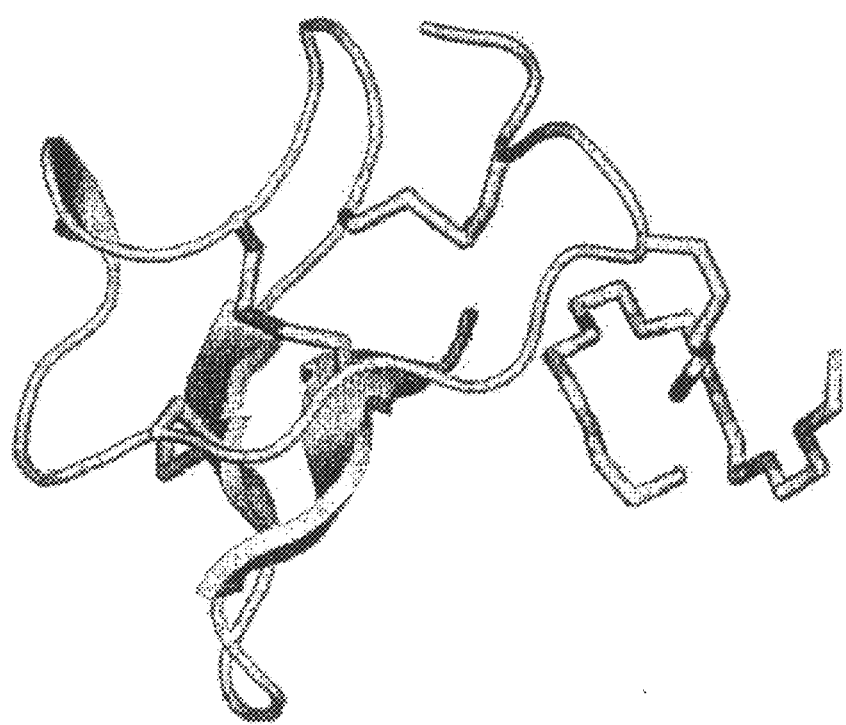

FIG. 19 shows MCoTi-II from the A monomer in cartoon representation. Side chains of cysteines and Lys 10 are shown in ball-and stick representation. A PEG molecule is located next to the side chain of Lys 10 with its oxygens in hydrogen bonding distance to the terminal amino group of Lys 10.

FIG. 20 presents an overlay of the MCoTi-II monomer with the first state of the MCoTi-II NMR ensembles 1HA9 (A), 1IB9 (B) and with the high resolution crystal structure of the squash-type trypsin inhibitor MCTI-I (C). MCoTi-II is shown in green in all panels.

The following Examples illustrate the invention:

EXPERIMENTAL SET-UP

Molecular Biological Techniques

Unless stated otherwise in the Examples, all recombinant DNA techniques are performed according to protocols as described in Sambrook and Russell (2001), Molecular Cloning: A Laboratory Manual, CSH Press, Cold Spring Harbor, N.Y., USA or in Volumes 1 and 2 of Ausubel et al. (1994), Current Protocols in Molecular Biology, Current Protocols.

EXAMPLE 1

Chemical Synthesis of Open Chain McoTI

Materials and Methods

All the chemicals used were of the highest grade available. Solvents were of analytical grade and used as supplied. $N_\alpha$-Fmoc protected amino acids were used with the following side-chain protecting groups: t-Bu (Asp, Tyr), Boc (Lys), Trt (Cys, Asn), Pbf (Arg). Pseudo-proline dipeptide Fmoc-Asp(O$^t$Bu)-Ser($\psi^{Me,Me}$)pro-OH was purchased from Calbiochem-Novabiochem GmbH. ESI mass spectra were measured with a TSQ 700 Finnegan spectrometer. High-resolution ESI mass spectra were recorded with a Bruker APEX-Q III 7T. HPLC were performed on a Pharmacia Äcta basic system using YMC J'sphere ODS H-80, RP C-18 columns for preparative runs (250×4.6 mm, 4 µm, 80 Å) and for the analytical samples (250×4.6 µm, 80 Å).

Synthesis of the Linear McoTI-o

The linear peptide McoTI-o (see FIG. 1B; SEQ ID NO: 1) was assembled using a combination of automated and manual Fmoc-assisted SPPS on PEG-type amide NovaSyn® TGR resin (Calbiochem-NovaBiochem GmbH) with a loading capacity of 0.23 mmol/g. The C-terminal glycine (5 equiv. respective to resin loading) was activated by HATU/DIEA (5 equiv. and 10 equiv., respectively) and attached without pre-activation onto the resin within six hours. The loading with the first amino acid was determined UV-spectroscopically by monitoring of Fmoc deprotection (Chan et al., 2000). Chain elongation was performed using the Applied Biosystems peptide synthesizer ABI 433. Starting from 0.435 g (0.1 mmol) of amide resin, FastMoc 0.1 MPP CondMon mode with conditional monitoring was used for all amino acid cycles including pseudo-proline dipeptide, except cysteine. After pre-swelling first in DCM, then in NMP, each amino acid cycle has been programmed to include basically 16 min Fmoc deprotection with conditional conductivity monitoring, 8 min activation with HBTU/HOBt/DIEA; and 30 min coupling. Depending on the Fmoc-monitoring, additional 20 min of Fmoc deprotection and 50 min coupling followed by acetic anhydride capping were added to the regular cycles automatically.

Cysteine was coupled manually in DCM/NMP using the standard DIC/HOBt protocol (Albericio et al., 2000). The peptide-resin was transferred from the peptide synthesizer reaction vessel into an SPPS reactor and treated by nitrogen bubbling in the presence of activated cysteine until a negative Kaiser test was obtained. Then the resin was thoroughly washed with NMP and DCM and transferred back to the peptide synthesizer reaction vessel.

Cleavage of the peptide from the resin was achieved using TFA/DTT/TIS/anisole (23:1:0.5:0.5 v:w:v:v, 5 mL per 200 mg peptide-resin). The resin was gently shaken for 2.5 h, filtered, washed with TFA (3×1 mL). The combined filtrates were concentrated in vacuo, and the peptide was precipitated with MTBE. The peptide was centrifuged, washed with MTBE, dried, dissolved in water containing 0.1% TFA, and lyophilized. The crude, reduced peptide (18 mg, 66.6% calculated using the program of the ABI 433 peptide synthesizer) was purified using preparative RP-HPLC. The gradients of 0.1% TFA-water (eluent A) and 90% acetonitrile-0.1% TFA (eluent B) were employed with a flow rate of 10 ml/min within 30 min. The linear peptide was characterized by ESI mass spectrometry as well as by high-resolution ESI-FT-ICR-MS.

Folding Procedure

Oxidation of the linear McoTI-o to the cystine knot was performed by dissolving the reduced lyophilized peptide in 50 µl 10 mM HCl per mg of peptide followed by addition of $NH_4HCO_3$ (200 mM, pH 9.1) to a final concentration of 1-1.5 mg/ml (Wentzel et al., 1999). The reaction mixture was incubated overnight in a PET container under vigorous shaking at room temperature. Purification of folded peptide was done by RP-HPLC using Phenomenex $C_{18}$ columns (analytical: 250× 4.60 mm; preparative: 250×10.00 mm). Conditions were as follows: Eluent A: $H_2O$ containing 0.1% TFA, eluent B: 50% acetonitrile, 50% 2-propanol containing 0.1% (v/v) TFA. A linear gradient of 10-37% B was performed with flow rates of 1 ml/min for analytical purposes and 3.5 ml/min for preparative runs, respectively. With monitoring at 217 nm the oxidized peptide-containing fraction was collected and lyophilized. Successful oxidation was confirmed by ESI mass spectrometry and by measurement of inhibitory activity against trypsin, which is strictly dependent on correct disulfide bond formation (Wentzel et al., 1999).

EXAMPLE 2

Recombinant Production in E. coli of McoEeTi

Construction of Expression Vector pBar100-McoETI

Two halves of the coding sequence for Bacillus amyloliquefaciens RNAse (Barnase) were separately PCR amplified with Taq polymerase (Eppendorf) using Bacillus amyloliquefaciens DNA and the primer pairs Barnase-up (5'-CCGGCGATGGCCATGGATGCACAG GTTATCAACACGTTTG-3'; SEQ ID NO: 25) and Barmitte-lo (5'-GTTCGTCCGCTTTTGCCCGGAAGT TTGCCTTC-CCTGTTTGAG-3'; SEQ ID NO: 26) and Barmitte-up (5'-CTTCCGGGCAAAAGCGGACGAAC-3'; SEQ ID NO: 27) and Barnase-lo (5'-GAATTCGGTCTGA TTTTTGTAAAG-GTCTGATAATGG GCCGTTGTTTTGTA-3'; SEQ ID NO: 28), respectively. The two halves of the resulting barnase' coding sequence were combined by PCR using the oligonucleotide pair Barnase-up and Barnase-lo. This barnase' PCR product was digested with Nco I and EcoR I and ligated with similarly cleaved pET22b (Novagen). From this vector, the barnase gene was PCR amplified using the primers bar'-Nhe-up (5' GCGCACTAGTGCTAGCGATCTCGATC-CCGCGAA 3'; SEQ ID NO: 29) and bar'-Sma-lo (5' CTGTC-CCGGGCGAATTCGGTCTGATTTTTGTAA AGGTCTGAT-AGGCGTCCGTTGTTTTG 3'; SEQ ID NO: 30), cleaved with Nhe I and Sma I and ligated into similarly cleaved pASK21-CKSend (Christmann et al., 1999). The resulting barnase'-EETI-II expression cassette was excised with Aat II and Pst I and ligated into similarly cleaved pMT416 (Hartley, 1988). The resulting plasmid contains a phoA leader sequence and the barnase' gene under tac promotor control (Hartley, 1988). This expression cassette was then transplanted by cleavage with Ecl 136 II and Xba I and ligation into similarly cleaved pASKInt200, a derivate of pASKInt100 (Wentzel et al., 2001) that lacks the tetR promotor, to give pASKBarInt200. This plasmid was finally cleaved with Sap I and Sma I and overlapping DNA ends were filled up using T4 DNA Polymerase (MBI Fermentas). Blunt end ligation of the vector fragment resulted in pBar100-EETI-II M7I. The nucleotide and corresponding amino acid sequence of rMcoEeTi is shown in FIG. 5 and SEQ ID NOs: 20 and 21.

For construction of plasmid pBar100-McoEeTI, the McoEeTI gene was assembled with synthetic oligonucleotides cotiup2 (5' GCATGCGCTCTTC-TAACTGCATAT-GCGG GCCCAACGGTTACTGCGGTTCCGGATCC 3'; SEQ ID NO: 31), cotilink (5' CGTCGACATTTTTTCAG GATTTTCGGGCAAACACCA-CCGTCGGATCCG-GAACCGCAG 3'; SEQ ID NO: 32) and cotilo (5'GCAT-GCGCTCTTCTGCAAGCAC-CCGGGCAGTCGGAGTCACGTCGACA-TTTTTTCAGG 3'; SEQ ID NO: 33) by polymerase chain reaction, assembled in vector pMalp-2 (New England BioLabs) and transplanted by cleavage with NcoI and Bsp120 I to similarly cleaved cloning vector pASKBar100-EETI-II M7I (see also FIG. 4).

Expression of Fusion Genes

The steps of expressing, purifying and cleaning the fusion protein are schematically outlined in FIG. 6. *E. coli* strain 71-18 [F' lacI$^q$ (lacZ.M15) proA+B+ (lac-proAB) supE thi1] (source B. Müller-Hill) containing helper plasmid pRep4 (Qiagen) was transformed with pBar100-McoEeTI by electroporation and grown in 50 ml dYT liquid media containing 25 µg/ml chloramphenicol and 37.5 µg/ml kanamycin overnight at 37° C. This culture was then used to inoculate 5 l of TB medium containing 25 µg/ml chloramphenicol and 37.5 µg/ml kanamycin in a 5 l fermenter (Bioengineering). Fermentation was performed at 30° C. At an O.D.$_{600}$ of 3-5 IPTG was added to a final concentration of 1 mM. After overnight incubation, the bacterial liquid culture was cooled to 4° C. and 55 ml of glacial acetic acid per liter of cell culture was added under continuous stirring. Acidification of the culture results in additional release of barnase' fusion protein into the medium (Hartley, 1988). Stirring was continued for another 15 min followed by centrifugation at 4000 rpm for 60 min at 4° C. Insoluble particles were removed by filtration.

Purification of Fusion Proteins

The filtered culture supernatant was diluted 5-fold with H$_2$O and applied to a Perseptive HS20 cation exchance column (1.0×10 cm, 7.6 ml bed volume) mounted to a Vision™ BioCad workstation (PerSeptive Biosystems) at 8 ml/min. Elution was performed with a gradient ranging from 0 to 0.5 M NaCl. Peak fractions ranging from 166 mM to 500 mM NaCl were directly applied to a Perseptive R2 reversed phase column. After washing with H$_2$O/0.1% (v/v) TFA, the fusion protein was eluted from the column using a gradient from 5 to 50% acetonitrile/0.1% (v/v) TFA. Fusion protein containing fractions were combined and lyophilized. The fusion protein peptides was dissolved in 0.1 M Tris-HCl pH 7.8 containing 8 M urea, dialyzed overnight against 50 mM ammonium acetate and further purified by Perseptive HS20 cation exchance chromatography. Elution was performed with a gradient ranging from 90 to 330 mM NaCl. Barnase-McoEeTi containing fractions were dialysed against 50 mM ammonium acetate and lyophilised.

Thrombin Cleavage of Fusion Proteins

Lyophilized proteins were solubilized in 20 mM Tris-HCl pH 8.45, 150 mM NaCl and 2.5 mM CaCl$_2$ and 1 unit of thrombin from human plasma (Sigma, T-7009) per mg of fusion protein was added. The reaction was incubated overnight at 37° C. and analysed by SDS polyacrylamide gel electrophoresis (FIG. 7) or reversed phase HPLC using a Phenomenex C$_{18}$ column (Synergi 4u Hydro-RP 80A; 250× 4.60 mm). Buffer A: H$_2$O containing 0.1% (v/v) trifluoroacetic add, buffer B acetonitrile containing 0.1% (v/v) trifluoroacetic acid. A linear gradient ranging from 10-37% buffer B was run at flow rate of 1 ml/min. Chromatography was monitored at 217 nm (FIG. 8). ICK peptide containing fractions were collected and lyophilized. The expected molecular mass of the McoETi peptide (3168.75) was confirmed by ESI mass spectrometry.

EXAMPLE 3

Determination of Trypsin and Tryptase Inhibitory Activity

Titration of the Inhibitor

The concentration of inhibitory active inhibitor was determined by titration with trypsin. Therefore, bovine pancreatic trypsin was standardised by active-site titration using p-Nitrophenyl p'-guanidinobenzoate (Chase & Shaw, 1970). The concentration of active inhibitor was calculated assuming a 1:1 interaction between the inhibitor and trypsin.

Determination of Equilibrium Constants:

Apparent equilibrium dissociation constants (Ki$_{app}$) for the complexes of the inhibitor with trypsin and tryptase were determined essentially as described by Bieth (Bull. Eur. Physiopathol. Respir. 16 (Suppl.) (1980), 183-197). Briefly, increasing concentrations of an inhibitor were incubated with a constant concentration of an enzyme. Substrate was then added, and the residual enzyme activity measured. Ki$_{app}$-values were calculated by fitting the steady state velocities to the equation for tight binding inhibitors (Morrison, 1969) using non-linear regression analysis. FIGS. 9 and 10 show tryptase inhibition curves for the microproteins McoTi-KKV and McoEeTi taken according to the above-described method.

In the following Table 1, an overview is provided of microproteins that have been produced in accordance with the procedure described in Example 1 or 2. Note that the microproteins for which neither "Barnase-Fusion" nor "Chemical Synthesis" is indicated have been expressed as a barnase fusion and the microprotein afterwards cleaved off by CNBr and purified.

Microproteins showing an inhibitory activity upon tryptase of above a Ki$_{app}$ of 1 mM can in principle not be considered as having a therapeutic utility. In some cases, the measurement of the inhibitory effect on tryptase apparently showed no activity at all. In other cases, there was inhibitory activity, however, only above a Ki$_{app}$ of 1 mM.

| No. | Substance | New Nomenclature | Barnase-Fusion | Chemical Synthesis | Sequence | Kiapp [82 mol/l]-Trypsin | Kiapp [µmol/l]-β3-Tryptase |
|---|---|---|---|---|---|---|---|
| 1 | SE-MC-K | SE-MC | | x | GVCPKILKKCRRDSDCPGACICRGNGYCG (SEQ ID NO: 1) | 0.0003 | 0.02 |
| 2 | SE-MA-0 | SE-MC-TR-010 | | x | GVCPAILKKCRRDSDCPGACICRGNGYCG (SEQ_ID NO:34) | no inhibition | 110 |
| 3 | SE-MG-0 | SE-MG | | | GVCPKILKKCRRDSDCLAGCVCGPNGFCGS (SEQ ID NO:2) | 0.0003 | 0.1 |
| 4 | SE-BMG-0 | SE-MG (Bar) | x | | Barnase'-SSSMGVCPKILKKCRRDSDCLAGCVCGPNGFCGS (SEQ ID NO:3) | 0.0002 | 0.1 |
| 5 | SE-BME | | x | | Barnase'-SSSMGIEGREERICPLIWMECKRDSDCLAGCVCGPNGFCGS (SEQ ID NO:35) | no inhibition | no inhibition |
| 6 | SE-EM-0 | SE-ET | | | GCPRILIRCKQDSDCLAGCVCGPNGFCGS (SEQ ID NO:36) | 0.0001 | 1.3 |
| 7 | MCoEeTI-2R-10 | SE-MG-TR-010 (Bar) | x | | Barnase'-SSSMGVCPRNRCKCRRDSDCLAGCVCGPNGCGS (SEQ ID NO:37) | 0.03 | no inhibition* |
| 8 | MCoEeTI-3R-3 | SE-MG-TR-020 (Bar) | x | | Barnase'-SSSMGVCPRILRRCRRDSDCLAGCVCGPNGFCGS (SEQ ID NO:4) | 0.0002 | 0.03 |
| 9 | MCoEeTI-QRT-7 | SE-MG-TR-030 (Bar) | x | | Barnase'-SSSMGVCPRNRQRCRRDSDCLAGCVCTNNKFCGS (SEQ ID NO:38) | 0.001 | no inhibition* |
| 10 | MCoEeTI-KKV-1 | SE-MG-TR-040 (Bar) | x | | Ba'-SSSMGKKVGVCPKILKKCRRDSDCLAGCVCGPNGFCGS (SEQ ID NO:5) | 0.0002 | 0.02 |
| 11 | MCoEeTI-ARD-2 | SE-MG-TR-050 (Bar) | x | | Barnase'-SSSMGVCPKILKACARDSDCLAGCVCGPNGFCGS (SEQ ID NO:39) | 0.0002 | no inhibition* |
| 12 | MCoEeTI-LKA-7 | SE-MG-TR-060 (Bar) | x | | Bar'-SSSMGVCPKILKACRRDSDCLAGCVCGPNGFCGS (SEQ ID NO:40) | 0.0002 | no inhibition* |
| 13 | MCoEeTI-T-1 | SE-MG-TR-080 (Bar) | x | | Barnase'-SSSMGVCPKILKKCRRDSDCLAGCVCTNNKFCGS (SEQ ID NO:6) | 0.0001 | 0.15 |
| 14 | MCoTI-KKV | SE-MC-TR-020 | | x | KKVGVCPKILKKCRRDSDCPGACICRGNGYCG (SEQ ID NO:7) | 0.0004 | 0.002 |
| 15 | MCoTI-R | SE-MC-TR-030 | | x | GVCPRILKKCRRDSDCPGACICRGNGYCG (SEQ tD NO:8) | 0.0008 | 0.02 |
| 16 | MCoEeTI | SE-MG-TR-090 | | | GSVCPKILKKCRRDSDCLAGCVCGPNGFCGS (SEQ ID NO:9) | ≈0.00003 | 0.20 |

-continued

| No. | Substance | New Nomenclature | Barnase-Fusion | Chemical Synthesis | Sequence | Kiapp [82 mol/l]-Trypsin | Kiapp [µmol/l]-β3-Tryptase |
|---|---|---|---|---|---|---|---|
| 17 | MCoTI-LAKC | SE-MC-TR-040 | | x | GVCPKILAKCRRDSDCPG ACICRGNGYCG (SEQ ID NO:10) | 0.0002 | 0.1 |
| 18 | MCoTI-LKAC | SE-MC-TR-050 | | x | GVCPKILKACRRDSDCPG ACICRGNGYCG (SEQ ID NO:11) | 0.0004 | 0.03 |
| 19 | MCoTI-LRKC | SE-MC-TR-060 | | x | GVCPKILRKCRRDSDCPG ACICRGNGYCG (SEQ ID NO: 12) | 0.0005 | 0.01 |
| 20 | MCoTI-LKRC | SE-MC-TR-070 | | x | GVCPKILKRCRRDSDCPG ACICRGNGYCG (SEQ ID NO:13) | 0.0004 | 0.01 |
| 21 | MCoTI-AlaG | SE-MC-TR-080 | | x | GVCP(AlaG)ILKKCRRD SDCPGACICRGNGYCG (SEQ ID NO:41) | 1 | ≈10 |
| 22 | MCoEeTI-ARDs | SE-MG-TR-110 (Bar) | x | | Barnase'-SSSMGVCPKILKKCARDS DCLAGCVCGPNGFCGS (SEQ ID NO:42) | | |
| 23 | MCoEeTI-RAD | SE-MG-TR-120 (Bar) | x | | Barnase'-SSSMGVCPKILKKCRADS DCLAGCVCGPNGFCGS (SEQ ID NO:43) | | |
| 24 | MCoEeTI-KKV-3R | SE-MG-TR-130 (Bar) | x | | Barnase'-SSSMGKKVCPRILRRCRR DSDCLAGCVCGPNGFCGS (SEQ ID NO:44) | | |

Table 1 gives an overview of the microproteins produced and tested in connection with the present invention.
*, at 0.5 µM protein concentration.

Three microproteins, among which the best inhibiting one (i.e. SE-MC-TR-020), were tested for tryptase selectivity. The results of these binding assays are shown in Table 2. As can be seen, SE-MC-TR-020 has a good selectivity for tryptase and does not inhibit other proteases apart from trypsin, or only to a significantly reduced degree when compared to tryptase inhibition.

TABLE 2

| Protease Family | Protease | Species | $K_{iapp}$ [nM] | | |
|---|---|---|---|---|---|
| | | | SE-MG | SE-MC-TR-020 | SE-MC-TR-030 |
| Tryptase | β-III | Human | 100 | 2 | 20 |
| | β-Ia | Human | 70 | 3 | 40 |
| | β-II | Human | 70 | 4 | 40 |
| | ST2 | Sheep | 4000 | 100 | 1000 |
| Pankreas proteases | Trypsin | Porcine | 0.3 | 0.4 | 0.8 |
| | Chymotrypsin | Porcine | >1000 | >1000 | >1000 |
| | Elastase | Porcine | >1000 | >1000 | >1000 |
| Koagulation | Thrombin | Human | >1000 | >1000 | >1000 |
| | Faktor XA | Human | >1000 | >1000 | >1000 |
| Fibrinolysis | Plasmin | Human | ~600 | ~400 | >1000 |
| | tPA | Human | >1000 | >1000 | >1000 |
| Neutrophiles | Elastase | Human | >1000 | >1000 | >1000 |
| | Cathepsin G | Human | >1000 | >1000 | >1000 |
| Kallikreines | pK1 | Human | >1000 | >1000 | >1000 |
| | hK3 | Human | >1000 | >1000 | ~100 |

EXAMPLE 4

Recombinant Production of Microproteins Fused to Barnase, Using the Barnase Moiety as a Purification Handle Materials and Methods Enzymes were obtained from NEB or MBI Fermentas. All chemicals used were of the highest grade available. Solvents were of analytical grade and used as supplied. ESI mass spectra were measured with a TSQ 700 Finnegan spectrometer. Liquid chromatography was performed on a Vision Bio-Cad workstation (PerSeptive Biosystems). RP-HPLC was done on a Kontron or an Äcta (Pharmacia Biotech) basic HPLC system.

Construction of pBar100 Vectors

A schematic representation of expression vector pBar100 vector and additional sequence information of the construct is given in FIG. 4. Plasmids pBar100-EETI-II M7I, pBar100-EETI-II, pBar100-McoEeTI and pBar100ThromMcoEeTI were constructed as follows: The 5' and the 3' half of the barnase coding sequence were separately PCR amplified with Taq polymerase (Eppendorf) using *Bacillus amyloliquefaciens* DNA and the primer pairs barnase-up (5'-CCGGC-GATGGCCATGGATGCACAG GTTATCAACACGTTTG-3'; SEQ ID NO: 45), barmitte-lo (5'-GTTCGTCCGCTTTTGCCCGGAAGT TTGCCTTCCCTGTTTGAG-3'; SEQ ID NO: 46) and barmitte-up (5'-CTTCCGGGCAAAAGCGGACGAAC-3'; SEQ ID NO: 47), barnase-lo (5'-GAATTCGGTCTGA TTTTTGTAAAGGTCTGATAATGG GCCGTGTTTTGTA-3'; SEQ ID NO: 48), respectively. Oligonucleotides were designed such that a Sma I site at codon #63 is eliminated and active site histidine codon #102 is converted to alanine. This mutation leads to an inactivation of the ribonuclease activity of the resulting barnase' protein (Jucovic, 1995).

The two halfs of the barnase' coding sequence were combined by PCR using the oligonucleotide pair barnase-up and barnase-lo. The resulting barnase' PCR product was digested with Nco I and EcoR I and ligated with similarly cleaved pET22b (Novagen). From this vector, the barnase gene was PCR amplified using the primers bar'-Nhe-up (5' GCGCAC-TAGTGCTAGCGATCTCGATCCCGCGAA 3'; SEQ ID NO: 49) and bar'-Sma-lo (5' CTGTCCCGGGCGAATTCG-GTCTGATTTTTGTAA AGGTCTGATAGGCGTCCGT-TGTTTTG 3'; SEQ ID NO: 50), cleaved with Nhe I and Sma I and ligated into similarly cleaved pASK21-CK$^{send}$ (Christmann, 1999). The resulting barnase-EETI-II expression cassette was excised with Aat II and Pst I and ligated into similarly cleaved pMT416 (Hartley, 1988) kindly provided by L. Leveneki (University of Marburg, Germany). The resulting plasmid contains a phoA leader sequence and the barnase' gene under tac promotor control (Hartley, 1988). This expression cassette was then transplanted by cleavage with Ecl 136 II and Xba I and ligation into similarly cleaved pASKInt200, a derivate of pASKInt100 (Wentzel, 2001) that lacks the tetR promoter, to give pASKBarInt200. The resulting plasmid was finally cleaved with Sap I and Sma I and overlapping DNA ends were filled up using T4 DNA polymerase (MBI Fermentas). Blunt end ligation of the vector fragment resulted in pBar100-EETI-II M7I.

pBar100-EETI-II M7I was used as a template for the construction of pBar100-EETI-II. To this end, the EETI-II encoding gene was PCR amplified from pBar100-EETI-II M7I with primers Nco-XA-eti-up (5' GACTCCGGCCATGGGGATC-GAGGGAAGGGGGTGCCC GCGCATTCTGATGCGCT-GCAAACAGGACTC 3'; SEQ ID NO: 51) and cat-hind-mittelo (CCACAAGCTTGAAAACGTTTCAG, SEQ ID NO: 52). The resulting product was cleaved with Nco I and Hind III and ligated into similarly digested pBar100-EETI-II M7I. For construction of plasmid pBar100-McoEeTI, the McoEeTI gene was assembled with synthetic oligonucleotides cotiup2 (5' GCATGCGCTCTTCTAACTGCATAT-GCGGGCCCAACGGTTACTGCGGTTCCGGAT CC 3'; SEQ ID NO: 53), cotilink (5' CGTCGACATTTTTTCAG GATTTTCGGGCAAACACCACCGTCG-GATCCGGAACCGCAG 3'; SEQ ID NO: 54) and cotilo (5'GCATGCGCTCTTCTGCAAGCAC-CCGGGCAGTCGGAGTCA-CGTCGACATTTTTTCAGG 3'; SEQ ID NO: 55) by polymerase chain reaction, assembled in vector pMalp-2 (New England BioLabs) and transplanted by cleavage with NcoI and Bsp120 I to similarly cleaved cloning vector pASKBar100-EETI-II M7I.

Plasmid pBar100-ThromMcoEeTI was constructed as described above for pBar100-EETI-II using pBar100-McoEeTI as a template and primers NcoThromMCoTi-up (5' AGCTCTTCCATGGGGCTGGTTC-CGCGTGGGTCCGTTGCCCGAAAATCCTGAAA AAATG 3'; SEQ ID NO: 56), which encodes a thrombin protease recognition sequence, and cat-hind-mittelo (SEQ ID NO: 52).

Fusion Protein Production

E. coli strain 71-18 [F' lacI$^q$ lacZΔM15 proA$^+$B$^+$ Δlac-proAB supE thi1] (source B. Müller-Hill) containing helper plasmid pRep4 (Qiagen) which contains a lacI gene was transformed with pBar100-EETI-II M7I, pBar100-EETI-II, pBar100-McoEeTI and pBar100-ThromMcoEeTI, respectively by electroporation and grown overnight at 37° C. in 50 ml rich media containing 25 µg/ml chloramphenicol and 37.5 µg/ml kanamycin. This culture was then used to inoculate 5 l of TB medium containing 25 µg/ml chloramphenicol and 37.5 µg/ml kanamycin in a 5 l fermenter (Bioengineering) or 1 l of TB medium in a 1 l fermenter (Biostat M, Braun Biotech). TB medium contains 12 g bacto-tryptone, 24 g bacto-yeast extract, 4 ml glycerol and 100 ml of a sterile solution of 0.17 M KH$_2$PO$_4$, 0.72 M K$_2$HPO$_4$ per liter. Fermentation was performed at 30° C. At an O.D.$_{600}$ of 3 to 5, IPTG was added to a final concentration of 1 mM. After overnight incubation, the bacterial liquid culture was cooled to 4° C. and 55 ml of glacial acetic acid per liter of cell culture was added under continuous stirring. Acidification of the culture results in release of barnase' fusion protein into the medium (Hartley, 1988). Stirring was continued for another 15 min followed by centrifugation at 4000 rpm for 60 min at 4° C. Insoluble particles were removed by filtration.

Purification of Fusion Proteins

The filtered culture supernatant was diluted 5-fold with H$_2$O and applied to a Perseptive HS20 cation exchance chromatography column (1.0×10 cm, 7.6 ml bed volume) mounted to a Vision BioCad workstation (PerSeptive Biosystems) at a flow rate of 8 ml/min. Elution was performed with a gradient ranging from 0 to 0.5 M NaCl. Peak fractions from 166 mM to 500 mM NaCl were directly applied to a Perseptive R2 reverse-phase column. After washing with H$_2$O/0.1% (v/v) TFA, the fusion protein was eluted from the column using a gradient from 5% (v/v) to 50% acetonitrile/0.1% (v/v) TFA. Fusion protein containing fractions were combined and lyophilized. For the purification of barnase'-ThromMcoEeTI, the fusion protein was pre-adsorbed to phosphocellulose prior to cation exchange chromatography as described (Hartley, 1972). Briefly, phosphocellulose P11 (Whatman) was treated with 0.5 N NaOH, H$_2$O, 0.5 N H$_2$SO$_4$ and 0.1 M Na-citrate as described and added to the acidified culture supernant (0.25 g/l liquid culture). After stirring at room temperature for 30 min, the phosphocellulose was filled into a 15×4 cm column, washed with 0.01 M ammonium acetate and the bound proteins were eluted with 2 M ammonium acetate. The protein solution was further concentrated with a rotation evaporator, lyophilized and re-solubilized in 25 mM Na-acetate pH 5.0 containing 8 M urea and applied to the combined cation exchange/reverse-phase HPLC (see above). Finally, lyophilized fusion protein was re-solubilized in 0.1 M Tris-HCl pH 7.8 containing 8 M urea, dialyzed overnight against 50 mM ammonium acetate and re-applied to the HS20 cation exchance column. Elution was performed with a gradient ranging from 90 to 330 mM NaCl.

CNBr Cleavage of Fusion Proteins

Lyophilized proteins were solubilized in 20 µl 70% formic acid per milligram of protein. Per milligram of fusion protein 0.6 µl of 5 M cyanogen bromide solution (Fluka) was added. After overnight incubation in a Teflon vial with a screw cap, the sample was either lyophilized or diluted 1:10 with 5% acetonitrile containing 0.1% (v/v) H$_2$O/TFA and directly used for RP-HPLC.

Thrombin Cleavage of Fusion Proteins

Lyophilized proteins were solubilized in 20 mM Tris-HCl pH 8.45, 150 mM NaCl and 2.5 mM CaCl$_2$ and 1 unit of thrombin from human plasma (Sigma, T-7009) per milligram of fusion protein was added. The reaction was incubated overnight at 37° C. and analysed by SDS polyacrylamide gel electrophoresis or RP-HPLC.

Purification of ICK Peptides

For separation of cleaved ICK peptide variants from the barnase' carrier protein standard RP-HPLC was performed on a Kontron or an Äcta (Pharmacia Biotech) basic HPLC system using a Phenomenex $C_{18}$ column (Synergi 4u Hydro-RP 80 Å; 250×4.60 mm). Buffer A: $H_2O$ containing 0.1% (v/v) trifluoroacetic acid, buffer B: acetonitrile containing 0.1% (v/v) trifluoroacetic acid. Linear gradients of 10-37% buffer B were run with flow rates of 1 ml/min. Chromatography was monitored at 217 nm, ICK peptide containing fractions were collected and lyophilized.

Determination of $K_i$ Values

The inhibitory activity of the protein variants was measured according to van Nostrand et al. (1990) and Sinha et al. (1991). The remaining activity of bovine trypsin (Serva) was determined after incubation with the respective inhibitor for 10 min at 37° C. by monitoring hydrolysis of the chromogenic substrate Boc-Leu-Gly-Arg-pNA (Bachem, solubilized in $Me_2SO$) at 405 nm. Assays were performed in a final volume of 100 μl in 50 mM Tris-HCl, pH 7.5, 150 mM NaCl, 5 mM $CaCl_2$ at 37° C. containing 5 nM of trypsin, 1.5 nM substrate and varying amounts of inhibitor ($10^{-10}$-$10^{-6}$ M). For calculation of $K_{iapp}$-values, $v_{max}$ values were determined and the curve fitting tool of SigmaPlot (Jandel Scientific) was applied on the basis of the following formula, that describes the case of competitive tight binding inhibitors (Morrison, 1969):

$$\frac{v_1}{v_0} = 1 - \frac{[E_t] + [I_t] + K_{iapp} - \{([E_t] + [I_t] + K_{iapp})^2 - 4[E_t] \cdot [I_t]\}^{\frac{1}{2}}}{2[E_t]}$$

$v_i = v_{max}$ value of inhibited reaction
$v_0 = v_{max}$ value of uninhibited reaction
$[E_t]$=total enzyme concentration (free and in complex)
$[I_t]$=total inhibitor concentration (free and in complex)
$K_{iapp}$=apparent dissociation constant of the enzyme-inhibitor complex.

Results and Discussion

Choice of Carrier Protein and Production Strategy

Barnase, an extracellular ribonuclease from *Bacillus amyloliquefaciens* is a well-characterized enzyme which has been extensively used in structure-function studies Fersht, 1993; Paddon, 1987). Barnase is a relatively small protein with a $M_r$ of approximately 12300 that can be produced in *Escherichia coli* via secretion into the periplasmic space and the culture medium in yields up to 100 mg of bacterial liquid culture (Hartley, 1988). It is composed of only 110 amino acid residues, contains no cysteine residues that might negatively interfere with disulfide bond formation of the fused ICK peptide and in addition it also contains no CNBr cleavable methionine residue. Furthermore, barnase can easily be purified by cation exchange chromatography (Hartley, 1988). To abolish the intrinsic RNAse activity of barnase we have constructed an enzymatically inactive variant (Jucovic, 1995) where the active site residue histidine #102 is replaced by alanine to give barnase'. Expression vector pBar100 which is shown in FIG. 4A contains the barnase' gene under tac promoter control and the respective ICK peptide coding sequence that was placed in frame to the barnase' gene together with a short linker sequence (FIG. 4B).

Fusion Protein Production and Purification

Four different ICK peptide variants have been successfully expressed in *E. coli* via fusion to barnase' that are derived from the *Ecballium elaterium* trypsin inhibitor EETI-II (Chiche, 1989). McoEeTI is a hybrid ICK peptide that is composed of the 13 aminoterminal residues of EETI-II and the 16 carboxyterminal residues of the *Momordica cochinchinensis* trypsin inhibitor McoTI-II (Hernandez, 2000). Sequences and yields of purified cystine knot protein variants are shown in Table 3.

TABLE 3

ICK peptides expressed as fusions to barnase'.

| ICK peptide | Peptide sequence | Fusion protein yield[a] [mg] | Kiapp[b] [M] |
| --- | --- | --- | --- |
| EETI-II M7I | GCPRILIRCKQDSDCLAGCVCGPNGFCGS (SEQ ID NO:57) | 12 | n.d. |
| EETI-II | GCPPILMRCKQDSDCLAGCVCGPNGFCGS (SEQ ID NO:58) | 6.7 | 9.0 +− 4.2 × 10-9 |
| McoEeTI | GVCPRILKKCRRDSDCLAGCVCGPNGFCGS (SEQ ID NO:23) | 24.3 | 7.1 +− 0.9 × 10-8 |
| ThromMcoEeTI | GSVCPRILKKCRRDSDCLAGCVCGPNGFCGS (SEQ ID NO:59) | 7.4 | n.d. |

[a]yield corresponds to the amount of purified fusion protein obtained from 1l *E. coli* culture.
[b]inhibition constants were determined by incubation of varying amounts of the respective ICK peptide with trypsin and monitoring the residual trypsin activity using the trypsin substrate Boc-Leu-Gly-Arg-pNA (Wentzel, 1999).
n.d.: not determined.

The underlying strategy for expression and purification is outlined in FIG. 6. Barnase'-ICK fusion proteins are directed into the periplasm of the host cell, where folding of the fusion protein and intramolecular disulfide bond formation of the ICK peptide can occur in the oxidative extracellular milieu. Acidification of the culture with glacial acidic acid results in the complete release of the barnase'-fusions from the periplasmic space into the culture medium (Hartley, 1988) (FIG. 7). The diluted culture medium is applied to cation exchange chromatography as a first purification step. Alternatively, to reduce the sample volume, the fusion protein can be preadsorbed to phosphocellulose followed by batch elution with ammonium acetate and lyophilization (Hartley, 1972) (data not shown). Subsequent RP-HPLC results in the removal of small peptides derived from tryptone and yeast extract of the culture medium. On average, 12 mg fusion protein have been obtained from 1 liter of bacterial liquid culture (Table 3). No efforts have been made yet to enhance protein yield via optimization of fermentation conditions towards high cell densities or by placing the barnase' gene under control of a promoter that is stronger than the tac promoter used in these studies.

It is important to check whether the cystine knot peptides obtained are fully oxidized and contain the desired three pairs of disulfide bonds, where the first cysteine residue in the sequence is connected to the fourth, the second to the fifth, and the third to the sixth (FIG. 11). The ICK peptides of this study are trypsin inhibitors and inhibition of trypsin activity can be used as a sensitive probe of correct folding, since correct disulfide connectivity is strictly required for high affinity trypsin binding (Wetzel, 1999). As can be seen in Table 3, both EETI-II and McoEeTI act as inhibitors of bovine trypsin as barnase' fusion proteins and display strong inhibitory activity.

Fusion Protein Cleavage and Isolation of the ICK Peptides

A unique methionine residue was introduced at the junction of barnase' and the respective ICK peptide. As a consequence, the ICK peptide can be released from the fusion protein by cyanogen bromide cleavage. As can be seen in FIG. 8B, the released ICK peptide elutes from a C18 column at lower acetonitrile concentrations than the barnase' carrier, from which it can easily be separated. After overnight incubation of the fusion protein with CNBr in 70% formic acid at least 80% of the fusion was completely cleaved as judged by gel electrophoresis (data not shown). The expected molecular mass of the resulting fully oxidized cystine knot protein was confirmed by ESI-MS (FIG. 8B).

CNBr cleavage cannot be applied for the removal of the barnase' carrier if the particular ICK peptide to be processed contains internal methionine residues as it is the case for the EETI-II ICK peptide. To have an alternative to CNBr cleavage at a methionine residue, expression vector pBar100ThromMcoEeTI was constructed, which gives rise to the synthesis of a fusion protein with a recognition sequence for the site-specific protease thrombin at the junction of barnase' and the ICK peptide McoEeTI. Thrombin cleavage was performed in 20 mM Tris-HCl buffer pH 8.45 containing 150 mM NaCl and 2.5 mM $CaCl_2$ at 37° C. and was almost complete after overnight incubation (FIG. 7) The ICK peptide was isolated by reverse-phase HPLC and the expected molecular mass of Throm-McoEeTI was confirmed by ESI-MS (FIG. 8A).

Conclusions and Outlook

Peptides of the inhibitor cystine knot family share a common architecture that is defined by a combination of three intramolecular disulfide bonds. These interesting molecules show diverse biological activities including for example neurotoxins (Narasimhan, 1994) and enzyme inhibitors (Hamato, 1995; Chakraborty, 2001). Because of their enormous intrinsic stability and the possibility to apply methods of molecular evolution for the isolation of variants with predefined binding capabilities (Wentzel, 1999; Baggio, 2002), cystine knot proteins are considered to be ideal scaffolds for drug design (Craik, 2001). We have devised an expression and purification strategy that is based on ICK peptide synthesis via fusion to barnase'. Expression of functional barnase is lethal to the host cell and requires co-expression of the barnase inhibitor, barstar (Hartley, 1988). Our approach to use an enzymatically inactive variant obviates this necessity and may in addition allow one to purify the barnase' fusion in a simple single step procedure via affinity chromatography on immobilized barstar, provided that the barnase H102A active site variant retains sufficient affinity to bind the inhibitor (see also Example 5, infra).

Recently, barnase fusions of antibody $V_L$ domains and single chain Fv fragments have been described (Martsev, 2004; Deyev, 2003). A solubilizing effect of barnase was observed both in vitro and in vivo, which was explained by a chaperone-like role that barnase may exert on the fused antibody domain (Martsev, 2004). It appears as if barnase' fusion generally supports folding and correct disulfide bond formation of the fused ICK peptide since we have also successfully expressed a number of other cystine knot peptides having a sequence different to that of the EETI-II and McoEeTI peptides shown in this Example. For these, we observed similar expression levels and high yields of folded peptides forming a cystine knot (see Example 3, supra).

In conclusion, the fusion protein system described here using barnase' as a carrier for secretion and export and as a convenient purification handle allows for the production of folded cystine knot proteins that can be directly used for biological assays. If required, the barnase' moiety can be removed, for example by chemical cleavage with cyanogen bromide or enzymatic cleavage with thrombin and the disulfide-bond containing ICK peptide can be isolated without the requirement of in vitro oxidation which often becomes the yield limiting step of cystine knot peptide production (Martsev, 2004).

EXAMPLE 5

Purification of Microprotein-Barnase Fusion Using Immobilized Barstar

Barstar was purified as described (Jones et al., 1993, FEBS Lett. 331, p. 165). The purified protein was covalently immobilized to a Affi-gel matrix (BioRad). To this end, 20 mg of Barstar in PBS buffer was coupled to 1 ml AffiGel (BioRad) as described by the manufacturer. To show that Barnase can be purified by affinity chromatography via binding to immobilized barstar, the column was equilibrated with 50 mM ammonium acetate pH 7. A sample solution (S) containing the fusion protein consisting of barnase' (the inactive mutant of barnase; see Example 3, supra) and the cystine knot microprotein SE-MG in PBS-buffer was applied to the column. The flow through (FT) was collected for analysis. The column was washed three times with 2.5 ml 50 mM ammonium acetate (W1, W2, W3). Bound protein was eluted by applying two times 2.5 ml 50 mM ammonium acetate, 8 M urea to the column (E1, E2). By addition of urea, both barstar and barnase are denatured and the barnase elutes from the column. The column was regenerated with 5 ml 50 mM ammonium acetate pH 7, 4 M urea (R1) followed by 5 ml 50 mM ammonium acetate pH 7 (R2). Aliquots of each fraction were analysed by SDS-polyacrylamide gel electrophoresis (see FIG. 12). The column could be reused at least three times (not shown).

The results of this experiment prove that tight interaction between barnase and barstar can be applied in order to purify fusion proteins comprising barnase. It is of particular note that this experiment has been carried out using an inactive variant of barnase. This means that the corresponding fusion protein can advantageously be expressed without the co-expression of barstar as it is described in the prior art to be necessary to avoid death of the host cell (see, e.g., Martsev, 2004; Deyev, 2003).

EXAMPLE 6

Crystallization of a Microprotein and Structure Analysis

Protein Crystallization and Data Collection

Initial screening using Jena Bioscience screens yielded small crystals under several conditions. Condition C3 from screen 6 (2 M ammonium sulphate, 5% PEG 400, 01.M MES pH 6.5) was further optimised and crystals used for data collection were grown by the sitting drop method at 4° C. with 1.3 M ammonium sulphate, 7% PEG 400 (v/v), 0.1 M MES pH 6.5 as reservoir solution. Droplets were mixed from 8 ml protein (30 mg/ml) and 4 ml reservoir solution. Crystals were plate shaped and grew over several weeks to a final size of about 500×500×35 mm (FIG. 13). Typically, stacks of plates were obtained, that had to be broken apart to isolate single plates for data collection. For cryoprotection crystals were immersed in mother liquor containing 25% glycerol and flash frozen in liquid nitrogen. Before data collection, crystals were annealed three times by blocking the cryo stream for several seconds. Annealing improved spot shape and resolution (FIG. 14). Data were collected to a resolution of 1.3 Å at DESY beamline BW6 at 100 K and a wavelength of 1.050 Å using a MarCCD detector. Data were processed with XDS and scaled with XSCALE (Kabsch 1993). Data statistics are given in Table 4. The raw data are given in PDB format in Table 6.

Structure Solution and Refinement

Initial phases were determined using in-house data to 2.9 Å by molecular replacement as implemented in the program EPMR (Kissinger, Gehlhaar et al. 1999) using a monomer of barnase (PDB ID 1A2P) as search model. Matthews probability predicted the asymmetric unit to most likely contain three molecules based on all entries in the PDB or four molecules given the resolution of the crystal (Kantardjieff and Rupp 2003). The search for three molecules in the asymmetric unit in EPMR yielded the highest correlation coefficient and lowest R factor upon placing the second molecule, while adding a third molecule gave worse results. Packing was checked in O (Jones, Zou et al. 1991). Barnase monomers packed against each other with their C-terminus pointing towards empty space available to the MCoTi-II part of the fusion protein (FIG. 15A). This indicated a correct solution and means that the crystals actually contain only 2 molecules per asymmetric unit. Accordingly, the Matthew's coefficient is 3.76 and the solvent content 67.3% (FIG. 15B), which is very unusual for crystals diffracting to 1.3 Å. Rigid body refinement of barnase was carried out in Refmac (Winn, Murshudov et al. 2003) followed by restrained refinement. An attempt to place the MCoTi-II part by molecular replacement using EPMR with barnase fixed and one state of the MCoTi-II NMR structure (PDB ID 1HA9) as search model failed. Hence, the MCoTi-II part was built manually using the initial 2.9 Å data. The model refined at 2.9 Å was used later for refinement with the high resolution data set keeping the free R set. ARP/wARP was used for finding water molecules. The current model contains all residues of the fusion protein, 477 water molecules, 2 PEG molecules, 6 sulfate ions and 3 glycerol molecules. Each barnase and each MCoTi-II was defined as a separate group for TLS refinement in REFMAC. Statistics of refinement are given in Table 4. Structure analysis, fitting of homologous structures and calculation of rmsds was carried out in Swiss PDB Viewer (Guex and Peitsch 1997). Figures were rendered in PyMol (DeLano 2002).

Results

A variant of the squash trypsin inhibitor MCoTi-II, which naturally occurs as a cyclic peptide in *Momordica cochinchinensis* (spiny bitter cucumber), was crystallized as a fusion protein with a catalytically inactive mutant of barnase, barnase' (see Example 4, supra). The fusion protein (SEQ ID NO: 17) had been recombinantly expressed in *E. coli* and purified to homogeneity (Example 4, supra). The structure of the fusion protein (FIG. 16) was solved at a resolution of 1.3 Å by molecular replacement using the barnase wild-type structure as search model. There are two molecules of the fusion protein in the asymmetric unit. The two molecules can be aligned with an rmsd of 0.71 Å for 572 backbone atoms and an rmsd of 0.85 for all atoms (FIG. 17). The difference is mainly caused by a rigid body movement of barnase and MCoTi-II relative to one another, as the individual domains in the fusion protein can be overlaid with considerably lower rmsd (FIG. 18) 0.3 Å for 120 backbone atoms in MCoTi-II and 0.34 Å for 436 backbone atoms in barnase (see Table 5). The two proteins are joined by a four residue linker (SSSM) which allows for this flexibility. In both molecules of the asymmetric unit, a PEG molecule is found near Lys 10 of MCoTi-II (FIGS. 18 and 19). By analogy with the crystal structure of the complex formed between bovine beta-trypsin and MCTI-A, another squash-type trypsin inhibitor, Lys10 is the residue, which is inserted into the active site of trypsin. Although in different overall orientation, the PEGs in both molecules adopt a conformation similar to crown ethers, positioning four to six oxygens favourably for hydrogen bond formation. Lys 10 is among the residues varying most between the two MCoTi-II monomers. The largest differences are in residues Gly6 to Leu12 and around Pro29. When overlaid with the first states of two NMR structures available in the PDB (1HA9 and 1IB9) and with the crystal structure of MCTI-I (1F2S), another squashtype trypsin inhibitor, the agreement is best with the crystal structure of MCTI-I (FIG. 20).

Table 4 provides an overview of the data statistics for data collection and refinement statistics carried out when analyzing the crystal structure of fusion protein McoTi-II-barnase'

| Data collection | |
| --- | --- |
| Space group | C222$_1$ |
| Cell dimensions | a = 73.981, b = 217.820, c = 58.322 |
| | α = β = γ = 90°. |
| Resolution range (Å) | 40-1.3 (1.4-1.3) |
| Measured reflections | 356629 (59959) |
| Unique reflections | 114401 (2246) |
| Completeness (%) | 98.7 (98.1) |
| R$_{iym}$ | 3.9 (41.8) |
| I/σI | 14.01 (2.42) |
| Refinement | |
| Atoms | |
| Protein | 2292 |
| Water | 477 |
| PEG, sulfate, glycerol | 94 |
| R$_{cryst}$/R$_{free}$ (%)[1] | 18.7/20.8 |
| R.m.s. deviation from ideal | |
| Bonds (Å) | 0.008 |
| Angles (°) | 1.569 |
| Most favored/additionally allowed Φ, ψ (%) | 91/9 |

[1] The test set comprised 2292 reflections (2%).

Table 5 is a comparison of the two crystallographically independent fusion proteins contained in the asymmetrical unit of the McoTi-II-barnase' fusion

| Molecules compared | Rmsd (Å) | # of atoms (bb = backbone a = all atoms) |
|---|---|---|
| Fusion protein | 0.71 | 572 |
|  | 0.85 | 1102 |
| Barnase | 0.34 | 436 |
|  | 0.51 | 867 |
| MCoTi-II | 0.3 | 120 |
|  | 0.79 | 209 |

Table 6 (next pages) depicts the raw data obtained by X-ray diffraction structure analysis of the McoTi-II-barnase' crystal described herein. The data is in PDB format. The two monomers contained in the asymmetrical unit are annoted in the data set as "A" and "B". The coordinates of barnase' including linker have order numbers 1-114, those of the microprotein portion 115-144.

```
HEADER    ----                                                    XX-XXX-XX    xxxx
COMPND    ---
REMARK  3
REMARK  3  REFINEMENT.
REMARK  3    PROGRAM     : REFMAC 5.1.24
REMARK  3    AUTHORS     : MURSHUDOV, VAGIN, DODSON
REMARK  3
REMARK  3    REFINEMENT TARGET: MAXIMUM LIKELIHOOD
REMARK  3
REMARK  3  DATA USED IN REFINEMENT.
REMARK  3    RESOLUTION RANGE HIGH       (ANGSTROMS) :   1.90
REMARK  3    RESOLUTION RANGE LOW        (ANGSTROMS) :  19.28
REMARK  3    DATA CUTOFF                    (SIGMA(F)) : NONE
REMARK  3    COMPLETENESS FOR RANGE             (%) : 100.00
REMARK  3    NUMBER OF REFLECTIONS              :  35284
REMARK  3
REMARK  3  FIT TO DATA USED IN REFINEMENT.
REMARK  3    CROSS-VALIDATION METHOD        : THROUGHOUT
REMARK  3    FREE R VALUE TEST SET SELECTION   : RANDOM
REMARK  3    R VALUE       (WORKING + TEST SET) : 0.18176
REMARK  3    R VALUE              (WORKING SET) : 0.17918
REMARK  3    FREE R VALUE                       : 0.23111
REMARK  3    FREE R VALUE TEST SET SIZE    (%) :   5.0
REMARK  3    FREE R VALUE TEST SET COUNT       :   1858
REMARK  3
REMARK  3  FIT IN THE HIGHEST RESOLUTION BIN.
REMARK  3    TOTAL NUMBER OF BINS USED          :     20
REMARK  3    BIN RESOLUTION RANGE HIGH          :  1.900
REMARK  3    BIN RESOLUTION RANGE LOW           :  1.949
REMARK  3    REFLECTION IN BIN      (WORKING SET) :  2544
REMARK  3    BIN R VALUE            (WORKING SET) :  0.320
REMARK  3    BIN FREE R VALUE SET COUNT         :    134
REMARK  3    BIN FREE R VALUE                   :  0.358
REMARK  3
REMARK  3  NUMBER OF NON-HYDROGEN ATOMS USED IN REFINEMENT.
REMARK  3    ALL ATOMS           :    2666
REMARK  3
REMARK  3  B VALUES.
REMARK  3    FROM WILSON PLOT           (A**2) : NULL
REMARK  3    MEAN B VALUE      (OVERALL, A**2) : 13.186
REMARK  3    OVERALL ANISOTROPIC B VALUE.
REMARK  3     B11 (A**2) :     1.01
REMARK  3     B22 (A**2) :    -1.55
REMARK  3     B33 (A**2) :     0.54
REMARK  3     B12 (A**2) :     0.00
REMARK  3     B13 (A**2) :     0.00
REMARK  3     B23 (A**2) :     0.00
REMARK  3
REMARK  3  ESTIMATED OVERALL COORDINATE ERROR.
REMARK  3    ESU BASED ON R VALUE                       (A) :  0.114
REMARK  3    ESU BASED ON FREE R VALUE                  (A) :  0.123
REMARK  3    ESU BASED ON MAXIMUM LIKELIHOOD            (A) :  0.090
REMARK  3    ESU FOR B VALUES BASED ON MAXIMUM LIKELIHOOD (A**2) :  3.289
REMARK  3
REMARK  3  CORRELATION COEFFICIENTS.
REMARK  3    CORRELATION COEFFICIENT FO-FC      :  0.947
REMARK  3    CORRELATION COEFFICIENT FO-FC FREE :  0.916
REMARK  3
REMARK  3  RMS DEVIATIONS FROM IDEAL VALUES        COUNT      RMS    WEIGHT
REMARK  3    BOND LENGTHS REFINED ATOMS       (A):  2298;   0.029;   0.021
REMARK  3    BOND LENGTHS OTHERS              (A):  2000;   0.002;   0.020
```

-continued

| | | | | | |
|---|---|---|---|---|---|
| REMARK 3 | BOND ANGLES REFINED ATOMS | (DEGREES): | 3096; | 3.569; | 1.965 |
| REMARK 3 | BOND ANGLES OTHERS | (DEGREES): | 4678; | 1.425; | 3.000 |
| REMARK 3 | TORSION ANGLES, PERIOD 1 | (DEGREES): | 284; | 6.563; | 5.000 |
| REMARK 3 | CHIRAL-CENTER RESTRAINTS | (A**3): | 322; | 0.442; | 0.200 |
| REMARK 3 | GENERAL PLANES REFINED ATOMS | (A): | 2540; | 0.021; | 0.020 |
| REMARK 3 | GENERAL PLANES OTHERS | (A): | 478; | 0.019; | 0.020 |
| REMARK 3 | NON-BONDED CONTACTS REFINED ATOMS | (A): | 493; | 0.216; | 0.300 |
| REMARK 3 | NON-BONDED CONTACTS OTHERS | (A): | 2588; | 0.275; | 0.300 |
| REMARK 3 | NON-BONDED TORSION OTHERS | (A): | 1402; | 0.109; | 0.500 |
| REMARK 3 | H-BOND (X...Y) REFINED ATOMS | (A): | 474; | 0.292; | 0.500 |
| REMARK 3 | SYMMETRY VDW REFINED ATOMS | (A): | 11; | 0.190; | 0.300 |
| REMARK 3 | SYMMETRY VDW OTHERS | (A): | 59; | 0.269; | 0.300 |
| REMARK 3 | SYMMETRY H-BOND REFINED ATOMS | (A): | 44; | 0.277; | 0.500 |
| REMARK 3 | | | | | |
| REMARK 3 | ISOTROPIC THERMAL FACTOR RESTRAINTS. | | COUNT | RMS | WEIGHT |
| REMARK 3 | MAIN-CHAIN BOND REFINED ATOMS | (A**2): | 1410; | 1.920; | 2.000 |
| REMARK 3 | MAIN-CHAIN ANGLE REFINED ATOMS | (A**2): | 2254; | 2.794; | 3.000 |
| REMARK 3 | SIDE-CHAIN BOND REFINED ATOMS | (A**2): | 888; | 2.293; | 2.000 |
| REMARK 3 | SIDE-CHAIN ANGLE REFINED ATOMS | (A**2): | 842; | 3.356; | 3.000 |

```
REMARK 3
REMARK 3   NCS RESTRAINTS STATISTICS
REMARK 3    NUMBER OF NCS GROUPS: NULL
REMARK 3
REMARK 3
REMARK 3   TLS DETAILS
REMARK 3    NUMBER OF TLS GROUPS :    4
REMARK 3
REMARK 3    TLS GROUP :    1
REMARK 3     NUMBER OF COMPONENTS GROUP :    1
REMARK 3     COMPONENTS         C SSSEQI   TO   C SSSEQI
REMARK 3     RESIDUE RANGE :     A    2      A    110
REMARK 3     ORIGIN FOR THE GROUP (A):    9.5430    68.2450   26.2250
REMARK 3     T TENSOR
REMARK 3      T11:     0.0557  T22:     0.1193
REMARK 3      T33:     0.1386  T12:     0.0268
REMARK 3      T13:    -0.0867  T23:    -0.0367
REMARK 3     L TENSOR
REMARK 3      L11:     2.3675  L22:     1.2064
REMARK 3      L33:     1.0960  L12:     0.8409
REMARK 3      L13:     0.7086  L23:     0.1284
REMARK 3     S TENSOR
REMARK 3      S11:    -0.1261  S12:    -0.1671  S13:     0.2670
REMARK 3      S21:     0.0795  S22:    -0.0329  S23:     0.0422
REMARK 3      S31:    -0.1451  S32:    -0.0618  S33:     0.1590
REMARK 3
REMARK 3    TLS GROUP :    2
REMARK 3     NUMBER OF COMPONENTS GROUP :    1
REMARK 3     COMPONENTS         C SSSEQI   TO   C SSSEQI
REMARK 3     RESIDUE RANGE :     A    115    A    144
REMARK 3     ORIGIN FOR THE GROUP (A):   12.2140    42.0860   17.9500
REMARK 3     T TENSOR
REMARK 3      T11:     0.0566  T22:     0.1455
REMARK 3      T33:     0.1138  T12:     0.0113
REMARK 3      T13:     0.0248  T23:     0.0103
REMARK 3     L TENSOR
REMARK 3      L11:     2.3057  L22:     5.5183
REMARK 3      L33:     2.7772  L12:     1.8588
REMARK 3      L13:    -0.9244  L23:    -2.0762
REMARK 3     S TENSOR
REMARK 3      S11:    -0.3277  S12:    -0.0677  S13:    -0.0462
REMARK 3      S21:     0.0131  S22:     0.1046  S23:    -0.3114
REMARK 3      S31:     0.2482  S32:     0.1350  S33:     0.2231
REMARK 3
REMARK 3    TLS GROUP :    3
REMARK 3     NUMBER OF COMPONENTS GROUP :    1
REMARK 3     COMPONENTS         C SSSEQI   TO   C SSSEQI
REMARK 3     RESIDUE RANGE :     B    2      B    110
REMARK 3     ORIGIN FOR THE GROUP (A):    8.1830    15.5270   27.3540
REMARK 3     T TENSOR
REMARK 3      T11:     0.1252  T22:     0.1062
REMARK 3      T33:     0.0617  T12:    -0.0050
REMARK 3      T13:     0.0228  T23:     0.0100
REMARK 3     L TENSOR
REMARK 3      L11:     0.5175  L22:     2.2632
REMARK 3      L33:     2.3909  L12:    -0.0338
REMARK 3      L13:    -0.0735  L23:    -1.3985
REMARK 3     S TENSOR
REMARK 3      S11:     0.0663  S12:    -0.0226  S13:    -0.0235
REMARK 3      S21:     0.1096  S22:    -0.1191  S23:    -0.2038
REMARK 3      S31:     0.1755  S32:     0.0797  S33:     0.0529
```

-continued

```
REMARK   3
REMARK   3      TLS GROUP :    4
REMARK   3          NUMBER OF COMPONENTS GROUP :    1
REMARK   3          COMPONENTS          C SSSEQI    TO   C SSSEQI
REMARK   3          RESIDUE RANGE :       B   115       B   144
REMARK   3          ORIGIN FOR THE GROUP (A):   -1.2080    42.0850    26.2740
REMARK   3          T TENSOR
REMARK   3             T11:     0.0583  T22:    0.1343
REMARK   3             T33:     0.0798  T12:    0.0154
REMARK   3             T13:     0.0490  T23:   -0.0002
REMARK   3          L TENSOR
REMARK   3             L11:     4.7339  L22:    6.5857
REMARK   3             L33:     2.7012  L12:   -0.8531
REMARK   3             L13:     1.2150  L23:    0.2365
REMARK   3          S TENSOR
REMARK   3             S11:    -0.2007  S12:   -0.3160  S13:    0.1082
REMARK   3             S21:     0.3828  S22:    0.0444  S23:    0.1488
REMARK   3             S31:    -0.1538  S32:    0.0224  S33:    0.1563
REMARK   3
REMARK   3
REMARK   3      BULK SOLVENT MODELLING.
REMARK   3       METHOD USED : BABINET MODEL WITH MASK
REMARK   3       PARAMETERS FOR MASK CALCULATION
REMARK   3       VDW PROBE RADIUS      :   1.40
REMARK   3       ION PROBE RADIUS      :   0.80
REMARK   3       SHRINKAGE RADIUS      :   0.80
REMARK   3
REMARK   3      OTHER REFINEMENT REMARKS:
REMARK   3       HYDROGENS HAVE BEEN ADDED IN THE RIDING POSITIONS
REMARK   3
CISPEP   1   GLN  A     2    VAL  A     3           0.00
SSBOND   1   CYS  A   117    CYS  A   134
SSBOND   2   CYS  A   124    CYS  A   136
SSBOND   3   CYS  A   130    CYS  A   142
SSBOND   4   CYS  B   117    CYS  B   134
SSBOND   5   CYS  B   124    CYS  B   136
SSBOND   6   CYS  B   130    CYS  B   142
CRYST1   73.640   216.650   58.160   90.00   90.00   90.00  C 2 2 21
SCALE1      0.013580  0.000000  0.000000      0.00000
SCALE2      0.000000  0.004616  0.000000      0.00000
SCALE3      0.000000  0.000000  0.017194      0.00000
ATOM     1   N    GLN  A    2      22.714  65.533  17.841  1.00  51.42   N
ATOM     3   CA   GLN  A    2      23.297  65.293  16.498  1.00  52.25   C
ATOM     5   CB   GLN  A    2      23.615  63.798  16.334  1.00  54.95   C
ATOM     8   CG   GLN  A    2      25.085  63.453  16.110  1.00  57.21   C
ATOM    11   CD   GLN  A    2      25.383  62.940  14.662  1.00  59.28   C
ATOM    12   OE1  GLN  A    2      24.475  62.435  13.953  1.00  59.58   O
ATOM    13   NE2  GLN  A    2      26.667  63.055  14.238  1.00  59.05   N
ATOM    16   C    GLN  A    2      22.329  65.811  15.433  1.00  48.06   C
ATOM    17   O    GLN  A    2      22.618  65.730  14.219  1.00  49.79   O
ATOM    20   N    VAL  A    3      21.234  66.449  15.853  1.00  41.37   N
ATOM    22   CA   VAL  A    3      20.732  66.626  17.234  1.00  34.29   C
ATOM    24   CB   VAL  A    3      20.931  68.077  17.865  1.00  36.02   C
ATOM    26   CG1  VAL  A    3      19.746  68.645  18.566  1.00  35.76   C
ATOM    30   CG2  VAL  A    3      22.043  68.143  18.980  1.00  38.59   C
ATOM    34   C    VAL  A    3      19.240  66.436  16.849  1.00  25.30   C
ATOM    35   O    VAL  A    3      18.798  67.055  15.915  1.00  25.57   O
ATOM    36   N    ILE  A    4      18.489  65.685  17.631  1.00  14.79   N
ATOM    38   CA   ILE  A    4      17.032  65.562  17.436  1.00   9.63   C
ATOM    40   CB   ILE  A    4      16.733  64.041  17.614  1.00  10.11   C
ATOM    42   CG1  ILE  A    4      17.699  63.151  16.725  1.00  12.96   C
ATOM    45   CD1  ILE  A    4      17.501  61.602  16.749  1.00  15.54   C
ATOM    49   CG2  ILE  A    4      15.401  63.628  17.280  1.00  11.19   C
ATOM    53   C    ILE  A    4      16.259  66.398  18.463  1.00   9.80   C
ATOM    54   O    ILE  A    4      16.006  66.065  19.634  1.00  15.16   O
ATOM    55   N    ASN  A    5      15.703  67.414  17.886  1.00  11.17   N
ATOM    57   CA   ASN  A    5      15.339  68.738  18.336  1.00  12.63   C
ATOM    59   CB   ASN  A    5      16.186  69.932  17.409  1.00  11.32   C
ATOM    62   CG   ASN  A    5      16.346  70.863  18.372  1.00  17.03   C
ATOM    63   OD1  ASN  A    5      16.974  71.871  18.477  1.00  21.67   O
ATOM    64   ND2  ASN  A    5      15.869  70.160  19.472  1.00  20.49   N
ATOM    67   C    ASN  A    5      13.896  69.048  17.860  1.00  11.85   C
ATOM    68   O    ASN  A    5      13.354  70.061  18.270  1.00   8.88   O
ATOM    69   N    THR  A    6      13.521  68.490  16.731  1.00  11.41   N
ATOM    71   CA   THR  A    6      12.252  68.817  16.131  1.00  12.37   C
ATOM    73   CB   THR  A    6      12.284  68.692  14.624  1.00  14.14   C
ATOM    75   OG1  THR  A    6      12.544  67.323  14.245  1.00  13.81   O
ATOM    77   CG2  THR  A    6      13.475  69.517  14.095  1.00  15.31   C
ATOM    81   C    THR  A    6      11.029  68.075  16.682  1.00  12.95   C
ATOM    82   O    THR  A    6      11.163  66.971  17.180  1.00   9.25   O
```

| | | | | | | | | | | | |
|---|---|---|---|---|---|---|---|---|---|---|---|
| ATOM | 83 | N | PHE | A | 7 | 9.844 | 68.629 | 16.409 | 1.00 | 11.85 | N |
| ATOM | 85 | CA | PHE | A | 7 | 8.609 | 68.029 | 16.838 | 1.00 | 11.89 | C |
| ATOM | 87 | CB | PHE | A | 7 | 7.388 | 68.783 | 16.372 | 1.00 | 13.02 | C |
| ATOM | 90 | CG | PHE | A | 7 | 7.092 | 70.038 | 17.167 | 1.00 | 12.66 | C |
| ATOM | 91 | CD1 | PHE | A | 7 | 6.661 | 69.949 | 18.523 | 1.00 | 11.60 | C |
| ATOM | 93 | CE1 | PHE | A | 7 | 6.522 | 71.133 | 19.245 | 1.00 | 11.80 | C |
| ATOM | 95 | CZ | PHE | A | 7 | 6.788 | 72.375 | 18.623 | 1.00 | 9.66 | C |
| ATOM | 97 | CE2 | PHE | A | 7 | 7.164 | 72.444 | 17.311 | 1.00 | 12.14 | C |
| ATOM | 99 | CD2 | PHE | A | 7 | 7.393 | 71.295 | 16.613 | 1.00 | 11.78 | C |
| ATOM | 101 | C | PHE | A | 7 | 8.539 | 66.601 | 16.283 | 1.00 | 10.82 | C |
| ATOM | 102 | O | PHE | A | 7 | 8.203 | 65.682 | 17.077 | 1.00 | 10.87 | O |
| ATOM | 103 | N | ASP | A | 8 | 8.725 | 66.458 | 14.955 | 1.00 | 8.74 | N |
| ATOM | 105 | CA | ASP | A | 8 | 8.624 | 65.165 | 14.254 | 1.00 | 8.34 | C |
| ATOM | 107 | CB | ASP | A | 8 | 8.552 | 65.307 | 12.761 | 1.00 | 8.38 | C |
| ATOM | 110 | CG | ASP | A | 8 | 7.181 | 65.848 | 12.385 | 1.00 | 8.22 | C |
| ATOM | 111 | OD1 | ASP | A | 8 | 6.157 | 65.350 | 12.901 | 1.00 | 8.55 | O |
| ATOM | 112 | OD2 | ASP | A | 8 | 7.076 | 66.792 | 11.570 | 1.00 | 8.62 | O |
| ATOM | 113 | C | ASP | A | 8 | 9.761 | 64.248 | 14.650 | 1.00 | 9.81 | C |
| ATOM | 114 | O | ASP | A | 8 | 9.629 | 63.060 | 14.898 | 1.00 | 6.21 | O |
| ATOM | 115 | N | GLY | A | 9 | 10.927 | 64.821 | 14.778 | 1.00 | 8.66 | N |
| ATOM | 117 | CA | GLY | A | 9 | 11.972 | 63.899 | 15.115 | 1.00 | 8.43 | C |
| ATOM | 120 | C | GLY | A | 9 | 11.842 | 63.372 | 16.545 | 1.00 | 9.71 | C |
| ATOM | 121 | O | GLY | A | 9 | 12.204 | 62.235 | 16.774 | 1.00 | 11.69 | O |
| ATOM | 122 | N | VAL | A | 10 | 11.526 | 64.228 | 17.505 | 1.00 | 7.35 | N |
| ATOM | 124 | CA | VAL | A | 10 | 11.445 | 63.809 | 18.896 | 1.00 | 6.20 | C |
| ATOM | 126 | CB | VAL | A | 10 | 11.403 | 64.969 | 19.833 | 1.00 | 8.73 | C |
| ATOM | 128 | CG1 | VAL | A | 10 | 11.229 | 64.568 | 21.311 | 1.00 | 8.03 | C |
| ATOM | 132 | CG2 | VAL | A | 10 | 12.672 | 65.808 | 19.621 | 1.00 | 8.63 | C |
| ATOM | 136 | C | VAL | A | 10 | 10.187 | 62.955 | 18.973 | 1.00 | 8.44 | C |
| ATOM | 137 | O | VAL | A | 10 | 10.165 | 61.921 | 19.547 | 1.00 | 9.75 | O |
| ATOM | 138 | N | ALA | A | 11 | 9.145 | 63.249 | 18.235 | 1.00 | 8.06 | N |
| ATOM | 140 | CA | ALA | A | 11 | 7.956 | 62.404 | 18.296 | 1.00 | 6.38 | C |
| ATOM | 142 | CB | ALA | A | 11 | 6.871 | 63.013 | 17.484 | 1.00 | 7.54 | C |
| ATOM | 146 | C | ALA | A | 11 | 8.223 | 60.997 | 17.795 | 1.00 | 8.53 | C |
| ATOM | 147 | O | ALA | A | 11 | 7.773 | 59.998 | 18.394 | 1.00 | 8.60 | O |
| ATOM | 148 | N | ASP | A | 12 | 8.905 | 60.912 | 16.653 | 1.00 | 10.14 | N |
| ATOM | 150 | CA | ASP | A | 12 | 9.201 | 59.571 | 16.151 | 1.00 | 8.94 | C |
| ATOM | 152 | CB | ASP | A | 12 | 9.841 | 59.678 | 14.813 | 1.00 | 7.64 | C |
| ATOM | 155 | CG | ASP | A | 12 | 8.919 | 60.189 | 13.703 | 1.00 | 10.41 | C |
| ATOM | 156 | OD1 | ASP | A | 12 | 7.683 | 60.170 | 13.869 | 1.00 | 12.37 | O |
| ATOM | 157 | OD2 | ASP | A | 12 | 9.417 | 60.663 | 12.675 | 1.00 | 9.96 | O |
| ATOM | 158 | C | ASP | A | 12 | 10.084 | 58.849 | 17.163 | 1.00 | 9.46 | C |
| ATOM | 159 | O | ASP | A | 12 | 9.976 | 57.640 | 17.320 | 1.00 | 8.43 | O |
| ATOM | 160 | N | TYR | A | 13 | 11.142 | 59.531 | 17.599 | 1.00 | 9.27 | N |
| ATOM | 162 | CA | TYR | A | 13 | 12.082 | 58.969 | 18.538 | 1.00 | 8.06 | C |
| ATOM | 164 | CB | TYR | A | 13 | 13.273 | 59.911 | 18.868 | 1.00 | 8.94 | C |
| ATOM | 167 | CG | TYR | A | 13 | 14.422 | 59.228 | 19.526 | 1.00 | 7.46 | C |
| ATOM | 168 | CD1 | TYR | A | 13 | 14.454 | 58.988 | 20.878 | 1.00 | 7.54 | C |
| ATOM | 170 | CE1 | TYR | A | 13 | 15.513 | 58.373 | 21.475 | 1.00 | 7.44 | C |
| ATOM | 172 | CZ | TYR | A | 13 | 16.661 | 58.039 | 20.738 | 1.00 | 9.30 | C |
| ATOM | 173 | OH | TYR | A | 13 | 17.767 | 57.465 | 21.340 | 1.00 | 12.39 | O |
| ATOM | 175 | CE2 | TYR | A | 13 | 16.705 | 58.335 | 19.414 | 1.00 | 9.34 | C |
| ATOM | 177 | CD2 | TYR | A | 13 | 15.574 | 58.883 | 18.787 | 1.00 | 7.69 | C |
| ATOM | 179 | C | TYR | A | 13 | 11.416 | 58.397 | 19.783 | 1.00 | 11.59 | C |
| ATOM | 180 | O | TYR | A | 13 | 11.725 | 57.223 | 20.139 | 1.00 | 11.48 | O |
| ATOM | 181 | N | LEU | A | 14 | 10.496 | 59.177 | 20.357 | 1.00 | 9.26 | N |
| ATOM | 183 | CA | LEU | A | 14 | 9.752 | 58.756 | 21.573 | 1.00 | 10.40 | C |
| ATOM | 185 | CB | LEU | A | 14 | 8.804 | 59.847 | 22.009 | 1.00 | 10.03 | C |
| ATOM | 188 | CG | LEU | A | 14 | 9.544 | 60.946 | 22.748 | 1.00 | 10.37 | C |
| ATOM | 190 | CD1 | LEU | A | 14 | 8.744 | 62.140 | 22.732 | 1.00 | 10.65 | C |
| ATOM | 194 | CD2 | LEU | A | 14 | 9.956 | 60.569 | 24.104 | 1.00 | 9.47 | C |
| ATOM | 198 | C | LEU | A | 14 | 8.964 | 57.490 | 21.225 | 1.00 | 9.22 | C |
| ATOM | 199 | O | LEU | A | 14 | 8.879 | 56.536 | 21.962 | 1.00 | 8.39 | O |
| ATOM | 200 | N | GLN | A | 15 | 8.169 | 57.576 | 20.148 | 1.00 | 6.72 | N |
| ATOM | 202 | CA | GLN | A | 15 | 7.420 | 56.409 | 19.768 | 1.00 | 8.38 | C |
| ATOM | 204 | CB | GLN | A | 15 | 6.320 | 56.771 | 18.708 | 1.00 | 5.44 | C |
| ATOM | 207 | CG | GLN | A | 15 | 5.426 | 57.873 | 19.269 | 1.00 | 7.39 | C |
| ATOM | 210 | CD | GLN | A | 15 | 4.151 | 57.906 | 18.454 | 1.00 | 11.03 | C |
| ATOM | 211 | OE1 | GLN | A | 15 | 4.189 | 57.833 | 17.224 | 1.00 | 10.64 | O |
| ATOM | 212 | NE2 | GLN | A | 15 | 3.026 | 57.918 | 19.120 | 1.00 | 8.47 | N |
| ATOM | 215 | C | GLN | A | 15 | 8.180 | 55.150 | 19.370 | 1.00 | 6.72 | C |
| ATOM | 216 | O | GLN | A | 15 | 7.634 | 54.043 | 19.664 | 1.00 | 9.19 | O |
| ATOM | 217 | N | THR | A | 16 | 9.400 | 55.270 | 18.868 | 1.00 | 6.36 | N |
| ATOM | 219 | CA | THR | A | 16 | 10.178 | 54.114 | 18.658 | 1.00 | 6.80 | C |
| ATOM | 221 | CB | THR | A | 16 | 11.254 | 54.550 | 17.647 | 1.00 | 9.04 | C |
| ATOM | 223 | OG1 | THR | A | 16 | 10.557 | 55.015 | 16.509 | 1.00 | 7.21 | O |
| ATOM | 225 | CG2 | THR | A | 16 | 12.063 | 53.377 | 17.151 | 1.00 | 8.26 | C |
| ATOM | 229 | C | THR | A | 16 | 10.782 | 53.490 | 19.924 | 1.00 | 7.67 | C |
| ATOM | 230 | O | THR | A | 16 | 10.765 | 52.278 | 20.163 | 1.00 | 7.74 | O |
| ATOM | 231 | N | TYR | A | 17 | 11.577 | 54.349 | 20.551 | 1.00 | 10.58 | N |

-continued

| | | | | | | | | | | | |
|---|---|---|---|---|---|---|---|---|---|---|---|
| ATOM | 233 | CA | TYR | A | 17 | 12.373 | 53.971 | 21.706 | 1.00 | 8.90 | C |
| ATOM | 235 | CB | TYR | A | 17 | 13.663 | 54.748 | 21.646 | 1.00 | 10.32 | C |
| ATOM | 238 | CG | TYR | A | 17 | 14.368 | 54.411 | 20.386 | 1.00 | 10.81 | C |
| ATOM | 239 | CD1 | TYR | A | 17 | 14.456 | 55.350 | 19.366 | 1.00 | 10.23 | C |
| ATOM | 241 | CE1 | TYR | A | 17 | 15.098 | 55.069 | 18.144 | 1.00 | 11.90 | C |
| ATOM | 243 | CZ | TYR | A | 17 | 15.689 | 53.811 | 17.935 | 1.00 | 14.28 | C |
| ATOM | 244 | OH | TYR | A | 17 | 16.254 | 53.477 | 16.702 | 1.00 | 10.14 | O |
| ATOM | 246 | CE2 | TYR | A | 17 | 15.619 | 52.827 | 18.981 | 1.00 | 15.09 | C |
| ATOM | 248 | CD2 | TYR | A | 17 | 14.874 | 53.126 | 20.198 | 1.00 | 12.77 | C |
| ATOM | 250 | C | TYR | A | 17 | 11.812 | 54.155 | 23.088 | 1.00 | 9.09 | C |
| ATOM | 251 | O | TYR | A | 17 | 12.393 | 53.597 | 23.993 | 1.00 | 8.25 | O |
| ATOM | 252 | N | HIS | A | 18 | 10.744 | 54.926 | 23.201 | 1.00 | 8.12 | N |
| ATOM | 254 | CA | HIS | A | 18 | 10.096 | 55.214 | 24.508 | 1.00 | 10.80 | C |
| ATOM | 256 | CB | HIS | A | 18 | 9.635 | 53.948 | 25.185 | 1.00 | 8.03 | C |
| ATOM | 259 | CG | HIS | A | 18 | 8.345 | 53.390 | 24.684 | 1.00 | 8.19 | C |
| ATOM | 260 | ND1 | HIS | A | 18 | 7.755 | 53.675 | 23.466 | 1.00 | 11.32 | N |
| ATOM | 262 | CE1 | HIS | A | 18 | 6.644 | 52.958 | 23.315 | 1.00 | 7.41 | C |
| ATOM | 264 | NE2 | HIS | A | 18 | 6.516 | 52.210 | 24.401 | 1.00 | 9.71 | N |
| ATOM | 266 | CD2 | HIS | A | 18 | 7.598 | 52.410 | 25.220 | 1.00 | 7.11 | C |
| ATOM | 268 | C | HIS | A | 18 | 10.945 | 55.950 | 25.536 | 1.00 | 9.81 | C |
| ATOM | 269 | O | HIS | A | 18 | 11.005 | 55.597 | 26.692 | 1.00 | 10.04 | O |
| ATOM | 270 | N | LYS | A | 19 | 11.799 | 56.783 | 25.001 | 1.00 | 11.80 | N |
| ATOM | 272 | CA | LYS | A | 19 | 12.712 | 57.645 | 25.737 | 1.00 | 12.16 | C |
| ATOM | 274 | CB | LYS | A | 19 | 14.025 | 56.952 | 26.188 | 1.00 | 13.25 | C |
| ATOM | 277 | CG | LYS | A | 19 | 14.911 | 56.337 | 25.134 | 1.00 | 14.23 | C |
| ATOM | 280 | CD | LYS | A | 19 | 16.081 | 55.623 | 25.742 | 1.00 | 18.80 | C |
| ATOM | 283 | CE | LYS | A | 19 | 16.757 | 54.993 | 24.442 | 1.00 | 19.86 | C |
| ATOM | 286 | NZ | LYS | A | 19 | 18.114 | 54.638 | 24.964 | 1.00 | 21.92 | N |
| ATOM | 290 | C | LYS | A | 19 | 13.036 | 58.804 | 24.789 | 1.00 | 14.37 | C |
| ATOM | 291 | O | LYS | A | 19 | 12.850 | 58.709 | 23.596 | 1.00 | 12.39 | O |
| ATOM | 292 | N | LEU | A | 20 | 13.512 | 59.902 | 25.369 | 1.00 | 13.18 | N |
| ATOM | 294 | CA | LEU | A | 20 | 13.955 | 61.071 | 24.623 | 1.00 | 12.39 | C |
| ATOM | 296 | CB | LEU | A | 20 | 13.959 | 62.266 | 25.581 | 1.00 | 11.63 | C |
| ATOM | 299 | CG | LEU | A | 20 | 12.572 | 62.858 | 25.874 | 1.00 | 12.36 | C |
| ATOM | 301 | CD1 | LEU | A | 20 | 12.842 | 63.805 | 27.067 | 1.00 | 14.63 | C |
| ATOM | 305 | CD2 | LEU | A | 20 | 12.006 | 63.572 | 24.678 | 1.00 | 12.86 | C |
| ATOM | 309 | C | LEU | A | 20 | 15.282 | 60.747 | 24.083 | 1.00 | 8.62 | C |
| ATOM | 310 | O | LEU | A | 20 | 16.027 | 59.887 | 24.673 | 1.00 | 11.07 | O |
| ATOM | 311 | N | PRO | A | 21 | 15.669 | 61.396 | 22.978 | 1.00 | 7.66 | N |
| ATOM | 312 | CA | PRO | A | 21 | 17.030 | 61.185 | 22.536 | 1.00 | 11.67 | C |
| ATOM | 314 | CB | PRO | A | 21 | 17.153 | 62.065 | 21.298 | 1.00 | 13.63 | C |
| ATOM | 317 | CG | PRO | A | 21 | 15.921 | 62.790 | 21.172 | 1.00 | 12.59 | C |
| ATOM | 320 | CD | PRO | A | 21 | 14.933 | 62.257 | 22.050 | 1.00 | 11.31 | C |
| ATOM | 323 | C | PRO | A | 21 | 18.066 | 61.784 | 23.470 | 1.00 | 13.18 | C |
| ATOM | 324 | O | PRO | A | 21 | 17.658 | 62.525 | 24.351 | 1.00 | 10.88 | O |
| ATOM | 325 | N | ASP | A | 22 | 19.333 | 61.502 | 23.188 | 1.00 | 15.40 | N |
| ATOM | 327 | CA | ASP | A | 22 | 20.443 | 61.785 | 24.122 | 1.00 | 17.57 | C |
| ATOM | 329 | CB | ASP | A | 22 | 21.662 | 61.062 | 23.593 | 1.00 | 24.41 | C |
| ATOM | 332 | CG | ASP | A | 22 | 21.513 | 59.510 | 23.725 | 1.00 | 31.16 | C |
| ATOM | 333 | OD1 | ASP | A | 22 | 20.568 | 59.028 | 24.453 | 1.00 | 32.54 | O |
| ATOM | 334 | OD2 | ASP | A | 22 | 22.254 | 58.691 | 23.046 | 1.00 | 35.54 | O |
| ATOM | 335 | C | ASP | A | 22 | 20.810 | 63.259 | 24.412 | 1.00 | 16.73 | C |
| ATOM | 336 | O | ASP | A | 22 | 21.558 | 63.592 | 25.341 | 1.00 | 13.24 | O |
| ATOM | 337 | N | ASN | A | 23 | 20.170 | 64.169 | 23.684 | 1.00 | 13.14 | N |
| ATOM | 339 | CA | ASN | A | 23 | 20.316 | 65.548 | 23.904 | 1.00 | 12.64 | C |
| ATOM | 341 | CB | ASN | A | 23 | 20.273 | 66.304 | 22.595 | 1.00 | 13.51 | C |
| ATOM | 344 | CG | ASN | A | 23 | 18.946 | 66.065 | 21.843 | 1.00 | 12.48 | C |
| ATOM | 345 | OD1 | ASN | A | 23 | 18.757 | 64.931 | 21.412 | 1.00 | 14.44 | O |
| ATOM | 346 | ND2 | ASN | A | 23 | 18.107 | 67.103 | 21.605 | 1.00 | 11.53 | N |
| ATOM | 349 | C | ASN | A | 23 | 19.407 | 66.138 | 24.931 | 1.00 | 12.26 | C |
| ATOM | 350 | O | ASN | A | 23 | 19.483 | 67.323 | 25.099 | 1.00 | 12.57 | O |
| ATOM | 351 | N | TYR | A | 24 | 18.532 | 65.358 | 25.568 | 1.00 | 13.29 | N |
| ATOM | 353 | CA | TYR | A | 24 | 17.668 | 65.811 | 26.648 | 1.00 | 10.21 | C |
| ATOM | 355 | CB | TYR | A | 24 | 16.312 | 65.214 | 26.465 | 1.00 | 10.68 | C |
| ATOM | 358 | CG | TYR | A | 24 | 15.655 | 65.918 | 25.280 | 1.00 | 10.21 | C |
| ATOM | 359 | CD1 | TYR | A | 24 | 14.960 | 67.105 | 25.486 | 1.00 | 11.90 | C |
| ATOM | 361 | CE1 | TYR | A | 24 | 14.371 | 67.769 | 24.470 | 1.00 | 12.10 | C |
| ATOM | 363 | CZ | TYR | A | 24 | 14.359 | 67.244 | 23.188 | 1.00 | 9.06 | C |
| ATOM | 364 | OH | TYR | A | 24 | 13.856 | 67.954 | 22.080 | 1.00 | 9.96 | O |
| ATOM | 366 | CE2 | TYR | A | 24 | 14.989 | 66.015 | 22.966 | 1.00 | 11.14 | C |
| ATOM | 368 | CD2 | TYR | A | 24 | 15.701 | 65.379 | 23.959 | 1.00 | 11.66 | C |
| ATOM | 370 | C | TYR | A | 24 | 18.209 | 65.569 | 28.048 | 1.00 | 12.21 | C |
| ATOM | 371 | O | TYR | A | 24 | 18.776 | 64.512 | 28.261 | 1.00 | 10.15 | O |
| ATOM | 372 | N | ILE | A | 25 | 18.012 | 66.559 | 28.917 | 1.00 | 9.70 | N |
| ATOM | 374 | CA | ILE | A | 25 | 18.206 | 66.459 | 30.306 | 1.00 | 11.83 | C |
| ATOM | 376 | CB | ILE | A | 25 | 19.506 | 67.213 | 30.728 | 1.00 | 11.40 | C |
| ATOM | 378 | CG1 | ILE | A | 25 | 19.440 | 68.693 | 30.416 | 1.00 | 9.91 | C |
| ATOM | 381 | CD1 | ILE | A | 25 | 20.762 | 69.389 | 30.853 | 1.00 | 10.20 | C |
| ATOM | 385 | CG2 | ILE | A | 25 | 20.708 | 66.655 | 30.035 | 1.00 | 11.11 | C |
| ATOM | 389 | C | ILE | A | 25 | 17.027 | 67.000 | 30.988 | 1.00 | 11.74 | C |

-continued

| ATOM | 390 | O | ILE | A | 25 | 16.385 | 67.972 | 30.528 | 1.00 | 8.70 | O |
|---|---|---|---|---|---|---|---|---|---|---|---|
| ATOM | 391 | N | THR | A | 26 | 16.734 | 66.404 | 32.127 | 1.00 | 11.03 | N |
| ATOM | 393 | CA | THR | A | 26 | 15.652 | 67.030 | 32.872 | 1.00 | 9.56 | C |
| ATOM | 395 | CB | THR | A | 26 | 15.130 | 66.092 | 33.987 | 1.00 | 11.31 | C |
| ATOM | 397 | OG1 | THR | A | 26 | 16.152 | 65.889 | 34.971 | 1.00 | 10.67 | O |
| ATOM | 399 | CG2 | THR | A | 26 | 14.797 | 64.684 | 33.576 | 1.00 | 12.02 | C |
| ATOM | 403 | C | THR | A | 26 | 15.942 | 68.370 | 33.479 | 1.00 | 11.08 | C |
| ATOM | 404 | O | THR | A | 26 | 17.095 | 68.793 | 33.616 | 1.00 | 14.78 | O |
| ATOM | 405 | N | LYS | A | 27 | 14.906 | 68.974 | 34.062 | 1.00 | 13.18 | N |
| ATOM | 407 | CA | LYS | A | 27 | 15.031 | 70.284 | 34.711 | 1.00 | 15.98 | C |
| ATOM | 409 | CB | LYS | A | 27 | 13.708 | 70.925 | 35.272 | 1.00 | 17.62 | C |
| ATOM | 412 | CG | LYS | A | 27 | 12.763 | 71.828 | 34.349 | 1.00 | 25.05 | C |
| ATOM | 415 | CD | LYS | A | 27 | 11.112 | 71.441 | 34.443 | 1.00 | 26.12 | C |
| ATOM | 418 | CE | LYS | A | 27 | 10.193 | 71.244 | 33.189 | 1.00 | 27.01 | C |
| ATOM | 421 | NZ | LYS | A | 27 | 9.557 | 72.396 | 32.193 | 1.00 | 26.80 | N |
| ATOM | 425 | C | LYS | A | 27 | 16.068 | 70.157 | 35.809 | 1.00 | 13.27 | C |
| ATOM | 426 | O | LYS | A | 27 | 16.999 | 70.916 | 35.857 | 1.00 | 14.27 | O |
| ATOM | 427 | N | SER | A | 28 | 15.877 | 69.187 | 36.707 | 1.00 | 9.50 | N |
| ATOM | 429 | CA | SER | A | 28 | 16.734 | 68.983 | 37.841 | 1.00 | 10.56 | C |
| ATOM | 431 | CB | SER | A | 28 | 16.099 | 67.834 | 38.613 | 1.00 | 11.46 | C |
| ATOM | 434 | OG | SER | A | 28 | 15.088 | 68.316 | 39.454 | 1.00 | 9.88 | O |
| ATOM | 436 | C | SER | A | 28 | 18.135 | 68.602 | 37.415 | 1.00 | 9.36 | C |
| ATOM | 437 | O | SER | A | 28 | 19.085 | 69.048 | 38.030 | 1.00 | 6.96 | O |
| ATOM | 438 | N | GLU | A | 29 | 18.255 | 67.802 | 36.373 | 1.00 | 11.20 | N |
| ATOM | 440 | CA | GLU | A | 29 | 19.645 | 67.503 | 35.960 | 1.00 | 12.45 | C |
| ATOM | 442 | CB | GLU | A | 29 | 19.714 | 66.495 | 34.796 | 1.00 | 14.00 | C |
| ATOM | 445 | CG | GLU | A | 29 | 19.473 | 65.002 | 35.018 | 1.00 | 19.06 | C |
| ATOM | 448 | CD | GLU | A | 29 | 19.686 | 64.358 | 33.618 | 1.00 | 21.71 | C |
| ATOM | 449 | OE1 | GLU | A | 29 | 20.911 | 64.341 | 33.214 | 1.00 | 25.61 | O |
| ATOM | 450 | OE2 | GLU | A | 29 | 18.719 | 64.383 | 32.868 | 1.00 | 15.51 | O |
| ATOM | 451 | C | GLU | A | 29 | 20.303 | 68.763 | 35.454 | 1.00 | 8.44 | C |
| ATOM | 452 | O | GLU | A | 29 | 21.504 | 69.019 | 35.698 | 1.00 | 10.70 | O |
| ATOM | 453 | N | ALA | A | 30 | 19.563 | 69.564 | 34.720 | 1.00 | 7.23 | N |
| ATOM | 455 | CA | ALA | A | 30 | 20.122 | 70.807 | 34.135 | 1.00 | 7.75 | C |
| ATOM | 457 | CB | ALA | A | 30 | 19.039 | 71.472 | 33.362 | 1.00 | 9.55 | C |
| ATOM | 461 | C | ALA | A | 30 | 20.596 | 71.777 | 35.251 | 1.00 | 8.76 | C |
| ATOM | 462 | O | ALA | A | 30 | 21.699 | 72.300 | 35.197 | 1.00 | 11.39 | O |
| ATOM | 463 | N | GLN | A | 31 | 19.833 | 71.804 | 36.339 | 1.00 | 9.29 | N |
| ATOM | 465 | CA | GLN | A | 31 | 20.103 | 72.676 | 37.441 | 1.00 | 11.25 | C |
| ATOM | 467 | CB | GLN | A | 31 | 18.966 | 72.692 | 38.463 | 1.00 | 11.04 | C |
| ATOM | 470 | CG | GLN | A | 31 | 17.718 | 73.425 | 37.952 | 1.00 | 14.12 | C |
| ATOM | 473 | CD | GLN | A | 31 | 16.494 | 73.253 | 38.898 | 1.00 | 19.64 | C |
| ATOM | 474 | OE1 | GLN | A | 31 | 16.506 | 72.345 | 39.712 | 1.00 | 23.07 | O |
| ATOM | 475 | NE2 | GLN | A | 31 | 15.471 | 74.101 | 38.819 | 1.00 | 20.34 | N |
| ATOM | 478 | C | GLN | A | 31 | 21.429 | 72.201 | 38.077 | 1.00 | 9.02 | C |
| ATOM | 479 | O | GLN | A | 31 | 22.183 | 73.029 | 38.506 | 1.00 | 11.78 | O |
| ATOM | 480 | N | ALA | A | 32 | 21.561 | 70.901 | 38.279 | 1.00 | 10.18 | N |
| ATOM | 482 | CA | ALA | A | 32 | 22.677 | 70.236 | 38.989 | 1.00 | 11.47 | C |
| ATOM | 484 | CB | ALA | A | 32 | 22.481 | 68.753 | 39.034 | 1.00 | 12.44 | C |
| ATOM | 488 | C | ALA | A | 32 | 23.870 | 70.518 | 38.116 | 1.00 | 13.28 | C |
| ATOM | 489 | O | ALA | A | 32 | 24.914 | 70.888 | 38.646 | 1.00 | 11.93 | O |
| ATOM | 490 | N | LEU | A | 33 | 23.662 | 70.518 | 36.792 | 1.00 | 13.42 | N |
| ATOM | 492 | CA | LEU | A | 33 | 24.793 | 70.844 | 35.892 | 1.00 | 14.02 | C |
| ATOM | 494 | CB | LEU | A | 33 | 24.534 | 70.318 | 34.443 | 1.00 | 15.03 | C |
| ATOM | 497 | CG | LEU | A | 33 | 24.448 | 68.788 | 34.388 | 1.00 | 16.07 | C |
| ATOM | 499 | CD1 | LEU | A | 33 | 23.979 | 68.378 | 32.994 | 1.00 | 18.21 | C |
| ATOM | 503 | CD2 | LEU | A | 33 | 25.736 | 68.108 | 34.800 | 1.00 | 18.74 | C |
| ATOM | 507 | C | LEU | A | 33 | 25.104 | 72.313 | 35.800 | 1.00 | 11.26 | C |
| ATOM | 508 | O | LEU | A | 33 | 26.052 | 72.707 | 35.094 | 1.00 | 14.47 | O |
| ATOM | 509 | N | GLY | A | 34 | 24.303 | 73.160 | 36.434 | 1.00 | 10.53 | N |
| ATOM | 511 | CA | GLY | A | 34 | 24.621 | 74.592 | 36.558 | 1.00 | 9.48 | C |
| ATOM | 514 | C | GLY | A | 34 | 23.644 | 75.540 | 35.935 | 1.00 | 9.94 | C |
| ATOM | 515 | O | GLY | A | 34 | 23.762 | 76.720 | 36.109 | 1.00 | 11.20 | O |
| ATOM | 516 | N | TRP | A | 35 | 22.552 | 75.045 | 35.343 | 1.00 | 8.51 | N |
| ATOM | 518 | CA | TRP | A | 35 | 21.516 | 75.886 | 34.712 | 1.00 | 10.37 | C |
| ATOM | 520 | CB | TRP | A | 35 | 20.516 | 75.006 | 33.978 | 1.00 | 9.49 | C |
| ATOM | 523 | CG | TRP | A | 35 | 19.403 | 75.797 | 33.464 | 1.00 | 10.46 | C |
| ATOM | 524 | CD1 | TRP | A | 35 | 19.413 | 76.830 | 32.588 | 1.00 | 10.67 | C |
| ATOM | 526 | NE1 | TRP | A | 35 | 18.126 | 77.221 | 32.338 | 1.00 | 10.69 | N |
| ATOM | 528 | CE2 | TRP | A | 35 | 17.276 | 76.364 | 32.953 | 1.00 | 10.95 | C |
| ATOM | 529 | CD2 | TRP | A | 35 | 18.055 | 75.494 | 33.714 | 1.00 | 11.03 | C |
| ATOM | 530 | CE3 | TRP | A | 35 | 17.421 | 74.517 | 34.474 | 1.00 | 12.02 | C |
| ATOM | 532 | CZ3 | TRP | A | 35 | 16.043 | 74.477 | 34.433 | 1.00 | 16.19 | C |
| ATOM | 534 | CH2 | TRP | A | 35 | 15.298 | 75.423 | 33.759 | 1.00 | 14.45 | C |
| ATOM | 536 | CZ2 | TRP | A | 35 | 15.912 | 76.386 | 33.026 | 1.00 | 13.57 | C |
| ATOM | 538 | C | TRP | A | 35 | 20.759 | 76.563 | 35.769 | 1.00 | 11.80 | C |
| ATOM | 539 | O | TRP | A | 35 | 20.480 | 75.978 | 36.787 | 1.00 | 13.46 | O |
| ATOM | 540 | N | VAL | A | 36 | 20.642 | 77.854 | 35.568 | 1.00 | 13.51 | N |
| ATOM | 542 | CA | VAL | A | 36 | 19.850 | 78.721 | 36.411 | 1.00 | 14.52 | C |
| ATOM | 544 | CB | VAL | A | 36 | 20.709 | 79.850 | 37.056 | 1.00 | 14.17 | C |

-continued

| | | | | | | | | | | | |
|---|---|---|---|---|---|---|---|---|---|---|---|
| ATOM | 546 | CG1 | VAL | A | 36 | 19.720 | 80.804 | 37.721 | 1.00 | 14.44 | C |
| ATOM | 550 | CG2 | VAL | A | 36 | 21.728 | 79.251 | 37.936 | 1.00 | 15.02 | C |
| ATOM | 554 | C | VAL | A | 36 | 18.845 | 79.361 | 35.471 | 1.00 | 14.86 | C |
| ATOM | 555 | O | VAL | A | 36 | 19.280 | 80.072 | 34.565 | 1.00 | 14.15 | O |
| ATOM | 556 | N | ALA | A | 37 | 17.552 | 79.152 | 35.681 | 1.00 | 16.80 | N |
| ATOM | 558 | CA | ALA | A | 37 | 16.602 | 79.612 | 34.642 | 1.00 | 19.03 | C |
| ATOM | 560 | CB | ALA | A | 37 | 15.185 | 79.302 | 35.065 | 1.00 | 19.86 | C |
| ATOM | 564 | C | ALA | A | 37 | 16.761 | 81.111 | 34.322 | 1.00 | 21.10 | C |
| ATOM | 565 | O | ALA | A | 37 | 16.893 | 81.598 | 33.201 | 1.00 | 22.32 | O |
| ATOM | 566 | N | SER | A | 38 | 16.864 | 81.921 | 35.342 | 1.00 | 21.48 | N |
| ATOM | 568 | CA | SER | A | 38 | 16.846 | 83.354 | 35.069 | 1.00 | 21.38 | C |
| ATOM | 570 | CB | SER | A | 38 | 16.521 | 84.067 | 36.372 | 1.00 | 19.41 | C |
| ATOM | 573 | OG | SER | A | 38 | 17.599 | 83.864 | 37.277 | 1.00 | 17.79 | O |
| ATOM | 575 | C | SER | A | 38 | 18.165 | 83.861 | 34.440 | 1.00 | 22.75 | C |
| ATOM | 576 | O | SER | A | 38 | 18.301 | 85.070 | 34.290 | 1.00 | 24.55 | O |
| ATOM | 577 | N | LYS | A | 39 | 19.210 | 83.047 | 34.266 | 1.00 | 21.17 | N |
| ATOM | 579 | CA | LYS | A | 39 | 20.406 | 83.423 | 33.529 | 1.00 | 21.64 | C |
| ATOM | 581 | CB | LYS | A | 39 | 21.725 | 82.845 | 34.110 | 1.00 | 24.13 | C |
| ATOM | 584 | CG | LYS | A | 39 | 22.192 | 83.242 | 35.464 | 1.00 | 26.02 | C |
| ATOM | 587 | CD | LYS | A | 39 | 23.733 | 83.693 | 35.579 | 1.00 | 28.80 | C |
| ATOM | 590 | CE | LYS | A | 39 | 24.843 | 82.596 | 35.622 | 1.00 | 29.09 | C |
| ATOM | 593 | NZ | LYS | A | 39 | 26.213 | 83.289 | 35.676 | 1.00 | 27.36 | N |
| ATOM | 597 | C | LYS | A | 39 | 20.403 | 83.022 | 32.048 | 1.00 | 19.45 | C |
| ATOM | 598 | O | LYS | A | 39 | 21.295 | 83.409 | 31.286 | 1.00 | 20.46 | O |
| ATOM | 599 | N | GLY | A | 40 | 19.470 | 82.199 | 31.602 | 1.00 | 15.53 | N |
| ATOM | 601 | CA | GLY | A | 40 | 19.449 | 81.892 | 30.173 | 1.00 | 16.20 | C |
| ATOM | 604 | C | GLY | A | 40 | 20.691 | 81.083 | 29.799 | 1.00 | 14.65 | C |
| ATOM | 605 | O | GLY | A | 40 | 21.128 | 81.158 | 28.663 | 1.00 | 14.14 | O |
| ATOM | 606 | N | ASN | A | 41 | 21.246 | 80.304 | 30.737 | 1.00 | 13.48 | N |
| ATOM | 608 | CA | ASN | A | 41 | 22.602 | 79.734 | 30.524 | 1.00 | 12.48 | C |
| ATOM | 610 | CB | ASN | A | 41 | 23.431 | 80.019 | 31.766 | 1.00 | 11.98 | C |
| ATOM | 613 | CG | ASN | A | 41 | 23.007 | 79.186 | 33.011 | 1.00 | 12.56 | C |
| ATOM | 614 | OD1 | ASN | A | 41 | 21.840 | 78.779 | 33.155 | 1.00 | 10.26 | O |
| ATOM | 615 | ND2 | ASN | A | 41 | 23.956 | 79.002 | 33.944 | 1.00 | 9.96 | N |
| ATOM | 618 | C | ASN | A | 41 | 22.632 | 78.213 | 30.191 | 1.00 | 11.89 | C |
| ATOM | 619 | O | ASN | A | 41 | 23.673 | 77.509 | 30.256 | 1.00 | 14.37 | O |
| ATOM | 620 | N | LEU | A | 42 | 21.514 | 77.703 | 29.710 | 1.00 | 12.36 | N |
| ATOM | 622 | CA | LEU | A | 42 | 21.402 | 76.226 | 29.582 | 1.00 | 12.49 | C |
| ATOM | 624 | CB | LEU | A | 42 | 20.084 | 75.745 | 29.009 | 1.00 | 10.42 | C |
| ATOM | 627 | CG | LEU | A | 42 | 19.937 | 74.236 | 28.890 | 1.00 | 11.23 | C |
| ATOM | 629 | CD1 | LEU | A | 42 | 20.038 | 73.626 | 30.265 | 1.00 | 12.26 | C |
| ATOM | 633 | CD2 | LEU | A | 42 | 18.518 | 74.008 | 28.264 | 1.00 | 11.52 | C |
| ATOM | 637 | C | LEU | A | 42 | 22.519 | 75.702 | 28.653 | 1.00 | 11.43 | C |
| ATOM | 638 | O | LEU | A | 42 | 23.242 | 74.740 | 28.955 | 1.00 | 9.65 | O |
| ATOM | 639 | N | ALA | A | 43 | 22.647 | 76.369 | 27.522 | 1.00 | 10.58 | N |
| ATOM | 641 | CA | ALA | A | 43 | 23.583 | 75.901 | 26.544 | 1.00 | 10.42 | C |
| ATOM | 643 | CB | ALA | A | 43 | 23.235 | 76.524 | 25.214 | 1.00 | 12.50 | C |
| ATOM | 647 | C | ALA | A | 43 | 25.004 | 76.298 | 26.884 | 1.00 | 12.63 | C |
| ATOM | 648 | O | ALA | A | 43 | 25.954 | 75.777 | 26.273 | 1.00 | 10.33 | O |
| ATOM | 649 | N | ASP | A | 44 | 25.173 | 77.151 | 27.882 | 1.00 | 11.19 | N |
| ATOM | 651 | CA | ASP | A | 44 | 26.547 | 77.343 | 28.254 | 1.00 | 12.65 | C |
| ATOM | 653 | CB | ASP | A | 44 | 26.698 | 78.658 | 28.997 | 1.00 | 13.47 | C |
| ATOM | 656 | CG | ASP | A | 44 | 26.281 | 79.841 | 28.157 | 1.00 | 15.50 | C |
| ATOM | 657 | OD1 | ASP | A | 44 | 26.671 | 79.946 | 26.990 | 1.00 | 13.20 | O |
| ATOM | 658 | OD2 | ASP | A | 44 | 25.532 | 80.690 | 28.634 | 1.00 | 19.68 | O |
| ATOM | 659 | C | ASP | A | 44 | 26.966 | 76.197 | 29.189 | 1.00 | 13.99 | C |
| ATOM | 660 | O | ASP | A | 44 | 28.062 | 75.754 | 29.121 | 1.00 | 11.77 | O |
| ATOM | 661 | N | VAL | A | 45 | 26.076 | 75.730 | 30.064 | 1.00 | 12.97 | N |
| ATOM | 663 | CA | VAL | A | 45 | 26.468 | 74.688 | 30.983 | 1.00 | 8.34 | C |
| ATOM | 665 | CB | VAL | A | 45 | 25.779 | 74.756 | 32.343 | 1.00 | 9.15 | C |
| ATOM | 667 | CG1 | VAL | A | 45 | 26.054 | 76.076 | 33.087 | 1.00 | 11.49 | C |
| ATOM | 671 | CG2 | VAL | A | 45 | 24.267 | 74.554 | 32.247 | 1.00 | 7.95 | C |
| ATOM | 675 | C | VAL | A | 45 | 26.299 | 73.328 | 30.373 | 1.00 | 8.80 | C |
| ATOM | 676 | O | VAL | A | 45 | 26.934 | 72.410 | 30.809 | 1.00 | 8.81 | O |
| ATOM | 677 | N | ALA | A | 46 | 25.474 | 73.205 | 29.359 | 1.00 | 8.48 | N |
| ATOM | 679 | CA | ALA | A | 46 | 25.183 | 71.921 | 28.744 | 1.00 | 10.55 | C |
| ATOM | 681 | CB | ALA | A | 46 | 23.884 | 71.323 | 29.281 | 1.00 | 9.59 | C |
| ATOM | 685 | C | ALA | A | 46 | 25.117 | 72.035 | 27.257 | 1.00 | 9.69 | C |
| ATOM | 686 | O | ALA | A | 46 | 24.005 | 72.015 | 26.706 | 1.00 | 8.90 | O |
| ATOM | 687 | N | PRO | A | 47 | 26.247 | 72.282 | 26.617 | 1.00 | 11.83 | N |
| ATOM | 688 | CA | PRO | A | 47 | 26.241 | 72.537 | 25.155 | 1.00 | 12.60 | C |
| ATOM | 690 | CB | PRO | A | 47 | 27.722 | 72.459 | 24.751 | 1.00 | 12.43 | C |
| ATOM | 693 | CG | PRO | A | 47 | 28.426 | 73.045 | 25.923 | 1.00 | 12.70 | C |
| ATOM | 696 | CD | PRO | A | 47 | 27.605 | 72.438 | 27.159 | 1.00 | 12.26 | C |
| ATOM | 699 | C | PRO | A | 47 | 25.458 | 71.487 | 24.393 | 1.00 | 11.89 | C |
| ATOM | 700 | O | PRO | A | 47 | 25.723 | 70.339 | 24.669 | 1.00 | 14.14 | O |
| ATOM | 701 | N | GLY | A | 48 | 24.579 | 71.821 | 23.457 | 1.00 | 11.22 | N |
| ATOM | 703 | CA | GLY | A | 48 | 23.812 | 70.835 | 22.738 | 1.00 | 12.82 | C |
| ATOM | 706 | C | GLY | A | 48 | 22.614 | 70.235 | 23.430 | 1.00 | 13.24 | C |
| ATOM | 707 | O | GLY | A | 48 | 21.888 | 69.530 | 22.788 | 1.00 | 9.40 | O |

-continued

| | | | | | | | | | | | |
|---|---|---|---|---|---|---|---|---|---|---|---|
| ATOM | 708 | N | LYS | A | 49 | 22.376 | 70.531 | 24.694 | 1.00 | 13.30 | N |
| ATOM | 710 | CA | LYS | A | 49 | 21.263 | 69.942 | 25.439 | 1.00 | 11.44 | C |
| ATOM | 712 | CB | LYS | A | 49 | 21.695 | 69.461 | 26.844 | 1.00 | 10.85 | C |
| ATOM | 715 | CG | LYS | A | 49 | 22.941 | 68.549 | 26.822 | 1.00 | 11.14 | C |
| ATOM | 718 | CD | LYS | A | 49 | 22.764 | 67.266 | 26.000 | 1.00 | 13.18 | C |
| ATOM | 721 | CE | LYS | A | 49 | 24.006 | 66.318 | 26.094 | 1.00 | 15.17 | C |
| ATOM | 724 | NZ | LYS | A | 49 | 23.634 | 64.958 | 25.791 | 1.00 | 15.55 | N |
| ATOM | 728 | C | LYS | A | 49 | 20.044 | 70.839 | 25.492 | 1.00 | 12.76 | C |
| ATOM | 729 | O | LYS | A | 49 | 20.112 | 72.030 | 25.213 | 1.00 | 14.86 | O |
| ATOM | 730 | N | SER | A | 50 | 18.913 | 70.163 | 25.630 | 1.00 | 10.73 | N |
| ATOM | 732 | CA | SER | A | 50 | 17.619 | 70.741 | 25.875 | 1.00 | 7.36 | C |
| ATOM | 734 | CB | SER | A | 50 | 16.736 | 70.450 | 24.697 | 1.00 | 8.47 | C |
| ATOM | 737 | OG | SER | A | 50 | 17.234 | 70.891 | 23.425 | 1.00 | 8.66 | O |
| ATOM | 739 | C | SER | A | 50 | 17.026 | 70.165 | 27.140 | 1.00 | 11.33 | C |
| ATOM | 740 | O | SER | A | 50 | 17.261 | 68.990 | 27.459 | 1.00 | 13.01 | O |
| ATOM | 741 | N | ILE | A | 51 | 16.097 | 70.924 | 27.762 | 1.00 | 11.26 | N |
| ATOM | 743 | CA | ILE | A | 51 | 15.379 | 70.391 | 28.867 | 1.00 | 10.46 | C |
| ATOM | 745 | CB | ILE | A | 51 | 14.534 | 71.580 | 29.537 | 1.00 | 13.60 | C |
| ATOM | 747 | CG1 | ILE | A | 51 | 15.343 | 72.572 | 30.368 | 1.00 | 14.63 | C |
| ATOM | 750 | CD1 | ILE | A | 51 | 16.482 | 72.131 | 30.836 | 1.00 | 14.11 | C |
| ATOM | 754 | CG2 | ILE | A | 51 | 13.746 | 70.994 | 30.651 | 1.00 | 13.76 | C |
| ATOM | 758 | C | ILE | A | 51 | 14.324 | 69.432 | 28.370 | 1.00 | 9.40 | C |
| ATOM | 759 | O | ILE | A | 51 | 13.584 | 69.744 | 27.406 | 1.00 | 10.07 | O |
| ATOM | 760 | N | GLY | A | 52 | 14.145 | 68.308 | 29.068 | 1.00 | 7.01 | N |
| ATOM | 762 | CA | GLY | A | 52 | 13.082 | 67.410 | 28.665 | 1.00 | 11.07 | C |
| ATOM | 765 | C | GLY | A | 52 | 13.076 | 66.192 | 29.552 | 1.00 | 9.40 | C |
| ATOM | 766 | O | GLY | A | 52 | 13.998 | 65.806 | 30.274 | 1.00 | 10.01 | O |
| ATOM | 767 | N | GLY | A | 53 | 11.854 | 65.731 | 29.690 | 1.00 | 7.49 | N |
| ATOM | 769 | CA | GLY | A | 53 | 11.526 | 64.546 | 30.398 | 1.00 | 7.92 | C |
| ATOM | 772 | C | GLY | A | 53 | 10.708 | 64.622 | 31.623 | 1.00 | 9.77 | C |
| ATOM | 773 | O | GLY | A | 53 | 10.445 | 63.577 | 32.196 | 1.00 | 10.62 | O |
| ATOM | 774 | N | ASP | A | 54 | 10.367 | 65.820 | 32.046 | 1.00 | 11.61 | N |
| ATOM | 776 | CA | ASP | A | 54 | 9.672 | 65.998 | 33.300 | 1.00 | 9.49 | C |
| ATOM | 778 | CB | ASP | A | 54 | 9.877 | 67.375 | 33.845 | 1.00 | 11.50 | C |
| ATOM | 781 | CG | ASP | A | 54 | 11.409 | 67.642 | 34.138 | 1.00 | 14.34 | C |
| ATOM | 782 | OD1 | ASP | A | 54 | 11.970 | 66.760 | 34.820 | 1.00 | 16.87 | O |
| ATOM | 783 | OD2 | ASP | A | 54 | 12.053 | 68.563 | 33.625 | 1.00 | 9.69 | O |
| ATOM | 784 | C | ASP | A | 54 | 8.205 | 65.732 | 33.154 | 1.00 | 10.32 | C |
| ATOM | 785 | O | ASP | A | 54 | 7.671 | 65.938 | 32.090 | 1.00 | 8.97 | O |
| ATOM | 786 | N | ILE | A | 55 | 7.556 | 65.472 | 34.266 | 1.00 | 9.81 | N |
| ATOM | 788 | CA | ILE | A | 55 | 6.112 | 65.406 | 34.259 | 1.00 | 12.28 | C |
| ATOM | 790 | CB | ILE | A | 55 | 5.632 | 64.968 | 35.646 | 1.00 | 11.93 | C |
| ATOM | 792 | CG1 | ILE | A | 55 | 5.794 | 63.507 | 35.611 | 1.00 | 15.09 | C |
| ATOM | 795 | CD1 | ILE | A | 55 | 6.656 | 63.222 | 36.568 | 1.00 | 19.15 | C |
| ATOM | 799 | CG2 | ILE | A | 55 | 4.080 | 65.112 | 35.721 | 1.00 | 13.77 | C |
| ATOM | 803 | C | ILE | A | 55 | 5.456 | 66.735 | 33.987 | 1.00 | 12.40 | C |
| ATOM | 804 | O | ILE | A | 55 | 5.821 | 67.753 | 34.489 | 1.00 | 12.96 | O |
| ATOM | 805 | N | PHE | A | 56 | 4.494 | 66.722 | 33.104 | 1.00 | 12.87 | N |
| ATOM | 807 | CA | PHE | A | 56 | 3.594 | 67.817 | 32.876 | 1.00 | 14.48 | C |
| ATOM | 809 | CB | PHE | A | 56 | 3.292 | 67.952 | 31.372 | 1.00 | 15.22 | C |
| ATOM | 812 | CG | PHE | A | 56 | 2.394 | 69.048 | 31.061 | 1.00 | 13.94 | C |
| ATOM | 813 | CD1 | PHE | A | 56 | 2.756 | 70.358 | 31.243 | 1.00 | 14.54 | C |
| ATOM | 815 | CE1 | PHE | A | 56 | 1.835 | 71.387 | 30.916 | 1.00 | 14.29 | C |
| ATOM | 817 | CZ | PHE | A | 56 | 0.550 | 71.078 | 30.557 | 1.00 | 15.46 | C |
| ATOM | 819 | CE2 | PHE | A | 56 | 0.226 | 69.794 | 30.283 | 1.00 | 14.32 | C |
| ATOM | 821 | CD2 | PHE | A | 56 | 1.111 | 68.779 | 30.589 | 1.00 | 17.12 | C |
| ATOM | 823 | C | PHE | A | 56 | 2.315 | 67.389 | 33.561 | 1.00 | 14.02 | C |
| ATOM | 824 | O | PHE | A | 56 | 1.619 | 66.341 | 33.309 | 1.00 | 14.15 | O |
| ATOM | 825 | N | SER | A | 57 | 1.999 | 68.276 | 34.478 | 1.00 | 14.80 | N |
| ATOM | 827 | CA | SER | A | 57 | 0.886 | 68.019 | 35.361 | 1.00 | 16.86 | C |
| ATOM | 829 | CB | SER | A | 57 | 1.077 | 68.915 | 36.606 | 1.00 | 19.01 | C |
| ATOM | 832 | OG | SER | A | 57 | 0.349 | 70.078 | 36.232 | 1.00 | 23.78 | O |
| ATOM | 834 | C | SER | A | 57 | −0.490 | 68.175 | 34.686 | 1.00 | 14.80 | C |
| ATOM | 835 | O | SER | A | 57 | −1.423 | 67.551 | 35.126 | 1.00 | 13.55 | O |
| ATOM | 836 | N | ASN | A | 58 | −0.639 | 68.880 | 33.566 | 1.00 | 14.70 | N |
| ATOM | 838 | CA | ASN | A | 58 | −1.909 | 68.934 | 32.798 | 1.00 | 13.86 | C |
| ATOM | 840 | CB | ASN | A | 58 | −2.305 | 67.579 | 32.253 | 1.00 | 12.61 | C |
| ATOM | 843 | CG | ASN | A | 58 | −3.415 | 67.687 | 31.230 | 1.00 | 12.21 | C |
| ATOM | 844 | OD1 | ASN | A | 58 | −3.457 | 68.669 | 30.508 | 1.00 | 14.42 | O |
| ATOM | 845 | ND2 | ASN | A | 58 | −4.234 | 66.664 | 31.077 | 1.00 | 10.60 | N |
| ATOM | 848 | C | ASN | A | 58 | −3.061 | 69.513 | 33.640 | 1.00 | 16.38 | C |
| ATOM | 849 | O | ASN | A | 58 | −4.238 | 69.071 | 33.529 | 1.00 | 15.38 | O |
| ATOM | 850 | N | ARG | A | 59 | −2.648 | 70.538 | 34.401 | 1.00 | 18.42 | N |
| ATOM | 852 | CA | ARG | A | 59 | −3.475 | 71.224 | 35.413 | 1.00 | 23.61 | C |
| ATOM | 854 | CB | ARG | A | 59 | −2.735 | 72.444 | 36.041 | 1.00 | 26.92 | C |
| ATOM | 857 | CG | ARG | A | 59 | −2.301 | 72.317 | 37.549 | 1.00 | 32.22 | C |
| ATOM | 860 | CD | ARG | A | 59 | −1.041 | 73.159 | 38.035 | 1.00 | 35.70 | C |
| ATOM | 863 | NE | ARG | A | 59 | 0.042 | 72.323 | 38.633 | 1.00 | 39.31 | N |
| ATOM | 865 | CZ | ARG | A | 59 | 1.377 | 72.328 | 38.378 | 1.00 | 41.80 | C |
| ATOM | 866 | NH1 | ARG | A | 59 | 1.975 | 73.090 | 37.445 | 1.00 | 42.97 | N |

-continued

| | | | | | | | | | | |
|---|---|---|---|---|---|---|---|---|---|---|
| ATOM | 869 | NH2 | ARG | A | 59 | 2.145 | 71.456 | 39.033 | 1.00 | 41.96 | N |
| ATOM | 872 | C | ARG | A | 59 | −4.808 | 71.680 | 34.787 | 1.00 | 20.35 | C |
| ATOM | 873 | O | ARG | A | 59 | −5.877 | 71.410 | 35.299 | 1.00 | 24.33 | O |
| ATOM | 874 | N | GLU | A | 60 | −4.731 | 72.368 | 33.665 | 1.00 | 19.25 | N |
| ATOM | 876 | CA | GLU | A | 60 | −5.905 | 72.954 | 32.977 | 1.00 | 20.37 | C |
| ATOM | 878 | CB | GLU | A | 60 | −5.385 | 74.077 | 32.036 | 1.00 | 23.39 | C |
| ATOM | 881 | CG | GLU | A | 60 | −4.458 | 75.170 | 32.640 | 1.00 | 26.33 | C |
| ATOM | 884 | CD | GLU | A | 60 | −4.214 | 76.380 | 31.668 | 1.00 | 30.05 | C |
| ATOM | 885 | OE1 | GLU | A | 60 | −5.095 | 77.283 | 31.635 | 1.00 | 31.61 | O |
| ATOM | 886 | OE2 | GLU | A | 60 | −3.236 | 76.514 | 30.835 | 1.00 | 30.87 | O |
| ATOM | 887 | C | GLU | A | 60 | −6.709 | 71.902 | 32.209 | 1.00 | 16.43 | C |
| ATOM | 888 | O | GLU | A | 60 | −7.791 | 72.180 | 31.655 | 1.00 | 17.87 | O |
| ATOM | 889 | N | GLY | A | 61 | −6.229 | 70.661 | 32.169 | 1.00 | 15.60 | N |
| ATOM | 891 | CA | GLY | A | 61 | −6.946 | 69.555 | 31.558 | 1.00 | 14.04 | C |
| ATOM | 894 | C | GLY | A | 61 | −7.052 | 69.738 | 30.057 | 1.00 | 13.71 | C |
| ATOM | 895 | O | GLY | A | 61 | −7.874 | 69.132 | 29.405 | 1.00 | 11.69 | O |
| ATOM | 896 | N | LYS | A | 62 | −6.209 | 70.566 | 29.473 | 1.00 | 14.43 | N |
| ATOM | 898 | CA | LYS | A | 62 | −6.166 | 70.684 | 28.018 | 1.00 | 15.74 | C |
| ATOM | 900 | CB | LYS | A | 62 | −5.296 | 71.872 | 27.609 | 1.00 | 16.93 | C |
| ATOM | 903 | CG | LYS | A | 62 | −5.987 | 73.225 | 27.903 | 1.00 | 18.53 | C |
| ATOM | 906 | CD | LYS | A | 62 | −5.027 | 74.380 | 28.045 | 1.00 | 18.80 | C |
| ATOM | 909 | CE | LYS | A | 62 | −5.824 | 75.691 | 28.420 | 1.00 | 19.77 | C |
| ATOM | 912 | NZ | LYS | A | 62 | −4.845 | 76.708 | 28.828 | 1.00 | 20.13 | N |
| ATOM | 916 | C | LYS | A | 62 | −5.702 | 69.470 | 27.267 | 1.00 | 16.16 | C |
| ATOM | 917 | O | LYS | A | 62 | −6.122 | 69.221 | 26.138 | 1.00 | 17.96 | O |
| ATOM | 918 | N | LEU | A | 63 | −4.817 | 68.680 | 27.844 | 1.00 | 15.98 | N |
| ATOM | 920 | CA | LEU | A | 63 | −4.536 | 67.419 | 27.210 | 1.00 | 14.10 | C |
| ATOM | 922 | CB | LEU | A | 63 | −3.202 | 67.029 | 27.637 | 1.00 | 15.14 | C |
| ATOM | 925 | CG | LEU | A | 63 | −2.182 | 67.945 | 27.006 | 1.00 | 18.20 | C |
| ATOM | 927 | CD1 | LEU | A | 63 | −0.936 | 67.468 | 27.771 | 1.00 | 17.41 | C |
| ATOM | 931 | CD2 | LEU | A | 63 | −1.957 | 67.758 | 25.449 | 1.00 | 18.52 | C |
| ATOM | 935 | C | LEU | A | 63 | −5.494 | 66.341 | 27.686 | 1.00 | 15.09 | C |
| ATOM | 936 | O | LEU | A | 63 | −5.976 | 66.439 | 28.819 | 1.00 | 11.32 | O |
| ATOM | 937 | N | PRO | A | 64 | −5.941 | 65.420 | 26.829 | 1.00 | 12.99 | N |
| ATOM | 938 | CA | PRO | A | 64 | −6.831 | 64.396 | 27.386 | 1.00 | 15.31 | C |
| ATOM | 940 | CB | PRO | A | 64 | −7.160 | 63.478 | 26.232 | 1.00 | 14.87 | C |
| ATOM | 943 | CG | PRO | A | 64 | −6.007 | 63.679 | 25.152 | 1.00 | 15.10 | C |
| ATOM | 946 | CD | PRO | A | 64 | −5.456 | 65.079 | 25.495 | 1.00 | 14.91 | C |
| ATOM | 949 | C | PRO | A | 64 | −6.345 | 63.488 | 28.528 | 1.00 | 15.62 | C |
| ATOM | 950 | O | PRO | A | 64 | −5.276 | 62.915 | 28.427 | 1.00 | 15.46 | O |
| ATOM | 951 | N | GLY | A | 65 | −7.239 | 63.267 | 29.472 | 1.00 | 17.38 | N |
| ATOM | 953 | CA | GLY | A | 65 | −6.995 | 62.584 | 30.724 | 1.00 | 19.51 | C |
| ATOM | 956 | C | GLY | A | 65 | −7.455 | 61.157 | 30.634 | 1.00 | 19.61 | C |
| ATOM | 957 | O | GLY | A | 65 | −8.458 | 60.920 | 29.978 | 1.00 | 18.11 | O |
| ATOM | 958 | N | LYS | A | 66 | −6.798 | 60.211 | 31.308 | 1.00 | 21.09 | N |
| ATOM | 960 | CA | LYS | A | 66 | −7.378 | 58.848 | 31.254 | 1.00 | 23.49 | C |
| ATOM | 962 | CB | LYS | A | 66 | −6.770 | 57.952 | 30.182 | 1.00 | 25.72 | C |
| ATOM | 965 | CG | LYS | A | 66 | −7.570 | 56.786 | 29.647 | 1.00 | 28.00 | C |
| ATOM | 968 | CD | LYS | A | 66 | −6.737 | 55.758 | 28.714 | 1.00 | 29.97 | C |
| ATOM | 971 | CE | LYS | A | 66 | −7.418 | 54.358 | 28.638 | 1.00 | 30.91 | C |
| ATOM | 974 | NZ | LYS | A | 66 | −7.560 | 53.792 | 27.285 | 1.00 | 31.32 | N |
| ATOM | 978 | C | LYS | A | 66 | −6.901 | 58.312 | 32.524 | 1.00 | 23.01 | C |
| ATOM | 979 | O | LYS | A | 66 | −5.834 | 58.738 | 32.962 | 1.00 | 22.45 | O |
| ATOM | 980 | N | SER | A | 67 | −7.622 | 57.331 | 33.061 | 1.00 | 21.46 | N |
| ATOM | 982 | CA | SER | A | 67 | −7.136 | 56.739 | 34.323 | 1.00 | 21.32 | C |
| ATOM | 984 | CB | SER | A | 67 | −8.240 | 55.791 | 34.802 | 1.00 | 24.97 | C |
| ATOM | 987 | OG | SER | A | 67 | −7.681 | 55.050 | 35.861 | 1.00 | 27.07 | O |
| ATOM | 989 | C | SER | A | 67 | −5.787 | 55.980 | 34.098 | 1.00 | 18.02 | C |
| ATOM | 990 | O | SER | A | 67 | −5.592 | 55.247 | 33.116 | 1.00 | 19.08 | O |
| ATOM | 991 | N | GLY | A | 68 | −4.800 | 56.276 | 34.899 | 1.00 | 14.53 | N |
| ATOM | 993 | CA | GLY | A | 68 | −3.446 | 55.766 | 34.748 | 1.00 | 14.52 | C |
| ATOM | 996 | C | GLY | A | 68 | −2.518 | 56.476 | 33.766 | 1.00 | 11.70 | C |
| ATOM | 997 | O | GLY | A | 68 | −1.377 | 56.160 | 33.668 | 1.00 | 11.23 | O |
| ATOM | 998 | N | ARG | A | 69 | −2.997 | 57.470 | 33.062 | 1.00 | 12.48 | N |
| ATOM | 1000 | CA | ARG | A | 69 | −2.153 | 58.194 | 32.121 | 1.00 | 12.39 | C |
| ATOM | 1002 | CB | ARG | A | 69 | −3.080 | 58.611 | 30.974 | 1.00 | 10.55 | C |
| ATOM | 1005 | CG | ARG | A | 69 | −2.345 | 59.529 | 30.015 | 1.00 | 12.38 | C |
| ATOM | 1008 | CD | ARG | A | 69 | −3.161 | 60.232 | 28.957 | 1.00 | 13.48 | C |
| ATOM | 1011 | NE | ARG | A | 69 | −3.600 | 59.225 | 27.992 | 1.00 | 13.13 | N |
| ATOM | 1013 | CZ | ARG | A | 69 | −4.757 | 59.251 | 27.381 | 1.00 | 15.18 | C |
| ATOM | 1014 | NH1 | ARG | A | 69 | −5.675 | 60.230 | 27.544 | 1.00 | 13.45 | N |
| ATOM | 1017 | NH2 | ARG | A | 69 | −5.086 | 58.182 | 26.639 | 1.00 | 15.98 | N |
| ATOM | 1020 | C | ARG | A | 69 | −1.486 | 59.400 | 32.714 | 1.00 | 10.39 | C |
| ATOM | 1021 | O | ARG | A | 69 | −2.146 | 60.226 | 33.368 | 1.00 | 13.47 | O |
| ATOM | 1022 | N | THR | A | 70 | −0.184 | 59.494 | 32.567 | 1.00 | 9.24 | N |
| ATOM | 1024 | CA | THR | A | 70 | 0.531 | 60.610 | 32.964 | 1.00 | 10.73 | C |
| ATOM | 1026 | CB | THR | A | 70 | 1.641 | 60.202 | 33.945 | 1.00 | 15.19 | C |
| ATOM | 1028 | OG1 | THR | A | 70 | 2.094 | 58.921 | 33.584 | 1.00 | 18.14 | O |
| ATOM | 1030 | CG2 | THR | A | 70 | 1.016 | 59.865 | 35.338 | 1.00 | 17.68 | C |
| ATOM | 1034 | C | THR | A | 70 | 1.091 | 61.251 | 31.715 | 1.00 | 11.07 | C |

-continued

| | | | | | | | | | | |
|---|---|---|---|---|---|---|---|---|---|---|
| ATOM | 1035 | O | THR | A | 70 | 1.206 | 60.564 | 30.704 | 1.00 | 9.88 | O |
| ATOM | 1036 | N | TRP | A | 71 | 1.639 | 62.466 | 31.834 | 1.00 | 9.15 | N |
| ATOM | 1038 | CA | TRP | A | 71 | 2.141 | 63.188 | 30.673 | 1.00 | 9.48 | C |
| ATOM | 1040 | CB | TRP | A | 71 | 1.238 | 64.391 | 30.336 | 1.00 | 9.88 | C |
| ATOM | 1043 | CG | TRP | A | 71 | −0.079 | 64.100 | 29.723 | 1.00 | 10.12 | C |
| ATOM | 1044 | CD1 | TRP | A | 71 | −1.244 | 63.942 | 30.410 | 1.00 | 9.86 | C |
| ATOM | 1046 | NE1 | TRP | A | 71 | −2.246 | 63.682 | 29.513 | 1.00 | 13.26 | N |
| ATOM | 1048 | CE2 | TRP | A | 71 | −1.707 | 63.641 | 28.245 | 1.00 | 10.61 | C |
| ATOM | 1049 | CD2 | TRP | A | 71 | −0.379 | 63.953 | 28.342 | 1.00 | 8.98 | C |
| ATOM | 1050 | CE3 | TRP | A | 71 | 0.398 | 63.946 | 27.152 | 1.00 | 10.37 | C |
| ATOM | 1052 | CZ3 | TRP | A | 71 | −0.162 | 63.667 | 25.981 | 1.00 | 8.20 | C |
| ATOM | 1054 | CH2 | TRP | A | 71 | −1.485 | 63.405 | 25.876 | 1.00 | 10.45 | C |
| ATOM | 1056 | CZ2 | TRP | A | 71 | −2.293 | 63.358 | 27.006 | 1.00 | 11.14 | C |
| ATOM | 1058 | C | TRP | A | 71 | 3.527 | 63.726 | 31.033 | 1.00 | 10.14 | C |
| ATOM | 1059 | O | TRP | A | 71 | 3.738 | 64.165 | 32.188 | 1.00 | 8.24 | O |
| ATOM | 1060 | N | ARG | A | 72 | 4.385 | 63.889 | 30.029 | 1.00 | 8.38 | N |
| ATOM | 1062 | CA | ARG | A | 72 | 5.687 | 64.373 | 30.238 | 1.00 | 9.32 | C |
| ATOM | 1064 | CB | ARG | A | 72 | 6.717 | 63.216 | 30.167 | 1.00 | 11.31 | C |
| ATOM | 1067 | CG | ARG | A | 72 | 6.993 | 62.457 | 31.497 | 1.00 | 13.27 | C |
| ATOM | 1070 | CD | ARG | A | 72 | 7.894 | 61.261 | 31.445 | 1.00 | 13.70 | C |
| ATOM | 1073 | NE | ARG | A | 72 | 7.765 | 60.444 | 32.612 | 1.00 | 16.16 | N |
| ATOM | 1075 | CZ | ARG | A | 72 | 8.301 | 60.753 | 33.805 | 1.00 | 20.44 | C |
| ATOM | 1076 | NH1 | ARG | A | 72 | 9.077 | 61.831 | 33.985 | 1.00 | 17.83 | N |
| ATOM | 1079 | NH2 | ARG | A | 72 | 8.008 | 60.008 | 34.861 | 1.00 | 21.24 | N |
| ATOM | 1082 | C | ARG | A | 72 | 5.905 | 65.353 | 29.118 | 1.00 | 10.57 | C |
| ATOM | 1083 | O | ARG | A | 72 | 5.276 | 65.342 | 28.063 | 1.00 | 12.04 | O |
| ATOM | 1084 | N | GLU | A | 73 | 6.918 | 66.176 | 29.292 | 1.00 | 12.14 | N |
| ATOM | 1086 | CA | GLU | A | 73 | 7.159 | 67.189 | 28.257 | 1.00 | 12.34 | C |
| ATOM | 1088 | CB | GLU | A | 73 | 6.705 | 68.554 | 28.815 | 1.00 | 13.21 | C |
| ATOM | 1091 | CG | GLU | A | 73 | 7.474 | 68.977 | 30.056 | 1.00 | 11.26 | C |
| ATOM | 1094 | CD | GLU | A | 73 | 7.316 | 70.435 | 30.333 | 1.00 | 12.31 | C |
| ATOM | 1095 | OE1 | GLU | A | 73 | 7.794 | 71.274 | 29.566 | 1.00 | 14.70 | O |
| ATOM | 1096 | OE2 | GLU | A | 73 | 6.628 | 70.788 | 31.316 | 1.00 | 17.26 | O |
| ATOM | 1097 | C | GLU | A | 73 | 8.621 | 67.330 | 27.931 | 1.00 | 11.97 | C |
| ATOM | 1098 | O | GLU | A | 73 | 9.498 | 66.851 | 28.673 | 1.00 | 10.83 | O |
| ATOM | 1099 | N | ALA | A | 74 | 8.920 | 67.876 | 26.764 | 1.00 | 11.65 | N |
| ATOM | 1101 | CA | ALA | A | 74 | 10.303 | 68.128 | 26.423 | 1.00 | 9.14 | C |
| ATOM | 1103 | CB | ALA | A | 74 | 10.934 | 67.030 | 25.740 | 1.00 | 7.95 | C |
| ATOM | 1107 | C | ALA | A | 74 | 10.313 | 69.384 | 25.559 | 1.00 | 10.16 | C |
| ATOM | 1108 | O | ALA | A | 74 | 9.341 | 69.674 | 24.900 | 1.00 | 13.65 | O |
| ATOM | 1109 | N | ASP | A | 75 | 11.402 | 70.174 | 25.667 | 1.00 | 9.31 | N |
| ATOM | 1111 | CA | ASP | A | 75 | 11.577 | 71.351 | 24.833 | 1.00 | 8.31 | C |
| ATOM | 1113 | CB | ASP | A | 75 | 12.737 | 72.217 | 25.364 | 1.00 | 8.64 | C |
| ATOM | 1116 | CG | ASP | A | 75 | 12.404 | 72.980 | 26.649 | 1.00 | 9.50 | C |
| ATOM | 1117 | OD1 | ASP | A | 75 | 11.471 | 72.519 | 27.347 | 1.00 | 11.90 | O |
| ATOM | 1118 | OD2 | ASP | A | 75 | 13.015 | 74.057 | 26.968 | 1.00 | 14.38 | O |
| ATOM | 1119 | C | ASP | A | 75 | 11.904 | 70.993 | 23.414 | 1.00 | 7.79 | C |
| ATOM | 1120 | O | ASP | A | 75 | 12.755 | 70.147 | 23.183 | 1.00 | 8.59 | O |
| ATOM | 1121 | N | ILE | A | 76 | 11.279 | 71.673 | 22.447 | 1.00 | 11.70 | N |
| ATOM | 1123 | CA | ILE | A | 76 | 11.618 | 71.533 | 21.068 | 1.00 | 11.46 | C |
| ATOM | 1125 | CB | ILE | A | 76 | 10.285 | 71.222 | 20.407 | 1.00 | 12.87 | C |
| ATOM | 1127 | CG1 | ILE | A | 76 | 9.829 | 69.860 | 20.914 | 1.00 | 13.71 | C |
| ATOM | 1130 | CD1 | ILE | A | 76 | 10.590 | 68.697 | 20.238 | 1.00 | 11.84 | C |
| ATOM | 1134 | CG2 | ILE | A | 76 | 10.407 | 71.190 | 18.939 | 1.00 | 12.63 | C |
| ATOM | 1138 | C | ILE | A | 76 | 12.130 | 72.855 | 20.595 | 1.00 | 11.92 | C |
| ATOM | 1139 | O | ILE | A | 76 | 11.713 | 73.953 | 21.039 | 1.00 | 11.71 | O |
| ATOM | 1140 | N | ASN | A | 77 | 12.929 | 72.701 | 19.563 | 1.00 | 10.75 | N |
| ATOM | 1142 | CA | ASN | A | 77 | 13.606 | 73.727 | 18.759 | 1.00 | 11.46 | C |
| ATOM | 1144 | CB | ASN | A | 77 | 12.614 | 74.609 | 18.043 | 1.00 | 12.26 | C |
| ATOM | 1147 | CG | ASN | A | 77 | 11.806 | 73.898 | 17.003 | 1.00 | 11.68 | C |
| ATOM | 1148 | OD1 | ASN | A | 77 | 12.299 | 73.103 | 16.183 | 1.00 | 12.28 | O |
| ATOM | 1149 | ND2 | ASN | A | 77 | 10.549 | 74.329 | 16.919 | 1.00 | 11.36 | N |
| ATOM | 1152 | C | ASN | A | 77 | 14.607 | 74.614 | 19.557 | 1.00 | 11.79 | C |
| ATOM | 1153 | O | ASN | A | 77 | 14.834 | 75.788 | 19.262 | 1.00 | 15.08 | O |
| ATOM | 1154 | N | TYR | A | 78 | 15.059 | 74.083 | 20.655 | 1.00 | 8.82 | N |
| ATOM | 1156 | CA | TYR | A | 78 | 15.853 | 74.919 | 21.572 | 1.00 | 12.79 | C |
| ATOM | 1158 | CB | TYR | A | 78 | 15.783 | 74.407 | 23.024 | 1.00 | 11.72 | C |
| ATOM | 1161 | CG | TYR | A | 78 | 16.794 | 75.115 | 23.878 | 1.00 | 12.22 | C |
| ATOM | 1162 | CD1 | TYR | A | 78 | 16.509 | 76.414 | 24.352 | 1.00 | 12.36 | C |
| ATOM | 1164 | CE1 | TYR | A | 78 | 17.467 | 77.153 | 25.060 | 1.00 | 9.98 | C |
| ATOM | 1166 | CZ | TYR | A | 78 | 18.672 | 76.533 | 25.448 | 1.00 | 10.27 | C |
| ATOM | 1167 | OH | TYR | A | 78 | 19.622 | 77.324 | 26.132 | 1.00 | 5.54 | O |
| ATOM | 1169 | CE2 | TYR | A | 78 | 18.975 | 75.269 | 24.957 | 1.00 | 10.03 | C |
| ATOM | 1171 | CD2 | TYR | A | 78 | 17.993 | 74.516 | 24.210 | 1.00 | 10.21 | C |
| ATOM | 1173 | C | TYR | A | 78 | 17.252 | 74.731 | 21.065 | 1.00 | 12.05 | C |
| ATOM | 1174 | O | TYR | A | 78 | 17.672 | 73.633 | 20.748 | 1.00 | 13.73 | O |
| ATOM | 1175 | N | THR | A | 79 | 18.004 | 75.793 | 20.946 | 1.00 | 13.40 | N |
| ATOM | 1177 | CA | THR | A | 79 | 19.414 | 75.608 | 20.674 | 1.00 | 14.31 | C |
| ATOM | 1179 | CB | THR | A | 79 | 19.869 | 76.190 | 19.342 | 1.00 | 17.06 | C |
| ATOM | 1181 | OG1 | THR | A | 79 | 19.411 | 77.531 | 19.282 | 1.00 | 19.07 | O |

-continued

| | | | | | | | | | | | |
|---|---|---|---|---|---|---|---|---|---|---|---|
| ATOM | 1183 | CG2 | THR | A | 79 | 19.086 | 75.686 | 18.246 | 1.00 | 17.91 | C |
| ATOM | 1187 | C | THR | A | 79 | 20.225 | 76.294 | 21.792 | 1.00 | 15.43 | C |
| ATOM | 1188 | O | THR | A | 79 | 21.186 | 75.669 | 22.306 | 1.00 | 10.46 | O |
| ATOM | 1189 | N | SER | A | 80 | 19.972 | 77.563 | 22.081 | 1.00 | 15.52 | N |
| ATOM | 1191 | CA | SER | A | 80 | 20.640 | 78.312 | 23.169 | 1.00 | 12.87 | C |
| ATOM | 1193 | CB | SER | A | 80 | 21.973 | 78.925 | 22.719 | 1.00 | 15.98 | C |
| ATOM | 1196 | OG | SER | A | 80 | 21.837 | 79.840 | 21.699 | 1.00 | 14.14 | O |
| ATOM | 1198 | C | SER | A | 80 | 19.864 | 79.500 | 23.677 | 1.00 | 12.72 | C |
| ATOM | 1199 | O | SER | A | 80 | 18.930 | 79.946 | 22.960 | 1.00 | 10.08 | O |
| ATOM | 1200 | N | GLY | A | 81 | 20.375 | 80.144 | 24.745 | 1.00 | 10.93 | N |
| ATOM | 1202 | CA | GLY | A | 81 | 19.645 | 81.253 | 25.352 | 1.00 | 13.73 | C |
| ATOM | 1205 | C | GLY | A | 81 | 18.495 | 80.776 | 26.227 | 1.00 | 12.83 | C |
| ATOM | 1206 | O | GLY | A | 81 | 18.544 | 79.680 | 26.738 | 1.00 | 13.82 | O |
| ATOM | 1207 | N | PHE | A | 82 | 17.545 | 81.650 | 26.484 | 1.00 | 13.00 | N |
| ATOM | 1209 | CA | PHE | A | 82 | 16.395 | 81.365 | 27.314 | 1.00 | 13.93 | C |
| ATOM | 1211 | CB | PHE | A | 82 | 15.515 | 82.598 | 27.558 | 1.00 | 14.16 | C |
| ATOM | 1214 | CG | PHE | A | 82 | 16.223 | 83.611 | 28.473 | 1.00 | 17.70 | C |
| ATOM | 1215 | CD1 | PHE | A | 82 | 16.312 | 83.392 | 29.863 | 1.00 | 16.63 | C |
| ATOM | 1217 | CE1 | PHE | A | 82 | 16.977 | 84.300 | 30.671 | 1.00 | 18.98 | C |
| ATOM | 1219 | CZ | PHE | A | 82 | 17.696 | 85.376 | 30.113 | 1.00 | 18.91 | C |
| ATOM | 1221 | CE2 | PHE | A | 82 | 17.645 | 85.629 | 28.745 | 1.00 | 19.29 | C |
| ATOM | 1223 | CD2 | PHE | A | 82 | 16.931 | 84.676 | 27.914 | 1.00 | 20.12 | C |
| ATOM | 1225 | C | PHE | A | 82 | 15.618 | 80.300 | 26.564 | 1.00 | 14.38 | C |
| ATOM | 1226 | O | PHE | A | 82 | 15.784 | 80.111 | 25.357 | 1.00 | 11.55 | O |
| ATOM | 1227 | N | ARG | A | 83 | 14.815 | 79.548 | 27.299 | 1.00 | 14.65 | N |
| ATOM | 1229 | CA | ARG | A | 83 | 13.906 | 78.568 | 26.648 | 1.00 | 13.87 | C |
| ATOM | 1231 | CB | ARG | A | 83 | 13.285 | 77.699 | 27.778 | 1.00 | 14.41 | C |
| ATOM | 1234 | CG | ARG | A | 83 | 14.287 | 76.834 | 28.511 | 1.00 | 12.33 | C |
| ATOM | 1237 | CD | ARG | A | 83 | 13.749 | 76.304 | 29.814 | 1.00 | 14.68 | C |
| ATOM | 1240 | NE | ARG | A | 83 | 12.799 | 75.237 | 29.520 | 1.00 | 15.04 | N |
| ATOM | 1242 | CZ | ARG | A | 83 | 11.848 | 74.782 | 30.335 | 1.00 | 18.82 | C |
| ATOM | 1243 | NH1 | ARG | A | 83 | 11.698 | 75.249 | 31.591 | 1.00 | 19.87 | N |
| ATOM | 1246 | NH2 | ARG | A | 83 | 11.000 | 73.846 | 29.896 | 1.00 | 14.39 | N |
| ATOM | 1249 | C | ARG | A | 83 | 12.865 | 79.267 | 25.827 | 1.00 | 12.96 | C |
| ATOM | 1250 | O | ARG | A | 83 | 12.495 | 80.387 | 26.099 | 1.00 | 10.42 | O |
| ATOM | 1251 | N | ASN | A | 84 | 12.289 | 78.576 | 24.851 | 1.00 | 13.03 | N |
| ATOM | 1253 | CA | ASN | A | 84 | 11.323 | 79.134 | 23.959 | 1.00 | 13.01 | C |
| ATOM | 1255 | CB | ASN | A | 84 | 11.742 | 78.687 | 22.560 | 1.00 | 12.53 | C |
| ATOM | 1258 | CG | ASN | A | 84 | 11.750 | 77.170 | 22.374 | 1.00 | 12.31 | C |
| ATOM | 1259 | OD1 | ASN | A | 84 | 11.008 | 76.464 | 23.075 | 1.00 | 9.23 | O |
| ATOM | 1260 | ND2 | ASN | A | 84 | 12.484 | 76.678 | 21.338 | 1.00 | 10.53 | N |
| ATOM | 1263 | C | ASN | A | 84 | 9.966 | 78.652 | 24.436 | 1.00 | 11.61 | C |
| ATOM | 1264 | O | ASN | A | 84 | 9.901 | 78.122 | 25.523 | 1.00 | 10.55 | O |
| ATOM | 1265 | N | SER | A | 85 | 8.981 | 78.746 | 23.580 | 1.00 | 11.49 | N |
| ATOM | 1267 | CA | SER | A | 85 | 7.587 | 78.334 | 23.820 | 1.00 | 12.14 | C |
| ATOM | 1269 | CB | SER | A | 85 | 6.672 | 79.458 | 23.268 | 1.00 | 12.72 | C |
| ATOM | 1272 | OG | SER | A | 85 | 6.979 | 80.668 | 23.991 | 1.00 | 15.95 | O |
| ATOM | 1274 | C | SER | A | 85 | 7.183 | 76.990 | 23.312 | 1.00 | 10.02 | C |
| ATOM | 1275 | O | SER | A | 85 | 6.000 | 76.636 | 23.266 | 1.00 | 12.61 | O |
| ATOM | 1276 | N | ASP | A | 86 | 8.124 | 76.267 | 22.739 | 1.00 | 10.38 | N |
| ATOM | 1278 | CA | ASP | A | 86 | 7.807 | 75.024 | 21.992 | 1.00 | 12.12 | C |
| ATOM | 1280 | CB | ASP | A | 86 | 8.722 | 74.836 | 20.753 | 1.00 | 10.98 | C |
| ATOM | 1283 | CG | ASP | A | 86 | 8.434 | 75.862 | 19.673 | 1.00 | 11.98 | C |
| ATOM | 1284 | OD1 | ASP | A | 86 | 7.319 | 76.457 | 19.720 | 1.00 | 17.86 | O |
| ATOM | 1285 | OD2 | ASP | A | 86 | 9.278 | 76.215 | 18.820 | 1.00 | 15.19 | O |
| ATOM | 1286 | C | ASP | A | 86 | 8.001 | 73.810 | 22.869 | 1.00 | 13.31 | C |
| ATOM | 1287 | O | ASP | A | 86 | 9.112 | 73.636 | 23.348 | 1.00 | 11.28 | O |
| ATOM | 1288 | N | ARG | A | 87 | 7.014 | 72.937 | 23.016 | 1.00 | 12.84 | N |
| ATOM | 1290 | CA | ARG | A | 87 | 7.255 | 71.747 | 23.867 | 1.00 | 12.00 | C |
| ATOM | 1292 | CB | ARG | A | 87 | 6.505 | 71.952 | 25.193 | 1.00 | 11.15 | C |
| ATOM | 1295 | CG | ARG | A | 87 | 6.899 | 73.103 | 26.000 | 1.00 | 12.23 | C |
| ATOM | 1298 | CD | ARG | A | 87 | 8.318 | 72.972 | 26.588 | 1.00 | 12.58 | C |
| ATOM | 1301 | NE | ARG | A | 87 | 8.677 | 74.154 | 27.329 | 1.00 | 11.57 | N |
| ATOM | 1303 | CZ | ARG | A | 87 | 9.343 | 75.184 | 26.833 | 1.00 | 12.24 | C |
| ATOM | 1304 | NH1 | ARG | A | 87 | 9.763 | 75.273 | 25.583 | 1.00 | 10.06 | N |
| ATOM | 1307 | NH2 | ARG | A | 87 | 9.599 | 76.167 | 27.669 | 1.00 | 14.03 | N |
| ATOM | 1310 | C | ARG | A | 87 | 6.512 | 70.600 | 23.165 | 1.00 | 11.13 | C |
| ATOM | 1311 | O | ARG | A | 87 | 5.416 | 70.798 | 22.610 | 1.00 | 11.33 | O |
| ATOM | 1312 | N | ILE | A | 88 | 7.093 | 69.399 | 23.231 | 1.00 | 13.28 | N |
| ATOM | 1314 | CA | ILE | A | 88 | 6.374 | 68.184 | 22.818 | 1.00 | 11.08 | C |
| ATOM | 1316 | CB | ILE | A | 88 | 7.271 | 67.247 | 22.097 | 1.00 | 11.24 | C |
| ATOM | 1318 | CG1 | ILE | A | 88 | 6.492 | 66.079 | 21.388 | 1.00 | 12.25 | C |
| ATOM | 1321 | CD1 | ILE | A | 88 | 7.496 | 65.321 | 20.368 | 1.00 | 12.64 | C |
| ATOM | 1325 | CG2 | ILE | A | 88 | 8.343 | 66.729 | 22.879 | 1.00 | 12.59 | C |
| ATOM | 1329 | C | ILE | A | 88 | 5.833 | 67.536 | 24.067 | 1.00 | 11.22 | C |
| ATOM | 1330 | O | ILE | A | 88 | 6.473 | 67.617 | 25.116 | 1.00 | 10.61 | O |
| ATOM | 1331 | N | LEU | A | 89 | 4.607 | 67.018 | 24.031 | 1.00 | 11.36 | N |
| ATOM | 1333 | CA | LEU | A | 89 | 4.013 | 66.418 | 25.233 | 1.00 | 7.65 | C |
| ATOM | 1335 | CB | LEU | A | 89 | 2.676 | 67.053 | 25.495 | 1.00 | 10.94 | C |
| ATOM | 1338 | CG | LEU | A | 89 | 2.648 | 68.432 | 26.158 | 1.00 | 13.79 | C |

-continued

| | | | | | | | | | | |
|---|---|---|---|---|---|---|---|---|---|---|
| ATOM | 1340 | CD1 | LEU | A | 89 | 3.199 | 68.234 | 27.549 | 1.00 | 10.56 | C |
| ATOM | 1344 | CD2 | LEU | A | 89 | 3.612 | 69.415 | 25.636 | 1.00 | 15.11 | C |
| ATOM | 1348 | C | LEU | A | 89 | 3.710 | 64.952 | 24.885 | 1.00 | 8.75 | C |
| ATOM | 1349 | O | LEU | A | 89 | 3.147 | 64.655 | 23.793 | 1.00 | 9.80 | O |
| ATOM | 1350 | N | TYR | A | 90 | 4.136 | 64.000 | 25.721 | 1.00 | 9.87 | N |
| ATOM | 1352 | CA | TYR | A | 90 | 3.927 | 62.607 | 25.370 | 1.00 | 7.26 | C |
| ATOM | 1354 | CB | TYR | A | 90 | 5.260 | 62.014 | 24.875 | 1.00 | 8.09 | C |
| ATOM | 1357 | CG | TYR | A | 90 | 6.383 | 62.142 | 25.902 | 1.00 | 7.48 | C |
| ATOM | 1358 | CD1 | TYR | A | 90 | 7.188 | 63.276 | 25.937 | 1.00 | 10.00 | C |
| ATOM | 1360 | CE1 | TYR | A | 90 | 8.334 | 63.339 | 26.814 | 1.00 | 9.09 | C |
| ATOM | 1362 | CZ | TYR | A | 90 | 8.740 | 62.238 | 27.462 | 1.00 | 10.59 | C |
| ATOM | 1363 | OH | TYR | A | 90 | 9.855 | 62.410 | 28.240 | 1.00 | 8.93 | O |
| ATOM | 1365 | CE2 | TYR | A | 90 | 7.993 | 61.064 | 27.410 | 1.00 | 9.27 | C |
| ATOM | 1367 | CD2 | TYR | A | 90 | 6.880 | 61.023 | 26.507 | 1.00 | 8.29 | C |
| ATOM | 1369 | C | TYR | A | 90 | 3.343 | 61.906 | 26.563 | 1.00 | 6.89 | C |
| ATOM | 1370 | O | TYR | A | 90 | 3.700 | 62.186 | 27.732 | 1.00 | 6.04 | O |
| ATOM | 1371 | N | SER | A | 91 | 2.368 | 61.039 | 26.288 | 1.00 | 6.48 | N |
| ATOM | 1373 | CA | SER | A | 91 | 1.711 | 60.417 | 27.421 | 1.00 | 7.31 | C |
| ATOM | 1375 | CB | SER | A | 91 | 0.253 | 60.198 | 27.184 | 1.00 | 8.94 | C |
| ATOM | 1378 | OG | SER | A | 91 | 0.034 | 59.301 | 26.095 | 1.00 | 8.89 | O |
| ATOM | 1380 | C | SER | A | 91 | 2.252 | 59.043 | 27.718 | 1.00 | 8.33 | C |
| ATOM | 1381 | O | SER | A | 91 | 3.011 | 58.478 | 26.933 | 1.00 | 11.09 | O |
| ATOM | 1382 | N | SER | A | 92 | 1.899 | 58.477 | 28.863 | 1.00 | 9.72 | N |
| ATOM | 1384 | CA | SER | A | 92 | 2.390 | 57.161 | 29.299 | 1.00 | 9.97 | C |
| ATOM | 1386 | CB | SER | A | 92 | 2.074 | 56.942 | 30.818 | 1.00 | 11.10 | C |
| ATOM | 1389 | OG | SER | A | 92 | 0.656 | 57.088 | 30.900 | 1.00 | 8.24 | O |
| ATOM | 1391 | C | SER | A | 92 | 1.817 | 56.051 | 28.374 | 1.00 | 11.05 | C |
| ATOM | 1392 | O | SER | A | 92 | 2.383 | 55.007 | 28.335 | 1.00 | 10.47 | O |
| ATOM | 1393 | N | ASP | A | 93 | 0.798 | 56.316 | 27.543 | 1.00 | 9.26 | N |
| ATOM | 1395 | CA | ASP | A | 93 | 0.286 | 55.419 | 26.559 | 1.00 | 11.54 | C |
| ATOM | 1397 | CB | ASP | A | 93 | −1.228 | 55.144 | 26.689 | 1.00 | 11.21 | C |
| ATOM | 1400 | CG | ASP | A | 93 | −2.095 | 56.428 | 26.740 | 1.00 | 12.30 | C |
| ATOM | 1401 | OD1 | ASP | A | 93 | −3.343 | 56.275 | 26.563 | 1.00 | 11.48 | O |
| ATOM | 1402 | OD2 | ASP | A | 93 | −1.664 | 57.550 | 27.003 | 1.00 | 11.90 | O |
| ATOM | 1403 | C | ASP | A | 93 | 0.673 | 55.946 | 25.176 | 1.00 | 10.07 | C |
| ATOM | 1404 | O | ASP | A | 93 | 0.104 | 55.590 | 24.162 | 1.00 | 11.29 | O |
| ATOM | 1405 | N | TRP | A | 94 | 1.674 | 56.837 | 25.143 | 1.00 | 11.35 | N |
| ATOM | 1407 | CA | TRP | A | 94 | 2.197 | 57.300 | 23.899 | 1.00 | 10.73 | C |
| ATOM | 1409 | CB | TRP | A | 94 | 3.016 | 56.177 | 23.212 | 1.00 | 11.67 | C |
| ATOM | 1412 | CG | TRP | A | 94 | 3.921 | 55.528 | 24.202 | 1.00 | 11.04 | C |
| ATOM | 1413 | CD1 | TRP | A | 94 | 3.591 | 54.410 | 25.005 | 1.00 | 7.89 | C |
| ATOM | 1415 | NE1 | TRP | A | 94 | 4.628 | 54.240 | 25.903 | 1.00 | 10.25 | N |
| ATOM | 1417 | CE2 | TRP | A | 94 | 5.574 | 55.213 | 25.732 | 1.00 | 7.45 | C |
| ATOM | 1418 | CD2 | TRP | A | 94 | 5.114 | 56.099 | 24.764 | 1.00 | 7.97 | C |
| ATOM | 1419 | CE3 | TRP | A | 94 | 5.941 | 57.157 | 24.388 | 1.00 | 10.30 | C |
| ATOM | 1421 | CZ3 | TRP | A | 94 | 7.056 | 57.427 | 25.166 | 1.00 | 12.75 | C |
| ATOM | 1423 | CH2 | TRP | A | 94 | 7.458 | 56.540 | 26.199 | 1.00 | 11.02 | C |
| ATOM | 1425 | CZ2 | TRP | A | 94 | 6.655 | 55.477 | 26.550 | 1.00 | 7.10 | C |
| ATOM | 1427 | C | TRP | A | 94 | 1.474 | 58.105 | 22.846 | 1.00 | 10.80 | C |
| ATOM | 1428 | O | TRP | A | 94 | 1.820 | 57.930 | 21.666 | 1.00 | 12.07 | O |
| ATOM | 1429 | N | LEU | A | 95 | 0.493 | 58.902 | 23.240 | 1.00 | 12.80 | N |
| ATOM | 1431 | CA | LEU | A | 95 | −0.057 | 59.966 | 22.440 | 1.00 | 11.32 | C |
| ATOM | 1433 | CB | LEU | A | 95 | −1.187 | 60.616 | 23.203 | 1.00 | 12.25 | C |
| ATOM | 1436 | CG | LEU | A | 95 | −2.329 | 59.624 | 23.549 | 1.00 | 13.74 | C |
| ATOM | 1438 | CD1 | LEU | A | 95 | −3.386 | 60.269 | 24.382 | 1.00 | 15.01 | C |
| ATOM | 1442 | CD2 | LEU | A | 95 | −2.918 | 59.103 | 22.351 | 1.00 | 12.90 | C |
| ATOM | 1446 | C | LEU | A | 95 | 1.050 | 61.020 | 22.438 | 1.00 | 12.56 | C |
| ATOM | 1447 | O | LEU | A | 95 | 1.802 | 61.072 | 23.397 | 1.00 | 11.37 | O |
| ATOM | 1448 | N | ILE | A | 96 | 1.130 | 61.821 | 21.382 | 1.00 | 10.65 | N |
| ATOM | 1450 | CA | ILE | A | 96 | 2.115 | 62.885 | 21.249 | 1.00 | 10.60 | C |
| ATOM | 1452 | CB | ILE | A | 96 | 3.185 | 62.608 | 20.202 | 1.00 | 9.27 | C |
| ATOM | 1454 | CG1 | ILE | A | 96 | 3.887 | 61.268 | 20.383 | 1.00 | 9.17 | C |
| ATOM | 1457 | CD1 | ILE | A | 96 | 4.677 | 61.085 | 21.606 | 1.00 | 6.17 | C |
| ATOM | 1461 | CG2 | ILE | A | 96 | 4.263 | 63.708 | 20.223 | 1.00 | 10.74 | C |
| ATOM | 1465 | C | ILE | A | 96 | 1.365 | 64.113 | 20.885 | 1.00 | 13.34 | C |
| ATOM | 1466 | O | ILE | A | 96 | 0.580 | 64.133 | 19.898 | 1.00 | 11.17 | O |
| ATOM | 1467 | N | TYR | A | 97 | 1.507 | 65.142 | 21.698 | 1.00 | 10.99 | N |
| ATOM | 1469 | CA | TYR | A | 97 | 0.948 | 66.448 | 21.389 | 1.00 | 10.40 | C |
| ATOM | 1471 | CB | TYR | A | 97 | −0.071 | 66.827 | 22.457 | 1.00 | 9.13 | C |
| ATOM | 1474 | CG | TYR | A | 97 | −1.476 | 66.205 | 22.338 | 1.00 | 11.66 | C |
| ATOM | 1475 | CD1 | TYR | A | 97 | −1.685 | 64.842 | 22.516 | 1.00 | 10.97 | C |
| ATOM | 1477 | CE1 | TYR | A | 97 | −2.954 | 64.364 | 22.408 | 1.00 | 10.97 | C |
| ATOM | 1479 | CZ | TYR | A | 97 | −4.022 | 65.180 | 22.159 | 1.00 | 9.89 | C |
| ATOM | 1480 | OH | TYR | A | 97 | −5.198 | 64.549 | 22.083 | 1.00 | 12.29 | O |
| ATOM | 1482 | CE2 | TYR | A | 97 | −3.858 | 66.528 | 21.939 | 1.00 | 8.64 | C |
| ATOM | 1484 | CD2 | TYR | A | 97 | −2.565 | 66.987 | 21.999 | 1.00 | 9.70 | C |
| ATOM | 1486 | C | TYR | A | 97 | 2.111 | 67.484 | 21.432 | 1.00 | 9.53 | C |
| ATOM | 1487 | O | TYR | A | 97 | 3.248 | 67.144 | 21.660 | 1.00 | 14.36 | O |
| ATOM | 1488 | N | LYS | A | 98 | 1.871 | 68.645 | 20.840 | 1.00 | 11.28 | N |
| ATOM | 1490 | CA | LYS | A | 98 | 2.723 | 69.809 | 20.826 | 1.00 | 8.69 | C |

-continued

| | | | | | | | | | | |
|---|---|---|---|---|---|---|---|---|---|---|
| ATOM | 1492 | CB | LYS | A | 98 | 3.322 | 70.137 | 19.432 | 1.00 | 10.99 | C |
| ATOM | 1495 | CG | LYS | A | 98 | 2.287 | 70.453 | 18.429 | 1.00 | 11.17 | C |
| ATOM | 1498 | CD | LYS | A | 98 | 2.737 | 70.559 | 17.046 | 1.00 | 12.80 | C |
| ATOM | 1501 | CE | LYS | A | 98 | 3.596 | 71.735 | 16.780 | 1.00 | 14.37 | C |
| ATOM | 1504 | NZ | LYS | A | 98 | 3.792 | 72.136 | 15.359 | 1.00 | 11.80 | N |
| ATOM | 1508 | C | LYS | A | 98 | 1.962 | 71.062 | 21.287 | 1.00 | 9.67 | C |
| ATOM | 1509 | O | LYS | A | 98 | 0.705 | 71.178 | 21.200 | 1.00 | 10.69 | O |
| ATOM | 1510 | N | THR | A | 99 | 2.802 | 71.949 | 21.791 | 1.00 | 11.10 | N |
| ATOM | 1512 | CA | THR | A | 99 | 2.478 | 73.322 | 22.083 | 1.00 | 11.12 | C |
| ATOM | 1514 | CB | THR | A | 99 | 2.279 | 73.630 | 23.530 | 1.00 | 11.10 | C |
| ATOM | 1516 | OG1 | THR | A | 99 | 1.848 | 75.009 | 23.663 | 1.00 | 12.60 | O |
| ATOM | 1518 | CG2 | THR | A | 99 | 3.664 | 73.409 | 24.231 | 1.00 | 14.35 | C |
| ATOM | 1522 | C | THR | A | 99 | 3.531 | 74.204 | 21.466 | 1.00 | 9.24 | C |
| ATOM | 1523 | O | THR | A | 99 | 4.699 | 73.886 | 21.462 | 1.00 | 12.21 | O |
| ATOM | 1524 | N | THR | A | 100 | 3.142 | 75.275 | 20.791 | 1.00 | 10.21 | N |
| ATOM | 1526 | CA | THR | A | 100 | 4.085 | 76.343 | 20.391 | 1.00 | 7.68 | C |
| ATOM | 1528 | CB | THR | A | 100 | 4.035 | 76.517 | 18.912 | 1.00 | 8.62 | C |
| ATOM | 1530 | OG1 | THR | A | 100 | 2.746 | 76.881 | 18.484 | 1.00 | 6.34 | O |
| ATOM | 1532 | CG2 | THR | A | 100 | 4.131 | 75.258 | 18.267 | 1.00 | 10.31 | C |
| ATOM | 1536 | C | THR | A | 100 | 3.816 | 77.679 | 21.115 | 1.00 | 10.03 | C |
| ATOM | 1537 | O | THR | A | 100 | 4.344 | 78.734 | 20.713 | 1.00 | 8.97 | O |
| ATOM | 1538 | N | ASP | A | 101 | 2.888 | 77.679 | 22.099 | 1.00 | 12.17 | N |
| ATOM | 1540 | CA | ASP | A | 101 | 2.480 | 78.926 | 22.827 | 1.00 | 11.94 | C |
| ATOM | 1542 | CB | ASP | A | 101 | 1.111 | 79.438 | 22.366 | 1.00 | 12.53 | C |
| ATOM | 1545 | CG | ASP | A | 101 | 0.017 | 78.428 | 22.586 | 1.00 | 12.67 | C |
| ATOM | 1546 | OD1 | ASP | A | 101 | 0.248 | 77.401 | 23.288 | 1.00 | 8.36 | O |
| ATOM | 1547 | OD2 | ASP | A | 101 | −1.154 | 78.592 | 22.146 | 1.00 | 16.13 | O |
| ATOM | 1548 | C | ASP | A | 101 | 2.637 | 78.764 | 24.353 | 1.00 | 12.93 | C |
| ATOM | 1549 | O | ASP | A | 101 | 1.823 | 79.275 | 25.139 | 1.00 | 13.24 | O |
| ATOM | 1550 | N | ALA | A | 102 | 3.625 | 77.957 | 24.771 | 1.00 | 11.21 | N |
| ATOM | 1552 | CA | ALA | A | 102 | 3.961 | 77.793 | 26.197 | 1.00 | 13.13 | C |
| ATOM | 1554 | CB | ALA | A | 102 | 4.537 | 79.124 | 26.793 | 1.00 | 15.01 | C |
| ATOM | 1558 | C | ALA | A | 102 | 2.768 | 77.206 | 26.945 | 1.00 | 12.35 | C |
| ATOM | 1559 | O | ALA | A | 102 | 2.301 | 77.790 | 27.907 | 1.00 | 8.75 | O |
| ATOM | 1560 | N | TYR | A | 103 | 2.246 | 76.082 | 26.425 | 1.00 | 8.76 | N |
| ATOM | 1562 | CA | TYR | A | 103 | 1.140 | 75.333 | 27.104 | 1.00 | 12.19 | C |
| ATOM | 1564 | CB | TYR | A | 103 | 1.476 | 75.002 | 28.562 | 1.00 | 15.30 | C |
| ATOM | 1567 | CG | TYR | A | 103 | 2.919 | 74.643 | 28.825 | 1.00 | 14.89 | C |
| ATOM | 1568 | CD1 | TYR | A | 103 | 3.379 | 73.369 | 28.624 | 1.00 | 16.53 | C |
| ATOM | 1570 | CE1 | TYR | A | 103 | 4.731 | 73.030 | 28.872 | 1.00 | 15.54 | C |
| ATOM | 1572 | CZ | TYR | A | 103 | 5.578 | 73.972 | 29.301 | 1.00 | 14.65 | C |
| ATOM | 1573 | OH | TYR | A | 103 | 6.856 | 73.644 | 29.477 | 1.00 | 10.93 | O |
| ATOM | 1575 | CE2 | TYR | A | 103 | 5.166 | 75.245 | 29.529 | 1.00 | 17.37 | C |
| ATOM | 1577 | CD2 | TYR | A | 103 | 3.819 | 75.586 | 29.288 | 1.00 | 17.19 | C |
| ATOM | 1579 | C | TYR | A | 103 | −0.261 | 75.975 | 27.097 | 1.00 | 14.30 | C |
| ATOM | 1580 | O | TYR | A | 103 | −1.242 | 75.482 | 27.722 | 1.00 | 11.25 | O |
| ATOM | 1581 | N | GLN | A | 104 | −0.401 | 77.056 | 26.344 | 1.00 | 15.15 | N |
| ATOM | 1583 | CA | GLN | A | 104 | −1.727 | 77.638 | 26.300 | 1.00 | 16.77 | C |
| ATOM | 1585 | CB | GLN | A | 104 | −1.639 | 79.064 | 25.757 | 1.00 | 20.34 | C |
| ATOM | 1588 | CG | GLN | A | 104 | −0.796 | 80.074 | 26.634 | 1.00 | 25.22 | C |
| ATOM | 1591 | CD | GLN | A | 104 | −0.824 | 81.541 | 26.069 | 1.00 | 28.73 | C |
| ATOM | 1592 | OE1 | GLN | A | 104 | −1.846 | 82.229 | 26.191 | 1.00 | 29.45 | O |
| ATOM | 1593 | NE2 | GLN | A | 104 | 0.280 | 81.975 | 25.393 | 1.00 | 30.51 | N |
| ATOM | 1596 | C | GLN | A | 104 | −2.675 | 76.767 | 25.445 | 1.00 | 14.55 | C |
| ATOM | 1597 | O | GLN | A | 104 | −3.878 | 76.706 | 25.696 | 1.00 | 15.19 | O |
| ATOM | 1598 | N | THR | A | 105 | −2.185 | 76.259 | 24.328 | 1.00 | 12.62 | N |
| ATOM | 1600 | CA | THR | A | 105 | −3.004 | 75.402 | 23.422 | 1.00 | 11.08 | C |
| ATOM | 1602 | CB | THR | A | 105 | −3.509 | 76.107 | 22.187 | 1.00 | 10.97 | C |
| ATOM | 1604 | OG1 | THR | A | 105 | −2.423 | 76.595 | 21.389 | 1.00 | 11.27 | O |
| ATOM | 1606 | CG2 | THR | A | 105 | −4.288 | 77.422 | 22.549 | 1.00 | 11.24 | C |
| ATOM | 1610 | C | THR | A | 105 | −2.092 | 74.272 | 22.929 | 1.00 | 12.45 | C |
| ATOM | 1611 | O | THR | A | 105 | −0.851 | 74.392 | 22.878 | 1.00 | 11.77 | O |
| ATOM | 1612 | N | PHE | A | 106 | −2.745 | 73.162 | 22.581 | 1.00 | 12.46 | N |
| ATOM | 1614 | CA | PHE | A | 106 | −2.052 | 71.958 | 22.188 | 1.00 | 13.94 | C |
| ATOM | 1616 | CB | PHE | A | 106 | −2.241 | 70.958 | 23.300 | 1.00 | 15.04 | C |
| ATOM | 1619 | CG | PHE | A | 106 | −1.644 | 71.393 | 24.580 | 1.00 | 17.01 | C |
| ATOM | 1620 | CD1 | PHE | A | 106 | −0.348 | 71.055 | 24.876 | 1.00 | 17.25 | C |
| ATOM | 1622 | CE1 | PHE | A | 106 | 0.203 | 71.431 | 26.083 | 1.00 | 19.41 | C |
| ATOM | 1624 | CZ | PHE | A | 106 | −0.596 | 72.104 | 27.017 | 1.00 | 18.42 | C |
| ATOM | 1626 | CE2 | PHE | A | 106 | −1.924 | 72.363 | 26.748 | 1.00 | 17.27 | C |
| ATOM | 1628 | CD2 | PHE | A | 106 | −2.426 | 72.041 | 25.525 | 1.00 | 18.01 | C |
| ATOM | 1630 | C | PHE | A | 106 | −2.624 | 71.412 | 20.915 | 1.00 | 12.39 | C |
| ATOM | 1631 | O | PHE | A | 106 | −3.806 | 71.598 | 20.631 | 1.00 | 10.59 | O |
| ATOM | 1632 | N | THR | A | 107 | −1.790 | 70.681 | 20.182 | 1.00 | 8.23 | N |
| ATOM | 1634 | CA | THR | A | 107 | −2.252 | 70.110 | 18.939 | 1.00 | 8.80 | C |
| ATOM | 1636 | CB | THR | A | 107 | −1.544 | 70.769 | 17.737 | 1.00 | 8.29 | C |
| ATOM | 1638 | OG1 | THR | A | 107 | −1.941 | 72.116 | 17.663 | 1.00 | 6.57 | O |
| ATOM | 1640 | CG2 | THR | A | 107 | −1.888 | 70.188 | 16.328 | 1.00 | 9.11 | C |
| ATOM | 1644 | C | THR | A | 107 | −1.722 | 68.685 | 18.979 | 1.00 | 9.08 | C |
| ATOM | 1645 | O | THR | A | 107 | −0.526 | 68.448 | 19.214 | 1.00 | 8.70 | O |

-continued

| | | | | | | | | | | | |
|---|---|---|---|---|---|---|---|---|---|---|---|
| ATOM | 1646 | N | LYS | A | 108 | −2.644 | 67.752 | 18.641 | 1.00 | 7.72 | N |
| ATOM | 1648 | CA | LYS | A | 108 | −2.313 | 66.334 | 18.620 | 1.00 | 10.16 | C |
| ATOM | 1650 | CB | LYS | A | 108 | −3.567 | 65.422 | 18.581 | 1.00 | 9.16 | C |
| ATOM | 1653 | CG | LYS | A | 108 | −3.278 | 63.953 | 18.663 | 1.00 | 7.26 | C |
| ATOM | 1656 | CD | LYS | A | 108 | −4.645 | 63.226 | 18.826 | 1.00 | 8.61 | C |
| ATOM | 1659 | CE | LYS | A | 108 | −4.416 | 61.782 | 18.664 | 1.00 | 11.16 | C |
| ATOM | 1662 | NZ | LYS | A | 108 | −5.542 | 60.906 | 19.154 | 1.00 | 5.13 | N |
| ATOM | 1666 | C | LYS | A | 108 | −1.515 | 66.072 | 17.398 | 1.00 | 8.51 | C |
| ATOM | 1667 | O | LYS | A | 108 | −1.983 | 66.354 | 16.308 | 1.00 | 10.06 | O |
| ATOM | 1668 | N | ILE | A | 109 | −0.374 | 65.450 | 17.573 | 1.00 | 7.29 | N |
| ATOM | 1670 | CA | ILE | A | 109 | 0.458 | 65.093 | 16.441 | 1.00 | 10.46 | C |
| ATOM | 1672 | CB | ILE | A | 109 | 1.838 | 65.833 | 16.410 | 1.00 | 8.44 | C |
| ATOM | 1674 | CG1 | ILE | A | 109 | 2.710 | 65.557 | 17.634 | 1.00 | 10.16 | C |
| ATOM | 1677 | CD1 | ILE | A | 109 | 4.081 | 66.272 | 17.332 | 1.00 | 7.91 | C |
| ATOM | 1681 | CG2 | ILE | A | 109 | 1.599 | 67.357 | 16.199 | 1.00 | 12.74 | C |
| ATOM | 1685 | C | ILE | A | 109 | 0.773 | 63.629 | 16.184 | 1.00 | 12.02 | C |
| ATOM | 1686 | O | ILE | A | 109 | 1.414 | 63.338 | 15.178 | 1.00 | 8.52 | O |
| ATOM | 1687 | N | ARG | A | 110 | 0.572 | 62.794 | 17.193 | 1.00 | 13.26 | N |
| ATOM | 1689 | CA | ARG | A | 110 | 0.591 | 61.359 | 16.992 | 1.00 | 13.26 | C |
| ATOM | 1691 | CB | ARG | A | 110 | 1.890 | 60.663 | 17.316 | 1.00 | 11.90 | C |
| ATOM | 1694 | CG | ARG | A | 110 | 3.052 | 61.153 | 16.489 | 1.00 | 11.81 | C |
| ATOM | 1697 | CD | ARG | A | 110 | 3.152 | 60.822 | 15.016 | 1.00 | 9.75 | C |
| ATOM | 1700 | NE | ARG | A | 110 | 4.549 | 61.145 | 14.559 | 1.00 | 5.77 | N |
| ATOM | 1702 | CZ | ARG | A | 110 | 4.863 | 62.377 | 14.133 | 1.00 | 5.92 | C |
| ATOM | 1703 | NH1 | ARG | A | 110 | 3.983 | 63.411 | 14.119 | 1.00 | 8.31 | N |
| ATOM | 1706 | NH2 | ARG | A | 110 | 6.026 | 62.568 | 13.645 | 1.00 | 5.94 | N |
| ATOM | 1709 | C | ARG | A | 110 | −0.519 | 60.667 | 17.721 | 1.00 | 11.42 | C |
| ATOM | 1710 | O | ARG | A | 110 | −0.696 | 61.007 | 18.840 | 1.00 | 8.70 | O |
| ATOM | 1711 | N | SER | A | 111 | −1.209 | 59.704 | 17.091 | 1.00 | 14.26 | N |
| ATOM | 1713 | CA | SER | A | 111 | −1.958 | 58.641 | 17.754 | 1.00 | 17.02 | C |
| ATOM | 1715 | CB | SER | A | 111 | −2.724 | 57.712 | 16.723 | 1.00 | 20.16 | C |
| ATOM | 1718 | OG | SER | A | 111 | −3.743 | 58.582 | 16.265 | 1.00 | 21.74 | O |
| ATOM | 1720 | C | SER | A | 111 | −0.919 | 57.829 | 18.544 | 1.00 | 14.70 | C |
| ATOM | 1721 | O | SER | A | 111 | 0.273 | 57.836 | 18.212 | 1.00 | 16.86 | O |
| ATOM | 1722 | N | SER | A | 112 | −1.445 | 57.078 | 19.469 | 1.00 | 15.33 | N |
| ATOM | 1724 | CA | SER | A | 112 | −0.660 | 56.086 | 20.204 | 1.00 | 16.21 | C |
| ATOM | 1726 | CB | SER | A | 112 | −1.475 | 55.242 | 21.153 | 1.00 | 16.36 | C |
| ATOM | 1729 | OG | SER | A | 112 | −0.683 | 54.311 | 21.872 | 1.00 | 15.39 | O |
| ATOM | 1731 | C | SER | A | 112 | −0.040 | 55.123 | 19.269 | 1.00 | 16.70 | C |
| ATOM | 1732 | O | SER | A | 112 | −0.684 | 54.627 | 18.315 | 1.00 | 20.34 | O |
| ATOM | 1733 | N | SER | A | 113 | 1.299 | 54.994 | 19.419 | 1.00 | 17.37 | N |
| ATOM | 1735 | CA | SER | A | 113 | 2.086 | 53.975 | 18.751 | 1.00 | 15.72 | C |
| ATOM | 1737 | CB | SER | A | 113 | 3.506 | 54.569 | 18.467 | 1.00 | 16.57 | C |
| ATOM | 1740 | OG | SER | A | 113 | 3.954 | 54.927 | 19.739 | 1.00 | 16.43 | O |
| ATOM | 1742 | C | SER | A | 113 | 2.165 | 52.631 | 19.489 | 1.00 | 14.13 | C |
| ATOM | 1743 | O | SER | A | 113 | 2.698 | 51.694 | 18.980 | 1.00 | 15.35 | O |
| ATOM | 1744 | N | MET | A | 114 | 1.461 | 52.409 | 20.599 | 1.00 | 13.09 | N |
| ATOM | 1746 | CA | MET | A | 114 | 1.406 | 51.112 | 21.222 | 1.00 | 12.38 | C |
| ATOM | 1748 | CB | MET | A | 114 | 0.459 | 51.169 | 22.415 | 1.00 | 15.07 | C |
| ATOM | 1751 | CG | MET | A | 114 | 1.178 | 52.022 | 23.536 | 1.00 | 19.87 | C |
| ATOM | 1754 | SD | MET | A | 114 | 0.264 | 52.200 | 25.023 | 1.00 | 21.07 | S |
| ATOM | 1755 | CE | MET | A | 114 | 0.298 | 50.494 | 25.805 | 1.00 | 23.70 | C |
| ATOM | 1759 | C | MET | A | 114 | 0.886 | 50.017 | 20.327 | 1.00 | 15.06 | C |
| ATOM | 1760 | O | MET | A | 114 | −0.020 | 50.332 | 19.607 | 1.00 | 15.11 | O |
| ATOM | 1761 | N | GLY | A | 115 | 1.654 | 48.922 | 20.220 | 1.00 | 9.36 | N |
| ATOM | 1763 | CA | GLY | A | 115 | 1.268 | 47.835 | 19.378 | 1.00 | 10.49 | C |
| ATOM | 1766 | C | GLY | A | 115 | 1.949 | 47.868 | 18.035 | 1.00 | 10.29 | C |
| ATOM | 1767 | O | GLY | A | 115 | 1.864 | 46.856 | 17.297 | 1.00 | 10.82 | O |
| ATOM | 1768 | N | VAL | A | 116 | 2.505 | 49.022 | 17.688 | 1.00 | 7.02 | N |
| ATOM | 1770 | CA | VAL | A | 116 | 3.178 | 49.172 | 16.391 | 1.00 | 9.43 | C |
| ATOM | 1772 | CB | VAL | A | 116 | 3.052 | 50.614 | 15.783 | 1.00 | 10.47 | C |
| ATOM | 1774 | CG1 | VAL | A | 116 | 3.941 | 50.829 | 14.510 | 1.00 | 10.78 | C |
| ATOM | 1778 | CG2 | VAL | A | 116 | 1.642 | 51.035 | 15.568 | 1.00 | 10.20 | C |
| ATOM | 1782 | C | VAL | A | 116 | 4.655 | 48.797 | 16.548 | 1.00 | 8.38 | C |
| ATOM | 1783 | O | VAL | A | 116 | 5.294 | 49.372 | 17.399 | 1.00 | 10.29 | O |
| ATOM | 1784 | N | CYS | A | 117 | 5.229 | 47.931 | 15.688 | 1.00 | 5.54 | N |
| ATOM | 1786 | CA | CYS | A | 117 | 6.624 | 47.576 | 15.832 | 1.00 | 6.25 | C |
| ATOM | 1788 | CB | CYS | A | 117 | 6.677 | 46.052 | 15.502 | 1.00 | 5.28 | C |
| ATOM | 1791 | SG | CYS | A | 117 | 8.354 | 45.441 | 15.452 | 1.00 | 8.44 | S |
| ATOM | 1792 | C | CYS | A | 117 | 7.411 | 48.304 | 14.769 | 1.00 | 9.64 | C |
| ATOM | 1793 | O | CYS | A | 117 | 7.075 | 48.159 | 13.586 | 1.00 | 10.64 | O |
| ATOM | 1794 | N | PRO | A | 118 | 8.347 | 49.144 | 15.166 | 1.00 | 9.31 | N |
| ATOM | 1795 | CA | PRO | A | 118 | 9.143 | 49.923 | 14.228 | 1.00 | 10.70 | C |
| ATOM | 1797 | CB | PRO | A | 118 | 10.164 | 50.594 | 15.173 | 1.00 | 8.88 | C |
| ATOM | 1800 | CG | PRO | A | 118 | 9.315 | 50.725 | 16.437 | 1.00 | 10.00 | C |
| ATOM | 1803 | CD | PRO | A | 118 | 8.747 | 49.349 | 16.572 | 1.00 | 6.82 | C |
| ATOM | 1806 | C | PRO | A | 118 | 9.838 | 48.934 | 13.269 | 1.00 | 10.27 | C |
| ATOM | 1807 | O | PRO | A | 118 | 10.321 | 47.864 | 13.627 | 1.00 | 10.68 | O |
| ATOM | 1808 | N | LYS | A | 119 | 10.089 | 49.409 | 12.064 | 1.00 | 12.58 | N |
| ATOM | 1810 | CA | LYS | A | 119 | 10.829 | 48.643 | 11.060 | 1.00 | 12.76 | C |

-continued

| ATOM | 1812 | CB | LYS | A | 119 | 10.568 | 49.228 | 9.653 | 1.00 | 15.68 | C |
| ATOM | 1815 | CG | LYS | A | 119 | 11.272 | 48.555 | 8.463 | 1.00 | 16.64 | C |
| ATOM | 1818 | CD | LYS | A | 119 | 11.111 | 46.997 | 8.542 | 1.00 | 18.87 | C |
| ATOM | 1821 | CE | LYS | A | 119 | 9.842 | 46.280 | 7.993 | 1.00 | 18.06 | C |
| ATOM | 1824 | NZ | LYS | A | 119 | 9.763 | 44.824 | 8.359 | 1.00 | 17.21 | N |
| ATOM | 1828 | C | LYS | A | 119 | 12.298 | 48.788 | 11.359 | 1.00 | 14.02 | C |
| ATOM | 1829 | O | LYS | A | 119 | 13.043 | 49.620 | 10.835 | 1.00 | 15.49 | O |
| ATOM | 1830 | N | ILE | A | 120 | 12.769 | 47.964 | 12.290 | 1.00 | 13.51 | N |
| ATOM | 1832 | CA | ILE | A | 120 | 14.178 | 48.094 | 12.694 | 1.00 | 9.14 | C |
| ATOM | 1834 | CB | ILE | A | 120 | 14.248 | 48.834 | 14.049 | 1.00 | 11.23 | C |
| ATOM | 1836 | CG1 | ILE | A | 120 | 14.036 | 50.319 | 13.716 | 1.00 | 13.36 | C |
| ATOM | 1839 | CD1 | ILE | A | 120 | 14.146 | 51.261 | 14.818 | 1.00 | 11.19 | C |
| ATOM | 1843 | CG2 | ILE | A | 120 | 15.702 | 48.607 | 14.704 | 1.00 | 11.91 | C |
| ATOM | 1847 | C | ILE | A | 120 | 14.643 | 46.647 | 12.985 | 1.00 | 9.77 | C |
| ATOM | 1848 | O | ILE | A | 120 | 13.918 | 45.854 | 13.625 | 1.00 | 9.24 | O |
| ATOM | 1849 | N | LEU | A | 121 | 15.794 | 46.275 | 12.450 | 1.00 | 9.71 | N |
| ATOM | 1851 | CA | LEU | A | 121 | 16.298 | 44.919 | 12.478 | 1.00 | 11.68 | C |
| ATOM | 1853 | CB | LEU | A | 121 | 17.380 | 44.869 | 11.407 | 1.00 | 15.05 | C |
| ATOM | 1856 | CG | LEU | A | 121 | 17.667 | 43.536 | 10.800 | 1.00 | 18.59 | C |
| ATOM | 1858 | CD1 | LEU | A | 121 | 16.393 | 42.688 | 10.319 | 1.00 | 20.06 | C |
| ATOM | 1862 | CD2 | LEU | A | 121 | 18.691 | 43.933 | 9.706 | 1.00 | 21.03 | C |
| ATOM | 1866 | C | LEU | A | 121 | 16.944 | 44.749 | 13.830 | 1.00 | 13.87 | C |
| ATOM | 1867 | O | LEU | A | 121 | 17.821 | 45.527 | 14.222 | 1.00 | 12.91 | O |
| ATOM | 1868 | N | LYS | A | 122 | 16.425 | 43.790 | 14.582 | 1.00 | 13.07 | N |
| ATOM | 1870 | CA | LYS | A | 122 | 16.842 | 43.595 | 15.962 | 1.00 | 13.86 | C |
| ATOM | 1872 | CB | LYS | A | 122 | 15.956 | 44.394 | 16.954 | 1.00 | 14.08 | C |
| ATOM | 1875 | CG | LYS | A | 122 | 16.400 | 44.389 | 18.454 | 1.00 | 19.57 | C |
| ATOM | 1878 | CD | LYS | A | 122 | 17.852 | 44.689 | 18.809 | 1.00 | 21.48 | C |
| ATOM | 1881 | CE | LYS | A | 122 | 18.343 | 44.220 | 20.262 | 1.00 | 24.39 | C |
| ATOM | 1884 | NZ | LYS | A | 122 | 19.234 | 42.945 | 20.283 | 1.00 | 22.59 | N |
| ATOM | 1888 | C | LYS | A | 122 | 16.860 | 42.115 | 16.279 | 1.00 | 9.69 | C |
| ATOM | 1889 | O | LYS | A | 122 | 15.856 | 41.522 | 16.259 | 1.00 | 10.32 | O |
| ATOM | 1890 | N | LYS | A | 123 | 17.944 | 41.530 | 16.778 | 1.00 | 7.24 | N |
| ATOM | 1892 | CA | LYS | A | 123 | 17.910 | 40.161 | 17.158 | 1.00 | 7.74 | C |
| ATOM | 1894 | CB | LYS | A | 123 | 19.343 | 39.669 | 17.314 | 1.00 | 8.85 | C |
| ATOM | 1897 | CG | LYS | A | 123 | 20.025 | 39.680 | 15.990 | 1.00 | 9.77 | C |
| ATOM | 1900 | CD | LYS | A | 123 | 21.433 | 39.034 | 16.157 | 1.00 | 13.94 | C |
| ATOM | 1903 | CE | LYS | A | 123 | 21.966 | 38.563 | 14.829 | 1.00 | 17.19 | C |
| ATOM | 1906 | NZ | LYS | A | 123 | 22.187 | 39.772 | 13.984 | 1.00 | 16.89 | N |
| ATOM | 1910 | C | LYS | A | 123 | 17.318 | 40.061 | 18.540 | 1.00 | 8.95 | C |
| ATOM | 1911 | O | LYS | A | 123 | 17.459 | 40.947 | 19.394 | 1.00 | 7.12 | O |
| ATOM | 1912 | N | CYS | A | 124 | 16.709 | 38.917 | 18.791 | 1.00 | 10.81 | N |
| ATOM | 1914 | CA | CYS | A | 124 | 16.102 | 38.662 | 20.074 | 1.00 | 10.25 | C |
| ATOM | 1916 | CB | CYS | A | 124 | 14.679 | 39.198 | 20.074 | 1.00 | 9.54 | C |
| ATOM | 1919 | SG | CYS | A | 124 | 13.811 | 38.420 | 18.689 | 1.00 | 8.73 | S |
| ATOM | 1920 | C | CYS | A | 124 | 16.097 | 37.162 | 20.431 | 1.00 | 10.85 | C |
| ATOM | 1921 | O | CYS | A | 124 | 16.179 | 36.263 | 19.594 | 1.00 | 9.26 | O |
| ATOM | 1922 | N | ARG | A | 125 | 15.845 | 36.927 | 21.706 | 1.00 | 12.03 | N |
| ATOM | 1924 | CA | ARG | A | 125 | 15.494 | 35.602 | 22.261 | 1.00 | 14.18 | C |
| ATOM | 1926 | CB | ARG | A | 125 | 16.547 | 35.142 | 23.312 | 1.00 | 18.03 | C |
| ATOM | 1929 | CG | ARG | A | 125 | 17.839 | 34.572 | 22.673 | 1.00 | 23.34 | C |
| ATOM | 1932 | CD | ARG | A | 125 | 19.191 | 34.637 | 23.511 | 1.00 | 28.34 | C |
| ATOM | 1935 | NE | ARG | A | 125 | 20.180 | 33.556 | 23.222 | 1.00 | 31.12 | N |
| ATOM | 1937 | CZ | ARG | A | 125 | 19.928 | 32.262 | 23.506 | 1.00 | 34.85 | C |
| ATOM | 1938 | NH1 | ARG | A | 125 | 18.765 | 31.934 | 24.100 | 1.00 | 37.06 | N |
| ATOM | 1941 | NH2 | ARG | A | 125 | 20.787 | 31.281 | 23.235 | 1.00 | 35.19 | N |
| ATOM | 1944 | C | ARG | A | 125 | 14.066 | 35.670 | 22.883 | 1.00 | 12.22 | C |
| ATOM | 1945 | O | ARG | A | 125 | 13.409 | 34.674 | 22.927 | 1.00 | 7.31 | O |
| ATOM | 1946 | N | ARG | A | 126 | 13.522 | 36.830 | 23.240 | 1.00 | 12.86 | N |
| ATOM | 1948 | CA | ARG | A | 126 | 12.234 | 36.928 | 23.840 | 1.00 | 14.85 | C |
| ATOM | 1950 | CB | ARG | A | 126 | 12.297 | 36.637 | 25.331 | 1.00 | 17.94 | C |
| ATOM | 1953 | CG | ARG | A | 126 | 13.257 | 37.535 | 26.061 | 1.00 | 19.22 | C |
| ATOM | 1956 | CD | ARG | A | 126 | 13.090 | 37.583 | 27.592 | 1.00 | 23.45 | C |
| ATOM | 1959 | NE | ARG | A | 126 | 11.702 | 37.396 | 28.055 | 1.00 | 26.65 | N |
| ATOM | 1961 | CZ | ARG | A | 126 | 11.341 | 36.720 | 29.159 | 1.00 | 29.80 | C |
| ATOM | 1962 | NH1 | ARG | A | 126 | 12.190 | 36.104 | 29.976 | 1.00 | 29.40 | N |
| ATOM | 1965 | NH2 | ARG | A | 126 | 10.054 | 36.585 | 29.456 | 1.00 | 31.54 | N |
| ATOM | 1968 | C | ARG | A | 126 | 11.723 | 38.301 | 23.507 | 1.00 | 13.43 | C |
| ATOM | 1969 | O | ARG | A | 126 | 12.499 | 39.161 | 23.074 | 1.00 | 11.02 | O |
| ATOM | 1970 | N | ASP | A | 127 | 10.432 | 38.511 | 23.751 | 1.00 | 8.99 | N |
| ATOM | 1972 | CA | ASP | A | 127 | 9.815 | 39.799 | 23.369 | 1.00 | 9.96 | C |
| ATOM | 1974 | CB | ASP | A | 127 | 8.301 | 39.815 | 23.730 | 1.00 | 9.55 | C |
| ATOM | 1977 | CG | ASP | A | 127 | 7.539 | 38.785 | 22.893 | 1.00 | 10.42 | C |
| ATOM | 1978 | OD1 | ASP | A | 127 | 6.398 | 38.465 | 23.319 | 1.00 | 8.22 | O |
| ATOM | 1979 | OD2 | ASP | A | 127 | 8.157 | 38.107 | 21.987 | 1.00 | 9.63 | O |
| ATOM | 1980 | C | ASP | A | 127 | 10.507 | 41.011 | 23.967 | 1.00 | 6.95 | C |
| ATOM | 1981 | O | ASP | A | 127 | 10.617 | 42.050 | 23.351 | 1.00 | 4.94 | O |
| ATOM | 1982 | N | SER | A | 128 | 10.916 | 40.905 | 25.209 | 1.00 | 9.26 | N |
| ATOM | 1984 | CA | SER | A | 128 | 11.467 | 42.058 | 25.882 | 1.00 | 10.08 | C |
| ATOM | 1986 | CB | SER | A | 128 | 11.599 | 41.822 | 27.397 | 1.00 | 12.52 | C |

|      |      |     |     |   |     | -continued |        |        |      |       |   |
|------|------|-----|-----|---|-----|--------|--------|--------|------|-------|---|
| ATOM | 1989 | OG  | SER | A | 128 | 12.320 | 40.648 | 27.732 | 1.00 | 11.88 | O |
| ATOM | 1991 | C   | SER | A | 128 | 12.779 | 42.492 | 25.315 | 1.00 | 9.99  | C |
| ATOM | 1992 | O   | SER | A | 128 | 13.299 | 43.506 | 25.763 | 1.00 | 9.39  | O |
| ATOM | 1993 | N   | ASP | A | 129 | 13.332 | 41.713 | 24.389 | 1.00 | 9.66  | N |
| ATOM | 1995 | CA  | ASP | A | 129 | 14.612 | 42.072 | 23.757 | 1.00 | 8.80  | C |
| ATOM | 1997 | CB  | ASP | A | 129 | 15.291 | 40.884 | 23.196 | 1.00 | 7.88  | C |
| ATOM | 2000 | CG  | ASP | A | 129 | 15.869 | 39.997 | 24.229 | 1.00 | 9.83  | C |
| ATOM | 2001 | OD1 | ASP | A | 129 | 16.317 | 40.424 | 25.331 | 1.00 | 12.63 | O |
| ATOM | 2002 | OD2 | ASP | A | 129 | 16.023 | 38.817 | 23.895 | 1.00 | 7.97  | O |
| ATOM | 2003 | C   | ASP | A | 129 | 14.247 | 42.999 | 22.580 | 1.00 | 10.66 | C |
| ATOM | 2004 | O   | ASP | A | 129 | 15.044 | 43.734 | 22.035 | 1.00 | 9.95  | O |
| ATOM | 2005 | N   | CYS | A | 130 | 12.966 | 43.125 | 22.304 | 1.00 | 9.69  | N |
| ATOM | 2007 | CA  | CYS | A | 130 | 12.596 | 43.961 | 21.202 | 1.00 | 10.40 | C |
| ATOM | 2009 | CB  | CYS | A | 130 | 11.546 | 43.241 | 20.368 | 1.00 | 10.66 | C |
| ATOM | 2012 | SG  | CYS | A | 130 | 11.959 | 41.602 | 19.702 | 1.00 | 10.81 | S |
| ATOM | 2013 | C   | CYS | A | 130 | 11.939 | 45.265 | 21.648 | 1.00 | 9.65  | C |
| ATOM | 2014 | O   | CYS | A | 130 | 11.417 | 45.435 | 22.752 | 1.00 | 12.43 | O |
| ATOM | 2015 | N   | LEU | A | 131 | 11.768 | 46.141 | 20.680 | 1.00 | 8.80  | N |
| ATOM | 2017 | CA  | LEU | A | 131 | 11.162 | 47.419 | 20.905 | 1.00 | 9.00  | C |
| ATOM | 2019 | CB  | LEU | A | 131 | 11.232 | 48.250 | 19.620 | 1.00 | 9.08  | C |
| ATOM | 2022 | CG  | LEU | A | 131 | 12.641 | 48.674 | 19.336 | 1.00 | 7.59  | C |
| ATOM | 2024 | CD1 | LEU | A | 131 | 12.884 | 49.341 | 18.066 | 1.00 | 8.36  | C |
| ATOM | 2028 | CD2 | LEU | A | 131 | 13.314 | 49.481 | 20.457 | 1.00 | 9.67  | C |
| ATOM | 2032 | C   | LEU | A | 131 | 9.692  | 47.224 | 21.237 | 1.00 | 8.20  | C |
| ATOM | 2033 | O   | LEU | A | 131 | 9.069  | 46.252 | 20.882 | 1.00 | 9.52  | O |
| ATOM | 2034 | N   | ALA | A | 132 | 9.123  | 48.267 | 21.809 | 1.00 | 5.72  | N |
| ATOM | 2036 | CA  | ALA | A | 132 | 7.712  | 48.167 | 22.036 | 1.00 | 6.14  | C |
| ATOM | 2038 | CB  | ALA | A | 132 | 7.272  | 49.392 | 22.713 | 1.00 | 4.65  | C |
| ATOM | 2042 | C   | ALA | A | 132 | 6.907  | 47.955 | 20.754 | 1.00 | 5.20  | C |
| ATOM | 2043 | O   | ALA | A | 132 | 7.109  | 48.660 | 19.731 | 1.00 | 7.05  | O |
| ATOM | 2044 | N   | GLY | A | 133 | 5.836  | 47.158 | 20.890 | 1.00 | 7.26  | N |
| ATOM | 2046 | CA  | GLY | A | 133 | 4.986  | 46.833 | 19.773 | 1.00 | 6.59  | C |
| ATOM | 2049 | C   | GLY | A | 133 | 5.551  | 45.630 | 18.983 | 1.00 | 7.38  | C |
| ATOM | 2050 | O   | GLY | A | 133 | 4.854  | 45.143 | 18.095 | 1.00 | 7.56  | O |
| ATOM | 2051 | N   | CYS | A | 134 | 6.715  | 45.096 | 19.316 | 1.00 | 6.87  | N |
| ATOM | 2053 | CA  | CYS | A | 134 | 7.395  | 44.072 | 18.598 | 1.00 | 6.03  | C |
| ATOM | 2055 | CB  | CYS | A | 134 | 8.849  | 44.449 | 18.295 | 1.00 | 7.35  | C |
| ATOM | 2058 | SG  | CYS | A | 134 | 9.007  | 45.911 | 17.270 | 1.00 | 8.44  | S |
| ATOM | 2059 | C   | CYS | A | 134 | 7.412  | 42.795 | 19.456 | 1.00 | 7.86  | C |
| ATOM | 2060 | O   | CYS | A | 134 | 7.613  | 42.827 | 20.697 | 1.00 | 7.10  | O |
| ATOM | 2061 | N   | VAL | A | 135 | 7.563  | 41.673 | 18.743 | 1.00 | 8.68  | N |
| ATOM | 2063 | CA  | VAL | A | 135 | 7.636  | 40.395 | 19.396 | 1.00 | 11.71 | C |
| ATOM | 2065 | CB  | VAL | A | 135 | 6.326  | 39.568 | 19.330 | 1.00 | 12.59 | C |
| ATOM | 2067 | CG1 | VAL | A | 135 | 5.239  | 40.261 | 20.132 | 1.00 | 12.03 | C |
| ATOM | 2071 | CG2 | VAL | A | 135 | 5.942  | 39.183 | 17.931 | 1.00 | 11.54 | C |
| ATOM | 2075 | C   | VAL | A | 135 | 8.754  | 39.610 | 18.731 | 1.00 | 12.89 | C |
| ATOM | 2076 | O   | VAL | A | 135 | 9.193  | 39.949 | 17.638 | 1.00 | 15.44 | O |
| ATOM | 2077 | N   | CYS | A | 136 | 9.347  | 38.690 | 19.514 | 1.00 | 12.32 | N |
| ATOM | 2079 | CA  | CYS | A | 136 | 10.425 | 37.864 | 19.038 | 1.00 | 9.14  | C |
| ATOM | 2081 | CB  | CYS | A | 136 | 11.351 | 37.414 | 20.162 | 1.00 | 9.24  | C |
| ATOM | 2084 | SG  | CYS | A | 136 | 12.853 | 36.730 | 19.489 | 1.00 | 9.57  | S |
| ATOM | 2085 | C   | CYS | A | 136 | 9.877  | 36.721 | 18.191 | 1.00 | 9.81  | C |
| ATOM | 2086 | O   | CYS | A | 136 | 8.999  | 35.948 | 18.560 | 1.00 | 10.22 | O |
| ATOM | 2087 | N   | GLY | A | 137 | 10.384 | 36.666 | 16.958 | 1.00 | 11.30 | N |
| ATOM | 2089 | CA  | GLY | A | 137 | 9.914  | 35.695 | 15.948 | 1.00 | 11.53 | C |
| ATOM | 2092 | C   | GLY | A | 137 | 10.704 | 34.425 | 15.986 | 1.00 | 10.87 | C |
| ATOM | 2093 | O   | GLY | A | 137 | 11.594 | 34.309 | 16.806 | 1.00 | 10.53 | O |
| ATOM | 2094 | N   | PRO | A | 138 | 10.362 | 33.432 | 15.175 | 1.00 | 10.27 | N |
| ATOM | 2095 | CA  | PRO | A | 138 | 11.060 | 32.150 | 15.353 | 1.00 | 10.62 | C |
| ATOM | 2097 | CB  | PRO | A | 138 | 10.114 | 31.148 | 14.663 | 1.00 | 11.02 | C |
| ATOM | 2100 | CG  | PRO | A | 138 | 9.523  | 32.010 | 13.541 | 1.00 | 9.49  | C |
| ATOM | 2103 | CD  | PRO | A | 138 | 9.185  | 33.314 | 14.275 | 1.00 | 9.58  | C |
| ATOM | 2106 | C   | PRO | A | 138 | 12.461 | 32.121 | 14.789 | 1.00 | 10.49 | C |
| ATOM | 2107 | O   | PRO | A | 138 | 13.013 | 31.031 | 14.849 | 1.00 | 7.78  | O |
| ATOM | 2108 | N   | ASN | A | 139 | 12.955 | 33.188 | 14.131 | 1.00 | 10.69 | N |
| ATOM | 2110 | CA  | ASN | A | 139 | 14.279 | 33.178 | 13.637 | 1.00 | 8.04  | C |
| ATOM | 2112 | CB  | ASN | A | 139 | 14.355 | 33.625 | 12.201 | 1.00 | 8.85  | C |
| ATOM | 2115 | CG  | ASN | A | 139 | 14.099 | 32.486 | 11.250 | 1.00 | 11.43 | C |
| ATOM | 2116 | OD1 | ASN | A | 139 | 13.582 | 31.405 | 11.673 | 1.00 | 12.02 | O |
| ATOM | 2117 | ND2 | ASN | A | 139 | 14.506 | 32.691 | 9.974  | 1.00 | 8.01  | N |
| ATOM | 2120 | C   | ASN | A | 139 | 15.231 | 34.047 | 14.428 | 1.00 | 10.21 | C |
| ATOM | 2121 | O   | ASN | A | 139 | 16.365 | 34.344 | 14.006 | 1.00 | 11.74 | O |
| ATOM | 2122 | N   | GLY | A | 140 | 14.815 | 34.372 | 15.607 | 1.00 | 9.67  | N |
| ATOM | 2124 | CA  | GLY | A | 140 | 15.589 | 35.221 | 16.463 | 1.00 | 10.04 | C |
| ATOM | 2127 | C   | GLY | A | 140 | 15.547 | 36.669 | 15.998 | 1.00 | 10.48 | C |
| ATOM | 2128 | O   | GLY | A | 140 | 16.426 | 37.390 | 16.407 | 1.00 | 9.32  | O |
| ATOM | 2129 | N   | PHE | A | 141 | 14.528 | 37.111 | 15.260 | 1.00 | 10.21 | N |
| ATOM | 2131 | CA  | PHE | A | 141 | 14.453 | 38.536 | 14.939 | 1.00 | 10.80 | C |
| ATOM | 2133 | CB  | PHE | A | 141 | 14.723 | 38.821 | 13.455 | 1.00 | 10.24 | C |
| ATOM | 2136 | CG  | PHE | A | 141 | 16.147 | 38.733 | 13.087 | 1.00 | 10.69 | C |

-continued

| | | | | | | | | | | |
|---|---|---|---|---|---|---|---|---|---|---|
| ATOM | 2137 | CD1 | PHE | A | 141 | 16.931 | 39.862 | 13.114 | 1.00 | 11.83 | C |
| ATOM | 2139 | CE1 | PHE | A | 141 | 18.217 | 39.837 | 12.812 | 1.00 | 10.05 | C |
| ATOM | 2141 | CZ | PHE | A | 141 | 18.775 | 38.651 | 12.386 | 1.00 | 7.45 | C |
| ATOM | 2143 | CE2 | PHE | A | 141 | 18.049 | 37.509 | 12.410 | 1.00 | 6.60 | C |
| ATOM | 2145 | CD2 | PHE | A | 141 | 16.752 | 37.523 | 12.759 | 1.00 | 9.67 | C |
| ATOM | 2147 | C | PHE | A | 141 | 13.132 | 39.101 | 15.382 | 1.00 | 11.58 | C |
| ATOM | 2148 | O | PHE | A | 141 | 12.080 | 38.398 | 15.451 | 1.00 | 14.86 | O |
| ATOM | 2149 | N | CYS | A | 142 | 13.184 | 40.385 | 15.742 | 1.00 | 10.60 | N |
| ATOM | 2151 | CA | CYS | A | 142 | 11.979 | 41.109 | 16.147 | 1.00 | 10.20 | C |
| ATOM | 2153 | CB | CYS | A | 142 | 12.321 | 42.364 | 16.941 | 1.00 | 10.04 | C |
| ATOM | 2156 | SG | CYS | A | 142 | 13.395 | 42.150 | 18.391 | 1.00 | 8.87 | S |
| ATOM | 2157 | C | CYS | A | 142 | 11.030 | 41.473 | 15.017 | 1.00 | 9.93 | C |
| ATOM | 2158 | O | CYS | A | 142 | 11.490 | 41.746 | 13.959 | 1.00 | 12.30 | O |
| ATOM | 2159 | N | GLY | A | 143 | 9.690 | 41.467 | 15.215 | 1.00 | 6.38 | N |
| ATOM | 2161 | CA | GLY | A | 143 | 8.764 | 41.871 | 14.194 | 1.00 | 8.97 | C |
| ATOM | 2164 | C | GLY | A | 143 | 7.380 | 42.086 | 14.827 | 1.00 | 9.03 | C |
| ATOM | 2165 | O | GLY | A | 143 | 7.277 | 42.013 | 16.034 | 1.00 | 4.04 | O |
| ATOM | 2166 | N | SER | A | 144 | 6.399 | 42.455 | 14.038 | 1.00 | 6.51 | N |
| ATOM | 2168 | CA | SER | A | 144 | 5.072 | 42.806 | 14.519 | 1.00 | 8.21 | C |
| ATOM | 2170 | CB | SER | A | 144 | 4.211 | 43.276 | 13.280 | 1.00 | 6.85 | C |
| ATOM | 2173 | OG | SER | A | 144 | 4.868 | 44.313 | 12.534 | 1.00 | 8.90 | O |
| ATOM | 2175 | C | SER | A | 144 | 4.545 | 41.514 | 15.054 | 1.00 | 11.77 | C |
| ATOM | 2176 | O | SER | A | 144 | 4.836 | 40.367 | 14.657 | 1.00 | 13.97 | O |
| ATOM | 2177 | OXT | SER | A | 144 | 3.644 | 41.553 | 15.871 | 1.00 | 17.62 | O |
| ATOM | 2178 | N | GLN | B | 2 | −7.652 | 18.523 | 35.984 | 1.00 | 47.13 | N |
| ATOM | 2180 | CA | GLN | B | 2 | −6.606 | 19.347 | 36.701 | 1.00 | 46.13 | C |
| ATOM | 2182 | CB | GLN | B | 2 | −6.839 | 19.145 | 38.193 | 1.00 | 48.68 | C |
| ATOM | 2185 | CG | GLN | B | 2 | −8.350 | 19.427 | 38.618 | 1.00 | 51.28 | C |
| ATOM | 2188 | CD | GLN | B | 2 | −9.116 | 18.300 | 39.436 | 1.00 | 53.84 | C |
| ATOM | 2189 | OE1 | GLN | B | 2 | −9.170 | 18.307 | 40.693 | 1.00 | 55.09 | O |
| ATOM | 2190 | NE2 | GLN | B | 2 | −9.777 | 17.382 | 38.706 | 1.00 | 54.79 | N |
| ATOM | 2193 | C | GLN | B | 2 | −5.133 | 19.105 | 36.229 | 1.00 | 42.32 | C |
| ATOM | 2194 | O | GLN | B | 2 | −4.350 | 20.059 | 36.029 | 1.00 | 40.81 | O |
| ATOM | 2197 | N | VAL | B | 3 | −4.756 | 17.840 | 35.983 | 1.00 | 36.38 | N |
| ATOM | 2199 | CA | VAL | B | 3 | −3.433 | 17.513 | 35.386 | 1.00 | 29.41 | C |
| ATOM | 2201 | CB | VAL | B | 3 | −3.025 | 16.089 | 35.713 | 1.00 | 30.90 | C |
| ATOM | 2203 | CG1 | VAL | B | 3 | −2.293 | 15.320 | 34.648 | 1.00 | 29.79 | C |
| ATOM | 2207 | CG2 | VAL | B | 3 | −2.305 | 16.044 | 37.089 | 1.00 | 32.67 | C |
| ATOM | 2211 | C | VAL | B | 3 | −3.532 | 17.692 | 33.876 | 1.00 | 22.75 | C |
| ATOM | 2212 | O | VAL | B | 3 | −4.500 | 17.320 | 33.231 | 1.00 | 20.09 | O |
| ATOM | 2213 | N | ILE | B | 4 | −2.494 | 18.302 | 33.309 | 1.00 | 17.63 | N |
| ATOM | 2215 | CA | ILE | B | 4 | −2.374 | 18.510 | 31.862 | 1.00 | 14.01 | C |
| ATOM | 2217 | CB | ILE | B | 4 | −2.148 | 19.960 | 31.544 | 1.00 | 13.99 | C |
| ATOM | 2219 | CG1 | ILE | B | 4 | −3.252 | 20.848 | 32.157 | 1.00 | 15.54 | C |
| ATOM | 2222 | CD1 | ILE | B | 4 | −3.042 | 22.418 | 31.823 | 1.00 | 14.33 | C |
| ATOM | 2226 | CG2 | ILE | B | 4 | −2.030 | 20.158 | 30.050 | 1.00 | 12.10 | C |
| ATOM | 2230 | C | ILE | B | 4 | −1.247 | 17.645 | 31.388 | 1.00 | 11.29 | C |
| ATOM | 2231 | O | ILE | B | 4 | −0.065 | 17.851 | 31.711 | 1.00 | 12.25 | O |
| ATOM | 2232 | N | ASN | B | 5 | −1.642 | 16.591 | 30.683 | 1.00 | 10.98 | N |
| ATOM | 2234 | CA | ASN | B | 5 | −0.749 | 15.581 | 30.162 | 1.00 | 7.79 | C |
| ATOM | 2236 | CB | ASN | B | 5 | −0.427 | 14.539 | 31.159 | 1.00 | 7.24 | C |
| ATOM | 2239 | CG | ASN | B | 5 | −1.512 | 13.458 | 31.336 | 1.00 | 9.99 | C |
| ATOM | 2240 | OD1 | ASN | B | 5 | −1.283 | 12.447 | 32.020 | 1.00 | 14.44 | O |
| ATOM | 2241 | ND2 | ASN | B | 5 | −2.679 | 13.706 | 30.877 | 1.00 | 5.64 | N |
| ATOM | 2244 | C | ASN | B | 5 | −1.121 | 14.874 | 28.892 | 1.00 | 9.61 | C |
| ATOM | 2245 | O | ASN | B | 5 | −0.656 | 13.757 | 28.698 | 1.00 | 11.34 | O |
| ATOM | 2246 | N | THR | B | 6 | −1.998 | 15.447 | 28.088 | 1.00 | 9.86 | N |
| ATOM | 2248 | CA | THR | B | 6 | −2.366 | 14.887 | 26.817 | 1.00 | 8.91 | C |
| ATOM | 2250 | CB | THR | B | 6 | −3.818 | 15.075 | 26.457 | 1.00 | 6.42 | C |
| ATOM | 2252 | OG1 | THR | B | 6 | −4.741 | 14.395 | 27.429 | 1.00 | 14.51 | O |
| ATOM | 2254 | CG2 | THR | B | 6 | −4.110 | 16.432 | 26.411 | 1.00 | 2.00 | C |
| ATOM | 2258 | C | THR | B | 6 | −1.455 | 15.671 | 25.807 | 1.00 | 10.95 | C |
| ATOM | 2259 | O | THR | B | 6 | −0.921 | 16.748 | 26.054 | 1.00 | 9.64 | O |
| ATOM | 2260 | N | PHE | B | 7 | −1.292 | 15.106 | 24.618 | 1.00 | 10.00 | N |
| ATOM | 2262 | CA | PHE | B | 7 | −0.470 | 15.699 | 23.620 | 1.00 | 8.08 | C |
| ATOM | 2264 | CB | PHE | B | 7 | −0.499 | 14.884 | 22.342 | 1.00 | 8.24 | C |
| ATOM | 2267 | CG | PHE | B | 7 | 0.343 | 13.605 | 22.376 | 1.00 | 9.14 | C |
| ATOM | 2268 | CD1 | PHE | B | 7 | 1.714 | 13.666 | 22.366 | 1.00 | 10.72 | C |
| ATOM | 2270 | CE1 | PHE | B | 7 | 2.478 | 12.542 | 22.402 | 1.00 | 12.63 | C |
| ATOM | 2272 | CZ | PHE | B | 7 | 1.929 | 11.326 | 22.385 | 1.00 | 11.51 | C |
| ATOM | 2274 | CE2 | PHE | B | 7 | 0.539 | 11.202 | 22.442 | 1.00 | 11.44 | C |
| ATOM | 2276 | CD2 | PHE | B | 7 | −0.263 | 12.356 | 22.468 | 1.00 | 10.83 | C |
| ATOM | 2278 | C | PHE | B | 7 | −1.049 | 17.081 | 23.251 | 1.00 | 8.06 | C |
| ATOM | 2279 | O | PHE | B | 7 | −0.322 | 18.035 | 23.253 | 1.00 | 7.93 | O |
| ATOM | 2280 | N | ASP | B | 8 | −2.321 | 17.256 | 22.965 | 1.00 | 6.86 | N |
| ATOM | 2282 | CA | ASP | B | 8 | −2.830 | 18.561 | 22.606 | 1.00 | 10.26 | C |
| ATOM | 2284 | CB | ASP | B | 8 | −4.203 | 18.473 | 22.030 | 1.00 | 8.76 | C |
| ATOM | 2287 | CG | ASP | B | 8 | −4.155 | 17.842 | 20.692 | 1.00 | 9.13 | C |
| ATOM | 2288 | OD1 | ASP | B | 8 | −3.323 | 18.263 | 19.835 | 1.00 | 6.14 | O |
| ATOM | 2289 | OD2 | ASP | B | 8 | −4.933 | 16.909 | 20.455 | 1.00 | 9.55 | O |

-continued

| | | | | | | | | | | | |
|---|---|---|---|---|---|---|---|---|---|---|---|
| ATOM | 2290 | C | ASP | B | 8 | −2.934 | 19.510 | 23.798 | 1.00 | 10.29 | C |
| ATOM | 2291 | O | ASP | B | 8 | −2.685 | 20.697 | 23.630 | 1.00 | 11.56 | O |
| ATOM | 2292 | N | GLY | B | 9 | −3.087 | 18.980 | 25.007 | 1.00 | 7.29 | N |
| ATOM | 2294 | CA | GLY | B | 9 | −3.174 | 19.910 | 26.104 | 1.00 | 8.84 | C |
| ATOM | 2297 | C | GLY | B | 9 | −1.801 | 20.412 | 26.478 | 1.00 | 9.08 | C |
| ATOM | 2298 | O | GLY | B | 9 | −1.625 | 21.602 | 26.761 | 1.00 | 8.49 | O |
| ATOM | 2299 | N | VAL | B | 10 | −0.795 | 19.565 | 26.363 | 1.00 | 10.58 | N |
| ATOM | 2301 | CA | VAL | B | 10 | 0.591 | 20.016 | 26.620 | 1.00 | 8.31 | C |
| ATOM | 2303 | CB | VAL | B | 10 | 1.507 | 18.863 | 27.007 | 1.00 | 9.15 | C |
| ATOM | 2305 | CG1 | VAL | B | 10 | 2.903 | 19.389 | 27.165 | 1.00 | 11.22 | C |
| ATOM | 2309 | CG2 | VAL | B | 10 | 1.009 | 18.122 | 28.215 | 1.00 | 11.83 | C |
| ATOM | 2313 | C | VAL | B | 10 | 1.040 | 20.954 | 25.527 | 1.00 | 9.51 | C |
| ATOM | 2314 | O | VAL | B | 10 | 1.647 | 21.983 | 25.807 | 1.00 | 9.75 | O |
| ATOM | 2315 | N | ALA | B | 11 | 0.772 | 20.592 | 24.273 | 1.00 | 7.97 | N |
| ATOM | 2317 | CA | ALA | B | 11 | 1.113 | 21.452 | 23.161 | 1.00 | 9.12 | C |
| ATOM | 2319 | CB | ALA | B | 11 | 0.636 | 20.894 | 21.831 | 1.00 | 9.88 | C |
| ATOM | 2323 | C | ALA | B | 11 | 0.580 | 22.870 | 23.301 | 1.00 | 7.14 | C |
| ATOM | 2324 | O | ALA | B | 11 | 1.305 | 23.856 | 23.113 | 1.00 | 9.85 | O |
| ATOM | 2325 | N | ASP | B | 12 | −0.691 | 22.975 | 23.599 | 1.00 | 9.02 | N |
| ATOM | 2327 | CA | ASP | B | 12 | −1.289 | 24.252 | 23.744 | 1.00 | 10.56 | C |
| ATOM | 2329 | CB | ASP | B | 12 | −2.792 | 24.074 | 24.009 | 1.00 | 8.87 | C |
| ATOM | 2332 | CG | ASP | B | 12 | −3.522 | 23.540 | 22.769 | 1.00 | 9.50 | C |
| ATOM | 2333 | OD1 | ASP | B | 12 | −2.930 | 23.532 | 21.660 | 1.00 | 7.65 | O |
| ATOM | 2334 | OD2 | ASP | B | 12 | −4.768 | 23.257 | 22.802 | 1.00 | 9.59 | O |
| ATOM | 2335 | C | ASP | B | 12 | −0.679 | 25.010 | 24.937 | 1.00 | 9.51 | C |
| ATOM | 2336 | O | ASP | B | 12 | −0.483 | 26.212 | 24.813 | 1.00 | 13.07 | O |
| ATOM | 2337 | N | TYR | B | 13 | −0.468 | 24.333 | 26.037 | 1.00 | 9.80 | N |
| ATOM | 2339 | CA | TYR | B | 13 | 0.066 | 24.973 | 27.238 | 1.00 | 7.80 | C |
| ATOM | 2341 | CB | TYR | B | 13 | 0.160 | 24.034 | 28.450 | 1.00 | 7.41 | C |
| ATOM | 2344 | CG | TYR | B | 13 | 0.391 | 24.735 | 29.769 | 1.00 | 8.08 | C |
| ATOM | 2345 | CD1 | TYR | B | 13 | 1.654 | 24.907 | 30.268 | 1.00 | 9.81 | C |
| ATOM | 2347 | CE1 | TYR | B | 13 | 1.923 | 25.538 | 31.426 | 1.00 | 9.09 | C |
| ATOM | 2349 | CZ | TYR | B | 13 | 0.882 | 25.868 | 32.302 | 1.00 | 13.91 | C |
| ATOM | 2350 | OH | TYR | B | 13 | 1.212 | 26.448 | 33.525 | 1.00 | 14.39 | O |
| ATOM | 2352 | CE2 | TYR | B | 13 | −0.458 | 25.581 | 31.903 | 1.00 | 10.49 | C |
| ATOM | 2354 | CD2 | TYR | B | 13 | −0.675 | 25.032 | 30.614 | 1.00 | 10.89 | C |
| ATOM | 2356 | C | TYR | B | 13 | 1.483 | 25.494 | 26.973 | 1.00 | 7.88 | C |
| ATOM | 2357 | O | TYR | B | 13 | 1.824 | 26.617 | 27.388 | 1.00 | 8.81 | O |
| ATOM | 2358 | N | LEU | B | 14 | 2.309 | 24.624 | 26.447 | 1.00 | 10.94 | N |
| ATOM | 2360 | CA | LEU | B | 14 | 3.638 | 25.014 | 25.990 | 1.00 | 7.43 | C |
| ATOM | 2362 | CB | LEU | B | 14 | 4.233 | 23.858 | 25.220 | 1.00 | 9.68 | C |
| ATOM | 2365 | CG | LEU | B | 14 | 4.871 | 22.796 | 26.149 | 1.00 | 10.03 | C |
| ATOM | 2367 | CD1 | LEU | B | 14 | 5.122 | 21.584 | 25.320 | 1.00 | 10.85 | C |
| ATOM | 2371 | CD2 | LEU | B | 14 | 6.178 | 23.145 | 26.903 | 1.00 | 9.85 | C |
| ATOM | 2375 | C | LEU | B | 14 | 3.652 | 26.252 | 25.101 | 1.00 | 11.17 | C |
| ATOM | 2376 | O | LEU | B | 14 | 4.475 | 27.159 | 25.320 | 1.00 | 10.57 | O |
| ATOM | 2377 | N | GLN | B | 15 | 2.822 | 26.232 | 24.039 | 1.00 | 9.73 | N |
| ATOM | 2379 | CA | GLN | B | 15 | 2.747 | 27.313 | 23.081 | 1.00 | 10.80 | C |
| ATOM | 2381 | CB | GLN | B | 15 | 1.999 | 26.859 | 21.797 | 1.00 | 8.56 | C |
| ATOM | 2384 | CG | GLN | B | 15 | 2.875 | 25.924 | 20.916 | 1.00 | 10.28 | C |
| ATOM | 2387 | CD | GLN | B | 15 | 2.426 | 25.805 | 19.520 | 1.00 | 8.91 | C |
| ATOM | 2388 | OE1 | GLN | B | 15 | 1.240 | 25.938 | 19.325 | 1.00 | 9.29 | O |
| ATOM | 2389 | NE2 | GLN | B | 15 | 3.323 | 25.676 | 18.500 | 1.00 | 3.81 | N |
| ATOM | 2392 | C | GLN | B | 15 | 2.186 | 28.597 | 23.639 | 1.00 | 10.08 | C |
| ATOM | 2393 | O | GLN | B | 15 | 2.541 | 29.651 | 23.182 | 1.00 | 11.20 | O |
| ATOM | 2394 | N | THR | B | 16 | 1.380 | 28.476 | 24.676 | 1.00 | 9.09 | N |
| ATOM | 2396 | CA | THR | B | 16 | 0.794 | 29.547 | 25.357 | 1.00 | 9.13 | C |
| ATOM | 2398 | CB | THR | B | 16 | −0.534 | 29.194 | 25.979 | 1.00 | 7.00 | C |
| ATOM | 2400 | OG1 | THR | B | 16 | −1.481 | 28.772 | 25.021 | 1.00 | 10.11 | O |
| ATOM | 2402 | CG2 | THR | B | 16 | −1.142 | 30.399 | 26.664 | 1.00 | 8.72 | C |
| ATOM | 2406 | C | THR | B | 16 | 1.736 | 30.206 | 26.395 | 1.00 | 7.73 | C |
| ATOM | 2407 | O | THR | B | 16 | 1.955 | 31.388 | 26.349 | 1.00 | 6.63 | O |
| ATOM | 2408 | N | TYR | B | 17 | 2.408 | 29.398 | 27.172 | 1.00 | 10.27 | N |
| ATOM | 2410 | CA | TYR | B | 17 | 3.082 | 29.809 | 28.377 | 1.00 | 11.55 | C |
| ATOM | 2412 | CB | TYR | B | 17 | 2.524 | 29.271 | 29.697 | 1.00 | 11.67 | C |
| ATOM | 2415 | CG | TYR | B | 17 | 1.052 | 29.571 | 29.949 | 1.00 | 11.49 | C |
| ATOM | 2416 | CD1 | TYR | B | 17 | 0.063 | 28.567 | 29.778 | 1.00 | 12.82 | C |
| ATOM | 2418 | CE1 | TYR | B | 17 | −1.313 | 28.791 | 30.003 | 1.00 | 11.99 | C |
| ATOM | 2420 | CZ | TYR | B | 17 | −1.685 | 30.091 | 30.334 | 1.00 | 12.14 | C |
| ATOM | 2421 | OH | TYR | B | 17 | −2.996 | 30.316 | 30.522 | 1.00 | 12.20 | O |
| ATOM | 2423 | CE2 | TYR | B | 17 | −0.737 | 31.122 | 30.513 | 1.00 | 12.43 | C |
| ATOM | 2425 | CD2 | TYR | B | 17 | 0.635 | 30.828 | 30.373 | 1.00 | 11.40 | C |
| ATOM | 2427 | C | TYR | B | 17 | 4.538 | 29.590 | 28.297 | 1.00 | 11.47 | C |
| ATOM | 2428 | O | TYR | B | 17 | 5.234 | 30.053 | 29.222 | 1.00 | 11.44 | O |
| ATOM | 2429 | N | HIS | B | 18 | 5.004 | 28.864 | 27.292 | 1.00 | 12.19 | N |
| ATOM | 2431 | CA | HIS | B | 18 | 6.454 | 28.628 | 27.117 | 1.00 | 14.05 | C |
| ATOM | 2433 | CB | HIS | B | 18 | 7.244 | 29.935 | 26.791 | 1.00 | 17.67 | C |
| ATOM | 2436 | CG | HIS | B | 18 | 6.897 | 30.535 | 25.469 | 1.00 | 24.43 | C |
| ATOM | 2437 | ND1 | HIS | B | 18 | 5.709 | 31.119 | 25.214 | 1.00 | 36.04 | N |
| ATOM | 2439 | CE1 | HIS | B | 18 | 5.598 | 31.493 | 23.944 | 1.00 | 34.79 | C |

-continued

| | | | | | | | | | | | |
|---|---|---|---|---|---|---|---|---|---|---|---|
| ATOM | 2441 | NE2 | HIS | B | 18 | 6.714 | 31.244 | 23.366 | 1.00 | 25.22 | N |
| ATOM | 2443 | CD2 | HIS | B | 18 | 7.500 | 30.600 | 24.282 | 1.00 | 30.50 | C |
| ATOM | 2445 | C | HIS | B | 18 | 7.135 | 27.925 | 28.303 | 1.00 | 13.17 | C |
| ATOM | 2446 | O | HIS | B | 18 | 8.278 | 28.237 | 28.732 | 1.00 | 9.99 | O |
| ATOM | 2447 | N | LYS | B | 19 | 6.359 | 27.047 | 28.905 | 1.00 | 11.45 | N |
| ATOM | 2449 | CA | LYS | B | 19 | 6.879 | 26.163 | 29.940 | 1.00 | 15.06 | C |
| ATOM | 2451 | CB | LYS | B | 19 | 6.989 | 26.910 | 31.307 | 1.00 | 15.74 | C |
| ATOM | 2454 | CG | LYS | B | 19 | 5.637 | 27.434 | 31.872 | 1.00 | 18.65 | C |
| ATOM | 2457 | CD | LYS | B | 19 | 5.833 | 28.453 | 33.009 | 1.00 | 21.85 | C |
| ATOM | 2460 | CE | LYS | B | 19 | 4.569 | 28.960 | 33.644 | 1.00 | 24.72 | C |
| ATOM | 2463 | NZ | LYS | B | 19 | 4.799 | 29.547 | 35.077 | 1.00 | 28.63 | N |
| ATOM | 2467 | C | LYS | B | 19 | 5.897 | 25.010 | 30.086 | 1.00 | 12.64 | C |
| ATOM | 2468 | O | LYS | B | 19 | 4.781 | 25.064 | 29.648 | 1.00 | 13.23 | O |
| ATOM | 2469 | N | LEU | B | 20 | 6.335 | 23.888 | 30.616 | 1.00 | 13.20 | N |
| ATOM | 2471 | CA | LEU | B | 20 | 5.414 | 22.809 | 30.925 | 1.00 | 10.09 | C |
| ATOM | 2473 | CB | LEU | B | 20 | 6.204 | 21.566 | 31.307 | 1.00 | 11.80 | C |
| ATOM | 2476 | CG | LEU | B | 20 | 7.128 | 21.060 | 30.215 | 1.00 | 11.10 | C |
| ATOM | 2478 | CD1 | LEU | B | 20 | 8.164 | 20.025 | 30.597 | 1.00 | 13.97 | C |
| ATOM | 2482 | CD2 | LEU | B | 20 | 6.205 | 20.302 | 29.184 | 1.00 | 12.08 | C |
| ATOM | 2486 | C | LEU | B | 20 | 4.530 | 23.131 | 32.047 | 1.00 | 10.11 | C |
| ATOM | 2487 | O | LEU | B | 20 | 4.832 | 23.921 | 32.929 | 1.00 | 11.78 | O |
| ATOM | 2488 | N | PRO | B | 21 | 3.380 | 22.493 | 32.024 | 1.00 | 11.42 | N |
| ATOM | 2489 | CA | PRO | B | 21 | 2.484 | 22.546 | 33.162 | 1.00 | 11.59 | C |
| ATOM | 2491 | CB | PRO | B | 21 | 1.421 | 21.465 | 32.816 | 1.00 | 13.68 | C |
| ATOM | 2494 | CG | PRO | B | 21 | 1.603 | 21.065 | 31.465 | 1.00 | 15.49 | C |
| ATOM | 2497 | CD | PRO | B | 21 | 2.840 | 21.697 | 30.918 | 1.00 | 12.52 | C |
| ATOM | 2500 | C | PRO | B | 21 | 3.197 | 22.133 | 34.490 | 1.00 | 11.12 | C |
| ATOM | 2501 | O | PRO | B | 21 | 4.193 | 21.367 | 34.474 | 1.00 | 9.47 | O |
| ATOM | 2502 | N | ASP | B | 22 | 2.542 | 22.447 | 35.582 | 1.00 | 10.82 | N |
| ATOM | 2504 | CA | ASP | B | 22 | 3.111 | 22.219 | 36.896 | 1.00 | 16.29 | C |
| ATOM | 2506 | CB | ASP | B | 22 | 2.227 | 22.925 | 37.937 | 1.00 | 19.70 | C |
| ATOM | 2509 | CG | ASP | B | 22 | 2.415 | 24.383 | 37.824 | 1.00 | 25.42 | C |
| ATOM | 2510 | OD1 | ASP | B | 22 | 1.646 | 25.091 | 38.504 | 1.00 | 28.81 | O |
| ATOM | 2511 | OD2 | ASP | B | 22 | 3.315 | 24.931 | 37.119 | 1.00 | 25.63 | O |
| ATOM | 2512 | C | ASP | B | 22 | 3.273 | 20.786 | 37.356 | 1.00 | 15.34 | C |
| ATOM | 2513 | O | ASP | B | 22 | 3.754 | 20.552 | 38.484 | 1.00 | 16.59 | O |
| ATOM | 2514 | N | ASN | B | 23 | 2.590 | 19.898 | 36.633 | 1.00 | 13.56 | N |
| ATOM | 2516 | CA | ASN | B | 23 | 2.646 | 18.495 | 36.907 | 1.00 | 11.91 | C |
| ATOM | 2518 | CB | ASN | B | 23 | 1.416 | 17.759 | 36.509 | 1.00 | 12.29 | C |
| ATOM | 2521 | CG | ASN | B | 23 | 1.057 | 17.932 | 35.001 | 1.00 | 13.95 | C |
| ATOM | 2522 | OD1 | ASN | B | 23 | 1.049 | 16.967 | 34.196 | 1.00 | 14.77 | O |
| ATOM | 2523 | ND2 | ASN | B | 23 | 0.582 | 19.128 | 34.684 | 1.00 | 14.82 | N |
| ATOM | 2526 | C | ASN | B | 23 | 3.849 | 17.836 | 36.358 | 1.00 | 11.72 | C |
| ATOM | 2527 | O | ASN | B | 23 | 3.966 | 16.596 | 36.447 | 1.00 | 14.87 | O |
| ATOM | 2528 | N | TYR | B | 24 | 4.781 | 18.628 | 35.847 | 1.00 | 10.27 | N |
| ATOM | 2530 | CA | TYR | B | 24 | 5.980 | 18.036 | 35.240 | 1.00 | 10.75 | C |
| ATOM | 2532 | CB | TYR | B | 24 | 6.294 | 18.529 | 33.842 | 1.00 | 10.64 | C |
| ATOM | 2535 | CG | TYR | B | 24 | 5.428 | 17.929 | 32.790 | 1.00 | 10.75 | C |
| ATOM | 2536 | CD1 | TYR | B | 24 | 5.774 | 16.719 | 32.234 | 1.00 | 9.86 | C |
| ATOM | 2538 | CE1 | TYR | B | 24 | 4.897 | 16.041 | 31.364 | 1.00 | 10.65 | C |
| ATOM | 2540 | CZ | TYR | B | 24 | 3.750 | 16.640 | 31.010 | 1.00 | 9.17 | C |
| ATOM | 2541 | OH | TYR | B | 24 | 2.926 | 16.023 | 30.114 | 1.00 | 10.54 | O |
| ATOM | 2543 | CE2 | TYR | B | 24 | 3.393 | 17.873 | 31.556 | 1.00 | 7.66 | C |
| ATOM | 2545 | CD2 | TYR | B | 24 | 4.211 | 18.537 | 32.448 | 1.00 | 7.74 | C |
| ATOM | 2547 | C | TYR | B | 24 | 7.237 | 18.279 | 36.101 | 1.00 | 11.32 | C |
| ATOM | 2548 | O | TYR | B | 24 | 7.282 | 19.342 | 36.700 | 1.00 | 12.80 | O |
| ATOM | 2549 | N | ILE | B | 25 | 8.156 | 17.313 | 36.205 | 1.00 | 11.07 | N |
| ATOM | 2551 | CA | ILE | B | 25 | 9.469 | 17.534 | 36.882 | 1.00 | 11.11 | C |
| ATOM | 2553 | CB | ILE | B | 25 | 9.525 | 16.893 | 38.258 | 1.00 | 12.23 | C |
| ATOM | 2555 | CG1 | ILE | B | 25 | 9.303 | 15.401 | 38.162 | 1.00 | 12.51 | C |
| ATOM | 2558 | CD1 | ILE | B | 25 | 9.362 | 14.819 | 39.651 | 1.00 | 13.73 | C |
| ATOM | 2562 | CG2 | ILE | B | 25 | 8.615 | 17.678 | 39.189 | 1.00 | 14.66 | C |
| ATOM | 2566 | C | ILE | B | 25 | 10.516 | 16.855 | 36.018 | 1.00 | 11.19 | C |
| ATOM | 2567 | O | ILE | B | 25 | 10.145 | 15.932 | 35.223 | 1.00 | 12.24 | O |
| ATOM | 2568 | N | THR | B | 26 | 11.731 | 17.382 | 36.073 | 1.00 | 11.68 | N |
| ATOM | 2570 | CA | THR | B | 26 | 12.787 | 16.862 | 35.229 | 1.00 | 13.65 | C |
| ATOM | 2572 | CB | THR | B | 26 | 14.052 | 17.739 | 35.301 | 1.00 | 14.60 | C |
| ATOM | 2574 | OG1 | THR | B | 26 | 14.575 | 17.871 | 36.623 | 1.00 | 11.50 | O |
| ATOM | 2576 | CG2 | THR | B | 26 | 13.809 | 19.193 | 34.703 | 1.00 | 15.85 | C |
| ATOM | 2580 | C | THR | B | 26 | 13.192 | 15.474 | 35.761 | 1.00 | 14.64 | C |
| ATOM | 2581 | O | THR | B | 26 | 12.920 | 15.113 | 36.936 | 1.00 | 12.25 | O |
| ATOM | 2582 | N | LYS | B | 27 | 14.006 | 14.793 | 34.963 | 1.00 | 11.43 | N |
| ATOM | 2584 | CA | LYS | B | 27 | 14.638 | 13.598 | 35.489 | 1.00 | 12.47 | C |
| ATOM | 2586 | CB | LYS | B | 27 | 15.419 | 12.810 | 34.447 | 1.00 | 14.64 | C |
| ATOM | 2589 | CG | LYS | B | 27 | 14.517 | 12.122 | 33.412 | 1.00 | 18.35 | C |
| ATOM | 2592 | CD | LYS | B | 27 | 15.265 | 11.145 | 32.477 | 1.00 | 19.42 | C |
| ATOM | 2595 | CE | LYS | B | 27 | 16.129 | 11.984 | 31.542 | 1.00 | 21.43 | C |
| ATOM | 2598 | NZ | LYS | B | 27 | 15.335 | 12.839 | 30.547 | 1.00 | 18.82 | N |
| ATOM | 2602 | C | LYS | B | 27 | 15.473 | 13.808 | 36.707 | 1.00 | 11.01 | C |
| ATOM | 2603 | O | LYS | B | 27 | 15.316 | 13.002 | 37.640 | 1.00 | 9.61 | O |

-continued

| | | | | | | | | | | |
|---|---|---|---|---|---|---|---|---|---|---|
| ATOM | 2604 | N | SER | B | 28 | 16.387 | 14.758 | 36.704 | 1.00 | 10.20 | N |
| ATOM | 2606 | CA | SER | B | 28 | 17.128 | 15.013 | 37.953 | 1.00 | 11.99 | C |
| ATOM | 2608 | CB | SER | B | 28 | 18.136 | 16.166 | 38.038 | 1.00 | 14.58 | C |
| ATOM | 2611 | OG | SER | B | 28 | 18.647 | 16.119 | 36.754 | 1.00 | 19.83 | O |
| ATOM | 2613 | C | SER | B | 28 | 16.234 | 15.291 | 39.135 | 1.00 | 11.22 | C |
| ATOM | 2614 | O | SER | B | 28 | 16.524 | 14.831 | 40.264 | 1.00 | 10.00 | O |
| ATOM | 2615 | N | GLU | B | 29 | 15.239 | 16.103 | 38.896 | 1.00 | 10.23 | N |
| ATOM | 2617 | CA | GLU | B | 29 | 14.316 | 16.394 | 39.989 | 1.00 | 11.87 | C |
| ATOM | 2619 | CB | GLU | B | 29 | 13.293 | 17.461 | 39.653 | 1.00 | 15.30 | C |
| ATOM | 2622 | CG | GLU | B | 29 | 13.879 | 18.873 | 39.597 | 1.00 | 17.38 | C |
| ATOM | 2625 | CD | GLU | B | 29 | 12.942 | 19.806 | 38.872 | 1.00 | 19.55 | C |
| ATOM | 2626 | OE1 | GLU | B | 29 | 13.272 | 21.005 | 38.905 | 1.00 | 23.69 | O |
| ATOM | 2627 | OE2 | GLU | B | 29 | 11.953 | 19.376 | 38.212 | 1.00 | 19.38 | O |
| ATOM | 2628 | C | GLU | B | 29 | 13.540 | 15.156 | 40.499 | 1.00 | 10.57 | C |
| ATOM | 2629 | O | GLU | B | 29 | 13.466 | 15.001 | 41.690 | 1.00 | 10.87 | O |
| ATOM | 2630 | N | ALA | B | 30 | 13.102 | 14.234 | 39.664 | 1.00 | 8.31 | N |
| ATOM | 2632 | CA | ALA | B | 30 | 12.557 | 12.968 | 40.051 | 1.00 | 10.34 | C |
| ATOM | 2634 | CB | ALA | B | 30 | 11.966 | 12.319 | 38.860 | 1.00 | 10.98 | C |
| ATOM | 2638 | C | ALA | B | 30 | 13.604 | 12.060 | 40.741 | 1.00 | 10.90 | C |
| ATOM | 2639 | O | ALA | B | 30 | 13.222 | 11.576 | 41.816 | 1.00 | 10.18 | O |
| ATOM | 2640 | N | GLN | B | 31 | 14.870 | 11.974 | 40.286 | 1.00 | 12.79 | N |
| ATOM | 2642 | CA | GLN | B | 31 | 15.934 | 11.215 | 40.895 | 1.00 | 14.39 | C |
| ATOM | 2644 | CB | GLN | B | 31 | 17.277 | 11.212 | 40.156 | 1.00 | 19.96 | C |
| ATOM | 2647 | CG | GLN | B | 31 | 17.216 | 10.729 | 38.640 | 1.00 | 24.22 | C |
| ATOM | 2650 | CD | GLN | B | 31 | 18.537 | 10.673 | 37.723 | 1.00 | 28.13 | C |
| ATOM | 2651 | OE1 | GLN | B | 31 | 19.059 | 11.660 | 37.122 | 1.00 | 29.70 | O |
| ATOM | 2652 | NE2 | GLN | B | 31 | 18.981 | 9.434 | 37.520 | 1.00 | 28.68 | N |
| ATOM | 2655 | C | GLN | B | 31 | 16.083 | 11.788 | 42.279 | 1.00 | 13.00 | C |
| ATOM | 2656 | O | GLN | B | 31 | 16.267 | 10.994 | 43.172 | 1.00 | 11.92 | O |
| ATOM | 2657 | N | ALA | B | 32 | 15.955 | 13.100 | 42.484 | 1.00 | 12.98 | N |
| ATOM | 2659 | CA | ALA | B | 32 | 16.197 | 13.648 | 43.825 | 1.00 | 13.91 | C |
| ATOM | 2661 | CB | ALA | B | 32 | 16.409 | 15.140 | 43.846 | 1.00 | 15.00 | C |
| ATOM | 2665 | C | ALA | B | 32 | 15.136 | 13.268 | 44.853 | 1.00 | 13.28 | C |
| ATOM | 2666 | O | ALA | B | 32 | 15.340 | 13.205 | 46.067 | 1.00 | 14.55 | O |
| ATOM | 2667 | N | LEU | B | 33 | 13.983 | 12.906 | 44.331 | 1.00 | 13.14 | N |
| ATOM | 2669 | CA | LEU | B | 33 | 12.881 | 12.507 | 45.171 | 1.00 | 12.01 | C |
| ATOM | 2671 | CB | LEU | B | 33 | 11.565 | 12.938 | 44.511 | 1.00 | 13.86 | C |
| ATOM | 2674 | CG | LEU | B | 33 | 11.274 | 14.421 | 44.500 | 1.00 | 15.58 | C |
| ATOM | 2676 | CD1 | LEU | B | 33 | 10.166 | 14.775 | 43.483 | 1.00 | 15.99 | C |
| ATOM | 2680 | CD2 | LEU | B | 33 | 10.908 | 14.822 | 46.002 | 1.00 | 17.33 | C |
| ATOM | 2684 | C | LEU | B | 33 | 12.903 | 11.024 | 45.362 | 1.00 | 12.31 | C |
| ATOM | 2685 | O | LEU | B | 33 | 12.048 | 10.518 | 46.123 | 1.00 | 11.39 | O |
| ATOM | 2686 | N | GLY | B | 34 | 13.843 | 10.325 | 44.702 | 1.00 | 10.75 | N |
| ATOM | 2688 | CA | GLY | B | 34 | 14.004 | 8.877 | 44.841 | 1.00 | 11.57 | C |
| ATOM | 2691 | C | GLY | B | 34 | 13.539 | 7.995 | 43.709 | 1.00 | 13.21 | C |
| ATOM | 2692 | O | GLY | B | 34 | 13.566 | 6.772 | 43.704 | 1.00 | 11.37 | O |
| ATOM | 2693 | N | TRP | B | 35 | 13.097 | 8.673 | 42.658 | 1.00 | 12.54 | N |
| ATOM | 2695 | CA | TRP | B | 35 | 12.875 | 8.003 | 41.406 | 1.00 | 14.11 | C |
| ATOM | 2697 | CB | TRP | B | 35 | 12.401 | 8.916 | 40.272 | 1.00 | 13.66 | C |
| ATOM | 2700 | CG | TRP | B | 35 | 12.205 | 8.174 | 38.906 | 1.00 | 13.56 | C |
| ATOM | 2701 | CD1 | TRP | B | 35 | 11.337 | 7.122 | 38.634 | 1.00 | 15.31 | C |
| ATOM | 2703 | NE1 | TRP | B | 35 | 11.394 | 6.748 | 37.311 | 1.00 | 13.91 | N |
| ATOM | 2705 | CE2 | TRP | B | 35 | 12.381 | 7.499 | 36.720 | 1.00 | 14.38 | C |
| ATOM | 2706 | CD2 | TRP | B | 35 | 12.925 | 8.375 | 37.714 | 1.00 | 13.95 | C |
| ATOM | 2707 | CE3 | TRP | B | 35 | 13.899 | 9.305 | 37.322 | 1.00 | 14.84 | C |
| ATOM | 2709 | CZ3 | TRP | B | 35 | 14.410 | 9.260 | 36.029 | 1.00 | 13.69 | C |
| ATOM | 2711 | CH2 | TRP | B | 35 | 13.893 | 8.324 | 35.067 | 1.00 | 13.19 | C |
| ATOM | 2713 | CZ2 | TRP | B | 35 | 12.887 | 7.448 | 35.416 | 1.00 | 14.36 | C |
| ATOM | 2715 | C | TRP | B | 35 | 14.115 | 7.243 | 40.896 | 1.00 | 14.04 | C |
| ATOM | 2716 | O | TRP | B | 35 | 15.190 | 7.801 | 40.716 | 1.00 | 15.29 | O |
| ATOM | 2717 | N | VAL | B | 36 | 13.881 | 6.010 | 40.477 | 1.00 | 13.88 | N |
| ATOM | 2719 | CA | VAL | B | 36 | 14.938 | 5.224 | 39.851 | 1.00 | 15.14 | C |
| ATOM | 2721 | CB | VAL | B | 36 | 15.528 | 4.160 | 40.879 | 1.00 | 16.48 | C |
| ATOM | 2723 | CG1 | VAL | B | 36 | 16.548 | 3.157 | 40.227 | 1.00 | 16.99 | C |
| ATOM | 2727 | CG2 | VAL | B | 36 | 16.171 | 4.808 | 42.113 | 1.00 | 17.44 | C |
| ATOM | 2731 | C | VAL | B | 36 | 14.267 | 4.521 | 38.670 | 1.00 | 14.82 | C |
| ATOM | 2732 | O | VAL | B | 36 | 13.314 | 3.811 | 38.897 | 1.00 | 12.15 | O |
| ATOM | 2733 | N | ALA | B | 37 | 14.782 | 4.608 | 37.446 | 1.00 | 16.44 | N |
| ATOM | 2735 | CA | ALA | B | 37 | 14.068 | 3.997 | 36.306 | 1.00 | 18.37 | C |
| ATOM | 2737 | CB | ALA | B | 37 | 14.815 | 4.224 | 35.074 | 1.00 | 18.92 | C |
| ATOM | 2741 | C | ALA | B | 37 | 13.684 | 2.542 | 36.399 | 1.00 | 20.89 | C |
| ATOM | 2742 | O | ALA | B | 37 | 12.480 | 2.155 | 36.213 | 1.00 | 24.01 | O |
| ATOM | 2743 | N | SER | B | 38 | 14.664 | 1.698 | 36.699 | 1.00 | 22.10 | N |
| ATOM | 2745 | CA | SER | B | 38 | 14.283 | 0.259 | 36.837 | 1.00 | 22.69 | C |
| ATOM | 2747 | CB | SER | B | 38 | 15.559 | −0.554 | 37.100 | 1.00 | 21.57 | C |
| ATOM | 2750 | OG | SER | B | 38 | 16.227 | −0.185 | 38.313 | 1.00 | 22.63 | O |
| ATOM | 2752 | C | SER | B | 38 | 13.211 | −0.060 | 37.961 | 1.00 | 22.94 | C |
| ATOM | 2753 | O | SER | B | 38 | 12.833 | −1.217 | 38.223 | 1.00 | 22.63 | O |
| ATOM | 2754 | N | LYS | B | 39 | 12.802 | 0.929 | 38.751 | 1.00 | 20.18 | N |
| ATOM | 2756 | CA | LYS | B | 39 | 11.882 | 0.673 | 39.846 | 1.00 | 20.50 | C |

-continued

| | | | | | | | | | | | |
|---|---|---|---|---|---|---|---|---|---|---|---|
| ATOM | 2758 | CB | LYS | B | 39 | 12.320 | 1.320 | 41.183 | 1.00 | 21.23 | C |
| ATOM | 2761 | CG | LYS | B | 39 | 13.561 | 0.765 | 41.893 | 1.00 | 24.77 | C |
| ATOM | 2764 | CD | LYS | B | 39 | 13.538 | 1.201 | 43.423 | 1.00 | 28.33 | C |
| ATOM | 2767 | CE | LYS | B | 39 | 14.880 | 1.154 | 44.242 | 1.00 | 29.68 | C |
| ATOM | 2770 | NZ | LYS | B | 39 | 15.134 | 2.247 | 45.316 | 1.00 | 28.89 | N |
| ATOM | 2774 | C | LYS | B | 39 | 10.403 | 0.992 | 39.492 | 1.00 | 17.00 | C |
| ATOM | 2775 | O | LYS | B | 39 | 9.506 | 0.664 | 40.253 | 1.00 | 13.44 | O |
| ATOM | 2776 | N | GLY | B | 40 | 10.178 | 1.681 | 38.387 | 1.00 | 14.62 | N |
| ATOM | 2778 | CA | GLY | B | 40 | 8.861 | 2.155 | 37.995 | 1.00 | 13.91 | C |
| ATOM | 2781 | C | GLY | B | 40 | 8.100 | 2.925 | 39.085 | 1.00 | 14.90 | C |
| ATOM | 2782 | O | GLY | B | 40 | 6.841 | 2.864 | 39.180 | 1.00 | 13.49 | O |
| ATOM | 2783 | N | ASN | B | 41 | 8.846 | 3.662 | 39.919 | 1.00 | 12.54 | N |
| ATOM | 2785 | CA | ASN | B | 41 | 8.311 | 4.283 | 41.124 | 1.00 | 12.94 | C |
| ATOM | 2787 | CB | ASN | B | 41 | 9.245 | 3.914 | 42.277 | 1.00 | 12.00 | C |
| ATOM | 2790 | CG | ASN | B | 41 | 10.602 | 4.641 | 42.160 | 1.00 | 11.23 | C |
| ATOM | 2791 | OD1 | ASN | B | 41 | 11.063 | 5.011 | 41.079 | 1.00 | 10.63 | O |
| ATOM | 2792 | ND2 | ASN | B | 41 | 11.235 | 4.830 | 43.312 | 1.00 | 10.22 | N |
| ATOM | 2795 | C | ASN | B | 41 | 8.030 | 5.836 | 41.123 | 1.00 | 11.22 | C |
| ATOM | 2796 | O | ASN | B | 41 | 8.079 | 6.456 | 42.186 | 1.00 | 13.26 | O |
| ATOM | 2797 | N | LEU | B | 42 | 7.855 | 6.431 | 39.942 | 1.00 | 13.90 | N |
| ATOM | 2799 | CA | LEU | B | 42 | 7.820 | 7.901 | 39.808 | 1.00 | 13.55 | C |
| ATOM | 2801 | CB | LEU | B | 42 | 7.718 | 8.373 | 38.389 | 1.00 | 14.14 | C |
| ATOM | 2804 | CG | LEU | B | 42 | 7.483 | 9.856 | 38.161 | 1.00 | 13.84 | C |
| ATOM | 2806 | CD1 | LEU | B | 42 | 8.631 | 10.589 | 38.839 | 1.00 | 14.77 | C |
| ATOM | 2810 | CD2 | LEU | B | 42 | 7.361 | 10.199 | 36.694 | 1.00 | 15.89 | C |
| ATOM | 2814 | C | LEU | B | 42 | 6.595 | 8.359 | 40.621 | 1.00 | 12.12 | C |
| ATOM | 2815 | O | LEU | B | 42 | 6.728 | 9.265 | 41.412 | 1.00 | 11.43 | O |
| ATOM | 2816 | N | ALA | B | 43 | 5.458 | 7.694 | 40.471 | 1.00 | 15.11 | N |
| ATOM | 2818 | CA | ALA | B | 43 | 4.210 | 8.094 | 41.091 | 1.00 | 16.61 | C |
| ATOM | 2820 | CB | ALA | B | 43 | 3.000 | 7.567 | 40.368 | 1.00 | 16.87 | C |
| ATOM | 2824 | C | ALA | B | 43 | 4.147 | 7.827 | 42.567 | 1.00 | 16.65 | C |
| ATOM | 2825 | O | ALA | B | 43 | 3.317 | 8.440 | 43.242 | 1.00 | 15.47 | O |
| ATOM | 2826 | N | ASP | B | 44 | 5.027 | 6.965 | 43.055 | 1.00 | 18.19 | N |
| ATOM | 2828 | CA | ASP | B | 44 | 5.135 | 6.790 | 44.497 | 1.00 | 19.89 | C |
| ATOM | 2830 | CB | ASP | B | 44 | 5.853 | 5.480 | 44.884 | 1.00 | 24.16 | C |
| ATOM | 2833 | CG | ASP | B | 44 | 5.218 | 4.261 | 44.280 | 1.00 | 27.36 | C |
| ATOM | 2834 | OD1 | ASP | B | 44 | 4.018 | 4.065 | 44.502 | 1.00 | 30.60 | O |
| ATOM | 2835 | OD2 | ASP | B | 44 | 5.786 | 3.464 | 43.507 | 1.00 | 30.35 | O |
| ATOM | 2836 | C | ASP | B | 44 | 5.942 | 7.921 | 45.115 | 1.00 | 17.87 | C |
| ATOM | 2837 | O | ASP | B | 44 | 5.640 | 8.343 | 46.217 | 1.00 | 18.04 | O |
| ATOM | 2838 | N | VAL | B | 45 | 6.999 | 8.399 | 44.440 | 1.00 | 15.56 | N |
| ATOM | 2840 | CA | VAL | B | 45 | 7.785 | 9.445 | 45.099 | 1.00 | 12.84 | C |
| ATOM | 2842 | CB | VAL | B | 45 | 9.255 | 9.309 | 44.795 | 1.00 | 14.45 | C |
| ATOM | 2844 | CG1 | VAL | B | 45 | 9.727 | 7.915 | 45.156 | 1.00 | 16.75 | C |
| ATOM | 2848 | CG2 | VAL | B | 45 | 9.571 | 9.462 | 43.280 | 1.00 | 13.91 | C |
| ATOM | 2852 | C | VAL | B | 45 | 7.389 | 10.830 | 44.658 | 1.00 | 12.95 | C |
| ATOM | 2853 | O | VAL | B | 45 | 7.815 | 11.800 | 45.278 | 1.00 | 12.61 | O |
| ATOM | 2854 | N | ALA | B | 46 | 6.672 | 10.937 | 43.529 | 1.00 | 11.48 | N |
| ATOM | 2856 | CA | ALA | B | 46 | 6.202 | 12.235 | 43.022 | 1.00 | 13.03 | C |
| ATOM | 2858 | CB | ALA | B | 46 | 7.091 | 12.748 | 41.873 | 1.00 | 12.22 | C |
| ATOM | 2862 | C | ALA | B | 46 | 4.760 | 12.084 | 42.499 | 1.00 | 11.88 | C |
| ATOM | 2863 | O | ALA | B | 46 | 4.468 | 12.032 | 41.324 | 1.00 | 14.30 | O |
| ATOM | 2864 | N | PRO | B | 47 | 3.838 | 12.052 | 43.426 | 1.00 | 13.53 | N |
| ATOM | 2865 | CA | PRO | B | 47 | 2.496 | 11.645 | 43.052 | 1.00 | 14.04 | C |
| ATOM | 2867 | CB | PRO | B | 47 | 1.741 | 11.717 | 44.404 | 1.00 | 14.16 | C |
| ATOM | 2870 | CG | PRO | B | 47 | 2.822 | 11.473 | 45.404 | 1.00 | 15.19 | C |
| ATOM | 2873 | CD | PRO | B | 47 | 4.046 | 12.158 | 44.894 | 1.00 | 15.11 | C |
| ATOM | 2876 | C | PRO | B | 47 | 1.920 | 12.675 | 42.107 | 1.00 | 13.57 | C |
| ATOM | 2877 | O | PRO | B | 47 | 2.089 | 13.855 | 42.339 | 1.00 | 14.43 | O |
| ATOM | 2878 | N | GLY | B | 48 | 1.333 | 12.257 | 40.997 | 1.00 | 13.92 | N |
| ATOM | 2880 | CA | GLY | B | 48 | 0.699 | 13.206 | 40.107 | 1.00 | 11.07 | C |
| ATOM | 2883 | C | GLY | B | 48 | 1.615 | 13.814 | 39.081 | 1.00 | 12.05 | C |
| ATOM | 2884 | O | GLY | B | 48 | 1.148 | 14.637 | 38.248 | 1.00 | 14.31 | O |
| ATOM | 2885 | N | LYS | B | 49 | 2.915 | 13.550 | 39.263 | 1.00 | 9.92 | N |
| ATOM | 2887 | CA | LYS | B | 49 | 3.885 | 14.055 | 38.328 | 1.00 | 9.15 | C |
| ATOM | 2889 | CB | LYS | B | 49 | 5.107 | 14.440 | 39.118 | 1.00 | 8.77 | C |
| ATOM | 2892 | CG | LYS | B | 49 | 4.764 | 15.397 | 40.227 | 1.00 | 10.89 | C |
| ATOM | 2895 | CD | LYS | B | 49 | 4.328 | 16.788 | 39.963 | 1.00 | 13.20 | C |
| ATOM | 2898 | CE | LYS | B | 49 | 4.423 | 17.615 | 41.294 | 1.00 | 15.89 | C |
| ATOM | 2901 | NZ | LYS | B | 49 | 4.288 | 18.964 | 40.734 | 1.00 | 18.50 | N |
| ATOM | 2905 | C | LYS | B | 49 | 4.295 | 13.129 | 37.237 | 1.00 | 11.64 | C |
| ATOM | 2906 | O | LYS | B | 49 | 3.919 | 11.969 | 37.234 | 1.00 | 11.93 | O |
| ATOM | 2907 | N | SER | B | 50 | 4.798 | 13.760 | 36.175 | 1.00 | 13.66 | N |
| ATOM | 2909 | CA | SER | B | 50 | 5.296 | 13.128 | 34.984 | 1.00 | 12.63 | C |
| ATOM | 2911 | CB | SER | B | 50 | 4.473 | 13.411 | 33.703 | 1.00 | 12.14 | C |
| ATOM | 2914 | OG | SER | B | 50 | 3.118 | 12.953 | 33.793 | 1.00 | 9.72 | O |
| ATOM | 2916 | C | SER | B | 50 | 6.698 | 13.748 | 34.777 | 1.00 | 13.09 | C |
| ATOM | 2917 | O | SER | B | 50 | 6.917 | 14.924 | 35.064 | 1.00 | 10.65 | O |
| ATOM | 2918 | N | ILE | B | 51 | 7.584 | 12.935 | 34.212 | 1.00 | 10.44 | N |
| ATOM | 2920 | CA | ILE | B | 51 | 8.850 | 13.427 | 33.834 | 1.00 | 11.52 | C |

-continued

| | | | | | | | | | | |
|---|---|---|---|---|---|---|---|---|---|---|
| ATOM | 2922 | CB | ILE | B | 51 | 9.737 | 12.216 | 33.416 | 1.00 | 13.32 | C |
| ATOM | 2924 | CG1 | ILE | B | 51 | 10.153 | 11.244 | 34.558 | 1.00 | 13.81 | C |
| ATOM | 2927 | CD1 | ILE | B | 51 | 10.718 | 12.028 | 35.481 | 1.00 | 15.55 | C |
| ATOM | 2931 | CG2 | ILE | B | 51 | 10.996 | 12.720 | 32.766 | 1.00 | 9.34 | C |
| ATOM | 2935 | C | ILE | B | 51 | 8.731 | 14.313 | 32.525 | 1.00 | 12.05 | C |
| ATOM | 2936 | O | ILE | B | 51 | 8.047 | 14.016 | 31.561 | 1.00 | 12.48 | O |
| ATOM | 2937 | N | GLY | B | 52 | 9.345 | 15.474 | 32.534 | 1.00 | 12.14 | N |
| ATOM | 2939 | CA | GLY | B | 52 | 9.413 | 16.324 | 31.357 | 1.00 | 11.66 | C |
| ATOM | 2942 | C | GLY | B | 52 | 10.335 | 17.490 | 31.576 | 1.00 | 12.77 | C |
| ATOM | 2943 | O | GLY | B | 52 | 10.646 | 17.884 | 32.723 | 1.00 | 10.85 | O |
| ATOM | 2944 | N | GLY | B | 53 | 10.697 | 18.089 | 30.445 | 1.00 | 10.59 | N |
| ATOM | 2946 | CA | GLY | B | 53 | 11.507 | 19.295 | 30.437 | 1.00 | 13.12 | C |
| ATOM | 2949 | C | GLY | B | 53 | 12.956 | 19.111 | 30.057 | 1.00 | 13.01 | C |
| ATOM | 2950 | O | GLY | B | 53 | 13.711 | 20.073 | 29.916 | 1.00 | 12.93 | O |
| ATOM | 2951 | N | ASP | B | 54 | 13.396 | 17.870 | 30.032 | 1.00 | 11.51 | N |
| ATOM | 2953 | CA | ASP | B | 54 | 14.787 | 17.675 | 29.793 | 1.00 | 13.36 | C |
| ATOM | 2955 | CB | ASP | B | 54 | 15.291 | 16.320 | 30.214 | 1.00 | 14.97 | C |
| ATOM | 2958 | CG | ASP | B | 54 | 15.028 | 16.059 | 31.664 | 1.00 | 17.99 | C |
| ATOM | 2959 | OD1 | ASP | B | 54 | 15.442 | 16.921 | 32.461 | 1.00 | 17.16 | O |
| ATOM | 2960 | OD2 | ASP | B | 54 | 14.309 | 15.092 | 32.022 | 1.00 | 16.58 | O |
| ATOM | 2961 | C | ASP | B | 54 | 15.066 | 17.807 | 28.306 | 1.00 | 14.77 | C |
| ATOM | 2962 | O | ASP | B | 54 | 14.227 | 17.691 | 27.416 | 1.00 | 12.24 | O |
| ATOM | 2963 | N | ILE | B | 55 | 16.316 | 18.144 | 28.050 | 1.00 | 13.38 | N |
| ATOM | 2965 | CA | ILE | B | 55 | 16.798 | 18.205 | 26.667 | 1.00 | 13.79 | C |
| ATOM | 2967 | CB | ILE | B | 55 | 18.301 | 18.698 | 26.674 | 1.00 | 13.55 | C |
| ATOM | 2969 | CG1 | ILE | B | 55 | 18.318 | 20.169 | 27.096 | 1.00 | 14.46 | C |
| ATOM | 2972 | CD1 | ILE | B | 55 | 18.098 | 21.020 | 25.908 | 1.00 | 17.36 | C |
| ATOM | 2976 | CG2 | ILE | B | 55 | 19.033 | 18.502 | 25.271 | 1.00 | 13.32 | C |
| ATOM | 2980 | C | ILE | B | 55 | 16.757 | 16.887 | 25.926 | 1.00 | 13.67 | C |
| ATOM | 2981 | O | ILE | B | 55 | 17.117 | 15.856 | 26.515 | 1.00 | 11.34 | O |
| ATOM | 2982 | N | PHE | B | 56 | 16.372 | 16.956 | 24.652 | 1.00 | 12.37 | N |
| ATOM | 2984 | CA | PHE | B | 56 | 16.420 | 15.781 | 23.781 | 1.00 | 14.85 | C |
| ATOM | 2986 | CB | PHE | B | 56 | 15.066 | 15.540 | 23.131 | 1.00 | 14.98 | C |
| ATOM | 2989 | CG | PHE | B | 56 | 15.045 | 14.462 | 22.122 | 1.00 | 14.15 | C |
| ATOM | 2990 | CD1 | PHE | B | 56 | 15.094 | 13.163 | 22.492 | 1.00 | 16.41 | C |
| ATOM | 2992 | CE1 | PHE | B | 56 | 15.080 | 12.101 | 21.579 | 1.00 | 15.50 | C |
| ATOM | 2994 | CZ | PHE | B | 56 | 14.954 | 12.359 | 20.275 | 1.00 | 17.62 | C |
| ATOM | 2996 | CE2 | PHE | B | 56 | 14.937 | 13.684 | 19.815 | 1.00 | 17.52 | C |
| ATOM | 2998 | CD2 | PHE | B | 56 | 14.927 | 14.754 | 20.797 | 1.00 | 17.22 | C |
| ATOM | 3000 | C | PHE | B | 56 | 17.495 | 16.046 | 22.751 | 1.00 | 16.47 | C |
| ATOM | 3001 | O | PHE | B | 56 | 17.319 | 16.988 | 21.993 | 1.00 | 17.74 | O |
| ATOM | 3002 | N | SER | B | 57 | 18.612 | 15.311 | 22.739 | 1.00 | 16.03 | N |
| ATOM | 3004 | CA | SER | B | 57 | 19.710 | 15.647 | 21.856 | 1.00 | 19.63 | C |
| ATOM | 3006 | CB | SER | B | 57 | 20.865 | 14.712 | 22.157 | 1.00 | 21.92 | C |
| ATOM | 3009 | OG | SER | B | 57 | 20.198 | 13.480 | 21.883 | 1.00 | 28.28 | O |
| ATOM | 3011 | C | SER | B | 57 | 19.377 | 15.424 | 20.380 | 1.00 | 19.52 | C |
| ATOM | 3012 | O | SER | B | 57 | 20.000 | 16.032 | 19.536 | 1.00 | 19.22 | O |
| ATOM | 3013 | N | ASN | B | 58 | 18.403 | 14.613 | 19.985 | 1.00 | 19.47 | N |
| ATOM | 3015 | CA | ASN | B | 58 | 18.061 | 14.614 | 18.532 | 1.00 | 19.30 | C |
| ATOM | 3017 | CB | ASN | B | 58 | 17.625 | 15.998 | 17.965 | 1.00 | 16.59 | C |
| ATOM | 3020 | CG | ASN | B | 58 | 16.947 | 15.904 | 16.623 | 1.00 | 14.55 | C |
| ATOM | 3021 | OD1 | ASN | B | 58 | 16.192 | 14.958 | 16.347 | 1.00 | 10.91 | O |
| ATOM | 3022 | ND2 | ASN | B | 58 | 17.143 | 16.939 | 15.797 | 1.00 | 13.94 | N |
| ATOM | 3025 | C | ASN | B | 58 | 19.192 | 14.060 | 17.696 | 1.00 | 21.21 | C |
| ATOM | 3026 | O | ASN | B | 58 | 19.395 | 14.477 | 16.557 | 1.00 | 18.51 | O |
| ATOM | 3027 | N | ARG | B | 59 | 19.879 | 13.089 | 18.291 | 1.00 | 25.14 | N |
| ATOM | 3029 | CA | ARG | B | 59 | 21.127 | 12.526 | 17.763 | 1.00 | 29.09 | C |
| ATOM | 3031 | CB | ARG | B | 59 | 21.680 | 11.481 | 18.820 | 1.00 | 33.53 | C |
| ATOM | 3034 | CG | ARG | B | 59 | 22.910 | 11.914 | 19.812 | 1.00 | 37.93 | C |
| ATOM | 3037 | CD | ARG | B | 59 | 23.254 | 11.163 | 21.216 | 1.00 | 40.80 | C |
| ATOM | 3040 | NE | ARG | B | 59 | 22.131 | 10.714 | 22.100 | 1.00 | 43.15 | N |
| ATOM | 3042 | CZ | ARG | B | 59 | 21.898 | 10.960 | 23.418 | 1.00 | 44.23 | C |
| ATOM | 3043 | NH1 | ARG | B | 59 | 22.695 | 11.724 | 24.163 | 1.00 | 44.03 | N |
| ATOM | 3046 | NH2 | ARG | B | 59 | 20.789 | 10.467 | 23.981 | 1.00 | 44.52 | N |
| ATOM | 3049 | C | ARG | B | 59 | 20.826 | 11.953 | 16.339 | 1.00 | 27.38 | C |
| ATOM | 3050 | O | ARG | B | 59 | 21.563 | 12.155 | 15.376 | 1.00 | 24.38 | O |
| ATOM | 3051 | N | GLU | B | 60 | 19.714 | 11.230 | 16.180 | 1.00 | 26.08 | N |
| ATOM | 3053 | CA | GLU | B | 60 | 19.389 | 10.662 | 14.876 | 1.00 | 25.44 | C |
| ATOM | 3055 | CB | GLU | B | 60 | 18.314 | 9.610 | 15.037 | 1.00 | 28.90 | C |
| ATOM | 3058 | CG | GLU | B | 60 | 18.542 | 8.639 | 16.184 | 1.00 | 33.14 | C |
| ATOM | 3061 | CD | GLU | B | 60 | 17.717 | 7.366 | 16.041 | 1.00 | 36.08 | C |
| ATOM | 3062 | OE1 | GLU | B | 60 | 16.456 | 7.363 | 16.154 | 1.00 | 38.14 | O |
| ATOM | 3063 | OE2 | GLU | B | 60 | 18.366 | 6.340 | 15.766 | 1.00 | 40.88 | O |
| ATOM | 3064 | C | GLU | B | 60 | 18.962 | 11.652 | 13.795 | 1.00 | 21.86 | C |
| ATOM | 3065 | O | GLU | B | 60 | 18.647 | 11.282 | 12.668 | 1.00 | 20.52 | O |
| ATOM | 3066 | N | GLY | B | 61 | 18.749 | 12.897 | 14.174 | 1.00 | 17.18 | N |
| ATOM | 3068 | CA | GLY | B | 61 | 18.395 | 13.868 | 13.195 | 1.00 | 15.80 | C |
| ATOM | 3071 | C | GLY | B | 61 | 16.964 | 13.696 | 12.721 | 1.00 | 14.53 | C |
| ATOM | 3072 | O | GLY | B | 61 | 16.660 | 14.211 | 11.681 | 1.00 | 10.59 | O |
| ATOM | 3073 | N | LYS | B | 62 | 16.111 | 12.944 | 13.380 | 1.00 | 13.39 | N |

-continued

| | | | | | | | | | | | |
|---|---|---|---|---|---|---|---|---|---|---|---|
| ATOM | 3075 | CA | LYS | B | 62 | 14.725 | 12.841 | 12.896 | 1.00 | 16.33 | C |
| ATOM | 3077 | CB | LYS | B | 62 | 14.036 | 11.690 | 13.652 | 1.00 | 17.63 | C |
| ATOM | 3080 | CG | LYS | B | 62 | 14.428 | 10.354 | 13.017 | 1.00 | 19.36 | C |
| ATOM | 3083 | CD | LYS | B | 62 | 14.161 | 9.185 | 14.019 | 1.00 | 19.12 | C |
| ATOM | 3086 | CE | LYS | B | 62 | 14.686 | 7.875 | 13.322 | 1.00 | 19.49 | C |
| ATOM | 3089 | NZ | LYS | B | 62 | 14.351 | 6.710 | 14.216 | 1.00 | 16.20 | N |
| ATOM | 3093 | C | LYS | B | 62 | 13.829 | 14.062 | 13.083 | 1.00 | 16.26 | C |
| ATOM | 3094 | O | LYS | B | 62 | 12.833 | 14.214 | 12.382 | 1.00 | 16.49 | O |
| ATOM | 3095 | N | LEU | B | 63 | 14.135 | 14.915 | 14.054 | 1.00 | 13.74 | N |
| ATOM | 3097 | CA | LEU | B | 63 | 13.442 | 16.167 | 14.120 | 1.00 | 14.01 | C |
| ATOM | 3099 | CB | LEU | B | 63 | 13.322 | 16.685 | 15.525 | 1.00 | 13.34 | C |
| ATOM | 3102 | CG | LEU | B | 63 | 12.510 | 15.779 | 16.426 | 1.00 | 14.81 | C |
| ATOM | 3104 | CD1 | LEU | B | 63 | 12.665 | 16.074 | 17.911 | 1.00 | 14.43 | C |
| ATOM | 3108 | CD2 | LEU | B | 63 | 10.991 | 15.726 | 15.995 | 1.00 | 14.13 | C |
| ATOM | 3112 | C | LEU | B | 63 | 14.242 | 17.186 | 13.315 | 1.00 | 15.51 | C |
| ATOM | 3113 | O | LEU | B | 63 | 15.480 | 17.144 | 13.327 | 1.00 | 10.44 | O |
| ATOM | 3114 | N | PRO | B | 64 | 13.572 | 18.214 | 12.783 | 1.00 | 14.48 | N |
| ATOM | 3115 | CA | PRO | B | 64 | 14.317 | 19.202 | 12.007 | 1.00 | 16.32 | C |
| ATOM | 3117 | CB | PRO | B | 64 | 13.199 | 20.032 | 11.353 | 1.00 | 16.04 | C |
| ATOM | 3120 | CG | PRO | B | 64 | 12.037 | 19.914 | 12.287 | 1.00 | 17.22 | C |
| ATOM | 3123 | CD | PRO | B | 64 | 12.165 | 18.574 | 12.919 | 1.00 | 16.49 | C |
| ATOM | 3126 | C | PRO | B | 64 | 15.157 | 20.030 | 12.963 | 1.00 | 15.25 | C |
| ATOM | 3127 | O | PRO | B | 64 | 14.728 | 20.446 | 14.048 | 1.00 | 13.62 | O |
| ATOM | 3128 | N | GLY | B | 65 | 16.358 | 20.297 | 12.528 | 1.00 | 14.61 | N |
| ATOM | 3130 | CA | GLY | B | 65 | 17.285 | 21.088 | 13.297 | 1.00 | 15.69 | C |
| ATOM | 3133 | C | GLY | B | 65 | 17.804 | 22.369 | 12.670 | 1.00 | 15.21 | C |
| ATOM | 3134 | O | GLY | B | 65 | 17.764 | 22.459 | 11.472 | 1.00 | 14.39 | O |
| ATOM | 3135 | N | LYS | B | 66 | 18.119 | 23.404 | 13.447 | 1.00 | 10.95 | N |
| ATOM | 3137 | CA | LYS | B | 66 | 18.781 | 24.548 | 12.841 | 1.00 | 13.11 | C |
| ATOM | 3139 | CB | LYS | B | 66 | 17.791 | 25.562 | 12.322 | 1.00 | 12.82 | C |
| ATOM | 3142 | CG | LYS | B | 66 | 17.007 | 26.296 | 13.407 | 1.00 | 13.39 | C |
| ATOM | 3145 | CD | LYS | B | 66 | 16.013 | 27.309 | 12.776 | 1.00 | 13.95 | C |
| ATOM | 3148 | CE | LYS | B | 66 | 15.176 | 28.166 | 13.786 | 1.00 | 16.36 | C |
| ATOM | 3151 | NZ | LYS | B | 66 | 14.165 | 29.115 | 13.158 | 1.00 | 11.77 | N |
| ATOM | 3155 | C | LYS | B | 66 | 19.614 | 25.165 | 13.933 | 1.00 | 14.09 | C |
| ATOM | 3156 | O | LYS | B | 66 | 19.343 | 24.994 | 15.142 | 1.00 | 12.00 | O |
| ATOM | 3157 | N | SER | B | 67 | 20.616 | 25.912 | 13.509 | 1.00 | 14.90 | N |
| ATOM | 3159 | CA | SER | B | 67 | 21.466 | 26.548 | 14.492 | 1.00 | 15.76 | C |
| ATOM | 3161 | CB | SER | B | 67 | 22.546 | 27.250 | 13.640 | 1.00 | 20.81 | C |
| ATOM | 3164 | OG | SER | B | 67 | 22.716 | 28.501 | 14.270 | 1.00 | 25.41 | O |
| ATOM | 3166 | C | SER | B | 67 | 20.676 | 27.446 | 15.495 | 1.00 | 15.12 | C |
| ATOM | 3167 | O | SER | B | 67 | 19.716 | 28.121 | 15.161 | 1.00 | 12.04 | O |
| ATOM | 3168 | N | GLY | B | 68 | 21.006 | 27.309 | 16.780 | 1.00 | 14.59 | N |
| ATOM | 3170 | CA | GLY | B | 68 | 20.321 | 27.923 | 17.881 | 1.00 | 15.20 | C |
| ATOM | 3173 | C | GLY | B | 68 | 19.087 | 27.131 | 18.370 | 1.00 | 16.18 | C |
| ATOM | 3174 | O | GLY | B | 68 | 18.508 | 27.506 | 19.432 | 1.00 | 16.23 | O |
| ATOM | 3175 | N | ARG | B | 69 | 18.602 | 26.098 | 17.644 | 1.00 | 12.19 | N |
| ATOM | 3177 | CA | ARG | B | 69 | 17.300 | 25.498 | 18.109 | 1.00 | 11.38 | C |
| ATOM | 3179 | CB | ARG | B | 69 | 16.581 | 24.937 | 16.919 | 1.00 | 11.11 | C |
| ATOM | 3182 | CG | ARG | B | 69 | 15.380 | 24.063 | 17.328 | 1.00 | 10.07 | C |
| ATOM | 3185 | CD | ARG | B | 69 | 14.825 | 23.413 | 16.057 | 1.00 | 10.96 | C |
| ATOM | 3188 | NE | ARG | B | 69 | 13.998 | 24.352 | 15.316 | 1.00 | 11.66 | N |
| ATOM | 3190 | CZ | ARG | B | 69 | 13.644 | 24.264 | 14.049 | 1.00 | 11.42 | C |
| ATOM | 3191 | NH1 | ARG | B | 69 | 14.074 | 23.229 | 13.293 | 1.00 | 13.20 | N |
| ATOM | 3194 | NH2 | ARG | B | 69 | 12.965 | 25.285 | 13.515 | 1.00 | 12.11 | N |
| ATOM | 3197 | C | ARG | B | 69 | 17.612 | 24.241 | 18.979 | 1.00 | 11.99 | C |
| ATOM | 3198 | O | ARG | B | 69 | 18.424 | 23.428 | 18.567 | 1.00 | 12.40 | O |
| ATOM | 3199 | N | THR | B | 70 | 17.037 | 24.125 | 20.169 | 1.00 | 13.86 | N |
| ATOM | 3201 | CA | THR | B | 70 | 17.180 | 22.979 | 20.966 | 1.00 | 13.56 | C |
| ATOM | 3203 | CB | THR | B | 70 | 17.851 | 23.241 | 22.332 | 1.00 | 15.52 | C |
| ATOM | 3205 | OG1 | THR | B | 70 | 17.244 | 24.348 | 22.902 | 1.00 | 18.34 | O |
| ATOM | 3207 | CG2 | THR | B | 70 | 19.246 | 23.871 | 22.193 | 1.00 | 14.51 | C |
| ATOM | 3211 | C | THR | B | 70 | 15.853 | 22.374 | 21.154 | 1.00 | 14.51 | C |
| ATOM | 3212 | O | THR | B | 70 | 14.787 | 23.010 | 21.002 | 1.00 | 13.92 | O |
| ATOM | 3213 | N | TRP | B | 71 | 15.943 | 21.072 | 21.403 | 1.00 | 11.24 | N |
| ATOM | 3215 | CA | TRP | B | 71 | 14.698 | 20.359 | 21.574 | 1.00 | 10.75 | C |
| ATOM | 3217 | CB | TRP | B | 71 | 14.701 | 19.142 | 20.651 | 1.00 | 10.35 | C |
| ATOM | 3220 | CG | TRP | B | 71 | 14.455 | 19.476 | 19.315 | 1.00 | 9.15 | C |
| ATOM | 3221 | CD1 | TRP | B | 71 | 15.385 | 19.661 | 18.348 | 1.00 | 10.42 | C |
| ATOM | 3223 | NE1 | TRP | B | 71 | 14.764 | 19.960 | 17.162 | 1.00 | 8.90 | N |
| ATOM | 3225 | CE2 | TRP | B | 71 | 13.405 | 19.886 | 17.349 | 1.00 | 9.90 | C |
| ATOM | 3226 | CD2 | TRP | B | 71 | 13.176 | 19.664 | 18.707 | 1.00 | 8.92 | C |
| ATOM | 3227 | CE3 | TRP | B | 71 | 11.850 | 19.587 | 19.162 | 1.00 | 8.43 | C |
| ATOM | 3229 | CZ3 | TRP | B | 71 | 10.798 | 19.818 | 18.226 | 1.00 | 9.38 | C |
| ATOM | 3231 | CH2 | TRP | B | 71 | 11.090 | 20.155 | 16.909 | 1.00 | 10.00 | C |
| ATOM | 3233 | CZ2 | TRP | B | 71 | 12.402 | 20.134 | 16.460 | 1.00 | 10.24 | C |
| ATOM | 3235 | C | TRP | B | 71 | 14.522 | 19.900 | 23.013 | 1.00 | 11.11 | C |
| ATOM | 3236 | O | TRP | B | 71 | 15.525 | 19.432 | 23.608 | 1.00 | 12.14 | O |
| ATOM | 3237 | N | ARG | B | 72 | 13.281 | 19.824 | 23.522 | 1.00 | 8.93 | N |
| ATOM | 3239 | CA | ARG | B | 72 | 13.148 | 19.254 | 24.831 | 1.00 | 8.99 | C |

-continued

| | | | | | | | | | | |
|---|---|---|---|---|---|---|---|---|---|---|
| ATOM | 3241 | CB | ARG | B | 72 | 12.781 | 20.436 | 25.772 | 1.00 | 10.59 | C |
| ATOM | 3244 | CG | ARG | B | 72 | 14.049 | 21.172 | 26.206 | 1.00 | 10.47 | C |
| ATOM | 3247 | CD | ARG | B | 72 | 13.698 | 22.350 | 27.185 | 1.00 | 13.16 | C |
| ATOM | 3250 | NE | ARG | B | 72 | 14.829 | 23.234 | 27.457 | 1.00 | 17.14 | N |
| ATOM | 3252 | CZ | ARG | B | 72 | 15.765 | 23.008 | 28.396 | 1.00 | 21.76 | C |
| ATOM | 3253 | NH1 | ARG | B | 72 | 15.799 | 21.977 | 29.248 | 1.00 | 19.74 | N |
| ATOM | 3256 | NH2 | ARG | B | 72 | 16.755 | 23.874 | 28.474 | 1.00 | 24.92 | N |
| ATOM | 3259 | C | ARG | B | 72 | 11.981 | 18.317 | 24.711 | 1.00 | 11.55 | C |
| ATOM | 3260 | O | ARG | B | 72 | 11.309 | 18.298 | 23.723 | 1.00 | 9.98 | O |
| ATOM | 3261 | N | GLU | B | 73 | 11.805 | 17.467 | 25.705 | 1.00 | 11.24 | N |
| ATOM | 3263 | CA | GLU | B | 73 | 10.800 | 16.416 | 25.686 | 1.00 | 11.94 | C |
| ATOM | 3265 | CB | GLU | B | 73 | 11.461 | 15.059 | 25.499 | 1.00 | 11.99 | C |
| ATOM | 3268 | CG | GLU | B | 73 | 12.550 | 14.639 | 26.507 | 1.00 | 12.70 | C |
| ATOM | 3271 | CD | GLU | B | 73 | 12.781 | 13.157 | 26.547 | 1.00 | 13.39 | C |
| ATOM | 3272 | OE1 | GLU | B | 73 | 11.866 | 12.343 | 26.858 | 1.00 | 14.56 | O |
| ATOM | 3273 | OE2 | GLU | B | 73 | 13.883 | 12.799 | 26.099 | 1.00 | 15.23 | O |
| ATOM | 3274 | C | GLU | B | 73 | 10.039 | 16.368 | 27.041 | 1.00 | 12.76 | C |
| ATOM | 3275 | O | GLU | B | 73 | 10.496 | 16.946 | 28.045 | 1.00 | 10.99 | O |
| ATOM | 3276 | N | ALA | B | 74 | 8.830 | 15.836 | 26.985 | 1.00 | 10.61 | N |
| ATOM | 3278 | CA | ALA | B | 74 | 8.102 | 15.625 | 28.176 | 1.00 | 9.54 | C |
| ATOM | 3280 | CB | ALA | B | 74 | 7.150 | 16.788 | 28.479 | 1.00 | 12.29 | C |
| ATOM | 3284 | C | ALA | B | 74 | 7.222 | 14.372 | 27.940 | 1.00 | 10.03 | C |
| ATOM | 3285 | O | ALA | B | 74 | 6.814 | 14.034 | 26.786 | 1.00 | 8.68 | O |
| ATOM | 3286 | N | ASP | B | 75 | 6.938 | 13.688 | 29.038 | 1.00 | 10.21 | N |
| ATOM | 3288 | CA | ASP | B | 75 | 6.139 | 12.457 | 28.976 | 1.00 | 10.00 | C |
| ATOM | 3290 | CB | ASP | B | 75 | 6.316 | 11.625 | 30.287 | 1.00 | 10.62 | C |
| ATOM | 3293 | CG | ASP | B | 75 | 7.582 | 10.826 | 30.281 | 1.00 | 11.53 | C |
| ATOM | 3294 | OD1 | ASP | B | 75 | 8.535 | 11.138 | 29.497 | 1.00 | 10.00 | O |
| ATOM | 3295 | OD2 | ASP | B | 75 | 7.689 | 9.813 | 31.005 | 1.00 | 8.42 | O |
| ATOM | 3296 | C | ASP | B | 75 | 4.694 | 12.806 | 28.893 | 1.00 | 10.82 | C |
| ATOM | 3297 | O | ASP | B | 75 | 4.156 | 13.698 | 29.619 | 1.00 | 10.82 | O |
| ATOM | 3298 | N | ILE | B | 76 | 4.017 | 12.065 | 28.004 | 1.00 | 10.07 | N |
| ATOM | 3300 | CA | ILE | B | 76 | 2.593 | 12.248 | 27.773 | 1.00 | 10.81 | C |
| ATOM | 3302 | CB | ILE | B | 76 | 2.402 | 12.577 | 26.295 | 1.00 | 11.34 | C |
| ATOM | 3304 | CG1 | ILE | B | 76 | 3.067 | 13.908 | 25.924 | 1.00 | 11.79 | C |
| ATOM | 3307 | CD1 | ILE | B | 76 | 2.244 | 15.072 | 26.633 | 1.00 | 9.59 | C |
| ATOM | 3311 | CG2 | ILE | B | 76 | 0.913 | 12.450 | 25.934 | 1.00 | 11.30 | C |
| ATOM | 3315 | C | ILE | B | 76 | 1.899 | 10.939 | 28.162 | 1.00 | 11.44 | C |
| ATOM | 3316 | O | ILE | B | 76 | 2.447 | 9.834 | 28.008 | 1.00 | 12.67 | O |
| ATOM | 3317 | N | ASN | B | 77 | 0.671 | 11.137 | 28.634 | 1.00 | 11.47 | N |
| ATOM | 3319 | CA | ASN | B | 77 | −0.308 | 10.132 | 28.985 | 1.00 | 11.42 | C |
| ATOM | 3321 | CB | ASN | B | 77 | −0.718 | 9.193 | 27.842 | 1.00 | 10.13 | C |
| ATOM | 3324 | CG | ASN | B | 77 | −1.413 | 9.887 | 26.689 | 1.00 | 10.02 | C |
| ATOM | 3325 | OD1 | ASN | B | 77 | −2.277 | 10.816 | 26.849 | 1.00 | 10.14 | O |
| ATOM | 3326 | ND2 | ASN | B | 77 | −1.086 | 9.387 | 25.484 | 1.00 | 5.55 | N |
| ATOM | 3329 | C | ASN | B | 77 | 0.203 | 9.321 | 30.171 | 1.00 | 10.23 | C |
| ATOM | 3330 | O | ASN | B | 77 | −0.293 | 8.237 | 30.365 | 1.00 | 8.49 | O |
| ATOM | 3331 | N | TYR | B | 78 | 1.223 | 9.787 | 30.881 | 1.00 | 10.59 | N |
| ATOM | 3333 | CA | TYR | B | 78 | 1.713 | 9.110 | 32.078 | 1.00 | 10.50 | C |
| ATOM | 3335 | CB | TYR | B | 78 | 3.165 | 9.533 | 32.418 | 1.00 | 13.30 | C |
| ATOM | 3338 | CG | TYR | B | 78 | 3.677 | 8.796 | 33.651 | 1.00 | 11.64 | C |
| ATOM | 3339 | CD1 | TYR | B | 78 | 4.238 | 7.543 | 33.513 | 1.00 | 9.95 | C |
| ATOM | 3341 | CE1 | TYR | B | 78 | 4.523 | 6.798 | 34.604 | 1.00 | 10.12 | C |
| ATOM | 3343 | CZ | TYR | B | 78 | 4.536 | 7.399 | 35.866 | 1.00 | 13.58 | C |
| ATOM | 3344 | OH | TYR | B | 78 | 4.921 | 6.680 | 37.002 | 1.00 | 11.86 | O |
| ATOM | 3346 | CE2 | TYR | B | 78 | 4.018 | 8.680 | 36.038 | 1.00 | 13.35 | C |
| ATOM | 3348 | CD2 | TYR | B | 78 | 3.609 | 9.363 | 34.905 | 1.00 | 13.98 | C |
| ATOM | 3350 | C | TYR | B | 78 | 0.830 | 9.346 | 33.299 | 1.00 | 13.49 | C |
| ATOM | 3351 | O | TYR | B | 78 | 0.502 | 10.501 | 33.576 | 1.00 | 12.46 | O |
| ATOM | 3352 | N | THR | B | 79 | 0.501 | 8.269 | 34.029 | 1.00 | 15.53 | N |
| ATOM | 3354 | CA | THR | B | 79 | −0.174 | 8.403 | 35.311 | 1.00 | 16.93 | C |
| ATOM | 3356 | CB | THR | B | 79 | −1.630 | 7.862 | 35.308 | 1.00 | 19.69 | C |
| ATOM | 3358 | OG1 | THR | B | 79 | −1.566 | 6.566 | 34.809 | 1.00 | 22.41 | O |
| ATOM | 3360 | CG2 | THR | B | 79 | −2.524 | 8.426 | 34.198 | 1.00 | 20.10 | C |
| ATOM | 3364 | C | THR | B | 79 | 0.608 | 7.691 | 36.442 | 1.00 | 16.57 | C |
| ATOM | 3365 | O | THR | B | 79 | 0.936 | 8.345 | 37.437 | 1.00 | 17.72 | O |
| ATOM | 3366 | N | SER | B | 80 | 1.012 | 6.438 | 36.273 | 1.00 | 14.71 | N |
| ATOM | 3368 | CA | SER | B | 80 | 1.693 | 5.684 | 37.324 | 1.00 | 17.33 | C |
| ATOM | 3370 | CB | SER | B | 80 | 0.768 | 5.182 | 38.478 | 1.00 | 17.59 | C |
| ATOM | 3373 | OG | SER | B | 80 | −0.117 | 4.227 | 37.922 | 1.00 | 16.70 | O |
| ATOM | 3375 | C | SER | B | 80 | 2.403 | 4.483 | 36.751 | 1.00 | 14.92 | C |
| ATOM | 3376 | O | SER | B | 80 | 2.137 | 4.104 | 35.610 | 1.00 | 16.85 | O |
| ATOM | 3377 | N | GLY | B | 81 | 3.424 | 4.035 | 37.455 | 1.00 | 11.29 | N |
| ATOM | 3379 | CA | GLY | B | 81 | 4.109 | 2.836 | 37.041 | 1.00 | 12.87 | C |
| ATOM | 3382 | C | GLY | B | 81 | 5.316 | 3.161 | 36.204 | 1.00 | 12.63 | C |
| ATOM | 3383 | O | GLY | B | 81 | 5.829 | 4.265 | 36.295 | 1.00 | 10.91 | O |
| ATOM | 3384 | N | PHE | B | 82 | 5.668 | 2.273 | 35.289 | 1.00 | 14.08 | N |
| ATOM | 3386 | CA | PHE | B | 82 | 6.868 | 2.483 | 34.496 | 1.00 | 15.62 | C |
| ATOM | 3388 | CB | PHE | B | 82 | 7.451 | 1.210 | 33.794 | 1.00 | 16.18 | C |
| ATOM | 3391 | CG | PHE | B | 82 | 8.098 | 0.281 | 34.762 | 1.00 | 16.15 | C |

-continued

| | | | | | | | | | | |
|---|---|---|---|---|---|---|---|---|---|---|
| ATOM | 3392 | CD1 | PHE | B | 82 | 9.459 | 0.374 | 35.054 | 1.00 | 16.99 | C |
| ATOM | 3394 | CE1 | PHE | B | 82 | 9.997 | −0.460 | 36.018 | 1.00 | 17.27 | C |
| ATOM | 3396 | CZ | PHE | B | 82 | 9.161 | −1.307 | 36.716 | 1.00 | 17.12 | C |
| ATOM | 3398 | CE2 | PHE | B | 82 | 7.825 | −1.460 | 36.320 | 1.00 | 16.78 | C |
| ATOM | 3400 | CD2 | PHE | B | 82 | 7.305 | −0.598 | 35.425 | 1.00 | 16.65 | C |
| ATOM | 3402 | C | PHE | B | 82 | 6.430 | 3.554 | 33.479 | 1.00 | 15.75 | C |
| ATOM | 3403 | O | PHE | B | 82 | 5.176 | 3.654 | 33.215 | 1.00 | 13.08 | O |
| ATOM | 3404 | N | ARG | B | 83 | 7.447 | 4.202 | 32.872 | 1.00 | 14.73 | N |
| ATOM | 3406 | CA | ARG | B | 83 | 7.168 | 5.264 | 31.864 | 1.00 | 14.03 | C |
| ATOM | 3408 | CB | ARG | B | 83 | 8.423 | 6.104 | 31.539 | 1.00 | 14.15 | C |
| ATOM | 3411 | CG | ARG | B | 83 | 8.896 | 6.789 | 32.802 | 1.00 | 12.57 | C |
| ATOM | 3414 | CD | ARG | B | 83 | 10.241 | 7.476 | 32.590 | 1.00 | 12.77 | C |
| ATOM | 3417 | NE | ARG | B | 83 | 10.149 | 8.493 | 31.525 | 1.00 | 12.31 | N |
| ATOM | 3419 | CZ | ARG | B | 83 | 11.192 | 9.088 | 30.968 | 1.00 | 13.30 | C |
| ATOM | 3420 | NH1 | ARG | B | 83 | 12.330 | 8.569 | 31.242 | 1.00 | 12.84 | N |
| ATOM | 3423 | NH2 | ARG | B | 83 | 11.094 | 10.007 | 29.995 | 1.00 | 13.50 | N |
| ATOM | 3426 | C | ARG | B | 83 | 6.746 | 4.523 | 30.603 | 1.00 | 14.98 | C |
| ATOM | 3427 | O | ARG | B | 83 | 7.169 | 3.385 | 30.333 | 1.00 | 13.79 | O |
| ATOM | 3428 | N | ASN | B | 84 | 5.827 | 5.172 | 29.929 | 1.00 | 13.06 | N |
| ATOM | 3430 | CA | ASN | B | 84 | 5.339 | 4.760 | 28.643 | 1.00 | 11.13 | C |
| ATOM | 3432 | CB | ASN | B | 84 | 3.862 | 5.136 | 28.564 | 1.00 | 9.88 | C |
| ATOM | 3435 | CG | ASN | B | 84 | 3.674 | 6.630 | 28.364 | 1.00 | 9.84 | C |
| ATOM | 3436 | OD1 | ASN | B | 84 | 4.576 | 7.309 | 27.879 | 1.00 | 7.46 | O |
| ATOM | 3437 | ND2 | ASN | B | 84 | 2.519 | 7.159 | 28.767 | 1.00 | 6.81 | N |
| ATOM | 3440 | C | ASN | B | 84 | 6.196 | 5.228 | 27.438 | 1.00 | 11.63 | C |
| ATOM | 3441 | O | ASN | B | 84 | 7.363 | 5.692 | 27.557 | 1.00 | 9.56 | O |
| ATOM | 3442 | N | SER | B | 85 | 5.646 | 5.064 | 26.239 | 1.00 | 8.08 | N |
| ATOM | 3444 | CA | SER | B | 85 | 6.395 | 5.370 | 25.021 | 1.00 | 11.21 | C |
| ATOM | 3446 | CB | SER | B | 85 | 6.078 | 4.253 | 23.981 | 1.00 | 11.13 | C |
| ATOM | 3449 | OG | SER | B | 85 | 6.861 | 3.227 | 24.572 | 1.00 | 16.57 | O |
| ATOM | 3451 | C | SER | B | 85 | 5.939 | 6.686 | 24.380 | 1.00 | 11.05 | C |
| ATOM | 3452 | O | SER | B | 85 | 6.348 | 7.024 | 23.288 | 1.00 | 12.31 | O |
| ATOM | 3453 | N | ASP | B | 86 | 5.041 | 7.414 | 25.025 | 1.00 | 12.04 | N |
| ATOM | 3455 | CA | ASP | B | 86 | 4.571 | 8.722 | 24.546 | 1.00 | 12.16 | C |
| ATOM | 3457 | CB | ASP | B | 86 | 3.114 | 8.874 | 24.995 | 1.00 | 14.37 | C |
| ATOM | 3460 | CG | ASP | B | 86 | 2.139 | 7.826 | 24.420 | 1.00 | 14.78 | C |
| ATOM | 3461 | OD1 | ASP | B | 86 | 2.352 | 7.224 | 23.339 | 1.00 | 13.22 | O |
| ATOM | 3462 | OD2 | ASP | B | 86 | 0.980 | 7.698 | 24.922 | 1.00 | 14.32 | O |
| ATOM | 3463 | C | ASP | B | 86 | 5.378 | 9.959 | 25.004 | 1.00 | 12.30 | C |
| ATOM | 3464 | O | ASP | B | 86 | 5.651 | 10.258 | 26.176 | 1.00 | 8.45 | O |
| ATOM | 3465 | N | ARG | B | 87 | 5.768 | 10.782 | 24.048 | 1.00 | 9.98 | N |
| ATOM | 3467 | CA | ARG | B | 87 | 6.458 | 11.956 | 24.434 | 1.00 | 11.52 | C |
| ATOM | 3469 | CB | ARG | B | 87 | 7.965 | 11.817 | 24.224 | 1.00 | 10.41 | C |
| ATOM | 3472 | CG | ARG | B | 87 | 8.570 | 10.637 | 24.919 | 1.00 | 10.56 | C |
| ATOM | 3475 | CD | ARG | B | 87 | 8.766 | 10.836 | 26.460 | 1.00 | 11.53 | C |
| ATOM | 3478 | NE | ARG | B | 87 | 9.441 | 9.647 | 26.971 | 1.00 | 15.77 | N |
| ATOM | 3480 | CZ | ARG | B | 87 | 8.853 | 8.594 | 27.512 | 1.00 | 15.46 | C |
| ATOM | 3481 | NH1 | ARG | B | 87 | 7.551 | 8.577 | 27.527 | 1.00 | 14.29 | N |
| ATOM | 3484 | NH2 | ARG | B | 87 | 9.539 | 7.514 | 27.917 | 1.00 | 16.26 | N |
| ATOM | 3487 | C | ARG | B | 87 | 6.017 | 13.076 | 23.494 | 1.00 | 12.84 | C |
| ATOM | 3488 | O | ARG | B | 87 | 5.953 | 12.916 | 22.285 | 1.00 | 10.06 | O |
| ATOM | 3489 | N | ILE | B | 88 | 5.998 | 14.277 | 24.058 | 1.00 | 11.60 | N |
| ATOM | 3491 | CA | ILE | B | 88 | 5.895 | 15.516 | 23.290 | 1.00 | 19.61 | C |
| ATOM | 3493 | CB | ILE | B | 88 | 4.870 | 16.429 | 24.022 | 1.00 | 12.82 | C |
| ATOM | 3495 | CG1 | ILE | B | 88 | 4.509 | 17.594 | 23.128 | 1.00 | 15.21 | C |
| ATOM | 3498 | CD1 | ILE | B | 88 | 3.329 | 18.393 | 23.515 | 1.00 | 17.41 | C |
| ATOM | 3502 | CG2 | ILE | B | 88 | 5.283 | 16.835 | 25.342 | 1.00 | 13.80 | C |
| ATOM | 3506 | C | ILE | B | 88 | 7.320 | 16.076 | 23.152 | 1.00 | 10.33 | C |
| ATOM | 3507 | O | ILE | B | 88 | 8.086 | 16.084 | 24.108 | 1.00 | 10.89 | O |
| ATOM | 3508 | N | LEU | B | 89 | 7.641 | 16.574 | 21.972 | 1.00 | 7.50 | N |
| ATOM | 3510 | CA | LEU | B | 89 | 8.899 | 17.219 | 21.665 | 1.00 | 10.76 | C |
| ATOM | 3512 | CB | LEU | B | 89 | 9.582 | 16.550 | 20.473 | 1.00 | 11.08 | C |
| ATOM | 3515 | CG | LEU | B | 89 | 10.371 | 15.310 | 20.923 | 1.00 | 15.57 | C |
| ATOM | 3517 | CD1 | LEU | B | 89 | 9.513 | 14.253 | 21.509 | 1.00 | 16.83 | C |
| ATOM | 3521 | CD2 | LEU | B | 89 | 11.614 | 15.587 | 21.738 | 1.00 | 14.08 | C |
| ATOM | 3525 | C | LEU | B | 89 | 8.605 | 18.664 | 21.313 | 1.00 | 10.88 | C |
| ATOM | 3526 | O | LEU | B | 89 | 7.825 | 18.955 | 20.448 | 1.00 | 14.16 | O |
| ATOM | 3527 | N | TYR | B | 90 | 9.384 | 19.561 | 21.879 | 1.00 | 12.66 | N |
| ATOM | 3529 | CA | TYR | B | 90 | 9.184 | 20.975 | 21.689 | 1.00 | 11.30 | C |
| ATOM | 3531 | CB | TYR | B | 90 | 8.419 | 21.593 | 22.845 | 1.00 | 7.36 | C |
| ATOM | 3534 | CG | TYR | B | 90 | 8.855 | 21.506 | 24.237 | 1.00 | 8.59 | C |
| ATOM | 3535 | CD1 | TYR | B | 90 | 8.753 | 20.356 | 24.947 | 1.00 | 11.37 | C |
| ATOM | 3537 | CE1 | TYR | B | 90 | 9.142 | 20.289 | 26.252 | 1.00 | 10.53 | C |
| ATOM | 3539 | CZ | TYR | B | 90 | 9.662 | 21.424 | 26.890 | 1.00 | 11.48 | C |
| ATOM | 3540 | OH | TYR | B | 90 | 10.100 | 21.305 | 28.179 | 1.00 | 12.87 | O |
| ATOM | 3542 | CE2 | TYR | B | 90 | 9.917 | 22.587 | 26.157 | 1.00 | 10.68 | C |
| ATOM | 3544 | CD2 | TYR | B | 90 | 9.482 | 22.600 | 24.856 | 1.00 | 11.87 | C |
| ATOM | 3546 | C | TYR | B | 90 | 10.506 | 21.669 | 21.549 | 1.00 | 9.65 | C |
| ATOM | 3547 | O | TYR | B | 90 | 11.449 | 21.401 | 22.255 | 1.00 | 10.81 | O |
| ATOM | 3548 | N | SER | B | 91 | 10.542 | 22.570 | 20.573 | 1.00 | 9.62 | N |

-continued

| | | | | | | | | | | |
|---|---|---|---|---|---|---|---|---|---|---|
| ATOM | 3550 | CA | SER | B | 91 | 11.779 | 23.283 | 20.183 | 1.00 | 9.56 | C |
| ATOM | 3552 | CB | SER | B | 91 | 11.885 | 23.361 | 18.667 | 1.00 | 7.45 | C |
| ATOM | 3555 | OG | SER | B | 91 | 10.990 | 24.322 | 18.077 | 1.00 | 11.78 | O |
| ATOM | 3557 | C | SER | B | 91 | 11.825 | 24.653 | 20.865 | 1.00 | 9.77 | C |
| ATOM | 3558 | O | SER | B | 91 | 10.806 | 25.180 | 21.252 | 1.00 | 10.48 | O |
| ATOM | 3559 | N | SER | B | 92 | 12.985 | 25.262 | 20.857 | 1.00 | 9.65 | N |
| ATOM | 3561 | CA | SER | B | 92 | 13.204 | 26.591 | 21.398 | 1.00 | 12.16 | C |
| ATOM | 3563 | CB | SER | B | 92 | 14.709 | 26.982 | 21.486 | 1.00 | 13.12 | C |
| ATOM | 3566 | OG | SER | B | 92 | 15.548 | 26.350 | 20.538 | 1.00 | 14.59 | O |
| ATOM | 3568 | C | SER | B | 92 | 12.576 | 27.644 | 20.544 | 1.00 | 11.62 | C |
| ATOM | 3569 | O | SER | B | 92 | 12.301 | 28.677 | 21.116 | 1.00 | 16.48 | O |
| ATOM | 3570 | N | ASP | B | 93 | 12.147 | 27.359 | 19.324 | 1.00 | 12.20 | N |
| ATOM | 3572 | CA | ASP | B | 93 | 11.293 | 28.188 | 18.525 | 1.00 | 12.09 | C |
| ATOM | 3574 | CB | ASP | B | 93 | 11.975 | 28.503 | 17.199 | 1.00 | 14.08 | C |
| ATOM | 3577 | CG | ASP | B | 93 | 12.197 | 27.261 | 16.309 | 1.00 | 16.23 | C |
| ATOM | 3578 | OD1 | ASP | B | 93 | 12.367 | 26.109 | 16.806 | 1.00 | 12.90 | O |
| ATOM | 3579 | OD2 | ASP | B | 93 | 12.125 | 27.398 | 15.051 | 1.00 | 17.42 | O |
| ATOM | 3580 | C | ASP | B | 93 | 9.817 | 27.694 | 18.452 | 1.00 | 12.38 | C |
| ATOM | 3581 | O | ASP | B | 93 | 8.979 | 28.180 | 17.657 | 1.00 | 14.03 | O |
| ATOM | 3582 | N | TRP | B | 94 | 9.488 | 26.774 | 19.347 | 1.00 | 10.13 | N |
| ATOM | 3584 | CA | TRP | B | 94 | 8.143 | 26.320 | 19.634 | 1.00 | 11.78 | C |
| ATOM | 3586 | CB | TRP | B | 94 | 7.312 | 27.516 | 20.139 | 1.00 | 10.64 | C |
| ATOM | 3589 | CG | TRP | B | 94 | 7.947 | 28.062 | 21.403 | 1.00 | 9.63 | C |
| ATOM | 3590 | CD1 | TRP | B | 94 | 8.580 | 29.206 | 21.514 | 1.00 | 10.05 | C |
| ATOM | 3592 | NE1 | TRP | B | 94 | 9.136 | 29.332 | 22.769 | 1.00 | 10.83 | N |
| ATOM | 3594 | CE2 | TRP | B | 94 | 8.827 | 28.239 | 23.524 | 1.00 | 12.03 | C |
| ATOM | 3595 | CD2 | TRP | B | 94 | 8.153 | 27.354 | 22.674 | 1.00 | 11.33 | C |
| ATOM | 3596 | CE3 | TRP | B | 94 | 7.634 | 26.176 | 23.225 | 1.00 | 12.54 | C |
| ATOM | 3598 | CZ3 | TRP | B | 94 | 7.860 | 25.884 | 24.533 | 1.00 | 11.99 | C |
| ATOM | 3600 | CH2 | TRP | B | 94 | 8.672 | 26.741 | 25.311 | 1.00 | 13.56 | C |
| ATOM | 3602 | CZ2 | TRP | B | 94 | 9.146 | 27.922 | 24.840 | 1.00 | 13.00 | C |
| ATOM | 3604 | C | TRP | B | 94 | 7.386 | 25.540 | 18.572 | 1.00 | 12.51 | C |
| ATOM | 3605 | O | TRP | B | 94 | 6.141 | 25.744 | 18.387 | 1.00 | 12.94 | O |
| ATOM | 3606 | N | LEU | B | 95 | 8.149 | 24.826 | 17.774 | 1.00 | 10.29 | N |
| ATOM | 3608 | CA | LEU | B | 95 | 7.617 | 23.705 | 17.007 | 1.00 | 10.18 | C |
| ATOM | 3610 | CB | LEU | B | 95 | 8.689 | 23.029 | 16.168 | 1.00 | 9.75 | C |
| ATOM | 3613 | CG | LEU | B | 95 | 9.283 | 23.906 | 15.153 | 1.00 | 12.77 | C |
| ATOM | 3615 | CD1 | LEU | B | 95 | 10.356 | 23.156 | 14.444 | 1.00 | 14.04 | C |
| ATOM | 3619 | CD2 | LEU | B | 95 | 8.234 | 24.220 | 14.093 | 1.00 | 15.77 | C |
| ATOM | 3623 | C | LEU | B | 95 | 7.230 | 22.636 | 18.046 | 1.00 | 11.53 | C |
| ATOM | 3624 | O | LEU | B | 95 | 7.882 | 22.490 | 19.086 | 1.00 | 9.60 | O |
| ATOM | 3625 | N | ILE | B | 96 | 6.152 | 21.909 | 17.786 | 1.00 | 11.73 | N |
| ATOM | 3627 | CA | ILE | B | 96 | 5.683 | 20.822 | 18.656 | 1.00 | 7.10 | C |
| ATOM | 3629 | CB | ILE | B | 96 | 4.329 | 21.102 | 19.314 | 1.00 | 10.09 | C |
| ATOM | 3631 | CG1 | ILE | B | 96 | 4.196 | 22.430 | 20.048 | 1.00 | 10.16 | C |
| ATOM | 3634 | CD1 | ILE | B | 96 | 5.269 | 22.658 | 21.147 | 1.00 | 13.15 | C |
| ATOM | 3638 | CG2 | ILE | B | 96 | 4.062 | 19.932 | 20.259 | 1.00 | 10.19 | C |
| ATOM | 3642 | C | ILE | B | 96 | 5.520 | 19.563 | 17.766 | 1.00 | 11.41 | C |
| ATOM | 3643 | O | ILE | B | 96 | 4.788 | 19.544 | 16.705 | 1.00 | 10.52 | O |
| ATOM | 3644 | N | TYR | B | 97 | 6.191 | 18.500 | 18.209 | 1.00 | 9.29 | N |
| ATOM | 3646 | CA | TYR | B | 97 | 6.092 | 17.186 | 17.649 | 1.00 | 10.84 | C |
| ATOM | 3648 | CB | TYR | B | 97 | 7.387 | 16.767 | 17.041 | 1.00 | 11.78 | C |
| ATOM | 3651 | CG | TYR | B | 97 | 7.812 | 17.398 | 15.692 | 1.00 | 8.80 | C |
| ATOM | 3652 | CD1 | TYR | B | 97 | 8.072 | 18.744 | 15.580 | 1.00 | 7.50 | C |
| ATOM | 3654 | CE1 | TYR | B | 97 | 8.426 | 19.267 | 14.297 | 1.00 | 10.82 | C |
| ATOM | 3656 | CZ | TYR | B | 97 | 8.496 | 18.470 | 13.186 | 1.00 | 9.25 | C |
| ATOM | 3657 | OH | TYR | B | 97 | 8.777 | 19.025 | 11.997 | 1.00 | 11.39 | O |
| ATOM | 3659 | CE2 | TYR | B | 97 | 8.176 | 17.146 | 13.256 | 1.00 | 8.97 | C |
| ATOM | 3661 | CD2 | TYR | B | 97 | 7.856 | 16.633 | 14.508 | 1.00 | 11.39 | C |
| ATOM | 3663 | C | TYR | B | 97 | 5.699 | 16.185 | 18.783 | 1.00 | 11.17 | C |
| ATOM | 3664 | O | TYR | B | 97 | 5.774 | 16.472 | 20.038 | 1.00 | 11.86 | O |
| ATOM | 3665 | N | LYS | B | 98 | 5.252 | 15.038 | 18.298 | 1.00 | 9.43 | N |
| ATOM | 3667 | CA | LYS | B | 98 | 4.912 | 13.885 | 19.152 | 1.00 | 8.78 | C |
| ATOM | 3669 | CB | LYS | B | 98 | 3.388 | 13.706 | 19.208 | 1.00 | 8.94 | C |
| ATOM | 3672 | CG | LYS | B | 98 | 2.805 | 13.227 | 17.865 | 1.00 | 8.95 | C |
| ATOM | 3675 | CD | LYS | B | 98 | 1.316 | 12.827 | 17.890 | 1.00 | 11.21 | C |
| ATOM | 3678 | CE | LYS | B | 98 | 0.869 | 11.736 | 18.861 | 1.00 | 9.75 | C |
| ATOM | 3681 | NZ | LYS | B | 98 | −0.569 | 11.508 | 18.832 | 1.00 | 10.33 | N |
| ATOM | 3685 | C | LYS | B | 98 | 5.599 | 12.617 | 18.681 | 1.00 | 10.84 | C |
| ATOM | 3686 | O | LYS | B | 98 | 5.933 | 12.460 | 17.487 | 1.00 | 11.21 | O |
| ATOM | 3687 | N | THR | B | 99 | 5.838 | 11.708 | 19.621 | 1.00 | 10.22 | N |
| ATOM | 3689 | CA | THR | B | 99 | 6.150 | 10.334 | 19.318 | 1.00 | 9.66 | C |
| ATOM | 3691 | CB | THR | B | 99 | 7.710 | 10.123 | 19.463 | 1.00 | 12.67 | C |
| ATOM | 3693 | OG1 | THR | B | 99 | 8.050 | 8.733 | 19.259 | 1.00 | 14.62 | O |
| ATOM | 3695 | CG2 | THR | B | 99 | 8.189 | 10.437 | 20.914 | 1.00 | 13.45 | C |
| ATOM | 3699 | C | THR | B | 99 | 5.340 | 9.493 | 20.252 | 1.00 | 10.54 | C |
| ATOM | 3700 | O | THR | B | 99 | 5.108 | 9.906 | 21.420 | 1.00 | 13.14 | O |
| ATOM | 3701 | N | THR | B | 100 | 4.784 | 8.413 | 19.688 | 1.00 | 11.05 | N |
| ATOM | 3703 | CA | THR | B | 100 | 4.122 | 7.347 | 20.395 | 1.00 | 10.71 | C |
| ATOM | 3705 | CB | THR | B | 100 | 2.688 | 7.046 | 19.838 | 1.00 | 12.11 | C |

-continued

| | | | | | | | | | | | |
|---|---|---|---|---|---|---|---|---|---|---|---|
| ATOM | 3707 | OG1 | THR | B | 100 | 2.831 | 6.710 | 18.481 | 1.00 | 10.59 | O |
| ATOM | 3709 | CG2 | THR | B | 100 | 1.831 | 8.385 | 19.771 | 1.00 | 9.70 | C |
| ATOM | 3713 | C | THR | B | 100 | 4.937 | 6.064 | 20.345 | 1.00 | 12.36 | C |
| ATOM | 3714 | O | THR | B | 100 | 4.463 | 5.051 | 20.882 | 1.00 | 9.43 | O |
| ATOM | 3715 | N | ASP | B | 101 | 6.147 | 6.064 | 19.768 | 1.00 | 11.48 | N |
| ATOM | 3717 | CA | ASP | B | 101 | 6.919 | 4.832 | 19.728 | 1.00 | 8.19 | C |
| ATOM | 3719 | CB | ASP | B | 101 | 6.931 | 4.333 | 18.253 | 1.00 | 9.42 | C |
| ATOM | 3722 | CG | ASP | B | 101 | 7.531 | 5.287 | 17.362 | 1.00 | 8.26 | C |
| ATOM | 3723 | OD1 | ASP | B | 101 | 8.060 | 6.361 | 17.787 | 1.00 | 6.48 | O |
| ATOM | 3724 | OD2 | ASP | B | 101 | 7.486 | 5.084 | 16.155 | 1.00 | 10.50 | O |
| ATOM | 3725 | C | ASP | B | 101 | 8.325 | 5.020 | 20.327 | 1.00 | 8.62 | C |
| ATOM | 3726 | O | ASP | B | 101 | 9.314 | 4.494 | 19.794 | 1.00 | 9.42 | O |
| ATOM | 3727 | N | ALA | B | 102 | 8.421 | 5.759 | 21.427 | 1.00 | 9.30 | N |
| ATOM | 3729 | CA | ALA | B | 102 | 9.684 | 5.959 | 22.146 | 1.00 | 8.92 | C |
| ATOM | 3731 | CB | ALA | B | 102 | 10.089 | 4.648 | 22.840 | 1.00 | 11.73 | C |
| ATOM | 3735 | C | ALA | B | 102 | 10.765 | 6.437 | 21.191 | 1.00 | 10.14 | C |
| ATOM | 3736 | O | ALA | B | 102 | 11.768 | 5.787 | 20.910 | 1.00 | 8.75 | O |
| ATOM | 3737 | N | TYR | B | 103 | 10.482 | 7.555 | 20.538 | 1.00 | 11.44 | N |
| ATOM | 3739 | CA | TYR | B | 103 | 11.508 | 8.278 | 19.720 | 1.00 | 11.53 | C |
| ATOM | 3741 | CB | TYR | B | 103 | 12.783 | 8.619 | 20.551 | 1.00 | 12.19 | C |
| ATOM | 3744 | CG | TYR | B | 103 | 12.597 | 8.999 | 22.025 | 1.00 | 12.00 | C |
| ATOM | 3745 | CD1 | TYR | B | 103 | 12.282 | 10.315 | 22.398 | 1.00 | 13.42 | C |
| ATOM | 3747 | CE1 | TYR | B | 103 | 12.129 | 10.692 | 23.733 | 1.00 | 10.35 | C |
| ATOM | 3749 | CZ | TYR | B | 103 | 12.307 | 9.737 | 24.714 | 1.00 | 12.04 | C |
| ATOM | 3750 | OH | TYR | B | 103 | 12.173 | 10.143 | 26.013 | 1.00 | 15.78 | O |
| ATOM | 3752 | CE2 | TYR | B | 103 | 12.639 | 8.441 | 24.401 | 1.00 | 12.70 | C |
| ATOM | 3754 | CD2 | TYR | B | 103 | 12.826 | 8.081 | 23.042 | 1.00 | 11.77 | C |
| ATOM | 3756 | C | TYR | B | 103 | 11.972 | 7.654 | 18.464 | 1.00 | 10.04 | C |
| ATOM | 3757 | O | TYR | B | 103 | 12.923 | 8.127 | 17.850 | 1.00 | 12.44 | O |
| ATOM | 3758 | N | GLN | B | 104 | 11.204 | 6.715 | 17.915 | 1.00 | 11.02 | N |
| ATOM | 3760 | CA | GLN | B | 104 | 11.661 | 6.200 | 16.655 | 1.00 | 11.75 | C |
| ATOM | 3762 | CB | GLN | B | 104 | 11.260 | 4.776 | 16.530 | 1.00 | 14.48 | C |
| ATOM | 3765 | CG | GLN | B | 104 | 11.996 | 3.789 | 17.446 | 1.00 | 18.18 | C |
| ATOM | 3768 | CD | GLN | B | 104 | 11.192 | 2.511 | 17.191 | 1.00 | 21.14 | C |
| ATOM | 3769 | OE1 | GLN | B | 104 | 11.534 | 1.628 | 16.363 | 1.00 | 22.36 | O |
| ATOM | 3770 | NE2 | GLN | B | 104 | 10.010 | 2.494 | 17.829 | 1.00 | 22.11 | N |
| ATOM | 3773 | C | GLN | B | 104 | 11.055 | 6.964 | 15.486 | 1.00 | 12.44 | C |
| ATOM | 3774 | O | GLN | B | 104 | 11.678 | 7.042 | 14.422 | 1.00 | 9.27 | O |
| ATOM | 3775 | N | THR | B | 105 | 9.805 | 7.402 | 15.648 | 1.00 | 10.73 | N |
| ATOM | 3777 | CA | THR | B | 105 | 9.231 | 8.256 | 14.622 | 1.00 | 12.47 | C |
| ATOM | 3779 | CB | THR | B | 105 | 8.302 | 7.521 | 13.660 | 1.00 | 12.84 | C |
| ATOM | 3781 | OG1 | THR | B | 105 | 7.148 | 7.143 | 14.391 | 1.00 | 9.11 | O |
| ATOM | 3783 | CG2 | THR | B | 105 | 8.971 | 6.206 | 13.051 | 1.00 | 13.18 | C |
| ATOM | 3787 | C | THR | B | 105 | 8.509 | 9.447 | 15.241 | 1.00 | 13.88 | C |
| ATOM | 3788 | O | THR | B | 105 | 8.150 | 9.366 | 16.412 | 1.00 | 10.75 | O |
| ATOM | 3789 | N | PHE | B | 106 | 8.458 | 10.577 | 14.513 | 1.00 | 11.94 | N |
| ATOM | 3791 | CA | PHE | B | 106 | 7.786 | 11.715 | 15.142 | 1.00 | 13.81 | C |
| ATOM | 3793 | CB | PHE | B | 106 | 8.804 | 12.815 | 15.394 | 1.00 | 12.48 | C |
| ATOM | 3796 | CG | PHE | B | 106 | 9.843 | 12.441 | 16.370 | 1.00 | 10.42 | C |
| ATOM | 3797 | CD1 | PHE | B | 106 | 9.657 | 12.688 | 17.722 | 1.00 | 10.90 | C |
| ATOM | 3799 | CE1 | PHE | B | 106 | 10.547 | 12.287 | 18.640 | 1.00 | 12.22 | C |
| ATOM | 3801 | CZ | PHE | B | 106 | 11.703 | 11.615 | 18.228 | 1.00 | 12.53 | C |
| ATOM | 3803 | CE2 | PHE | B | 106 | 11.879 | 11.316 | 16.847 | 1.00 | 10.73 | C |
| ATOM | 3805 | CD2 | PHE | B | 106 | 10.956 | 11.764 | 15.949 | 1.00 | 9.20 | C |
| ATOM | 3807 | C | PHE | B | 106 | 6.734 | 12.247 | 14.183 | 1.00 | 12.03 | C |
| ATOM | 3808 | O | PHE | B | 106 | 6.966 | 12.165 | 13.011 | 1.00 | 12.66 | O |
| ATOM | 3809 | N | THR | B | 107 | 5.745 | 12.961 | 14.690 | 1.00 | 10.03 | N |
| ATOM | 3811 | CA | THR | B | 107 | 4.715 | 13.610 | 13.897 | 1.00 | 12.09 | C |
| ATOM | 3813 | CB | THR | B | 107 | 3.327 | 12.936 | 14.011 | 1.00 | 10.99 | C |
| ATOM | 3815 | OG1 | THR | B | 107 | 2.231 | 13.621 | 13.261 | 1.00 | 13.44 | O |
| ATOM | 3817 | CG2 | THR | B | 107 | 3.534 | 11.546 | 13.696 | 1.00 | 6.47 | C |
| ATOM | 3821 | C | THR | B | 107 | 4.587 | 15.061 | 14.349 | 1.00 | 10.62 | C |
| ATOM | 3822 | O | THR | B | 107 | 4.529 | 15.328 | 15.516 | 1.00 | 11.81 | O |
| ATOM | 3823 | N | LYS | B | 108 | 4.675 | 15.981 | 13.414 | 1.00 | 8.19 | N |
| ATOM | 3825 | CA | LYS | B | 108 | 4.638 | 17.363 | 13.780 | 1.00 | 6.78 | C |
| ATOM | 3827 | CB | LYS | B | 108 | 4.980 | 18.239 | 12.589 | 1.00 | 6.97 | C |
| ATOM | 3830 | CG | LYS | B | 108 | 4.758 | 19.786 | 12.770 | 1.00 | 8.64 | C |
| ATOM | 3833 | CD | LYS | B | 108 | 5.346 | 20.499 | 11.468 | 1.00 | 10.24 | C |
| ATOM | 3836 | CE | LYS | B | 108 | 5.516 | 21.949 | 11.654 | 1.00 | 9.99 | C |
| ATOM | 3839 | NZ | LYS | B | 108 | 6.376 | 22.605 | 10.559 | 1.00 | 7.56 | N |
| ATOM | 3843 | C | LYS | B | 108 | 3.185 | 17.602 | 14.082 | 1.00 | 6.60 | C |
| ATOM | 3844 | O | LYS | B | 108 | 2.340 | 17.285 | 13.216 | 1.00 | 6.51 | O |
| ATOM | 3845 | N | ILE | B | 109 | 2.891 | 18.177 | 15.252 | 1.00 | 7.61 | N |
| ATOM | 3847 | CA | ILE | B | 109 | 1.503 | 18.514 | 15.573 | 1.00 | 8.50 | C |
| ATOM | 3849 | CB | ILE | B | 109 | 1.015 | 17.742 | 16.849 | 1.00 | 9.03 | C |
| ATOM | 3851 | CG1 | ILE | B | 109 | 1.990 | 18.037 | 18.017 | 1.00 | 8.97 | C |
| ATOM | 3854 | CD1 | ILE | B | 109 | 1.318 | 17.512 | 19.330 | 1.00 | 7.70 | C |
| ATOM | 3858 | CG2 | ILE | B | 109 | 1.045 | 16.280 | 16.573 | 1.00 | 8.27 | C |
| ATOM | 3862 | C | ILE | B | 109 | 1.235 | 20.014 | 15.852 | 1.00 | 9.66 | C |
| ATOM | 3863 | O | ILE | B | 109 | 0.088 | 20.353 | 16.058 | 1.00 | 11.91 | O |

-continued

| | | | | | | | | | | |
|---|---|---|---|---|---|---|---|---|---|---|
| ATOM | 3864 | N | ARG | B | 110 | 2.253 | 20.866 | 15.820 | 1.00 | 8.83 | N |
| ATOM | 3866 | CA | ARG | B | 110 | 2.081 | 22.304 | 15.741 | 1.00 | 10.67 | C |
| ATOM | 3868 | CB | ARG | B | 110 | 2.001 | 23.106 | 17.075 | 1.00 | 9.40 | C |
| ATOM | 3871 | CG | ARG | B | 110 | 1.019 | 22.512 | 18.056 | 1.00 | 10.12 | C |
| ATOM | 3874 | CD | ARG | B | 110 | −0.428 | 22.908 | 17.699 | 1.00 | 10.77 | C |
| ATOM | 3877 | NE | ARG | B | 110 | −1.329 | 22.540 | 18.795 | 1.00 | 11.62 | N |
| ATOM | 3879 | CZ | ARG | B | 110 | −1.885 | 21.356 | 19.014 | 1.00 | 10.50 | C |
| ATOM | 3880 | NH1 | ARG | B | 110 | −1.591 | 20.279 | 18.255 | 1.00 | 11.81 | N |
| ATOM | 3883 | NH2 | ARG | B | 110 | −2.671 | 21.248 | 20.061 | 1.00 | 13.24 | N |
| ATOM | 3886 | C | ARG | B | 110 | 3.156 | 22.952 | 14.909 | 1.00 | 11.39 | C |
| ATOM | 3887 | O | ARG | B | 110 | 4.293 | 22.627 | 15.119 | 1.00 | 9.56 | O |
| ATOM | 3888 | N | SER | B | 111 | 2.761 | 23.904 | 14.047 | 1.00 | 17.56 | N |
| ATOM | 3890 | CA | SER | B | 111 | 3.817 | 24.837 | 13.596 | 1.00 | 18.65 | C |
| ATOM | 3892 | CB | SER | B | 111 | 3.127 | 25.831 | 12.616 | 1.00 | 22.08 | C |
| ATOM | 3895 | OG | SER | B | 111 | 2.761 | 25.073 | 11.470 | 1.00 | 26.67 | O |
| ATOM | 3897 | C | SER | B | 111 | 4.330 | 25.682 | 14.763 | 1.00 | 19.94 | C |
| ATOM | 3898 | O | SER | B | 111 | 3.671 | 25.834 | 15.796 | 1.00 | 15.06 | O |
| ATOM | 3899 | N | SER | B | 112 | 5.413 | 26.431 | 14.518 | 1.00 | 16.03 | N |
| ATOM | 3901 | CA | SER | B | 112 | 5.894 | 27.372 | 15.454 | 1.00 | 16.28 | C |
| ATOM | 3903 | CB | SER | B | 112 | 7.111 | 28.164 | 14.987 | 1.00 | 17.02 | C |
| ATOM | 3906 | OG | SER | B | 112 | 7.529 | 29.153 | 15.859 | 1.00 | 20.34 | O |
| ATOM | 3908 | C | SER | B | 112 | 4.787 | 28.364 | 15.753 | 1.00 | 16.25 | C |
| ATOM | 3909 | O | SER | B | 112 | 4.290 | 28.999 | 14.870 | 1.00 | 15.95 | O |
| ATOM | 3910 | N | SER | B | 113 | 4.640 | 28.635 | 17.041 | 1.00 | 16.88 | N |
| ATOM | 3912 | CA | SER | B | 113 | 3.731 | 29.682 | 17.470 | 1.00 | 17.97 | C |
| ATOM | 3914 | CB | SER | B | 113 | 3.003 | 29.096 | 18.670 | 1.00 | 17.19 | C |
| ATOM | 3917 | OG | SER | B | 113 | 3.823 | 28.684 | 19.766 | 1.00 | 16.21 | O |
| ATOM | 3919 | C | SER | B | 113 | 4.457 | 30.939 | 17.914 | 1.00 | 17.85 | C |
| ATOM | 3920 | O | SER | B | 113 | 3.821 | 31.813 | 18.516 | 1.00 | 14.91 | O |
| ATOM | 3921 | N | MET | B | 114 | 5.771 | 30.898 | 17.685 | 1.00 | 16.90 | N |
| ATOM | 3923 | CA | MET | B | 114 | 6.546 | 31.955 | 18.261 | 1.00 | 19.52 | C |
| ATOM | 3925 | CB | MET | B | 114 | 8.034 | 31.609 | 18.110 | 1.00 | 19.35 | C |
| ATOM | 3928 | CG | MET | B | 114 | 8.865 | 32.525 | 18.911 | 1.00 | 20.21 | C |
| ATOM | 3931 | SD | MET | B | 114 | 10.507 | 31.849 | 19.144 | 1.00 | 22.34 | S |
| ATOM | 3932 | CE | MET | B | 114 | 11.231 | 33.131 | 19.753 | 1.00 | 22.35 | C |
| ATOM | 3936 | C | MET | B | 114 | 6.240 | 33.293 | 17.655 | 1.00 | 14.52 | C |
| ATOM | 3937 | O | MET | B | 114 | 6.246 | 33.425 | 16.397 | 1.00 | 17.95 | O |
| ATOM | 3938 | N | GLY | B | 115 | 5.853 | 34.241 | 18.487 | 1.00 | 12.58 | N |
| ATOM | 3940 | CA | GLY | B | 115 | 5.367 | 35.478 | 17.896 | 1.00 | 10.36 | C |
| ATOM | 3943 | C | GLY | B | 115 | 3.889 | 35.607 | 17.733 | 1.00 | 10.90 | C |
| ATOM | 3944 | O | GLY | B | 115 | 3.455 | 36.659 | 17.290 | 1.00 | 9.54 | O |
| ATOM | 3945 | N | VAL | B | 116 | 3.106 | 34.578 | 18.070 | 1.00 | 8.88 | N |
| ATOM | 3947 | CA | VAL | B | 116 | 1.685 | 34.684 | 17.836 | 1.00 | 6.16 | C |
| ATOM | 3949 | CB | VAL | B | 116 | 1.192 | 33.347 | 17.222 | 1.00 | 8.93 | C |
| ATOM | 3951 | CG1 | VAL | B | 116 | −0.277 | 33.381 | 16.954 | 1.00 | 12.38 | C |
| ATOM | 3955 | CG2 | VAL | B | 116 | 1.831 | 33.118 | 15.887 | 1.00 | 9.12 | C |
| ATOM | 3959 | C | VAL | B | 116 | 1.084 | 34.836 | 19.201 | 1.00 | 8.87 | C |
| ATOM | 3960 | O | VAL | B | 116 | 1.393 | 34.087 | 20.135 | 1.00 | 6.19 | O |
| ATOM | 3961 | N | CYS | B | 117 | 0.053 | 35.687 | 19.290 | 1.00 | 10.78 | N |
| ATOM | 3963 | CA | CYS | B | 117 | −0.424 | 36.085 | 20.603 | 1.00 | 9.89 | C |
| ATOM | 3965 | CB | CYS | B | 117 | −0.726 | 37.600 | 20.576 | 1.00 | 11.75 | C |
| ATOM | 3968 | SG | CYS | B | 117 | −1.669 | 38.165 | 22.037 | 1.00 | 10.46 | S |
| ATOM | 3969 | C | CYS | B | 117 | −1.676 | 35.307 | 21.025 | 1.00 | 11.58 | C |
| ATOM | 3970 | O | CYS | B | 117 | −2.592 | 35.281 | 20.309 | 1.00 | 11.90 | O |
| ATOM | 3971 | N | PRO | B | 118 | −1.677 | 34.581 | 22.146 | 1.00 | 12.58 | N |
| ATOM | 3972 | CA | PRO | B | 118 | −2.804 | 33.780 | 22.592 | 1.00 | 13.53 | C |
| ATOM | 3974 | CB | PRO | B | 118 | −2.317 | 33.153 | 23.909 | 1.00 | 13.68 | C |
| ATOM | 3977 | CG | PRO | B | 118 | −0.851 | 33.125 | 23.783 | 1.00 | 13.54 | C |
| ATOM | 3980 | CD | PRO | B | 118 | −0.466 | 34.285 | 22.923 | 1.00 | 12.24 | C |
| ATOM | 3983 | C | PRO | B | 118 | −3.925 | 34.758 | 23.014 | 1.00 | 15.56 | C |
| ATOM | 3984 | O | PRO | B | 118 | −3.691 | 35.809 | 23.599 | 1.00 | 11.88 | O |
| ATOM | 3985 | N | LYS | B | 119 | −5.144 | 34.341 | 22.695 | 1.00 | 15.70 | N |
| ATOM | 3987 | CA | LYS | B | 119 | −6.297 | 35.135 | 23.045 | 1.00 | 17.01 | C |
| ATOM | 3989 | CB | LYS | B | 119 | −7.383 | 34.887 | 22.004 | 1.00 | 22.58 | C |
| ATOM | 3992 | CG | LYS | B | 119 | −7.327 | 36.025 | 20.935 | 1.00 | 25.28 | C |
| ATOM | 3995 | CD | LYS | B | 119 | −7.787 | 35.752 | 19.474 | 1.00 | 28.00 | C |
| ATOM | 3998 | CE | LYS | B | 119 | −7.749 | 37.101 | 18.625 | 1.00 | 27.82 | C |
| ATOM | 4001 | NZ | LYS | B | 119 | −9.270 | 37.120 | 18.547 | 1.00 | 33.30 | N |
| ATOM | 4005 | C | LYS | B | 119 | −6.695 | 34.843 | 24.483 | 1.00 | 14.78 | C |
| ATOM | 4006 | O | LYS | B | 119 | −7.488 | 33.952 | 24.745 | 1.00 | 14.72 | O |
| ATOM | 4007 | N | ILE | B | 120 | −6.139 | 35.660 | 25.388 | 1.00 | 13.92 | N |
| ATOM | 4009 | CA | ILE | B | 120 | −6.426 | 35.657 | 26.829 | 1.00 | 13.11 | C |
| ATOM | 4011 | CB | ILE | B | 120 | −5.480 | 34.905 | 27.638 | 1.00 | 13.03 | C |
| ATOM | 4013 | CG1 | ILE | B | 120 | −5.391 | 33.465 | 27.084 | 1.00 | 13.72 | C |
| ATOM | 4016 | CD1 | ILE | B | 120 | −4.475 | 32.514 | 27.909 | 1.00 | 15.32 | C |
| ATOM | 4020 | CG2 | ILE | B | 120 | −5.836 | 35.055 | 29.195 | 1.00 | 13.02 | C |
| ATOM | 4024 | C | ILE | B | 120 | −6.460 | 37.114 | 27.256 | 1.00 | 14.74 | C |
| ATOM | 4025 | O | ILE | B | 120 | −5.460 | 37.769 | 27.127 | 1.00 | 13.53 | O |
| ATOM | 4026 | N | ILE | B | 121 | −7.643 | 37.640 | 27.540 | 1.00 | 10.64 | N |
| ATOM | 4028 | CA | LEU | B | 121 | −7.707 | 39.052 | 27.854 | 1.00 | 12.46 | C |

-continued

| | | | | | | | | | | |
|---|---|---|---|---|---|---|---|---|---|---|
| ATOM | 4030 | CB | LEU | B | 121 | −9.146 | 39.417 | 28.156 | 1.00 | 12.34 | C |
| ATOM | 4033 | CG | LEU | B | 121 | −9.636 | 40.815 | 28.565 | 1.00 | 12.97 | C |
| ATOM | 4035 | CD1 | LEU | B | 121 | −9.438 | 41.591 | 27.278 | 1.00 | 13.00 | C |
| ATOM | 4039 | CD2 | LEU | B | 121 | −11.102 | 40.869 | 28.910 | 1.00 | 14.52 | C |
| ATOM | 4043 | C | LEU | B | 121 | −6.882 | 39.419 | 29.071 | 1.00 | 11.66 | C |
| ATOM | 4044 | O | LEU | B | 121 | −7.171 | 38.974 | 30.186 | 1.00 | 17.63 | O |
| ATOM | 4045 | N | LYS | B | 122 | −6.036 | 40.414 | 28.943 | 1.00 | 12.56 | N |
| ATOM | 4047 | CA | LYS | B | 122 | −5.174 | 40.807 | 30.076 | 1.00 | 12.21 | C |
| ATOM | 4049 | CB | LYS | B | 122 | −3.875 | 39.996 | 29.854 | 1.00 | 14.60 | C |
| ATOM | 4052 | CG | LYS | B | 122 | −2.683 | 40.335 | 30.676 | 1.00 | 18.10 | C |
| ATOM | 4055 | CD | LYS | B | 122 | −3.084 | 40.179 | 32.127 | 1.00 | 20.56 | C |
| ATOM | 4058 | CE | LYS | B | 122 | −1.789 | 40.064 | 32.976 | 1.00 | 23.92 | C |
| ATOM | 4061 | NZ | LYS | B | 122 | −2.311 | 39.634 | 34.336 | 1.00 | 28.08 | N |
| ATOM | 4065 | C | LYS | B | 122 | −4.898 | 42.321 | 29.881 | 1.00 | 11.03 | C |
| ATOM | 4066 | O | LYS | B | 122 | −4.457 | 42.765 | 28.795 | 1.00 | 12.51 | O |
| ATOM | 4067 | N | LYS | B | 123 | −4.977 | 43.071 | 30.962 | 1.00 | 9.09 | N |
| ATOM | 4069 | CA | LYS | B | 123 | −4.695 | 44.494 | 30.960 | 1.00 | 10.54 | C |
| ATOM | 4071 | CB | LYS | B | 123 | −5.098 | 45.144 | 32.316 | 1.00 | 13.28 | C |
| ATOM | 4074 | CG | LYS | B | 123 | −6.591 | 45.411 | 32.338 | 1.00 | 18.06 | C |
| ATOM | 4077 | CD | LYS | B | 123 | −7.163 | 46.077 | 33.657 | 1.00 | 19.84 | C |
| ATOM | 4080 | CE | LYS | B | 123 | −8.710 | 46.448 | 33.621 | 1.00 | 21.27 | C |
| ATOM | 4083 | NZ | LYS | B | 123 | −9.164 | 47.071 | 34.941 | 1.00 | 22.45 | N |
| ATOM | 4087 | C | LYS | B | 123 | −3.165 | 44.612 | 30.948 | 1.00 | 11.75 | C |
| ATOM | 4088 | O | LYS | B | 123 | −2.444 | 43.790 | 31.522 | 1.00 | 11.87 | O |
| ATOM | 4089 | N | CYS | B | 124 | −2.678 | 45.719 | 30.408 | 1.00 | 10.18 | N |
| ATOM | 4091 | CA | CYS | B | 124 | −1.269 | 45.987 | 30.396 | 1.00 | 8.52 | C |
| ATOM | 4093 | CB | CYS | B | 124 | −0.601 | 45.310 | 29.211 | 1.00 | 9.48 | C |
| ATOM | 4096 | SG | CYS | B | 124 | −1.433 | 45.749 | 27.654 | 1.00 | 10.30 | S |
| ATOM | 4097 | C | CYS | B | 124 | −0.982 | 47.449 | 30.306 | 1.00 | 10.61 | C |
| ATOM | 4098 | O | CYS | B | 124 | −1.829 | 48.242 | 29.905 | 1.00 | 9.26 | O |
| ATOM | 4099 | N | ARG | B | 125 | 0.284 | 47.748 | 30.607 | 1.00 | 11.40 | N |
| ATOM | 4101 | CA | ARG | B | 125 | 0.849 | 49.061 | 30.435 | 1.00 | 11.65 | C |
| ATOM | 4103 | CB | ARG | B | 125 | 1.347 | 49.611 | 31.780 | 1.00 | 15.50 | C |
| ATOM | 4106 | CG | ARG | B | 125 | 0.223 | 50.109 | 32.599 | 1.00 | 19.98 | C |
| ATOM | 4109 | CD | ARG | B | 125 | 0.813 | 50.748 | 33.851 | 1.00 | 24.00 | C |
| ATOM | 4112 | NE | ARG | B | 125 | 0.168 | 51.936 | 34.448 | 1.00 | 31.02 | N |
| ATOM | 4114 | CZ | ARG | B | 125 | 0.243 | 52.222 | 35.802 | 1.00 | 33.95 | C |
| ATOM | 4115 | NH1 | ARG | B | 125 | 0.932 | 51.414 | 36.632 | 1.00 | 35.25 | N |
| ATOM | 4118 | NH2 | ARG | B | 125 | −0.328 | 53.293 | 36.385 | 1.00 | 34.45 | N |
| ATOM | 4121 | C | ARG | B | 125 | 1.984 | 48.994 | 29.427 | 1.00 | 9.67 | C |
| ATOM | 4122 | O | ARG | B | 125 | 2.250 | 49.965 | 28.726 | 1.00 | 10.41 | O |
| ATOM | 4123 | N | ARG | B | 126 | 2.688 | 47.872 | 29.345 | 1.00 | 7.73 | N |
| ATOM | 4125 | CA | ARG | B | 126 | 3.725 | 47.692 | 28.332 | 1.00 | 9.47 | C |
| ATOM | 4127 | CB | ARG | B | 126 | 5.117 | 48.052 | 29.000 | 1.00 | 12.34 | C |
| ATOM | 4130 | CG | ARG | B | 126 | 5.383 | 47.318 | 30.299 | 1.00 | 14.67 | C |
| ATOM | 4133 | CD | ARG | B | 126 | 6.628 | 47.869 | 31.019 | 1.00 | 15.55 | C |
| ATOM | 4136 | NE | ARG | B | 126 | 7.789 | 47.510 | 30.169 | 1.00 | 18.94 | N |
| ATOM | 4138 | CZ | ARG | B | 126 | 9.025 | 48.071 | 30.290 | 1.00 | 23.10 | C |
| ATOM | 4139 | NH1 | ARG | B | 126 | 9.273 | 48.985 | 31.232 | 1.00 | 21.13 | N |
| ATOM | 4142 | NH2 | ARG | B | 126 | 10.058 | 47.720 | 29.495 | 1.00 | 24.42 | N |
| ATOM | 4145 | C | ARG | B | 126 | 3.745 | 46.218 | 27.935 | 1.00 | 9.85 | C |
| ATOM | 4146 | O | ARG | B | 126 | 3.088 | 45.331 | 28.499 | 1.00 | 11.71 | O |
| ATOM | 4147 | N | ASP | B | 127 | 4.535 | 45.914 | 26.928 | 1.00 | 8.60 | N |
| ATOM | 4149 | CA | ASP | B | 127 | 4.497 | 44.553 | 26.371 | 1.00 | 9.89 | C |
| ATOM | 4151 | CB | ASP | B | 127 | 5.457 | 44.441 | 25.194 | 1.00 | 9.11 | C |
| ATOM | 4154 | CG | ASP | B | 127 | 5.114 | 45.420 | 24.054 | 1.00 | 11.38 | C |
| ATOM | 4155 | OD1 | ASP | B | 127 | 4.013 | 46.027 | 24.051 | 1.00 | 7.79 | O |
| ATOM | 4156 | OD2 | ASP | B | 127 | 5.990 | 45.632 | 23.156 | 1.00 | 9.54 | O |
| ATOM | 4157 | C | ASP | B | 127 | 4.814 | 43.402 | 27.338 | 1.00 | 8.70 | C |
| ATOM | 4158 | O | ASP | B | 127 | 4.234 | 42.332 | 27.204 | 1.00 | 6.87 | O |
| ATOM | 4159 | N | SER | B | 128 | 5.820 | 43.613 | 28.182 | 1.00 | 7.27 | N |
| ATOM | 4161 | CA | SER | B | 128 | 6.115 | 42.632 | 29.156 | 1.00 | 7.62 | C |
| ATOM | 4163 | CB | SER | B | 128 | 7.436 | 42.945 | 29.874 | 1.00 | 6.31 | C |
| ATOM | 4166 | OG | SER | B | 128 | 7.355 | 44.167 | 30.597 | 1.00 | 5.17 | O |
| ATOM | 4168 | C | SER | B | 128 | 5.031 | 42.266 | 30.191 | 1.00 | 7.45 | C |
| ATOM | 4169 | O | SER | B | 128 | 5.215 | 41.316 | 30.948 | 1.00 | 9.76 | O |
| ATOM | 4170 | N | ASP | B | 129 | 3.906 | 42.945 | 30.227 | 1.00 | 6.64 | N |
| ATOM | 4172 | CA | ASP | B | 129 | 2.845 | 42.526 | 31.076 | 1.00 | 5.36 | C |
| ATOM | 4174 | CB | ASP | B | 129 | 1.875 | 43.651 | 31.314 | 1.00 | 6.34 | C |
| ATOM | 4177 | CG | ASP | B | 129 | 2.481 | 44.812 | 32.036 | 1.00 | 6.51 | C |
| ATOM | 4178 | OD1 | ASP | B | 129 | 2.069 | 45.984 | 31.794 | 1.00 | 8.78 | O |
| ATOM | 4179 | OD2 | ASP | B | 129 | 3.267 | 44.674 | 32.939 | 1.00 | 6.56 | O |
| ATOM | 4180 | C | ASP | B | 129 | 2.032 | 41.489 | 30.333 | 1.00 | 6.90 | C |
| ATOM | 4181 | O | ASP | B | 129 | 1.201 | 40.847 | 30.961 | 1.00 | 9.35 | O |
| ATOM | 4182 | N | CYS | B | 130 | 2.361 | 41.241 | 29.064 | 1.00 | 8.72 | N |
| ATOM | 4184 | CA | CYS | B | 130 | 1.662 | 40.266 | 28.283 | 1.00 | 11.71 | C |
| ATOM | 4186 | CB | CYS | B | 130 | 1.347 | 40.888 | 26.943 | 1.00 | 9.14 | C |
| ATOM | 4189 | SG | CYS | B | 130 | 0.439 | 42.509 | 26.939 | 1.00 | 9.10 | S |
| ATOM | 4190 | C | CYS | B | 130 | 2.368 | 38.973 | 28.024 | 1.00 | 10.38 | C |
| ATOM | 4191 | O | CYS | B | 130 | 3.571 | 38.914 | 28.083 | 1.00 | 14.55 | O |

-continued

| | | | | | | | | | | |
|---|---|---|---|---|---|---|---|---|---|---|
| ATOM | 4192 | N | LEU | B | 131 | 1.610 | 37.961 | 27.661 | 1.00 | 11.47 | N |
| ATOM | 4194 | CA | LEU | B | 131 | 2.153 | 36.691 | 27.206 | 1.00 | 12.37 | C |
| ATOM | 4196 | CB | LEU | B | 131 | 1.016 | 35.770 | 26.768 | 1.00 | 15.31 | C |
| ATOM | 4199 | CG | LEU | B | 131 | 0.146 | 35.345 | 27.951 | 1.00 | 16.72 | C |
| ATOM | 4201 | CD1 | LEU | B | 131 | −1.022 | 34.671 | 27.445 | 1.00 | 15.47 | C |
| ATOM | 4205 | CD2 | LEU | B | 131 | 0.869 | 34.400 | 28.946 | 1.00 | 19.03 | C |
| ATOM | 4209 | C | LEU | B | 131 | 3.075 | 36.867 | 25.979 | 1.00 | 10.63 | C |
| ATOM | 4210 | O | LEU | B | 131 | 3.076 | 37.898 | 25.337 | 1.00 | 9.90 | O |
| ATOM | 4211 | N | ALA | B | 132 | 4.034 | 35.970 | 25.865 | 1.00 | 11.14 | N |
| ATOM | 4213 | CA | ALA | B | 132 | 4.919 | 35.829 | 24.726 | 1.00 | 8.75 | C |
| ATOM | 4215 | CB | ALA | B | 132 | 5.620 | 34.574 | 24.801 | 1.00 | 10.07 | C |
| ATOM | 4219 | C | ALA | B | 132 | 4.084 | 35.899 | 23.441 | 1.00 | 9.76 | C |
| ATOM | 4220 | O | ALA | B | 132 | 2.971 | 35.444 | 23.362 | 1.00 | 8.80 | O |
| ATOM | 4221 | N | GLY | B | 133 | 4.458 | 36.741 | 22.506 | 1.00 | 9.65 | N |
| ATOM | 4223 | CA | GLY | B | 133 | 3.751 | 36.937 | 21.247 | 1.00 | 10.68 | C |
| ATOM | 4226 | C | GLY | B | 133 | 2.702 | 38.018 | 21.306 | 1.00 | 12.09 | C |
| ATOM | 4227 | O | GLY | B | 133 | 2.216 | 38.349 | 20.251 | 1.00 | 9.81 | O |
| ATOM | 4228 | N | CYS | B | 134 | 2.450 | 38.606 | 22.488 | 1.00 | 12.02 | N |
| ATOM | 4230 | CA | CYS | B | 134 | 1.546 | 39.680 | 22.637 | 1.00 | 11.04 | C |
| ATOM | 4232 | CB | CYS | B | 134 | 0.570 | 39.306 | 23.730 | 1.00 | 12.03 | C |
| ATOM | 4235 | SG | CYS | B | 134 | −0.369 | 37.779 | 23.515 | 1.00 | 12.63 | S |
| ATOM | 4236 | C | CYS | B | 134 | 2.277 | 40.964 | 23.014 | 1.00 | 9.59 | C |
| ATOM | 4237 | O | CYS | B | 134 | 3.365 | 41.040 | 23.589 | 1.00 | 7.88 | O |
| ATOM | 4238 | N | VAL | B | 135 | 1.627 | 42.040 | 22.604 | 1.00 | 9.26 | N |
| ATOM | 4240 | CA | VAL | B | 135 | 2.034 | 43.417 | 22.845 | 1.00 | 8.42 | C |
| ATOM | 4242 | CB | VAL | B | 135 | 2.512 | 44.137 | 21.572 | 1.00 | 9.70 | C |
| ATOM | 4244 | CG1 | VAL | B | 135 | 3.695 | 43.379 | 21.044 | 1.00 | 7.35 | C |
| ATOM | 4248 | CG2 | VAL | B | 135 | 1.409 | 44.224 | 20.498 | 1.00 | 10.12 | C |
| ATOM | 4252 | C | VAL | B | 135 | 0.863 | 44.238 | 23.405 | 1.00 | 10.16 | C |
| ATOM | 4253 | O | VAL | B | 135 | −0.243 | 43.826 | 23.365 | 1.00 | 10.36 | O |
| ATOM | 4254 | N | CYS | B | 136 | 1.193 | 45.237 | 24.198 | 1.00 | 9.32 | N |
| ATOM | 4256 | CA | CYS | B | 136 | 0.230 | 46.046 | 24.823 | 1.00 | 8.81 | C |
| ATOM | 4258 | CB | CYS | B | 136 | 0.855 | 46.732 | 26.021 | 1.00 | 9.87 | C |
| ATOM | 4261 | SG | CYS | B | 136 | −0.426 | 47.442 | 27.058 | 1.00 | 9.28 | S |
| ATOM | 4262 | C | CYS | B | 136 | −0.286 | 47.049 | 23.783 | 1.00 | 6.94 | C |
| ATOM | 4263 | O | CYS | B | 136 | 0.375 | 47.951 | 23.242 | 1.00 | 8.86 | O |
| ATOM | 4264 | N | GLY | B | 137 | −1.528 | 46.918 | 23.504 | 1.00 | 6.75 | N |
| ATOM | 4266 | CA | GLY | B | 137 | −2.147 | 47.852 | 22.595 | 1.00 | 9.92 | C |
| ATOM | 4269 | C | GLY | B | 137 | −2.508 | 49.229 | 23.168 | 1.00 | 10.96 | C |
| ATOM | 4270 | O | GLY | B | 137 | −2.470 | 49.438 | 24.371 | 1.00 | 9.72 | O |
| ATOM | 4271 | N | PRO | B | 138 | −2.984 | 50.143 | 22.297 | 1.00 | 11.07 | N |
| ATOM | 4272 | CA | PRO | B | 138 | −3.165 | 51.514 | 22.722 | 1.00 | 10.23 | C |
| ATOM | 4274 | CB | PRO | B | 138 | −3.533 | 52.322 | 21.450 | 1.00 | 12.09 | C |
| ATOM | 4277 | CG | PRO | B | 138 | −3.656 | 51.346 | 20.402 | 1.00 | 12.93 | C |
| ATOM | 4280 | CD | PRO | B | 138 | −3.292 | 49.940 | 20.879 | 1.00 | 10.42 | C |
| ATOM | 4283 | C | PRO | B | 138 | −4.269 | 51.565 | 23.733 | 1.00 | 10.00 | C |
| ATOM | 4284 | O | PRO | B | 138 | −4.374 | 52.585 | 24.375 | 1.00 | 8.95 | O |
| ATOM | 4285 | N | ASN | B | 139 | −5.100 | 50.528 | 23.821 | 1.00 | 11.01 | N |
| ATOM | 4287 | CA | ASN | B | 139 | −6.229 | 50.453 | 24.757 | 1.00 | 11.73 | C |
| ATOM | 4289 | CB | ASN | B | 139 | −7.398 | 49.648 | 24.143 | 1.00 | 12.66 | C |
| ATOM | 4292 | CG | ASN | B | 139 | −7.043 | 48.164 | 23.935 | 1.00 | 15.97 | C |
| ATOM | 4293 | OD1 | ASN | B | 139 | −5.850 | 47.792 | 23.628 | 1.00 | 17.55 | O |
| ATOM | 4294 | ND2 | ASN | B | 139 | −8.102 | 47.349 | 23.816 | 1.00 | 16.59 | N |
| ATOM | 4297 | C | ASN | B | 139 | −5.851 | 49.894 | 26.113 | 1.00 | 11.34 | C |
| ATOM | 4298 | O | ASN | B | 139 | −6.692 | 49.722 | 26.961 | 1.00 | 11.56 | O |
| ATOM | 4299 | N | GLY | B | 140 | −4.580 | 49.571 | 26.321 | 1.00 | 11.16 | N |
| ATOM | 4301 | CA | GLY | B | 140 | −4.135 | 49.044 | 27.588 | 1.00 | 11.37 | C |
| ATOM | 4304 | C | GLY | B | 140 | −4.515 | 47.571 | 27.751 | 1.00 | 13.70 | C |
| ATOM | 4305 | O | GLY | B | 140 | −4.560 | 47.091 | 28.894 | 1.00 | 11.23 | O |
| ATOM | 4306 | N | PHE | B | 141 | −4.740 | 46.853 | 26.652 | 1.00 | 10.89 | N |
| ATOM | 4308 | CA | PHE | B | 141 | −4.891 | 45.423 | 26.705 | 1.00 | 12.78 | C |
| ATOM | 4310 | CB | PHE | B | 141 | −6.306 | 44.957 | 26.389 | 1.00 | 10.06 | C |
| ATOM | 4313 | CG | PHE | B | 141 | −7.336 | 45.362 | 27.436 | 1.00 | 11.78 | C |
| ATOM | 4314 | CD1 | PHE | B | 141 | −7.711 | 44.504 | 28.471 | 1.00 | 7.36 | C |
| ATOM | 4316 | CE1 | PHE | B | 141 | −8.597 | 44.947 | 29.489 | 1.00 | 9.72 | C |
| ATOM | 4318 | CZ | PHE | B | 141 | −9.128 | 46.180 | 29.446 | 1.00 | 12.47 | C |
| ATOM | 4320 | CE2 | PHE | B | 141 | −8.703 | 47.083 | 28.426 | 1.00 | 12.66 | C |
| ATOM | 4322 | CD2 | PHE | B | 141 | −7.866 | 46.658 | 27.409 | 1.00 | 11.40 | C |
| ATOM | 4324 | C | PHE | B | 141 | −3.889 | 44.781 | 25.793 | 1.00 | 9.78 | C |
| ATOM | 4325 | O | PHE | B | 141 | −3.560 | 45.224 | 24.695 | 1.00 | 12.17 | O |
| ATOM | 4326 | N | CYS | B | 142 | −3.707 | 43.526 | 26.091 | 1.00 | 7.08 | N |
| ATOM | 4328 | CA | CYS | B | 142 | −2.768 | 42.694 | 25.376 | 1.00 | 9.17 | C |
| ATOM | 4330 | CB | CYS | B | 142 | −2.189 | 41.557 | 26.226 | 1.00 | 9.73 | C |
| ATOM | 4333 | SG | CYS | B | 142 | −1.323 | 42.018 | 27.751 | 1.00 | 10.02 | S |
| ATOM | 4334 | C | CYS | B | 142 | −3.320 | 42.140 | 24.095 | 1.00 | 9.02 | C |
| ATOM | 4335 | O | CYS | B | 142 | −4.431 | 41.691 | 24.074 | 1.00 | 11.66 | O |
| ATOM | 4336 | N | GLY | B | 143 | −2.562 | 42.134 | 23.011 | 1.00 | 9.08 | N |
| ATOM | 4338 | CA | GLY | B | 143 | −3.060 | 41.566 | 21.754 | 1.00 | 10.12 | C |
| ATOM | 4341 | C | GLY | B | 143 | −2.022 | 41.372 | 20.679 | 1.00 | 10.66 | C |
| ATOM | 4342 | O | GLY | B | 143 | −0.853 | 41.535 | 21.057 | 1.00 | 6.24 | O |

-continued

| | | | | | | | | | | |
|---|---|---|---|---|---|---|---|---|---|---|
| ATOM | 4343 | N | SER | B | 144 | −2.373 | 40.993 | 19.468 | 1.00 | 10.91 | N |
| ATOM | 4345 | CA | SER | B | 144 | −1.348 | 40.819 | 18.471 | 1.00 | 12.34 | C |
| ATOM | 4347 | CB | SER | B | 144 | −1.704 | 40.101 | 17.211 | 1.00 | 14.54 | C |
| ATOM | 4350 | OG | SER | B | 144 | −2.592 | 39.027 | 17.539 | 1.00 | 17.92 | O |
| ATOM | 4352 | C | SER | B | 144 | −0.582 | 42.056 | 18.066 | 1.00 | 14.23 | C |
| ATOM | 4353 | O | SER | B | 144 | −1.210 | 43.081 | 18.067 | 1.00 | 14.50 | O |
| ATOM | 4354 | OXT | SER | B | 144 | 0.614 | 42.013 | 17.708 | 1.00 | 13.17 | O |
| ATOM | 4355 | S | SO4 | X | 1 | −8.456 | 59.328 | 25.375 | 1.00 | 62.73 | S |
| ATOM | 4356 | O1 | SO4 | X | 1 | −7.367 | 58.486 | 24.804 | 1.00 | 61.80 | O |
| ATOM | 4357 | O2 | SO4 | X | 1 | −8.232 | 60.230 | 26.492 | 1.00 | 59.94 | O |
| ATOM | 4358 | O3 | SO4 | X | 1 | −8.605 | 60.235 | 24.188 | 1.00 | 60.50 | O |
| ATOM | 4359 | O4 | SO4 | X | 1 | −9.327 | 58.362 | 26.132 | 1.00 | 58.47 | O |
| ATOM | 4360 | S | SO4 | X | 2 | 21.150 | 27.268 | 10.030 | 1.00 | 44.73 | S |
| ATOM | 4361 | O1 | SO4 | X | 2 | 22.620 | 27.325 | 10.129 | 1.00 | 45.48 | O |
| ATOM | 4362 | O2 | SO4 | X | 2 | 20.443 | 28.463 | 10.581 | 1.00 | 44.20 | O |
| ATOM | 4363 | O3 | SO4 | X | 2 | 20.634 | 27.169 | 8.666 | 1.00 | 44.34 | O |
| ATOM | 4364 | O4 | SO4 | X | 2 | 20.873 | 25.984 | 10.659 | 1.00 | 44.14 | O |
| ATOM | 4365 | S | SO4 | X | 3 | 11.477 | 23.840 | 10.225 | 1.00 | 54.03 | S |
| ATOM | 4366 | O1 | SO4 | X | 3 | 12.992 | 23.747 | 10.387 | 1.00 | 52.64 | O |
| ATOM | 4367 | O2 | SO4 | X | 3 | 10.500 | 24.718 | 10.950 | 1.00 | 52.07 | O |
| ATOM | 4368 | O3 | SO4 | X | 3 | 11.312 | 24.727 | 9.071 | 1.00 | 55.72 | O |
| ATOM | 4369 | O4 | SO4 | X | 3 | 11.011 | 22.642 | 9.534 | 1.00 | 52.59 | O |
| ATOM | 4370 | S | SO4 | X | 4 | 15.596 | 8.604 | 28.993 | 1.00 | 75.74 | S |
| ATOM | 4371 | O1 | SO4 | X | 4 | 16.683 | 9.569 | 29.222 | 1.00 | 76.36 | O |
| ATOM | 4372 | O2 | SO4 | X | 4 | 14.997 | 8.662 | 30.328 | 1.00 | 75.37 | O |
| ATOM | 4373 | O3 | SO4 | X | 4 | 14.478 | 8.820 | 28.043 | 1.00 | 74.08 | O |
| ATOM | 4374 | O4 | SO4 | X | 4 | 16.378 | 7.433 | 28.550 | 1.00 | 75.08 | O |
| ATOM | 4375 | O5 | PG4 | X | 100 | 12.072 | 43.213 | 7.525 | 1.00 | 39.50 | O |
| ATOM | 4377 | C8 | PG4 | X | 100 | 12.548 | 43.607 | 8.885 | 1.00 | 37.25 | C |
| ATOM | 4380 | C7 | PG4 | X | 100 | 11.817 | 43.689 | 10.251 | 1.00 | 33.81 | C |
| ATOM | 4383 | O4 | PG4 | X | 100 | 11.369 | 44.773 | 11.185 | 1.00 | 34.32 | O |
| ATOM | 4384 | C6 | PG4 | X | 100 | 9.889 | 44.956 | 11.391 | 1.00 | 24.12 | C |
| ATOM | 4387 | C5 | PG4 | X | 100 | 8.581 | 45.829 | 11.434 | 1.00 | 26.64 | C |
| ATOM | 4390 | O3 | PG4 | X | 100 | 7.471 | 45.386 | 10.455 | 1.00 | 29.66 | O |
| ATOM | 4391 | C4 | PG4 | X | 100 | 6.503 | 46.017 | 9.644 | 1.00 | 28.44 | C |
| ATOM | 4394 | C3 | PG4 | X | 100 | 5.903 | 45.321 | 8.386 | 1.00 | 30.07 | C |
| ATOM | 4397 | O2 | PG4 | X | 100 | 6.866 | 44.799 | 7.455 | 1.00 | 30.65 | O |
| ATOM | 4398 | C2 | PG4 | X | 100 | 6.761 | 43.940 | 6.323 | 1.00 | 32.24 | C |
| ATOM | 4401 | C1 | PG4 | X | 100 | 8.049 | 43.362 | 5.699 | 1.00 | 35.20 | C |
| ATOM | 4404 | O1 | PG4 | X | 100 | 8.996 | 44.184 | 4.980 | 1.00 | 36.32 | O |
| ATOM | 4406 | O5 | PG4 | X | 101 | −8.880 | 40.691 | 20.549 | 1.00 | 42.26 | O |
| ATOM | 4408 | C8 | PG4 | X | 101 | −9.332 | 39.861 | 19.445 | 1.00 | 37.50 | C |
| ATOM | 4411 | C7 | PG4 | X | 101 | −10.060 | 40.099 | 18.098 | 1.00 | 36.74 | C |
| ATOM | 4414 | O4 | PG4 | X | 101 | −9.381 | 39.225 | 17.139 | 1.00 | 35.25 | O |
| ATOM | 4415 | C6 | PG4 | X | 101 | −9.588 | 38.588 | 15.865 | 1.00 | 37.24 | C |
| ATOM | 4418 | C5 | PG4 | X | 101 | −8.334 | 38.332 | 15.007 | 1.00 | 38.38 | C |
| ATOM | 4421 | O3 | PG4 | X | 101 | −7.427 | 37.351 | 15.506 | 1.00 | 40.25 | O |
| ATOM | 4422 | C4 | PG4 | X | 101 | −6.369 | 36.662 | 14.847 | 1.00 | 42.96 | C |
| ATOM | 4425 | C3 | PG4 | X | 101 | −5.678 | 35.666 | 15.803 | 1.00 | 44.49 | C |
| ATOM | 4428 | O2 | PG4 | X | 101 | −4.238 | 35.808 | 16.035 | 1.00 | 47.79 | O |
| ATOM | 4429 | C2 | PG4 | X | 101 | −3.655 | 35.990 | 17.344 | 1.00 | 47.22 | C |
| ATOM | 4432 | C1 | PG4 | X | 101 | −4.649 | 36.586 | 18.393 | 1.00 | 46.24 | C |
| ATOM | 4435 | O1 | PG4 | X | 101 | −4.356 | 37.565 | 19.404 | 1.00 | 39.61 | O |
| ATOM | 4437 | O | HOH | W | 1 | 0.000 | 58.790 | 14.540 | 0.50 | 11.72 | O |
| ATOM | 4440 | O | HOH | W | 2 | 0.000 | 24.853 | 14.540 | 0.50 | 12.82 | O |
| ATOM | 4443 | O | HOH | W | 3 | 5.569 | 8.132 | 30.455 | 1.00 | 18.15 | O |
| ATOM | 4446 | O | HOH | W | 4 | 4.308 | 30.482 | 21.389 | 1.00 | 18.25 | O |
| ATOM | 4449 | O | HOH | W | 5 | 10.470 | 13.439 | 29.078 | 1.00 | 19.96 | O |
| ATOM | 4452 | O | HOH | W | 6 | 10.334 | 71.418 | 15.207 | 1.00 | 20.56 | O |
| ATOM | 4455 | O | HOH | W | 7 | 12.261 | 35.986 | 13.669 | 1.00 | 17.17 | O |
| ATOM | 4458 | O | HOH | W | 8 | 8.715 | 36.629 | 25.110 | 1.00 | 18.41 | O |
| ATOM | 4461 | O | HOH | W | 9 | −2.731 | 12.411 | 24.763 | 1.00 | 16.82 | O |
| ATOM | 4464 | O | HOH | W | 10 | 9.048 | 44.966 | 26.900 | 1.00 | 27.01 | O |
| ATOM | 4467 | O | HOH | W | 11 | 6.415 | 10.293 | 33.357 | 1.00 | 20.43 | O |
| ATOM | 4470 | O | HOH | W | 12 | 3.956 | 33.537 | 27.379 | 1.00 | 19.80 | O |
| ATOM | 4473 | O | HOH | W | 13 | 1.940 | 39.628 | 17.828 | 1.00 | 22.19 | O |
| ATOM | 4476 | O | HOH | W | 14 | −1.947 | 16.381 | 18.388 | 1.00 | 15.41 | O |
| ATOM | 4479 | O | HOH | W | 15 | 2.281 | 12.528 | 31.170 | 1.00 | 16.86 | O |
| ATOM | 4482 | O | HOH | W | 16 | 13.356 | 11.260 | 29.109 | 1.00 | 30.83 | O |
| ATOM | 4485 | O | HOH | W | 17 | 13.419 | 59.715 | 28.278 | 1.00 | 20.40 | O |
| ATOM | 4488 | O | HOH | W | 18 | 9.109 | 68.562 | 12.889 | 1.00 | 19.53 | O |
| ATOM | 4491 | O | HOH | W | 19 | 20.514 | 43.163 | 16.705 | 1.00 | 35.54 | O |
| ATOM | 4494 | O | HOH | W | 20 | 11.132 | 68.532 | 31.061 | 1.00 | 21.92 | O |
| ATOM | 4497 | O | HOH | W | 21 | 10.592 | 50.742 | 22.338 | 1.00 | 19.02 | O |
| ATOM | 4500 | O | HOH | W | 22 | 5.729 | 58.346 | 14.919 | 1.00 | 20.60 | O |
| ATOM | 4503 | O | HOH | W | 23 | 6.395 | 47.767 | 25.855 | 1.00 | 21.74 | O |
| ATOM | 4506 | O | HOH | W | 24 | −5.301 | 15.063 | 18.514 | 1.00 | 19.43 | O |
| ATOM | 4509 | O | HOH | W | 25 | 8.102 | 51.134 | 19.350 | 1.00 | 19.33 | O |
| ATOM | 4512 | O | HOH | W | 26 | 5.711 | 21.642 | 8.152 | 1.00 | 20.85 | O |
| ATOM | 4515 | O | HOH | W | 27 | 14.942 | 71.340 | 21.781 | 1.00 | 18.33 | O |

-continued

| | | | | | | | | | | |
|---|---|---|---|---|---|---|---|---|---|---|
| ATOM | 4518 | O | HOH | W | 28 | −7.820 | 61.894 | 18.143 | 1.00 | 22.35 | O |
| ATOM | 4521 | O | HOH | W | 29 | 12.150 | 15.157 | 30.288 | 1.00 | 23.42 | O |
| ATOM | 4524 | O | HOH | W | 30 | 15.645 | 73.649 | 26.582 | 1.00 | 24.21 | O |
| ATOM | 4527 | O | HOH | W | 31 | 27.619 | 71.256 | 33.365 | 1.00 | 28.16 | O |
| ATOM | 4530 | O | HOH | W | 32 | 11.082 | 30.951 | 10.399 | 1.00 | 27.41 | O |
| ATOM | 4533 | O | HOH | W | 33 | 5.396 | 8.177 | 16.702 | 1.00 | 19.60 | O |
| ATOM | 4536 | O | HOH | W | 34 | 5.838 | 58.094 | 28.696 | 1.00 | 27.76 | O |
| ATOM | 4539 | O | HOH | W | 35 | −4.247 | 15.097 | 22.657 | 1.00 | 19.58 | O |
| ATOM | 4542 | O | HOH | W | 36 | 4.961 | 50.326 | 20.161 | 1.00 | 15.13 | O |
| ATOM | 4545 | O | HOH | W | 37 | 2.553 | 43.907 | 16.824 | 1.00 | 19.84 | O |
| ATOM | 4548 | O | HOH | W | 38 | 3.560 | 44.117 | 10.280 | 1.00 | 26.18 | O |
| ATOM | 4551 | O | HOH | W | 39 | 10.369 | 70.392 | 29.020 | 1.00 | 23.61 | O |
| ATOM | 4554 | O | HOH | W | 40 | −4.440 | 61.433 | 32.419 | 1.00 | 32.08 | O |
| ATOM | 4557 | O | HOH | W | 41 | 5.516 | 52.935 | 20.837 | 1.00 | 15.86 | O |
| ATOM | 4560 | O | HOH | W | 42 | −5.375 | 40.911 | 18.995 | 1.00 | 24.57 | O |
| ATOM | 4563 | O | HOH | W | 43 | 5.490 | 39.538 | 12.342 | 1.00 | 31.58 | O |
| ATOM | 4566 | O | HOH | W | 44 | 7.558 | 35.834 | 20.807 | 1.00 | 19.05 | O |
| ATOM | 4569 | O | HOH | W | 45 | 4.729 | 60.236 | 29.586 | 1.00 | 15.57 | O |
| ATOM | 4572 | O | HOH | W | 46 | 2.279 | 32.794 | 23.898 | 1.00 | 18.78 | O |
| ATOM | 4575 | O | HOH | W | 47 | 7.077 | 42.538 | 11.012 | 1.00 | 18.63 | O |
| ATOM | 4578 | O | HOH | W | 48 | −1.052 | 10.367 | 16.178 | 1.00 | 28.44 | O |
| ATOM | 4581 | O | HOH | W | 49 | 1.958 | 57.209 | 15.560 | 1.00 | 22.98 | O |
| ATOM | 4584 | O | HOH | W | 50 | 18.613 | 78.830 | 29.537 | 1.00 | 23.72 | O |
| ATOM | 4587 | O | HOH | W | 51 | 3.528 | 15.368 | 44.050 | 1.00 | 29.21 | O |
| ATOM | 4590 | O | HOH | W | 52 | −6.051 | 41.809 | 33.733 | 1.00 | 28.67 | O |
| ATOM | 4593 | O | HOH | W | 53 | 1.499 | 14.231 | 35.574 | 1.00 | 21.04 | O |
| ATOM | 4596 | O | HOH | W | 54 | −4.121 | 67.336 | 15.091 | 1.00 | 22.73 | O |
| ATOM | 4599 | O | HOH | W | 55 | −0.324 | 37.396 | 17.017 | 1.00 | 24.78 | O |
| ATOM | 4602 | O | HOH | W | 56 | 9.434 | 33.285 | 26.515 | 1.00 | 29.61 | O |
| ATOM | 4605 | O | HOH | W | 57 | 18.143 | 33.757 | 12.186 | 1.00 | 29.20 | O |
| ATOM | 4608 | O | HOH | W | 58 | 13.968 | 43.052 | 13.635 | 1.00 | 19.33 | O |
| ATOM | 4611 | O | HOH | W | 59 | 12.408 | 28.178 | 11.443 | 1.00 | 26.19 | O |
| ATOM | 4614 | O | HOH | W | 60 | 18.506 | 19.558 | 21.258 | 1.00 | 24.26 | O |
| ATOM | 4617 | O | HOH | W | 61 | 18.217 | 58.246 | 23.895 | 1.00 | 26.84 | O |
| ATOM | 4620 | O | HOH | W | 62 | −1.232 | 38.434 | 27.190 | 1.00 | 22.02 | O |
| ATOM | 4623 | O | HOH | W | 63 | 4.995 | 69.915 | 14.221 | 1.00 | 20.73 | O |
| ATOM | 4626 | O | HOH | W | 64 | 5.965 | 33.589 | 21.250 | 1.00 | 16.38 | O |
| ATOM | 4629 | O | HOH | W | 65 | 5.460 | 68.539 | 10.698 | 1.00 | 22.04 | O |
| ATOM | 4632 | O | HOH | W | 66 | 3.600 | 33.068 | 21.336 | 1.00 | 20.02 | O |
| ATOM | 4635 | O | HOH | W | 67 | 19.422 | 69.743 | 22.196 | 1.00 | 20.58 | O |
| ATOM | 4638 | O | HOH | W | 68 | −1.767 | 73.135 | 14.951 | 1.00 | 36.16 | O |
| ATOM | 4641 | O | HOH | W | 69 | 1.423 | 10.955 | 37.687 | 1.00 | 24.08 | O |
| ATOM | 4644 | O | HOH | W | 70 | 14.952 | 66.300 | 14.549 | 1.00 | 25.64 | O |
| ATOM | 4647 | O | HOH | W | 71 | 8.446 | 76.529 | 30.667 | 1.00 | 28.89 | O |
| ATOM | 4650 | O | HOH | W | 72 | 11.897 | 46.124 | 15.353 | 1.00 | 19.96 | O |
| ATOM | 4653 | O | HOH | W | 73 | 13.452 | 67.576 | 36.982 | 1.00 | 24.13 | O |
| ATOM | 4656 | O | HOH | W | 74 | 6.475 | 25.912 | 11.779 | 1.00 | 23.93 | O |
| ATOM | 4659 | O | HOH | W | 75 | 0.016 | 23.977 | 35.410 | 1.00 | 34.89 | O |
| ATOM | 4662 | O | HOH | W | 76 | 8.360 | 44.168 | 23.192 | 1.00 | 21.03 | O |
| ATOM | 4665 | O | HOH | W | 77 | 6.253 | 52.072 | 17.601 | 1.00 | 18.19 | O |
| ATOM | 4668 | O | HOH | W | 78 | 10.791 | 23.588 | 29.362 | 1.00 | 29.93 | O |
| ATOM | 4671 | O | HOH | W | 79 | −0.729 | 47.967 | 15.636 | 1.00 | 24.15 | O |
| ATOM | 4674 | O | HOH | W | 80 | −5.946 | 41.064 | 26.119 | 1.00 | 25.29 | O |
| ATOM | 4677 | O | HOH | W | 81 | 12.859 | 22.724 | 30.930 | 1.00 | 26.81 | O |
| ATOM | 4680 | O | HOH | W | 82 | 12.877 | 23.410 | 23.827 | 1.00 | 21.68 | O |
| ATOM | 4683 | O | HOH | W | 83 | −0.579 | 45.550 | 17.331 | 1.00 | 19.14 | O |
| ATOM | 4686 | O | HOH | W | 84 | 12.717 | 45.547 | 17.915 | 1.00 | 18.82 | O |
| ATOM | 4689 | O | HOH | W | 85 | 4.653 | 54.216 | 29.700 | 1.00 | 27.98 | O |
| ATOM | 4692 | O | HOH | W | 86 | 8.433 | 5.156 | 37.077 | 1.00 | 22.40 | O |
| ATOM | 4695 | O | HOH | W | 87 | −6.017 | 69.464 | 20.826 | 1.00 | 39.33 | O |
| ATOM | 4698 | O | HOH | W | 88 | 2.994 | 48.232 | 22.818 | 1.00 | 15.43 | O |
| ATOM | 4701 | O | HOH | W | 89 | 9.112 | 75.208 | 34.001 | 1.00 | 37.26 | O |
| ATOM | 4704 | O | HOH | W | 90 | −0.072 | 73.879 | 18.702 | 1.00 | 33.81 | O |
| ATOM | 4707 | O | HOH | W | 91 | −3.833 | 23.229 | 27.552 | 1.00 | 26.34 | O |
| ATOM | 4710 | O | HOH | W | 92 | 8.797 | 34.594 | 22.914 | 1.00 | 19.91 | O |
| ATOM | 4713 | O | HOH | W | 93 | −5.093 | 38.811 | 23.433 | 1.00 | 26.55 | O |
| ATOM | 4716 | O | HOH | W | 94 | 3.630 | 46.545 | 13.630 | 1.00 | 20.19 | O |
| ATOM | 4719 | O | HOH | W | 95 | 12.956 | 75.740 | 24.756 | 1.00 | 17.89 | O |
| ATOM | 4722 | O | HOH | W | 96 | −2.191 | 46.712 | 19.298 | 1.00 | 19.11 | O |
| ATOM | 4725 | O | HOH | W | 97 | 0.254 | 26.340 | 16.863 | 1.00 | 28.81 | O |
| ATOM | 4728 | O | HOH | W | 98 | 18.526 | 19.241 | 16.363 | 1.00 | 26.18 | O |
| ATOM | 4731 | O | HOH | W | 99 | −1.153 | 25.253 | 20.015 | 1.00 | 25.87 | O |
| ATOM | 4734 | O | HOH | W | 100 | 18.488 | 22.025 | 16.032 | 1.00 | 33.45 | O |
| ATOM | 4737 | O | HOH | W | 101 | 17.029 | 78.337 | 21.107 | 1.00 | 24.35 | O |
| ATOM | 4740 | O | HOH | W | 102 | 9.100 | 17.423 | 9.981 | 1.00 | 25.36 | O |
| ATOM | 4743 | O | HOH | W | 103 | 13.927 | 80.205 | 30.359 | 1.00 | 32.23 | O |
| ATOM | 4746 | O | HOH | W | 104 | 16.562 | 30.601 | 12.293 | 1.00 | 31.46 | O |
| ATOM | 4749 | O | HOH | W | 105 | 0.233 | 75.590 | 20.523 | 1.00 | 22.05 | O |
| ATOM | 4752 | O | HOH | W | 106 | 5.911 | 74.458 | 14.901 | 1.00 | 34.42 | O |
| ATOM | 4755 | O | HOH | W | 107 | −3.053 | 9.843 | 23.060 | 1.00 | 33.67 | O |

-continued

| | | | | | | | | | | | |
|---|---|---|---|---|---|---|---|---|---|---|---|
| ATOM | 4758 | O | HOH | W | 108 | 13.624 | 60.717 | 14.932 | 1.00 | 22.75 | O |
| ATOM | 4761 | O | HOH | W | 109 | −11.385 | 35.553 | 17.771 | 1.00 | 25.06 | O |
| ATOM | 4764 | O | HOH | W | 110 | 9.197 | 52.364 | 11.557 | 1.00 | 33.98 | O |
| ATOM | 4767 | O | HOH | W | 111 | 15.172 | 64.468 | 37.267 | 1.00 | 34.40 | O |
| ATOM | 4770 | O | HOH | W | 112 | 3.808 | 9.889 | 15.981 | 1.00 | 32.38 | O |
| ATOM | 4773 | O | HOH | W | 113 | 3.113 | 38.346 | 15.162 | 1.00 | 28.61 | O |
| ATOM | 4776 | O | HOH | W | 114 | 10.293 | 33.312 | 10.568 | 1.00 | 36.43 | O |
| ATOM | 4779 | O | HOH | W | 115 | 17.095 | 48.164 | 10.932 | 1.00 | 31.46 | O |
| ATOM | 4782 | O | HOH | W | 116 | 0.976 | 52.541 | 28.901 | 1.00 | 28.51 | O |
| ATOM | 4785 | O | HOH | W | 117 | −3.666 | 54.865 | 23.887 | 1.00 | 34.22 | O |
| ATOM | 4788 | O | HOH | W | 118 | 16.943 | 16.288 | 34.339 | 1.00 | 25.43 | O |
| ATOM | 4791 | O | HOH | W | 119 | −10.149 | 64.450 | 29.311 | 1.00 | 32.72 | O |
| ATOM | 4794 | O | HOH | W | 120 | 19.689 | 59.775 | 21.082 | 1.00 | 26.63 | O |
| ATOM | 4797 | O | HOH | W | 121 | −3.691 | 48.425 | 17.743 | 1.00 | 19.17 | O |
| ATOM | 4800 | O | HOH | W | 122 | 21.430 | 73.034 | 23.048 | 1.00 | 28.42 | O |
| ATOM | 4803 | O | HOH | W | 123 | 10.265 | 27.752 | 12.773 | 1.00 | 31.81 | O |
| ATOM | 4806 | O | HOH | W | 124 | 0.806 | 63.954 | 34.184 | 1.00 | 23.12 | O |
| ATOM | 4809 | O | HOH | W | 125 | 12.287 | 7.157 | 27.671 | 1.00 | 24.45 | O |
| ATOM | 4812 | O | HOH | W | 126 | 18.944 | 29.156 | 12.709 | 1.00 | 26.63 | O |
| ATOM | 4815 | O | HOH | W | 127 | −7.243 | 66.210 | 21.853 | 1.00 | 29.41 | O |
| ATOM | 4818 | O | HOH | W | 128 | −0.149 | 12.004 | 35.548 | 1.00 | 27.14 | O |
| ATOM | 4821 | O | HOH | W | 129 | 4.382 | 24.565 | 9.438 | 1.00 | 28.77 | O |
| ATOM | 4824 | O | HOH | W | 130 | −3.342 | 25.747 | 27.914 | 1.00 | 29.86 | O |
| ATOM | 4827 | O | HOH | W | 131 | −1.529 | 50.070 | 17.418 | 1.00 | 22.20 | O |
| ATOM | 4830 | O | HOH | W | 132 | 14.650 | 72.436 | 15.638 | 1.00 | 25.05 | O |
| ATOM | 4833 | O | HOH | W | 133 | 17.878 | 62.716 | 31.362 | 1.00 | 25.14 | O |
| ATOM | 4836 | O | HOH | W | 134 | 9.227 | 79.817 | 20.659 | 1.00 | 29.29 | O |
| ATOM | 4839 | O | HOH | W | 135 | −3.314 | 37.852 | 25.395 | 1.00 | 23.68 | O |
| ATOM | 4842 | O | HOH | W | 136 | 0.000 | 73.500 | 14.540 | 0.50 | 41.45 | O |
| ATOM | 4845 | O | HOH | W | 137 | 4.068 | 51.191 | 26.923 | 1.00 | 23.45 | O |
| ATOM | 4848 | O | HOH | W | 138 | 20.008 | 71.988 | 20.726 | 1.00 | 27.68 | O |
| ATOM | 4851 | O | HOH | W | 139 | 13.234 | 5.847 | 32.263 | 1.00 | 26.27 | O |
| ATOM | 4854 | O | HOH | W | 140 | 21.749 | 63.563 | 28.203 | 1.00 | 39.60 | O |
| ATOM | 4857 | O | HOH | W | 141 | −5.465 | 73.144 | 23.338 | 1.00 | 32.11 | O |
| ATOM | 4860 | O | HOH | W | 142 | 6.574 | 53.636 | 15.141 | 1.00 | 33.57 | O |
| ATOM | 4863 | O | HOH | W | 143 | −4.638 | 57.202 | 19.896 | 1.00 | 36.81 | O |
| ATOM | 4866 | O | HOH | W | 144 | 23.482 | 65.349 | 22.878 | 1.00 | 40.79 | O |
| ATOM | 4869 | O | HOH | W | 145 | 0.000 | 36.784 | 14.540 | 0.50 | 36.06 | O |
| ATOM | 4872 | O | HOH | W | 146 | 11.619 | 25.587 | 27.445 | 1.00 | 38.30 | O |
| ATOM | 4875 | O | HOH | W | 147 | 3.678 | 0.181 | 34.918 | 1.00 | 35.60 | O |
| ATOM | 4878 | O | HOH | W | 148 | −0.922 | 55.118 | 30.320 | 1.00 | 34.56 | O |
| ATOM | 4881 | O | HOH | W | 149 | 10.578 | 21.194 | 36.599 | 1.00 | 24.21 | O |
| ATOM | 4884 | O | HOH | W | 150 | 6.844 | 79.063 | 19.415 | 1.00 | 27.87 | O |
| ATOM | 4887 | O | HOH | W | 151 | 6.947 | 33.486 | 28.230 | 1.00 | 35.70 | O |
| ATOM | 4890 | O | HOH | W | 152 | 9.923 | 10.379 | 12.113 | 1.00 | 24.52 | O |
| ATOM | 4893 | O | HOH | W | 153 | 16.798 | 8.264 | 42.844 | 1.00 | 32.24 | O |
| ATOM | 4896 | O | HOH | W | 154 | 17.274 | 19.428 | 9.768 | 1.00 | 27.77 | O |
| ATOM | 4899 | O | HOH | W | 155 | 8.826 | 21.865 | 11.163 | 1.00 | 26.29 | O |
| ATOM | 4902 | O | HOH | W | 156 | 27.143 | 68.891 | 26.526 | 1.00 | 36.72 | O |
| ATOM | 4905 | O | HOH | W | 157 | 16.246 | 79.665 | 31.172 | 1.00 | 29.11 | O |
| ATOM | 4908 | O | HOH | W | 158 | 11.534 | 25.541 | 24.515 | 1.00 | 26.28 | O |
| ATOM | 4911 | O | HOH | W | 159 | 10.685 | 45.664 | 4.374 | 1.00 | 37.97 | O |
| ATOM | 4914 | O | HOH | W | 160 | −5.673 | 61.783 | 21.945 | 1.00 | 24.53 | O |
| ATOM | 4917 | O | HOH | W | 161 | 22.240 | 79.362 | 26.912 | 1.00 | 29.20 | O |
| ATOM | 4920 | O | HOH | W | 162 | 0.803 | 5.435 | 33.148 | 1.00 | 26.13 | O |
| ATOM | 4923 | O | HOH | W | 163 | 2.950 | 3.896 | 25.431 | 1.00 | 32.10 | O |
| ATOM | 4926 | O | HOH | W | 164 | 8.803 | 73.744 | 14.259 | 1.00 | 34.41 | O |
| ATOM | 4929 | O | HOH | W | 165 | 18.289 | 18.636 | 29.961 | 1.00 | 28.63 | O |
| ATOM | 4932 | O | HOH | W | 166 | −5.968 | 58.836 | 17.376 | 1.00 | 37.46 | O |
| ATOM | 4935 | O | HOH | W | 167 | 10.900 | 60.135 | 29.293 | 1.00 | 33.46 | O |
| ATOM | 4938 | O | HOH | W | 168 | 15.619 | 63.656 | 29.877 | 1.00 | 29.28 | O |
| ATOM | 4941 | O | HOH | W | 169 | 19.391 | 35.752 | 15.989 | 1.00 | 33.30 | O |
| ATOM | 4944 | O | HOH | W | 170 | 4.391 | 49.703 | 24.737 | 1.00 | 29.63 | O |
| ATOM | 4947 | O | HOH | W | 171 | −3.594 | 71.525 | 30.335 | 1.00 | 41.73 | O |
| ATOM | 4950 | O | HOH | W | 172 | 9.494 | 60.912 | 37.398 | 1.00 | 38.36 | O |
| ATOM | 4953 | O | HOH | W | 173 | −6.047 | 39.285 | 21.011 | 1.00 | 43.07 | O |
| ATOM | 4956 | O | HOH | W | 174 | 3.638 | 25.697 | 34.715 | 1.00 | 27.03 | O |
| ATOM | 4959 | O | HOH | W | 175 | 8.238 | 39.535 | 27.775 | 1.00 | 20.24 | O |
| ATOM | 4962 | O | HOH | W | 176 | 9.002 | 24.171 | 31.532 | 1.00 | 19.88 | O |
| ATOM | 4965 | O | HOH | W | 177 | −1.497 | 9.498 | 20.373 | 1.00 | 28.11 | O |
| ATOM | 4968 | O | HOH | W | 178 | 6.540 | 52.061 | 12.149 | 1.00 | 28.41 | O |
| ATOM | 4971 | O | HOH | W | 179 | 17.795 | 51.254 | 16.536 | 1.00 | 28.05 | O |
| ATOM | 4974 | O | HOH | W | 180 | 23.668 | 63.439 | 29.730 | 1.00 | 34.47 | O |
| ATOM | 4977 | O | HOH | W | 181 | 13.724 | 58.071 | 15.406 | 1.00 | 28.65 | O |
| ATOM | 4980 | O | HOH | W | 182 | 1.468 | 63.179 | 36.696 | 1.00 | 37.17 | O |
| ATOM | 4983 | O | HOH | W | 183 | −4.503 | 17.545 | 28.757 | 1.00 | 31.69 | O |
| ATOM | 4986 | O | HOH | W | 184 | 1.190 | 54.806 | 14.848 | 1.00 | 40.39 | O |
| ATOM | 4989 | O | HOH | W | 185 | −5.451 | 48.707 | 30.980 | 1.00 | 47.15 | O |
| ATOM | 4992 | O | HOH | W | 186 | 26.237 | 64.077 | 25.969 | 1.00 | 34.48 | O |
| ATOM | 4995 | O | HOH | W | 187 | 4.495 | 59.364 | 32.171 | 1.00 | 47.06 | O |

-continued

| | | | | | | | | | | | |
|---|---|---|---|---|---|---|---|---|---|---|---|
| ATOM | 4998 | O | HOH | W | 188 | 18.371 | 17.436 | 12.446 | 1.00 | 31.73 | O |
| ATOM | 5001 | O | HOH | W | 189 | −4.452 | 13.028 | 19.551 | 1.00 | 42.23 | O |
| ATOM | 5004 | O | HOH | W | 190 | 6.392 | 20.193 | 39.348 | 1.00 | 34.18 | O |
| ATOM | 5007 | O | HOH | W | 191 | 11.097 | 47.282 | 24.689 | 1.00 | 27.20 | O |
| ATOM | 5010 | O | HOH | W | 192 | 6.759 | 70.006 | 33.832 | 1.00 | 30.32 | O |
| ATOM | 5013 | O | HOH | W | 193 | −5.313 | 55.974 | 21.971 | 1.00 | 37.30 | O |
| ATOM | 5016 | O | HOH | W | 194 | 11.186 | 33.502 | 23.735 | 1.00 | 31.59 | O |
| ATOM | 5019 | O | HOH | W | 195 | 5.132 | 39.962 | 25.444 | 1.00 | 26.14 | O |
| ATOM | 5022 | O | HOH | W | 196 | 15.843 | 61.406 | 28.650 | 1.00 | 37.75 | O |
| ATOM | 5025 | O | HOH | W | 197 | 6.121 | 49.560 | 11.474 | 1.00 | 19.12 | O |
| ATOM | 5028 | O | HOH | W | 198 | −3.691 | 64.262 | 32.648 | 1.00 | 33.48 | O |
| ATOM | 5031 | O | HOH | W | 199 | 11.259 | 30.201 | 26.404 | 1.00 | 39.04 | O |
| ATOM | 5034 | O | HOH | W | 200 | 15.467 | 10.721 | 25.734 | 1.00 | 30.17 | O |
| ATOM | 5037 | O | HOH | W | 201 | 17.074 | 37.421 | 26.045 | 1.00 | 35.86 | O |
| ATOM | 5040 | O | HOH | W | 202 | 11.016 | 31.027 | 23.765 | 1.00 | 36.02 | O |
| ATOM | 5043 | O | HOH | W | 203 | −7.480 | 39.258 | 24.530 | 1.00 | 29.90 | O |
| ATOM | 5046 | O | HOH | W | 204 | 20.829 | 20.177 | 22.398 | 1.00 | 31.08 | O |
| ATOM | 5049 | O | HOH | W | 205 | 12.637 | 77.832 | 32.808 | 1.00 | 35.88 | O |
| ATOM | 5052 | O | HOH | W | 206 | 0.194 | 9.694 | 40.528 | 1.00 | 37.33 | O |
| ATOM | 5055 | O | HOH | W | 207 | −0.188 | 5.179 | 28.683 | 1.00 | 39.12 | O |
| ATOM | 5058 | O | HOH | W | 208 | 5.619 | 72.852 | 32.734 | 1.00 | 30.88 | O |
| ATOM | 5061 | O | HOH | W | 209 | 10.039 | 20.268 | 34.085 | 1.00 | 23.56 | O |
| ATOM | 5064 | O | HOH | W | 210 | 4.491 | 1.662 | 26.042 | 1.00 | 36.43 | O |
| ATOM | 5067 | O | HOH | W | 211 | 9.543 | 34.268 | 32.189 | 1.00 | 44.91 | O |
| ATOM | 5070 | O | HOH | W | 212 | 18.162 | 14.065 | 30.634 | 1.00 | 40.62 | O |
| ATOM | 5073 | O | HOH | W | 213 | 19.262 | 76.397 | 39.166 | 1.00 | 33.47 | O |
| ATOM | 5076 | O | HOH | W | 214 | 6.323 | 57.214 | 33.232 | 1.00 | 31.54 | O |
| ATOM | 5079 | O | HOH | W | 215 | 21.017 | 16.074 | 15.221 | 1.00 | 46.56 | O |
| ATOM | 5082 | O | HOH | W | 216 | 11.669 | 67.591 | 11.375 | 1.00 | 42.53 | O |
| ATOM | 5085 | O | HOH | W | 217 | 11.940 | 61.510 | 12.504 | 1.00 | 33.55 | O |
| ATOM | 5088 | O | HOH | W | 218 | 9.102 | 63.809 | 9.568 | 1.00 | 39.79 | O |
| ATOM | 5091 | O | HOH | W | 219 | 18.537 | 12.895 | 24.532 | 1.00 | 33.67 | O |
| ATOM | 5094 | O | HOH | W | 220 | −3.399 | 32.781 | 31.853 | 1.00 | 42.62 | O |
| ATOM | 5097 | O | HOH | W | 221 | 19.656 | 30.684 | 9.101 | 1.00 | 30.56 | O |
| ATOM | 5100 | O | HOH | W | 222 | −7.746 | 31.604 | 23.654 | 1.00 | 51.51 | O |
| ATOM | 5103 | O | HOH | W | 223 | 6.410 | 70.578 | 12.271 | 1.00 | 43.62 | O |
| ATOM | 5106 | O | HOH | W | 224 | 18.414 | 26.816 | 21.935 | 1.00 | 33.30 | O |
| ATOM | 5109 | O | HOH | W | 225 | −4.562 | 73.658 | 18.557 | 1.00 | 40.27 | O |
| ATOM | 5112 | O | HOH | W | 226 | 1.834 | 45.214 | 14.792 | 1.00 | 33.35 | O |
| ATOM | 5115 | O | HOH | W | 227 | −6.456 | 16.978 | 25.284 | 1.00 | 42.58 | O |
| ATOM | 5118 | O | HOH | W | 228 | 1.485 | 47.197 | 34.415 | 1.00 | 43.14 | O |
| ATOM | 5121 | O | HOH | W | 229 | 8.518 | 58.008 | 29.660 | 1.00 | 46.30 | O |
| ATOM | 5124 | O | HOH | W | 230 | 13.320 | 17.345 | 43.256 | 1.00 | 36.98 | O |
| ATOM | 5127 | O | HOH | W | 231 | −2.219 | 27.551 | 21.949 | 1.00 | 36.33 | O |
| ATOM | 5130 | O | HOH | W | 232 | 20.763 | 34.788 | 14.546 | 1.00 | 43.67 | O |
| ATOM | 5133 | O | HOH | W | 233 | 25.392 | 78.634 | 37.424 | 1.00 | 50.95 | O |
| ATOM | 5136 | O | HOH | W | 234 | 29.860 | 76.534 | 27.279 | 1.00 | 28.22 | O |
| ATOM | 5139 | O | HOH | W | 235 | 8.669 | 29.399 | 11.804 | 1.00 | 41.52 | O |
| ATOM | 5142 | O | HOH | W | 236 | 18.163 | 30.488 | 20.723 | 1.00 | 54.55 | O |
| ATOM | 5145 | O | HOH | W | 237 | 26.581 | 79.924 | 33.310 | 1.00 | 41.69 | O |
| ATOM | 5148 | O | HOH | W | 238 | −7.320 | 17.258 | 21.238 | 1.00 | 34.51 | O |
| ATOM | 5151 | O | HOH | W | 239 | 15.141 | 41.048 | 27.454 | 1.00 | 28.78 | O |
| ATOM | 5154 | O | HOH | W | 240 | 15.351 | 24.118 | 24.643 | 1.00 | 36.57 | O |
| ATOM | 5157 | O | HOH | W | 241 | 10.464 | 50.247 | 25.346 | 1.00 | 40.45 | O |
| ATOM | 5160 | O | HOH | W | 242 | −7.555 | 20.139 | 21.792 | 1.00 | 33.87 | O |
| ATOM | 5163 | O | HOH | W | 243 | −3.365 | 10.200 | 32.114 | 1.00 | 37.80 | O |
| ATOM | 5166 | O | HOH | W | 244 | 7.111 | 14.218 | 46.259 | 1.00 | 37.31 | O |
| ATOM | 5169 | O | HOH | W | 245 | −0.497 | 7.203 | 22.295 | 1.00 | 35.75 | O |
| ATOM | 5172 | O | HOH | W | 246 | 5.000 | 4.810 | 39.815 | 1.00 | 26.98 | O |
| ATOM | 5175 | O | HOH | W | 247 | 7.136 | 49.342 | 8.646 | 1.00 | 26.65 | O |
| ATOM | 5178 | O | HOH | W | 248 | −5.792 | 22.456 | 25.116 | 1.00 | 32.36 | O |
| ATOM | 5181 | O | HOH | W | 249 | 16.203 | 12.016 | 16.320 | 1.00 | 31.39 | O |
| ATOM | 5184 | O | HOH | W | 250 | −4.880 | 16.340 | 30.695 | 1.00 | 42.96 | O |
| ATOM | 5187 | O | HOH | W | 251 | 5.949 | 42.046 | 22.980 | 1.00 | 36.30 | O |
| ATOM | 5190 | O | HOH | W | 252 | 0.573 | 29.971 | 34.228 | 1.00 | 47.16 | O |
| ATOM | 5193 | O | HOH | W | 253 | −0.987 | 29.373 | 20.834 | 1.00 | 36.44 | O |
| ATOM | 5196 | O | HOH | W | 254 | 19.444 | 19.199 | 18.718 | 1.00 | 37.77 | O |
| ATOM | 5199 | O | HOH | W | 255 | 24.736 | 80.148 | 25.329 | 1.00 | 39.85 | O |
| ATOM | 5202 | O | HOH | W | 256 | 11.691 | 61.111 | 31.739 | 1.00 | 32.31 | O |
| ATOM | 5205 | O | HOH | W | 257 | 2.864 | 3.875 | 17.924 | 1.00 | 38.15 | O |
| ATOM | 5208 | O | HOH | W | 258 | 14.511 | 16.067 | 9.859 | 1.00 | 49.07 | O |
| ATOM | 5211 | O | HOH | W | 259 | 6.041 | 15.719 | 44.019 | 1.00 | 38.12 | O |
| ATOM | 5214 | O | HOH | W | 260 | −3.500 | 11.317 | 28.973 | 1.00 | 31.78 | O |
| ATOM | 5217 | O | HOH | W | 261 | 20.113 | 18.209 | 14.238 | 1.00 | 39.21 | O |
| ATOM | 5220 | O | HOH | W | 262 | 12.901 | 53.061 | 26.970 | 1.00 | 43.64 | O |
| ATOM | 5223 | O | HOH | W | 263 | 13.748 | 78.590 | 19.665 | 1.00 | 45.08 | O |
| ATOM | 5226 | O | HOH | W | 264 | −5.789 | 32.286 | 21.059 | 1.00 | 36.44 | O |
| ATOM | 5229 | O | HOH | W | 265 | −2.186 | 52.836 | 16.940 | 1.00 | 30.43 | O |
| ATOM | 5232 | O | HOH | W | 266 | 7.623 | 9.946 | 10.664 | 1.00 | 39.43 | O |
| ATOM | 5235 | O | HOH | W | 267 | 12.879 | 65.624 | 39.396 | 1.00 | 46.93 | O |

-continued

| | | | | | | | | | | | |
|---|---|---|---|---|---|---|---|---|---|---|---|
| ATOM | 5238 | O | HOH | W | 268 | 3.762 | 3.939 | 41.903 | 1.00 | 46.14 | O |
| ATOM | 5241 | O | HOH | W | 269 | 17.828 | 31.637 | 16.048 | 1.00 | 47.28 | O |
| ATOM | 5244 | O | HOH | W | 270 | 3.542 | 70.692 | 35.072 | 1.00 | 36.22 | O |
| ATOM | 5247 | O | HOH | W | 271 | 9.189 | 65.423 | 36.649 | 1.00 | 36.55 | O |
| ATOM | 5250 | O | HOH | W | 272 | 18.089 | 19.294 | 34.947 | 1.00 | 32.14 | O |
| ATOM | 5253 | O | HOH | W | 273 | 12.998 | 3.363 | 21.479 | 1.00 | 27.18 | O |
| ATOM | 5256 | O | HOH | W | 274 | 0.719 | 28.723 | 15.348 | 1.00 | 38.43 | O |
| ATOM | 5259 | O | HOH | W | 275 | 15.569 | 18.739 | 42.772 | 1.00 | 42.03 | O |
| ATOM | 5262 | O | HOH | W | 276 | −3.457 | 55.073 | 30.607 | 1.00 | 45.58 | O |
| ATOM | 5265 | O | HOH | W | 277 | 5.522 | 31.715 | 14.294 | 1.00 | 32.09 | O |
| ATOM | 5268 | O | HOH | W | 278 | −2.657 | 35.531 | 31.044 | 1.00 | 34.38 | O |
| ATOM | 5271 | O | HOH | W | 279 | 12.105 | 63.958 | 11.282 | 1.00 | 37.18 | O |
| ATOM | 5274 | O | HOH | W | 280 | 18.747 | 47.105 | 16.449 | 1.00 | 34.97 | O |
| ATOM | 5277 | O | HOH | W | 281 | 5.977 | 55.901 | 30.172 | 1.00 | 38.23 | O |
| ATOM | 5280 | O | HOH | W | 282 | 25.844 | 78.740 | 23.059 | 1.00 | 40.40 | O |
| ATOM | 5283 | O | HOH | W | 283 | 15.278 | 9.678 | 17.509 | 1.00 | 38.76 | O |
| ATOM | 5286 | O | HOH | W | 284 | 21.498 | 72.061 | 18.923 | 1.00 | 37.11 | O |
| ATOM | 5289 | O | HOH | W | 285 | 18.724 | 50.881 | 14.447 | 1.00 | 44.73 | O |
| ATOM | 5292 | O | HOH | W | 286 | −11.218 | 48.480 | 24.128 | 1.00 | 42.03 | O |
| ATOM | 5295 | O | HOH | W | 287 | −1.136 | 28.910 | 34.251 | 1.00 | 38.99 | O |
| ATOM | 5298 | O | HOH | W | 288 | 11.120 | 58.787 | 33.554 | 1.00 | 34.94 | O |
| ATOM | 5301 | O | HOH | W | 289 | −10.583 | 56.470 | 31.910 | 1.00 | 43.90 | O |
| ATOM | 5304 | O | HOH | W | 290 | 2.255 | 4.906 | 22.735 | 1.00 | 33.76 | O |
| ATOM | 5307 | O | HOH | W | 291 | −4.463 | 53.493 | 27.131 | 1.00 | 37.65 | O |
| ATOM | 5310 | O | HOH | W | 292 | 26.026 | 81.949 | 31.499 | 1.00 | 45.48 | O |
| ATOM | 5313 | O | HOH | W | 293 | 7.442 | 76.447 | 16.369 | 1.00 | 41.23 | O |
| ATOM | 5316 | O | HOH | W | 294 | −3.686 | 27.401 | 26.198 | 1.00 | 35.10 | O |
| ATOM | 5319 | O | HOH | W | 295 | 21.577 | 22.219 | 15.316 | 1.00 | 41.70 | O |
| ATOM | 5322 | O | HOH | W | 296 | −2.025 | 13.772 | 19.436 | 1.00 | 19.84 | O |
| ATOM | 5325 | O | HOH | W | 297 | 4.552 | 56.197 | 33.298 | 1.00 | 45.25 | O |
| ATOM | 5328 | O | HOH | W | 298 | 14.647 | 47.199 | 23.522 | 1.00 | 48.24 | O |
| ATOM | 5331 | O | HOH | W | 299 | 15.390 | 62.007 | 13.636 | 1.00 | 42.37 | O |
| ATOM | 5334 | O | HOH | W | 300 | 10.428 | 26.350 | 31.879 | 1.00 | 42.60 | O |
| ATOM | 5337 | O | HOH | W | 301 | 14.718 | 5.189 | 45.549 | 1.00 | 45.54 | O |
| ATOM | 5340 | O | HOH | W | 302 | 8.946 | 22.508 | 33.873 | 1.00 | 40.76 | O |
| ATOM | 5343 | O | HOH | W | 303 | 16.384 | 27.295 | 24.851 | 1.00 | 41.97 | O |
| ATOM | 5346 | O | HOH | W | 304 | 3.772 | 7.760 | 47.728 | 1.00 | 41.52 | O |
| ATOM | 5349 | O | HOH | W | 305 | 10.504 | 78.455 | 18.240 | 1.00 | 40.71 | O |
| ATOM | 5352 | O | HOH | W | 306 | 1.711 | 18.621 | 39.993 | 1.00 | 46.98 | O |
| ATOM | 5355 | O | HOH | W | 307 | −2.232 | 37.318 | 29.555 | 1.00 | 52.79 | O |
| ATOM | 5358 | O | HOH | W | 308 | 17.695 | 84.082 | 24.846 | 1.00 | 35.15 | O |
| ATOM | 5361 | O | HOH | W | 309 | 9.444 | 81.936 | 21.257 | 1.00 | 43.21 | O |
| ATOM | 5364 | O | HOH | W | 310 | 18.962 | 14.586 | 41.000 | 1.00 | 33.95 | O |
| ATOM | 5367 | O | HOH | W | 311 | 17.224 | 59.864 | 27.056 | 1.00 | 44.86 | O |
| ATOM | 5370 | O | HOH | W | 312 | 8.196 | 32.729 | 30.403 | 1.00 | 46.43 | O |
| ATOM | 5373 | O | HOH | W | 313 | 6.716 | 21.920 | 35.622 | 1.00 | 40.07 | O |
| ATOM | 5376 | O | HOH | W | 314 | −8.178 | 51.601 | 21.128 | 1.00 | 26.96 | O |
| ATOM | 5379 | O | HOH | W | 315 | 21.626 | 23.241 | 10.371 | 1.00 | 46.41 | O |
| ATOM | 5382 | O | HOH | W | 316 | 1.992 | 8.600 | 16.619 | 1.00 | 47.59 | O |
| ATOM | 5385 | O | HOH | W | 317 | −9.110 | 62.976 | 22.532 | 1.00 | 41.04 | O |
| ATOM | 5388 | O | HOH | W | 318 | 10.186 | 78.289 | 31.815 | 1.00 | 35.64 | O |
| ATOM | 5391 | O | HOH | W | 319 | 7.452 | 56.107 | 15.200 | 1.00 | 47.41 | O |
| ATOM | 5394 | O | HOH | W | 320 | 16.416 | 21.307 | 39.421 | 1.00 | 47.41 | O |
| ATOM | 5397 | O | HOH | W | 321 | −0.758 | 31.033 | 19.795 | 1.00 | 50.41 | O |
| ATOM | 5400 | O | HOH | W | 322 | −0.518 | 16.247 | 39.461 | 1.00 | 34.97 | O |
| ATOM | 5403 | O | HOH | W | 323 | −1.833 | 51.374 | 29.019 | 1.00 | 40.40 | O |
| ATOM | 5406 | O | HOH | W | 324 | 15.835 | 54.684 | 14.540 | 1.00 | 41.84 | O |
| ATOM | 5409 | O | HOH | W | 325 | 2.870 | 15.482 | 46.756 | 1.00 | 35.83 | O |
| ATOM | 5412 | O | HOH | W | 326 | −4.606 | 53.769 | 17.686 | 1.00 | 34.90 | O |
| ATOM | 5415 | O | HOH | W | 327 | 16.007 | 35.046 | 26.985 | 1.00 | 43.92 | O |
| ATOM | 5418 | O | HOH | W | 328 | 16.481 | 19.803 | 36.607 | 1.00 | 33.16 | O |
| ATOM | 5421 | O | HOH | W | 329 | −3.099 | 12.154 | 36.959 | 1.00 | 43.78 | O |
| ATOM | 5424 | O | HOH | W | 330 | 8.836 | 66.515 | 9.394 | 1.00 | 38.90 | O |
| ATOM | 5427 | O | HOH | W | 331 | −5.196 | 55.555 | 14.903 | 1.00 | 41.11 | O |
| ATOM | 5430 | O | HOH | W | 332 | 3.673 | 20.670 | 43.076 | 1.00 | 49.53 | O |
| ATOM | 5433 | O | HOH | W | 333 | 14.210 | 57.558 | 29.654 | 1.00 | 38.52 | O |
| ATOM | 5436 | O | HOH | W | 334 | −4.440 | 26.268 | 30.382 | 1.00 | 41.01 | O |
| ATOM | 5439 | O | HOH | W | 335 | 0.303 | 5.327 | 26.203 | 1.00 | 40.13 | O |
| ATOM | 5442 | O | HOH | W | 336 | 23.927 | 25.223 | 17.079 | 1.00 | 49.07 | O |
| ATOM | 5445 | O | HOH | W | 337 | 18.154 | 2.532 | 36.875 | 1.00 | 48.40 | O |
| ATOM | 5448 | O | HOH | W | 338 | −1.578 | 9.589 | 38.800 | 1.00 | 45.45 | O |
| ATOM | 5451 | O | HOH | W | 339 | 10.755 | 44.148 | 30.134 | 1.00 | 44.26 | O |
| ATOM | 5454 | O | HOH | W | 340 | −5.779 | 19.722 | 29.027 | 1.00 | 44.44 | O |
| ATOM | 5457 | O | HOH | W | 341 | 2.605 | 2.158 | 29.438 | 1.00 | 45.14 | O |
| ATOM | 5460 | O | HOH | W | 342 | 13.174 | 27.958 | 25.103 | 1.00 | 47.67 | O |
| ATOM | 5463 | O | HOH | W | 343 | 2.644 | 4.022 | 32.067 | 1.00 | 44.27 | O |
| ATOM | 5466 | O | HOH | W | 344 | −6.107 | 51.428 | 30.348 | 1.00 | 37.84 | O |
| ATOM | 5469 | O | HOH | W | 345 | 8.444 | 46.539 | 25.407 | 1.00 | 27.68 | O |
| ATOM | 5472 | O | HOH | W | 346 | 0.216 | 9.594 | 15.345 | 0.50 | 19.30 | O |
| ATOM | 5475 | O | HOH | W | 347 | 7.419 | 52.115 | 28.750 | 1.00 | 43.60 | O |

-continued

| | | | | | | | | | | | |
|---|---|---|---|---|---|---|---|---|---|---|---|
| ATOM | 5478 | O | HOH | W | 348 | 1.084 | 74.672 | 17.236 | 1.00 | 43.61 | O |
| ATOM | 5481 | O | HOH | W | 349 | 9.086 | 56.763 | 13.070 | 1.00 | 32.67 | O |
| ATOM | 5484 | O | HOH | W | 350 | 10.168 | 36.128 | 33.057 | 1.00 | 46.83 | O |
| ATOM | 5487 | O | HOH | W | 351 | 6.222 | 30.908 | 12.092 | 1.00 | 40.82 | O |
| ATOM | 5490 | O | HOH | W | 352 | 18.711 | 54.082 | 21.232 | 1.00 | 40.98 | O |
| ATOM | 5493 | O | HOH | W | 353 | 7.045 | 24.081 | 34.543 | 1.00 | 40.00 | O |
| ATOM | 5496 | O | HOH | W | 354 | 19.551 | 36.122 | 18.141 | 1.00 | 39.80 | O |
| ATOM | 5499 | O | HOH | W | 355 | 8.323 | 35.863 | 26.985 | 1.00 | 42.79 | O |
| ATOM | 5502 | O | HOH | W | 356 | 15.768 | 76.605 | 17.198 | 1.00 | 41.62 | O |
| ATOM | 5505 | O | HOH | W | 357 | 7.713 | 14.211 | 11.015 | 1.00 | 38.48 | O |
| ATOM | 5508 | O | HOH | W | 358 | −0.007 | 19.970 | 39.379 | 1.00 | 40.86 | O |
| ATOM | 5511 | O | HOH | W | 359 | 4.894 | 10.472 | 11.299 | 1.00 | 43.58 | O |
| ATOM | 5514 | O | HOH | W | 360 | −7.013 | 19.983 | 24.789 | 1.00 | 41.53 | O |
| ATOM | 5517 | O | HOH | W | 361 | 11.882 | 69.046 | 38.268 | 1.00 | 37.09 | O |
| ATOM | 5520 | O | HOH | W | 362 | 0.847 | 38.127 | 31.394 | 1.00 | 44.71 | O |
| ATOM | 5523 | O | HOH | W | 363 | 12.543 | 77.215 | 35.944 | 1.00 | 46.47 | O |
| ATOM | 5526 | O | HOH | W | 364 | −0.275 | 5.281 | 20.527 | 1.00 | 49.03 | O |
| ATOM | 5529 | O | HOH | W | 365 | 3.852 | 47.193 | 33.824 | 1.00 | 45.52 | O |
| ATOM | 5532 | O | HOH | W | 366 | 5.374 | 28.678 | 10.725 | 1.00 | 55.58 | O |
| ATOM | 5535 | O | HOH | W | 367 | 7.148 | 2.729 | 15.160 | 1.00 | 47.51 | O |
| ATOM | 5538 | O | HOH | W | 368 | 5.850 | −0.340 | 39.838 | 1.00 | 45.55 | O |
| ATOM | 5541 | O | HOH | W | 369 | 20.182 | 18.359 | 34.879 | 1.00 | 43.84 | O |
| ATOM | 5544 | O | HOH | W | 370 | 9.912 | 3.925 | 45.795 | 1.00 | 45.61 | O |
| ATOM | 5547 | O | HOH | W | 371 | −8.844 | 50.990 | 27.544 | 1.00 | 43.80 | O |
| ATOM | 5550 | O | HOH | W | 372 | −8.869 | 42.344 | 32.264 | 1.00 | 36.72 | O |
| ATOM | 5553 | O | HOH | W | 373 | 15.800 | 13.628 | 27.582 | 1.00 | 41.13 | O |
| ATOM | 5556 | O | HOH | W | 374 | 18.901 | 14.505 | 33.218 | 1.00 | 41.62 | O |
| ATOM | 5559 | O | HOH | W | 375 | 1.853 | 79.517 | 18.137 | 1.00 | 46.62 | O |
| ATOM | 5562 | O | HOH | W | 376 | 16.236 | 86.830 | 33.769 | 1.00 | 41.68 | O |
| ATOM | 5565 | O | HOH | W | 377 | 4.608 | 27.482 | 37.133 | 1.00 | 45.58 | O |
| ATOM | 5568 | O | HOH | W | 378 | −3.757 | 32.642 | 19.402 | 1.00 | 46.75 | O |
| ATOM | 5571 | O | HOH | W | 379 | 14.471 | 32.910 | 26.576 | 1.00 | 53.42 | O |
| ATOM | 5574 | O | HOH | W | 380 | −1.037 | 46.322 | 34.315 | 1.00 | 47.01 | O |
| ATOM | 5577 | O | HOH | W | 381 | 1.793 | 32.853 | 32.560 | 1.00 | 42.76 | O |
| ATOM | 5580 | O | HOH | W | 382 | −2.051 | 73.756 | 29.908 | 1.00 | 44.88 | O |
| ATOM | 5583 | O | HOH | W | 383 | 14.083 | 81.363 | 21.948 | 1.00 | 41.19 | O |
| ATOM | 5586 | O | HOH | W | 384 | 17.211 | 49.125 | 17.870 | 1.00 | 49.94 | O |
| ATOM | 5589 | O | HOH | W | 385 | 6.061 | 38.796 | 30.019 | 1.00 | 37.05 | O |
| ATOM | 5592 | O | HOH | W | 386 | 3.701 | 38.468 | 32.113 | 1.00 | 49.50 | O |
| ATOM | 5595 | O | HOH | W | 387 | 11.997 | 45.720 | 26.358 | 1.00 | 43.58 | O |
| ATOM | 5598 | O | HOH | W | 388 | 3.891 | 33.001 | 30.507 | 1.00 | 47.99 | O |
| ATOM | 5601 | O | HOH | W | 389 | 14.616 | 70.545 | 40.365 | 1.00 | 45.64 | O |
| ATOM | 5604 | O | HOH | W | 390 | 14.574 | 22.055 | 41.425 | 1.00 | 52.12 | O |
| ATOM | 5607 | O | HOH | W | 391 | 4.346 | 13.355 | 48.148 | 1.00 | 52.19 | O |
| ATOM | 5610 | O | HOH | W | 392 | 27.169 | 76.192 | 24.082 | 1.00 | 39.17 | O |
| ATOM | 5613 | O | HOH | W | 393 | 9.571 | 38.797 | 27.006 | 1.00 | 32.47 | O |
| ATOM | 5616 | O | HOH | W | 394 | 8.508 | 43.203 | 25.738 | 1.00 | 39.98 | O |
| ATOM | 5619 | O | HOH | W | 395 | 19.082 | 54.659 | 19.221 | 1.00 | 40.35 | O |
| ATOM | 5622 | O | HOH | W | 396 | 20.830 | 42.893 | 13.607 | 1.00 | 39.95 | O |
| ATOM | 5625 | O | HOH | W | 397 | 5.319 | 20.544 | 43.801 | 1.00 | 49.19 | O |
| ATOM | 5628 | O | HOH | W | 398 | −0.686 | 77.185 | 18.682 | 1.00 | 48.70 | O |
| ATOM | 5631 | O | HOH | W | 399 | 13.037 | 80.375 | 31.401 | 1.00 | 34.60 | O |
| ATOM | 5634 | O | HOH | W | 400 | 9.194 | 62.157 | 37.713 | 1.00 | 52.16 | O |
| ATOM | 5637 | O | HOH | W | 401 | −7.980 | 17.818 | 43.735 | 1.00 | 46.19 | O |
| ATOM | 5640 | O | HOH | W | 402 | 23.280 | 74.562 | 20.442 | 1.00 | 52.69 | O |
| ATOM | 5643 | O | HOH | W | 403 | 14.240 | 61.150 | 32.356 | 1.00 | 47.70 | O |
| ATOM | 5646 | O | HOH | W | 404 | −0.769 | 78.275 | 30.180 | 1.00 | 50.98 | O |
| ATOM | 5649 | O | HOH | W | 405 | −5.626 | 22.219 | 29.113 | 1.00 | 46.52 | O |
| ATOM | 5652 | O | HOH | W | 406 | 15.541 | 64.739 | 13.428 | 1.00 | 46.05 | O |
| ATOM | 5655 | O | HOH | W | 407 | 7.527 | 37.758 | 26.580 | 1.00 | 25.51 | O |
| ATOM | 5658 | O | HOH | W | 408 | 24.624 | 74.521 | 22.385 | 1.00 | 38.85 | O |
| ATOM | 5661 | O | HOH | W | 409 | 7.728 | 50.654 | 28.168 | 1.00 | 47.15 | O |
| ATOM | 5664 | O | HOH | W | 410 | 15.960 | 6.626 | 32.420 | 1.00 | 43.54 | O |
| ATOM | 5667 | O | HOH | W | 411 | −7.813 | 53.566 | 25.122 | 1.00 | 52.09 | O |
| ATOM | 5670 | O | HOH | W | 412 | 7.890 | 45.778 | 27.572 | 1.00 | 30.54 | O |
| ATOM | 5673 | O | HOH | W | 413 | 21.095 | 43.371 | 18.127 | 1.00 | 38.67 | O |
| ATOM | 5676 | O | HOH | W | 414 | 12.440 | 22.432 | 33.478 | 1.00 | 44.89 | O |

REFERENCES

Albericio, F., Annis, I., Royo, M., Barany, G. 2000. In Chan, W. C., White, P. D. (Eds), Fmoc solid phase synthesis. A practical approach, Oxford University Press, NY, pp. 81-91.

Alter, S. C., Kramps, J. A., Janoff, A. & Schwartz, L. B. (1990) Interactions of human mast cell tryptase with biological protease inhibitors. Arch. Biochem. Biophys. 276, 26-31.

Atkins, P. C., Schwartz, L. B., Adkinson, N. F., von-Allmen, C., Valenzano, M. & Zweiman, B. (1990) In vivo antigen-induced cutaneous mediator release: simultaneous comparisons of histamine, tryptase, and prostaglandin D2 release and the effect of oral corticosteroid administration. J. Allergy Clin. Immunol. 86, 360-70.

Auerswald, E. A., Morenweiser, R., Sommerhoff, C. P. et al. (1994) Recombinant leech derived tryptase inhibitor: construction, production, protein chemical characterization and inhibition of HIV-1 replication. Biological Chemistn Hoppe-Seyler 375, 695-703.

R. Baggio, P. Burgstaller, S. P. Hale, A. R. Putney, M. Lane, D. Lipovsek, M. C. Wright, R. W. Roberts, R. Liu, J. W. Szostak, R. W. Wagner, Identification of epitope-like consensus motifs using mRNA display, J. Mol. Recognit. 15 (2002) 126-134.

Brockow K, Akin C, Huber M, Scott L M, Schwartz L B, Metcalfe D D. (2002) Levels of mast-cell growth factors in plasma and in suction skin blister fluid in adults with mastocytosis: correlation with dermal mast-cell numbers and mast-cell tryptase. J Allergy Clin Immunol. January; 109 (1):82-8.

Broide, D. H., Gleich, G. J., Cuomo, A. J., Coburn, D. A., Federman, E. C., Schwartz, L. B. & Wasserman, S. I. (1991) Evidence of ongoing mast cell and eosinophil degranulation in symptomatic asthma airway. J. Allergy Clin. Immunol. 88, 637-48.

Castells, M. & Schwartz, L. B. (1988) Tryptase levels in nasal-lavage fluid as an indicator of the immediate allergic response. J. Allergy Clin. Immunol. 82, 348-55.

Caughey, G. H., Leidig, F., Viro, N. F, Nadel, J. A (1989) Substance P and vasoactive intestinal peptide degradation by mast cell tryptase and chymase. J Pharmacol Exp Ther. 1988 January; 244(1):133-7.

S. Chakraborty, U. Haldar, A. K. Bera, A. K. Pal, S. Bhattacharya, S. Ghosh, B. P. Mukhopadhyay, A. Banerjee, Recognition and stabilization of a unique CPRI-structural motif in cucurbitaceae family trypsin inhibitor peptides: molecular dynamics based homology modeling using the X-ray structure of MCTI-II, J. Biomol. Struct. Dyn. 18 (2001) 569-577.

Chan, W. C., White, P. D. In Chan, W. C., White, P. D. (Eds), Fmoc solid phase synthesis. A practical approach, Oxford University Press, NY, 2000, p. 63.

Chase, T. & Shaw, E. (1970) in Meth. Enzymol. Vol. XIX (Perlman et al., eds), pp. 20-27.

X. M. Chen, Y. W. Qian, C. W. Chi, K. D. Gan, M. F. Zhang, C. Q. Chen, Chemical synthesis, molecular cloning, and expression of the gene coding for the *Trichosanthes* trypsin inhibitor—a squash family inhibitor, J. Biochem. (Tokyo) 112 (1992) 45-51.

L. Chiche, C. Gaboriaud, A. Heitz, J. P. Momon, B. Castro, P. A. Kollman, Use of restrained molecular dynamics in water to determine three-dimensional protein structure: prediction of the three-dimensional structure of *Ecballium elaterium* trypsin inhibitor II, Proteins 6 (1989) 405-417.

Christmann, A., Walter, K., Wentzel, A., Kratzner, R., Kolmar H. (1999) The cystine knot of a squash-type protease inhibitor as a structural scaffold for *Escherichia coli* cell surface display of conformationally constrained peptides. Protein Eng 12(9):797-806.

D. J. Craik, N. L. Daly, C. Waine, The cystine knot motif in toxins and implications for drug design, Toxicon 39 (2001) 43-60.

Craik, D. J., Simonsen, S., Daly, N. L. (2002) The cyclotides: novel macrocyclic peptides as scaffolds in drug design. Curr Opin Drug Discov Devel. March; 5(2):251-60.

Cregar L., Elrod K. C., Putnam D. et al. (1999) Neutrophil myeloperoxidase is a potent and selective inhibitor of mast cell tryptase. Archives of Biochemistry and Biophysics 366, 125-130.

Cox, S. W. & Eley, B. M. (1989) Tryptase-like activity in crevicular fluid from gingivitis and periodontitis patients. J. Period. Res. 24, 41-4.

Daly, N. L., Love, S., Alewood, P. F., and Craik, D. J. (1999) Chemical synthesis and folding pathways of large cyclic polypeptides: studies of the cystine knot polypeptide kalata B1. Biochemistry 38, 10606-10614

N. L. Daly, D. J. Craik, Acyclic permutants of naturally occurring cyclic proteins characterization of cystine knot and beta-sheet formation in the macrocyclic polypeptide kalata B1, J. Biol. Chem. 275 (2000) 19068-19075.

DeLano, W. L. (2002). "The PyMOL Molecular Graphics System." on World Wide Web http://www.pymol.org. DeLano Scientific, San Carlos, Calif., USA.

S. M. Deyev, R. Waibel, E. N. Lebedenko, A. P. Schubiger, A. Plückthun, Design of multivalent complexes using the barnase barstar module, Nat. Biotechnol. 21 (2003) 1486-1492.

Di Marco, S., Priestle, J. P. (1997) Structure of the complex of leech-derived tryptase inhibitor (LDTI) with trypsin and modeling of the LDTI-tryptase system. Structure. 1 November 15; 5(11):1465-74.

H. Döbeli, H. Andres, N. Breyer, N. Draeger, D. Sizmann, M. T. Zuber, B. Weinert, B. Wipf, Recombinant fusion proteins for the industrial production of disulfide bridge containing peptides: purification, oxidation without concatamer formation, and selective cleavage, Protein Expr. Purif. 12 (1998) 404-414.

Elrod, K. C., Moore, W. R., Abraham, W. M. et al. (1997) Lactoferrin, a potent tryptase inhibitor, abolishes late-phase airway responses in allergic sheep. American Journal of and Critical Care Medicine 156, 375-381.

W. D. Fairlie, A. D. Uboldi, D. P. De Souza, G. J. Hemmings, N. A. Nicola, M. Baca, A fusion protein system for the recombinant production of short disulfide-containing peptides, Protein Expr. Purif. 26 (2002) 171-178.

A. R. Fersht, The sixth Datta Lecture. Protein folding and stability: the pathway of folding of barnase, FEBS Lett. 325 (1993) 5-16.

Franconi, G. M., Graf, P. D., Lazarus, S. C., Nadel, J. A. & Caughey, G. H. (1989) Mast cell tryptase and chymase reverse airway smooth muscle relaxation induced by vasoactive intestinal peptide in the ferret. J. Pharmacol. Exp. Ther. 248, 947-51.

Gelly, J. C., Gracy, J., Kaas, Q., Le-Nguyen, D., Heitz, A., Chiche, L. (2004) The KNOTTIN website and database: a new information system dedicated to the knottin scaffold. Nucleic Acids Res. January 1; 32 Database issue:D156-9.

Guex, N. and M. C. Peitsch (1997). "SWISS-MODEL and the Swiss-PdbViewer: an environment for comparative protein modeling." Electrophoresis 18(15): 2714-23.

Gustafson, K. R., Sowder, R. C., II, Henderson, L. E., Parsons, I. C., Kashman, Y., Cardellina II, J. H., McMahon, J. B., Buckheit, R. W., Jr., Pannell, L. K., and Boyd, M. R. (1994) J. Am. Chem. Soc. 116, 9337-9338

Gustafson, K. R., Walton, L. K., Sowder, R. C. I., Johnson, D. G., Pannell, L. K., Cardellina, J. H. I., and Boyd, M. R. (2000) New circulin macrocyclic polypeptides from *Chassalia parvifolia* J. Nat. Prod. 63, 176-178

N. Hamato, T. Koshiba, T. N. Pham, Y. Tatsumi, D. Nakamura, R. Takano, K. Hayashi, Y. M. Hong, S. Hara, Trypsin and elastase inhibitors from bitter gourd (*Momordica charantia* LINN.) seeds: purification, amino acid sequences, and inhibitory activities of four new inhibitors, J. Biochem. (Tokyo) 117 (1995) 432-437.

R. W. Hartley, D. L. Rogerson, Jr., Production and purification of the extracellular ribonuclease of *Bacillus amyloliquefaciens* (barnase) and its intracellular inhibitor (barstar). I. Barnase, Prep. Biochem. 2 (1972) 229-242.

Hartley, R. W. (1988) Barnase and barstar. Expression of its cloned inhibitor permits expression of a cloned ribonuclease. J Mol. Biol. August 20; 202(4):913-5.

He, S H (2004) Key role of mast cells and their major secretory products in inflammatory bowel disease. World J. Gastroenterol. 2004 Feb. 1; 10(3):309-18.

Hernandez, J. F., Gagnon, J., Chiche, L., Nguyen, T. M., Andrieu, J. P., Heitz, A., Trinh Hong, T., Pham, T. T., and Le Nguyen, D. (2000) Squash trypsin inhibitors from *Momordica cochinchinensis* exhibit an atypical macrocyclic structure. Biochemistry 39, 5722-30

Hood, L. IMMUNOLOGY 2nd ed., Benjamin-Cummings 1984.

Howarth, P H (1995) The cellular basis for allergic rhinitis. Allergy. 1995; 50(23 Suppl):6-10.

Isaacs, N. W. (1995) Cystine knots. Curr. Biol. 5, 391-395

Jones, T. A., J. Y. Zou, et al. (1991). "Improved methods for building protein models in electron density maps and the location of errors in these models." Acta Crystallographica Section a Foundations of Crystallography 2(1): 110-19.

M. Jucovic, R. W. Hartley, In vivo system for the detection of low level activity barnase mutants, Protein Eng. 8 (1995) 497-499.

Juliusson, S., Holmberg, K., Baumgarten, C. R., Olsson, M., Enander, I. & Pipkorn, U. (1991) Tryptase in nasal lavage fluid after local allergen challenge. Relationship to histamine levels and TAME-esterase activity. Allergy 46, 459-65.

Kabsch, W. (1993). "Automatic processing of rotation diffraction data from crystals of initially unknown symmetry and cell constants." Journal of Applied Crystallography 26(6): 795-800.

Kantardjieff, K. A. and B. Rupp (2003). "Matthews coefficient probabilities: Improved estimates for unit cell contents of proteins, DNA, and protein-nucleic acid complex crystals." Protein Sci 12(9): 1865-71.

Kissinger, C. R., D. K. Gehlhaar, et al. (1999). "Rapid automated molecular replacement by evolutionary search." Acta Crystallogr D Biol Crystallogr 55 (Pt 2): 484-91.

Kohno, T., Kim, J. I., Kobayashi, K., Kodera, Y., Maeda, T., and Sato, K. (1995) Three-dimensional structure in solution of the calcium channel blocker omega-conotoxin MVIIA. Biochemistry. August 15; 34(32):10256-65.

S. Kojima, K. Miyoshi, K. Miura, Synthesis of a squash-type protease inhibitor by gene engineering and effects of replacements of conserved hydrophobic amino acid residues on its inhibitory activity, Protein Eng. 9 (1996) 1241-1246.

Le-Nguyen, D., Heitz, A., Chiche, L., Castro, B., Boigegrain, R. A., Favel, A., and Coletti-Previero, M. A. (1990) Molecular recognition between serine proteases and new bioactive microproteins with a knotted structure Biochimie, 72 431-435

S. P. Martsev, Y. I. Tsybovsky, O. A. Stremovskiy, S. G. Odintsov, T. G. Balandin, P. Arosio, Z. I. Kravchuk, S. M. Deyev, Fusion of the antiferritin antibody VL domain to barnase results in enhanced solubility and altered pH stability, Protein Eng. Des. Sel. 17 (2004) 85-93.

Michaelsson G, Kraaz W, Hagforsen E, Pihl-Lundin I, Loof L. (1997) Psoriasis patients have highly increased numbers of tryptase-positive mast cells in the duodenal stroma. Br J Dermatol. 1997 June; 136(6):866-70.

Miller, J. S., Westin, E. H., Schwartz, L. B. (1989) Cloning and characterization of complementary DNA for human tryptase J Clin Invest. October; 84(4):1188-95.

Miller, J. S., Moxley, G., Schwartz, L. B. (1990) Cloning and characterization of a second complementary DNA for human tryptase: J Clin Invest. 1990 September; 86(3):864-70.

J. F. Morrison, Kinetics of the reversible inhibition of enzyme-catalysed reactions by tight-binding inhibitors, Biochim. Biophys. Acta 185 (1969) 269-286.

L. Narasimhan, J. Singh, C. Humblet, K. Guruprasad, T. Blundell, Snail and spider toxins share a similar tertiary structure and 'cystine motif', Nat. Struct. Biol. 1 (1994) 850-852.

Newhouse, B. J. (2002) Tryptase inhibitors—review of the recent patent literature. IDrugs. 2002 July; 5(7):682-8.

R. S. Norton, P. K. Pallaghy, The cystine knot structure of ion channel toxins and related polypeptides, Toxicon 36 (1998) 1573-1583.

C. J. Paddon, R. W. Hartley, Expression of *Bacillus amyloliquefaciens* extracellular ribonuclease (barnase) in *Escherichia coli* following an inactivating mutation, Gene 53 (1987) 11-19.

Pallaghy, P. K., Nielsen, K. J., Craik, D. J., and Norton, R. (1994) A common structural motif incorporating a cystine knot and a triple-stranded beta-sheet in toxic and inhibitory polypeptides. Protein Sci. 3, 1833-1839.

A. Polanowski, T. Wilusz, B. Nienartowicz, E. Cieslar, A. Slominska, K. Nowak, Isolation and partial amino acid sequence of the trypsin inhibitor from the seeds of *Cucurbita maxima*, Acta Biochim. Pol. 27 (1980) 371-382.

Rees, D. C., Lipscomb, W. N. (1982) Refined crystal structure of the potato inhibitor complex of carboxypeptidase A at 2.5 A resolution. Proc. Natl. Acad. Sci. USA 77, 4633-4637.

Ruoss, S. J., Hartmann, T., Caughey, G. H (1991) Mast cell tryptase is a mitogen for cultured fibroblasts. J Clin Invest. 1991 August; 88(2):493-9.

Saether, O., Craik, D. J., Campbell, I. D., Sletten, K., Juul, J., and Norman, D. G. (1995) Elucidation of the primary and three-dimensional structure of the uterotonic polypeptide kalata B1 Biochemistry 34, 4147-4158

Sambrook J., Fritsch E. F. & Maniatis T. (1989) Molecular cloning: a laboratory manual. pp. Pages. New York: Cold Spring Harbor Laboratory Press.

Schwartz, L. B., Metcalfe, D. D., Miller, J. S., Earl, H. & Sullivan, T. (1987) Tryptase levels as an indicator of mast-cell activation in systemic anaphylaxis and mastocytosis. N. Engl. J. Med. 316, 1622-6.

Schwartz, L. B., Yunginger, J. W., Miller, J., Bokhari, R. & Dull, D. (1989) Time course of appearance and disappearance of human mast cell tryptase in the circulation after anaphylaxis. J. Clin. Invest. 83, 1551-5.

Schwartz L. B. (1994) Tryptase: a mast cell serine protease. Methods in Enzymology 244, 88-100.

Sekizawa, K., Caughey, G. H., Lazarus, S. C., Gold, W. M. & Nadel, J. A. (1989) Mast cell tryptase causes airway smooth muscle hyperresponsiveness in dogs. J. Clin. Invest. 83, 175-9.

Shalit, M., Schwartz, L. B., von-Allmen, C., Atkins, P. C., Lavker, R. M. & Zweiman, B. (1990) Release of histamine and tryptase in vivo after prolonged cutaneous challenge with allergen in humans. J. Immunol. 1988 Aug. 1; 141(3): 821-6. J. Allergy Clin. Immunol. 86, 117-25.

U. Sinha, S. A. Wolz, P. J. Lad, Two new extracellular serine proteases from *Streptomyces fradiae*, Int. J. Biochem. 23 (1991) 979-984.

Sommerhoff, C. P., Sollner, C., Mentele, R. et al. (1994) A Kazal-type inhibitor of human mast cell tryptase: isolation from the medical leech Hirudo medicinalis, characterization, and sequence analysis. Biological Chemistry Hoppe-Seyler 375, 685-694.

Sommerhoff, C. P., Bode, W., Pereira, P. J, Stubbs, M. T, Sturzebecher, J., Piechottka, G. P., Matschiner, G., Bergner, A. (1999) The structure of the human betaII-tryptase tetramer: fo(u)r better or worse. Proc Natl Acad Sci USA. September 28; 96(20):1098-491.

Sperr W. R., Jordan, J. H., Baghestanian, M, Kiener, H. P., Samorapoompichit, P., Semper, H., Hauswirth, A., Schernthaner, G. H., Chott, A., Natter, S., Kraft, D., Valenta, R., Schwartz, L. B., Geissler, K., Lechner, K., Valent, P. (2001) Expression of mast cell tryptase by myeloblasts in a group of patients with acute myeloid leukemia. Blood. October 1; 98(7):2200-9.

Sperr, W. R., Hauswirth, A. W., Valent, P. (2002) Tryptase a novel biochemical marker of acute myeloid leukemia. Leuk Lymphoma. 2002 December; 43(12):2257-61.

Stubbs, M. T., Morenweiser, R., Sturzebecher, J. et al. (1997) The three-dimensional structure of recombinant leech-derived tryptase inhibitor in complex with trypsin. Implications for the structure of human mast cell tryptase and its inhibition. Journal of Biological Chemistry 272, 19931-19937.

Tam, E. K., Franconi, G. M., Nadel, J. A. & Caughey, G. H. (1990) Protease inhibitors potentiate smooth muscle relaxation induced by vasoactive intestinal peptide in isolated human bronchi. Amer. J. Respir. Cell. Molec. Biol. 2, 449-52.

Tam, J. P., Lu, Y. A., Yang, J. L., and Chiu, K. W. (1999) An unusual structural motif of antimicrobial peptides containing end-to-end macrocycle and cystine-knot disulfides Proc. Natl. Acad. Sci. U.S.A. 96, 8913-8918

Towbin, H., Staehelin, T., Gordon, J. (1979) Electrophoretic transfer of proteins from polyacrylamide gels to nitrocellulose sheets: procedure and some applications. Proc Natl Acad Sci USA. September; 76(9):4350-4.

Vanderslice, P., Ballinger, S. M., Tam, E. K., Goldstein, S. M., Craik, C. S., Caughey, G. H. (1990) Human mast cell tryptase: multiple cDNAs and genes reveal a multigene serine protease family. Proc Natl Acad Sci USA. 1990 May; 87(10):3811-5.

W. E. Van Nostrand, S. L. Wagner, J. S. Farrow, D. D. Cunningham, Immunopurification and protease inhibitory properties of protease nexin-2/amyloid beta-protein precursor, J. Biol. Chem. 265 (1990) 9591-9594.

Walls, A. F., Bennett, A. R., Godfrey, R. C., Holgate, S. T. & Church, M. K. (1991) Mast cell tryptase and histamine concentrations in bronchoalveolar lavage fluid from patients with interstitial lung disease. Clin. Sci. 81, 183-8.

Wentzel, A., Christmann, A., Krätzner, R., Kolmar, H. (1999) Sequence requirements of the GPNG beta-turn of the *Ecballium elaterium* trypsin inhibitor II explored by combinatorial library screening, J. Biol. Chem., 274, 21037-21043.

Wentzel, A., Christmann, A., Adams, T., Kolmar, H. (2001) Display of passenger proteins on the surface of *Escherichia coli* K-12 by the enterohemorrhagic *E. coli* intimin EaeA. J. Bacteriol. December; 183(24):7273-84.

Wenzel, S. E., Fowler, A. A. 3d. & Schwartz, L. B. (1988) Activation of pulmonary mast cells by bronchoalveolar allergen challenge. In vivo release of histamine and tryptase in atopic subjects with and without asthma. Am. Rev. Respir. Dis. 137, 1002-8.

Winn, M. D., G. N. Murshudov, et al. (2003). "Macromolecular TLS refinement in REFMAC at moderate resolutions." Methods Enzymol 374: 300-21.

Witherup, K. M., Bogusky, M. J., Anderson, P. S., Ramjit, H., Ransom, R. W., Wood, T., and Sardana, M. (1994) Cyclopsychotride A, a biologically active, 31-residue cyclic peptide isolated from *Psychotria longipes*. J. Nat. Prod. 57, 1619-1625

---

The invention claimed is:

1. A method for treating or preventing-asthma that can be treated or prevented by inhibiting the activity of tryptase comprising administering to a subject in need thereof an isolated microprotein, wherein the microprotein comprises an amino acid sequence selected from the group consisting of:
    the amino acid sequence depicted in anyone of SEQ ID NOs: 1 to 17.

2. The method of claim 1, wherein the microprotein comprises at least six cysteine residues, of which six cysteine residues are connected via disulphide bonds so as to form a cystine knot.

3. The method of claim 1, wherein the microprotein has a peptide backbone with an open or a circular conformation.

4. The method of claim 1, wherein the microprotein is fused to barnase.

5. The method of claim 4, wherein the barnase is inactive.

6. The method of claim 1, wherein the microprotein is administered to the patient in the form of a gene delivery vector which expresses the microprotein.

7. The method of claim 6, wherein the cells are transformed with the vector ex vivo and the transformed cells are administered to the patient.

8. A method for the treatment of an individual with asthma comprising administering to said individual an effective amount of a pharmaceutical composition comprising the microprotein as defined in claim 1 and, optionally, a pharmaceutically acceptable carrier.

9. A method of diagnosing asthma related to an aberrant expression of tryptase, wherein the method comprises:
    contacting a sample from a cell, tissue, organ or organism with a microprotein, wherein the microprotein comprises an amino acid sequence selected from the group consisting of:
    the amino acid sequence depicted in anyone of SEQ ID NOs: 1 to 17;

determining the amount of the microprotein bound to tryptase;

comparing the determined amount bound to tryptase to a standard amount; and diagnosing asthma.

10. A kit comprising an isolated microprotein and a manual for carrying out a method of diagnosing asthma related to an aberrant expression of tryptase and, means of detection or a standard tryptase sample; wherein the microprotein consists of an amino acid sequence selected from the group consisting of:

the amino acid sequence depicted in anyone of SEQ ID NOs: 1 to 17.

11. A method for treating or preventing asthma comprising administering to a subject a fusion protein comprising barnase and a microprotein, wherein the microprotein comprises an amino acid sequence selected from the group consisting of:

the amino acid sequence depicted in anyone of SEQ ID NOs: 1 to 17.

12. The method of claim 11, wherein said barnase is inactive.

13. A method of treating or preventing asthma of claim 11, wherein the fusion protein is administered to the patient as a gene delivery vector comprising a nucleic acid molecule, wherein the nucleic acid molecule comprises a nucleotide sequence encoding the fusion protein of claim 11.

14. The method of claim 13, wherein the nucleic acid molecule comprises DNA, cDNA, or RNA.

15. The method of claim 13, wherein the nucleotide sequence encoding the fusion protein is operably linked to one or more expression control sequences allowing the expression of the fusion protein in a host cell.

16. The method of claim 13, wherein the subject is administered a host cell genetically engineered with the vector comprising said nucleic acid molecule.

17. A method for preparing a fusion protein comprising cultivating the host cell of claim 16 under conditions that the fusion protein encoded by said nucleic acid molecule or vector is expressed; and recovering the fusion protein from the culture.

18. The method of claim 17, wherein said recovering comprises a step in which the fusion protein is purified by way of binding the barnase moiety of the fusion protein to barstar.

19. A method of treating or preventing asthma comprising administering to a subject in need thereof a crystal of a microprotein fused with barnase, wherein the microprotein comprises an amino acid sequence selected from the group consisting of:

the amino acid sequence depicted in anyone of SEQ ID NOs: 1 to 17.

20. The method of claim 19, wherein the microprotein comprises the amino acid sequence depicted in SEQ ID NO: 7.

21. The method of claim 19, wherein the barnase is inactive.

22. The method of claim 19 wherein the microprotein fused with barnase comprises the amino acid sequence set forth in SEQ ID NO: 19.

23. The method of claim 19, wherein the crystal belongs to space group C2221.

24. The method of claim 19, wherein the crystal has the unit cell dimensions of a=73.981 Å, b=217.820 Å and c=58.322 Å, $\alpha=\beta=\gamma=90°$.

25. The method of claim 19 wherein the crystal has the crystal coordinates as depicted in Table 6.

26. The method of claim 19, wherein a pharmaceutical composition comprises the crystal and, optionally, a pharmaceutically acceptable carrier.

27. A method for preventing asthma that can be prevented by inhibiting the activity of tryptase comprising administering to a subject in need thereof an isolated microprotein, wherein the microprotein consists of an amino acid sequence selected from the group consisting of:

the amino acid sequence depicted in anyone of SEQ ID NOs: 1 to 17.

28. The method of claim 27, wherein the microprotein is fused to barnase.

29. The method of claim 28, wherein the barnase is inactive.

30. The method of claim 27, wherein the microprotein is administered to the patient in the form of a gene delivery vector which expresses the microprotein.

31. The method of claim 29, wherein the cells are transformed with the vector ex vivo and the transformed cells are administered to the patient.

* * * * *

SEQUENCE LISTING

```
<160> NUMBER OF SEQ ID NOS: 59

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 1

Gly Val Cys Pro Lys Ile Leu Lys Lys Cys Arg Arg Asp Ser Asp Cys
1               5                   10                  15

Pro Gly Ala Cys Ile Cys Arg Gly Asn Gly Tyr Cys Gly
            20                  25

<210> SEQ ID NO 2
```

```
<211> LENGTH: 30
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 2

Gly Val Cys Pro Lys Ile Leu Lys Lys Cys Arg Arg Asp Ser Asp Cys
1               5                   10                  15

Leu Ala Gly Cys Val Cys Gly Pro Asn Gly Phe Cys Gly Ser
            20                  25                  30

<210> SEQ ID NO 3
<211> LENGTH: 34
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 3

Ser Ser Ser Met Gly Val Cys Pro Lys Ile Leu Lys Lys Cys Arg Arg
1               5                   10                  15

Asp Ser Asp Cys Leu Ala Gly Cys Val Cys Gly Pro Asn Gly Phe Cys
            20                  25                  30

Gly Ser

<210> SEQ ID NO 4
<211> LENGTH: 34
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 4

Ser Ser Ser Met Gly Val Cys Pro Arg Ile Leu Arg Arg Cys Arg Arg
1               5                   10                  15

Asp Ser Asp Cys Leu Ala Gly Cys Val Cys Gly Pro Asn Gly Phe Cys
            20                  25                  30

Gly Ser

<210> SEQ ID NO 5
<211> LENGTH: 38
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 5

Ser Ser Ser Met Gly Lys Lys Val Gly Val Cys Pro Lys Ile Leu Lys
1               5                   10                  15

Lys Cys Arg Arg Asp Ser Asp Cys Leu Ala Gly Cys Val Cys Gly Pro
            20                  25                  30

Asn Gly Phe Cys Gly Ser
        35

<210> SEQ ID NO 6
<211> LENGTH: 34
<212> TYPE: PRT
<213> ORGANISM: Artificial Sequence
<220> FEATURE:
<223> OTHER INFORMATION: Description of Artificial Sequence: Synthetic
```

-continued mutant microprotein

<400> SEQUENCE: 6

Ser Ser Ser Met Gly Val Cys Pro Lys Ile Leu Lys Lys Cys Arg Arg
1               5                   10                  15

Asp Ser Asp Cys Leu Ala Gly Cys Val Cys Thr Asn Asn Lys Phe Cys
            20                  25                  30

Gly Ser

<210> SEQ ID NO 7
<211> LENGTH: 32
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 7

Lys Lys Val Gly Val Cys Pro Lys Ile Leu Lys Lys Cys Arg Arg Asp
1               5                   10                  15

Ser Asp Cys Pro Gly Ala Cys Ile Cys Arg Gly Asn Gly Tyr Cys Gly
            20                  25                  30

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 8

Gly Val Cys Pro Arg Ile Leu Lys Lys Cys Arg Arg Asp Ser Asp Cys
1               5                   10                  15

Pro Gly Ala Cys Ile Cys Arg Gly Asn Gly Tyr Cys Gly
            20                  25

<210> SEQ ID NO 9
<211> LENGTH: 31
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 9

Gly Ser Val Cys Pro Lys Ile Leu Lys Lys Cys Arg Arg Asp Ser Asp
1               5                   10                  15

Cys Leu Ala Gly Cys Val Cys Gly Pro Asn Gly Phe Cys Gly Ser
            20                  25                  30

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 10

Gly Val Cys Pro Lys Ile Leu Ala Lys Cys Arg Arg Asp Ser Asp Cys
1               5                   10                  15

Pro Gly Ala Cys Ile Cys Arg Gly Asn Gly Tyr Cys Gly
            20                  25

```
<210> SEQ ID NO 11
<211> LENGTH: 29
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 11

Gly Val Cys Pro Lys Ile Leu Lys Ala Cys Arg Arg Asp Ser Asp Cys
1               5                   10                  15

Pro Gly Ala Cys Ile Cys Arg Gly Asn Gly Tyr Cys Gly
            20                  25

<210> SEQ ID NO 12
<211> LENGTH: 29
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 12

Gly Val Cys Pro Lys Ile Leu Arg Lys Cys Arg Arg Asp Ser Asp Cys
1               5                   10                  15

Pro Gly Ala Cys Ile Cys Arg Gly Asn Gly Tyr Cys Gly
            20                  25

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 13

Gly Val Cys Pro Lys Ile Leu Lys Arg Cys Arg Arg Asp Ser Asp Cys
1               5                   10                  15

Pro Gly Ala Cys Ile Cys Arg Gly Asn Gly Tyr Cys Gly
            20                  25

<210> SEQ ID NO 14
<211> LENGTH: 32
<212> TYPE: PRT
<213> ORGANISM: Momordica cochinchinensis

<400> SEQUENCE: 14

Ser Gly Ser Gly Val Cys Pro Lys Ile Leu Gln Arg Cys Arg Arg Asp
1               5                   10                  15

Ser Asp Cys Pro Gly Ala Cys Ile Cys Arg Gly Asn Gly Tyr Cys Gly
            20                  25                  30

<210> SEQ ID NO 15
<211> LENGTH: 30
<212> TYPE: PRT
<213> ORGANISM: Momordica cochinchinensis

<400> SEQUENCE: 15

Gln Arg Ala Cys Pro Arg Ile Leu Lys Lys Cys Arg Arg Asp Ser Asp
1               5                   10                  15

Cys Pro Gly Glu Cys Ile Cys Lys Glu Asn Gly Tyr Cys Gly
            20                  25                  30
```

```
<210> SEQ ID NO 16
<211> LENGTH: 32
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(2)
<223> OTHER INFORMATION: Lys or Arg
<220> FEATURE:
<221> NAME/KEY: MOD_RES
<222> LOCATION: (8)..(8)
<223> OTHER INFORMATION: Lys or Arg
<220> FEATURE:
<221> NAME/KEY: MOD_RES
<222> LOCATION: (11)..(12)
<223> OTHER INFORMATION: Lys or Arg
<220> FEATURE:
<221> NAME/KEY: MOD_RES
<222> LOCATION: (14)..(15)
<223> OTHER INFORMATION: Lys or Arg

<400> SEQUENCE: 16

Xaa Xaa Val Gly Val Cys Pro Xaa Ile Leu Xaa Xaa Cys Xaa Xaa Asp
1               5                   10                  15

Ser Asp Cys Pro Gly Ala Cys Ile Cys Arg Gly Asn Gly Tyr Cys Gly
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(2)
<223> OTHER INFORMATION: Lys or Arg
<220> FEATURE:
<221> NAME/KEY: MOD_RES
<222> LOCATION: (8)..(8)
<223> OTHER INFORMATION: Lys or Arg
<220> FEATURE:
<221> NAME/KEY: MOD_RES
<222> LOCATION: (11)..(12)
<223> OTHER INFORMATION: Lys or Arg
<220> FEATURE:
<221> NAME/KEY: MOD_RES
<222> LOCATION: (14)..(15)
<223> OTHER INFORMATION: Lys or Arg

<400> SEQUENCE: 17

Xaa Xaa Val Gly Val Cys Pro Xaa Ile Leu Xaa Xaa Cys Xaa Xaa Asp
1               5                   10                  15

Ser Asp Cys Leu Ala Gly Cys Val Cys Gly Pro Asn Gly Phe Cys Gly
            20                  25                  30

<210> SEQ ID NO 18
<211> LENGTH: 33
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(9)
```

```
<223> OTHER INFORMATION: Any amino acid
<220> FEATURE:
<221> NAME/KEY: MOD_RES
<222> LOCATION: (11)..(14)
<223> OTHER INFORMATION: Any amino acid
<220> FEATURE:
<221> NAME/KEY: MOD_RES
<222> LOCATION: (15)..(17)
<223> OTHER INFORMATION: Any amino acid or absent
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid
<220> FEATURE:
<221> NAME/KEY: MOD_RES
<222> LOCATION: (27)..(31)
<223> OTHER INFORMATION: Any amino acid
<220> FEATURE:
<221> NAME/KEY: MOD_RES
<222> LOCATION: (32)..(33)
<223> OTHER INFORMATION: Any amino acid or absent

<400> SEQUENCE: 18

Cys Xaa Xaa Xaa Cys Xaa Xaa Xaa Cys Xaa Xaa Xaa Xaa Xaa
1               5                   10                  15

Xaa Cys Xaa Cys Xaa Xaa Xaa Xaa Xaa Cys Xaa Xaa Xaa Xaa Xaa
        20                  25                  30

Xaa

<210> SEQ ID NO 19
<211> LENGTH: 144
<212> TYPE: PRT
<213> ORGANISM: Artificial Sequence
<220> FEATURE:
<223> OTHER INFORMATION: Description of Artificial Sequence: Synthetic
      fusion protein of barnase and microprotein
      MCoTi-II

<400> SEQUENCE: 19

Met Gln Val Ile Asn Thr Phe Asp Gly Val Ala Asp Tyr Leu Gln Thr
1               5                   10                  15

Tyr His Lys Leu Pro Asp Asn Tyr Ile Thr Lys Ser Glu Ala Gln Ala
            20                  25                  30

Leu Gly Trp Val Ala Ser Lys Gly Asn Leu Ala Asp Val Ala Pro Gly
        35                  40                  45

Lys Ser Ile Gly Gly Asp Ile Phe Ser Asn Arg Glu Gly Lys Leu Pro
    50                  55                  60

Gly Lys Ser Gly Arg Thr Trp Arg Glu Ala Asp Ile Asn Tyr Thr Ser
65                  70                  75                  80

Gly Phe Arg Asn Ser Asp Arg Ile Leu Tyr Ser Ser Asp Trp Leu Ile
                85                  90                  95

Tyr Lys Thr Thr Asp Ala Tyr Gln Thr Phe Thr Lys Ile Arg Ser Ser
            100                 105                 110

Ser Met Gly Val Cys Pro Lys Ile Leu Lys Lys Cys Arg Arg Asp Ser
        115                 120                 125

Asp Cys Leu Ala Gly Cys Val Cys Gly Pro Asn Gly Phe Cys Gly Ser
    130                 135                 140

<210> SEQ ID NO 20
<211> LENGTH: 96
<212> TYPE: DNA
<213> ORGANISM: Artificial Sequence
```

```
<220> FEATURE:
<223> OTHER INFORMATION: Description of Artificial Sequence: Synthetic
      mutant oligonucleotide
<220> FEATURE:
<221> NAME/KEY: CDS
<222> LOCATION: (1)..(93)

<400> SEQUENCE: 20 ggg tcc gtt tgc ccg aaa atc ctg aaa aaa tgt cga cgt gac tcc gac      48
Gly Ser Val Cys Pro Lys Ile Leu Lys Lys Cys Arg Arg Asp Ser Asp
1               5                   10                  15 tgc ctg gct ggc tgc gtt tgc ggg ccc aac ggt ttc tgc ggg tcc taa      96
Cys Leu Ala Gly Cys Val Cys Gly Pro Asn Gly Phe Cys Gly Ser
            20                  25                  30

<210> SEQ ID NO 21
<211> LENGTH: 31
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 21

Gly Ser Val Cys Pro Lys Ile Leu Lys Lys Cys Arg Arg Asp Ser Asp
1               5                   10                  15

Cys Leu Ala Gly Cys Val Cys Gly Pro Asn Gly Phe Cys Gly Ser
            20                  25                  30

<210> SEQ ID NO 22
<211> LENGTH: 34
<212> TYPE: PRT
<213> ORGANISM: Momordica cochinchinensis

<400> SEQUENCE: 22

Cys Pro Lys Ile Leu Lys Lys Cys Arg Arg Asp Ser Asp Cys Pro Gly
1               5                   10                  15

Ala Cys Ile Cys Arg Gly Asn Gly Tyr Cys Gly Ser Gly Ser Asp Gly
            20                  25                  30

Gly Val

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Synthetic
      hybrid of proteins of McoTi-o and EETI-II

<400> SEQUENCE: 23

Gly Val Cys Pro Arg Ile Leu Met Arg Cys Arg Arg Asp Ser Asp Cys
1               5                   10                  15

Leu Ala Gly Cys Val Cys Gly Pro Asn Gly Phe Cys Gly
            20                  25

<210> SEQ ID NO 24
<211> LENGTH: 28
<212> TYPE: PRT
<213> ORGANISM: Ecballium elaterium

<400> SEQUENCE: 24

Gly Cys Pro Arg Ile Leu Met Arg Cys Lys Gln Asp Ser Asp Cys Leu
1               5                   10                  15

Ala Gly Cys Val Cys Gly Pro Asn Gly Phe Cys Gly
            20                  25
```

```
<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 25
ccggcgatgg ccatggatgc acaggttatc aacacgtttg                            40

<210> SEQ ID NO 26
<211> LENGTH: 42
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 26
gttcgtccgc ttttgcccgg aagtttgcct tccctgtttg ag                         42

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 27
cttccgggca aaagcggacg aac                                              23

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 28
gaattcggtc tgattttttgt aaaggtctga taatgggccg ttgttttgta                50

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 29
gcgcactagt gctagcgatc tcgatcccgc gaa                                   33

<210> SEQ ID NO 30
<211> LENGTH: 59
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 30
ctgtcccggg cgaattcggt ctgattttttg taaaggtctg ataggcgtcc gttgttttg      59
```

<210> SEQ ID NO 31
<211> LENGTH: 56
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 31
gcatgcgctc ttctaactgc atatgcgggc ccaacggtta ctgcggttcc ggatcc     56

<210> SEQ ID NO 32
<211> LENGTH: 57
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 32
cgtcgacatt ttttcaggat tttcgggcaa acaccaccgt cggatccgga accgcag    57

<210> SEQ ID NO 33
<211> LENGTH: 57
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 33
gcatgcgctc ttctgcaagc acccgggcag tcggagtcac gtcgacattt tttcagg    57

<210> SEQ ID NO 34
<211> LENGTH: 29
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 34

Gly Val Cys Pro Ala Ile Leu Lys Lys Cys Arg Arg Asp Ser Asp Cys
1               5                   10                  15

Pro Gly Ala Cys Ile Cys Arg Gly Asn Gly Tyr Cys Gly
            20                  25

<210> SEQ ID NO 35
<211> LENGTH: 41
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 35

Ser Ser Ser Met Gly Ile Glu Gly Arg Glu Glu Arg Ile Cys Pro Leu
1               5                   10                  15

Ile Trp Met Glu Cys Lys Arg Asp Ser Asp Cys Leu Ala Gly Cys Val
            20                  25                  30

Cys Gly Pro Asn Gly Phe Cys Gly Ser
        35                  40

<210> SEQ ID NO 36
<211> LENGTH: 29
<212> TYPE: PRT
<213> ORGANISM: Artificial Sequence

```
<220> FEATURE:
<223> OTHER INFORMATION: Description of Artificial Sequence: Synthetic
      mutant microprotein

<400> SEQUENCE: 36

Gly Cys Pro Arg Ile Leu Ile Arg Cys Lys Gln Asp Ser Asp Cys Leu
1               5                   10                  15

Ala Gly Cys Val Cys Gly Pro Asn Gly Phe Cys Gly Ser
            20                  25

<210> SEQ ID NO 37
<211> LENGTH: 34
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 37

Ser Ser Ser Met Gly Val Cys Pro Arg Asn Arg Gln Lys Cys Arg Arg
1               5                   10                  15

Asp Ser Asp Cys Leu Ala Gly Cys Val Cys Gly Pro Asn Gly Phe Cys
            20                  25                  30

Gly Ser

<210> SEQ ID NO 38
<211> LENGTH: 34
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 38

Ser Ser Ser Met Gly Val Cys Pro Arg Asn Arg Gln Arg Cys Arg Arg
1               5                   10                  15

Asp Ser Asp Cys Leu Ala Gly Cys Val Cys Thr Asn Asn Lys Phe Cys
            20                  25                  30

Gly Ser

<210> SEQ ID NO 39
<211> LENGTH: 34
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 39

Ser Ser Ser Met Gly Val Cys Pro Lys Ile Leu Lys Ala Cys Ala Arg
1               5                   10                  15

Asp Ser Asp Cys Leu Ala Gly Cys Val Cys Gly Pro Asn Gly Phe Cys
            20                  25                  30

Gly Ser

<210> SEQ ID NO 40
<211> LENGTH: 34
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 40
```

```
Ser Ser Ser Met Gly Val Cys Pro Lys Ile Leu Lys Ala Cys Arg Arg
1               5                   10                  15

Asp Ser Asp Cys Leu Ala Gly Cys Val Cys Pro Asn Gly Phe Cys
            20                  25                  30

Gly Ser
```

<210> SEQ ID NO 41
<211> LENGTH: 29
<212> TYPE: PRT
<213> ORGANISM: Artificial Sequence
<220> FEATURE:
<223> OTHER INFORMATION: Description of Artificial Sequence: Synthetic
      mutant microprotein
<220> FEATURE:
<221> NAME/KEY: MOD_RES
<222> LOCATION: (5)..(5)
<223> OTHER INFORMATION: Guaninyl-Alanine

<400> SEQUENCE: 41

```
Gly Val Cys Pro Ala Ile Leu Lys Lys Cys Arg Arg Asp Ser Asp Cys
1               5                   10                  15

Pro Gly Ala Cys Ile Cys Arg Gly Asn Gly Tyr Cys Gly
            20                  25
```

<210> SEQ ID NO 42
<211> LENGTH: 34
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 42

```
Ser Ser Ser Met Gly Val Cys Pro Lys Ile Leu Lys Lys Cys Ala Arg
1               5                   10                  15

Asp Ser Asp Cys Leu Ala Gly Cys Val Cys Gly Pro Asn Gly Phe Cys
            20                  25                  30

Gly Ser
```

<210> SEQ ID NO 43
<211> LENGTH: 34
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 43

```
Ser Ser Ser Met Gly Val Cys Pro Lys Ile Leu Lys Lys Cys Arg Ala
1               5                   10                  15

Asp Ser Asp Cys Leu Ala Gly Cys Val Cys Gly Pro Asn Gly Phe Cys
            20                  25                  30

Gly Ser
```

<210> SEQ ID NO 44
<211> LENGTH: 36
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 44

```
Ser Ser Ser Met Gly Lys Lys Val Cys Pro Arg Ile Leu Arg Arg Cys
1               5                   10                  15
```

```
Arg Arg Asp Ser Asp Cys Leu Ala Gly Cys Val Cys Gly Pro Asn Gly
         20                  25                  30

Phe Cys Gly Ser
         35

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 45
ccggcgatgg ccatggatgc acaggttatc aacacgtttg                           40

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 46
gttcgtccgc ttttgcccgg aagtttgcct tccctgtttg ag                        42

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 47
cttccgggca aaagcggacg aac                                             23

<210> SEQ ID NO 48
<211> LENGTH: 50
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 48
gaattcggtc tgattttgt aaaggtctga taatgggccg ttgttttgta                 50

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 49
gcgcactagt gctagcgatc tcgatcccgc gaa                                  33

<210> SEQ ID NO 50
<211> LENGTH: 59
<212> TYPE: DNA
<213> ORGANISM: Artificial Sequence
<220> FEATURE:
<223> OTHER INFORMATION: Description of Artificial Sequence: Synthetic
      PCR primer oligonucleotide
```

<400> SEQUENCE: 50
ctgtcccggg cgaattcggt ctgattttt g taaaggtctg ataggcgtcc gttgttttg    59

<210> SEQ ID NO 51
<211> LENGTH: 66
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 51
gactccggcc atggggatcg agggaagggg gtgcccgcgc attctgatgc gctgcaaaca    60
ggactc                                                              66

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 52
ccacaagctt gaaaacgttt cag                                           23

<210> SEQ ID NO 53
<211> LENGTH: 56
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 53
gcatgcgctc ttctaactgc atatgcgggc ccaacggtta ctgcggttcc ggatcc       56

<210> SEQ ID NO 54
<211> LENGTH: 57
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 54
cgtcgacatt ttttcaggat tttcgggcaa acaccaccgt cggatccgga accgcag      57

<210> SEQ ID NO 55
<211> LENGTH: 57
<212> TYPE: DNA
<213> ORGANISM: Artificial Sequence
<220> FEATURE:
<223> OTHER INFORMATION: Description of Artificial Sequence: Synthetic
      PCR primer oligonucleotide

<400> SEQUENCE: 55
gcatgcgctc ttctgcaagc acccgggcag tcggagtcac gtcgacattt tttcagg      57

<210> SEQ ID NO 56
<211> LENGTH: 59
<212> TYPE: DNA
<213> ORGANISM: Artificial Sequence
<220> FEATURE:
<223> OTHER INFORMATION: Description of Artificial Sequence: Synthetic
      PCR primer oligonucleotide

```
<400> SEQUENCE: 56
agctcttcca tggggctggt tccgcgtggg tccgtttgcc cgaaaatcct gaaaaaatg        59

<210> SEQ ID NO 57
<211> LENGTH: 29
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 57

Gly Cys Pro Arg Ile Leu Ile Arg Cys Lys Gln Asp Ser Asp Cys Leu
1               5                   10                  15

Ala Gly Cys Val Cys Gly Pro Asn Gly Phe Cys Gly Ser
            20                  25

<210> SEQ ID NO 58
<211> LENGTH: 29
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 58

Gly Cys Pro Arg Ile Leu Met Arg Cys Lys Gln Asp Ser Asp Cys Leu
1               5                   10                  15

Ala Gly Cys Val Cys Gly Pro Asn Gly Phe Cys Gly Ser
            20                  25

<210> SEQ ID NO 59
<211> LENGTH: 31
<212> TYPE: PRT
<213> ORGANISM: Artificial Sequence
<220> FEATURE:
<223> OTHER INFORMATION: Description of Artificial Sequence: Synthetic
      mutant microprotein

<400> SEQUENCE: 59

Gly Ser Val Cys Pro Arg Ile Leu Lys Lys Cys Arg Arg Asp Ser Asp
1               5                   10                  15

Cys Leu Ala Gly Cys Val Cys Gly Pro Asn Gly Phe Cys Gly Ser
            20                  25                  30
```